US011993651B2

(12) United States Patent
Wilson et al.

(10) Patent No.: US 11,993,651 B2
(45) Date of Patent: May 28, 2024

(54) ANTI-LAG-3 ANTIBODIES AND METHODS OF USE THEREOF

(71) Applicant: Agenus Inc., Lexington, MA (US)

(72) Inventors: Nicholas Stuart Wilson, San Carlos, CA (US); David Adam Savitsky, Boxford, MA (US); Shawn Michael Jennings, Acton, MA (US); Marc van Dijk, Bosch en Duin (NL); Cornelia Anne Mundt, Lörrach (DE)

(73) Assignee: AGENUS INC., Lexington, MA (US)

( * ) Notice: Subject to any disclaimer, the term of this patent is extended or adjusted under 35 U.S.C. 154(b) by 769 days.

(21) Appl. No.: 17/100,038

(22) Filed: Nov. 20, 2020

(65) Prior Publication Data

US 2021/0171634 A1 Jun. 10, 2021

Related U.S. Application Data

(63) Continuation of application No. 16/989,369, filed on Aug. 10, 2020, now Pat. No. 10,882,908, which is a continuation of application No. 15/730,249, filed on Oct. 11, 2017, now Pat. No. 10,844,119.

(60) Provisional application No. 62/420,280, filed on Nov. 10, 2016, provisional application No. 62/406,766, filed on Oct. 11, 2016.

(51) Int. Cl.
*C07K 16/00* (2006.01)
*A61K 47/68* (2017.01)
*A61P 35/00* (2006.01)
*C07K 16/28* (2006.01)

(52) U.S. Cl.
CPC ...... *C07K 16/2803* (2013.01); *A61K 47/6873* (2017.08); *A61P 35/00* (2018.01); *C07K 2317/20* (2013.01); *C07K 2317/24* (2013.01); *C07K 2317/34* (2013.01); *C07K 2317/55* (2013.01); *C07K 2317/76* (2013.01)

(58) Field of Classification Search
None
See application file for complete search history.

(56) References Cited

U.S. PATENT DOCUMENTS

| 5,225,539 A | 7/1993 | Winter |
| 5,403,484 A | 4/1995 | Ladner et al. |
| 5,413,923 A | 5/1995 | Kucherlapati et al. |
| 5,427,908 A | 6/1995 | Dower et al. |
| 5,516,637 A | 5/1996 | Huang et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,585,097 A | 12/1996 | Bolt et al. |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,658,727 A | 8/1997 | Barbas et al. |
| 5,661,016 A | 8/1997 | Lonberg et al. |
| 5,677,425 A | 10/1997 | Bodmer et al. |
| 5,698,426 A | 12/1997 | Huse |
| 5,709,874 A | 1/1998 | Hanson et al. |
| 5,733,743 A | 3/1998 | Johnson et al. |
| 5,750,753 A | 5/1998 | Kimae et al. |
| 5,759,542 A | 6/1998 | Gurewich |
| 5,766,886 A | 6/1998 | Studnicka et al. |
| 5,780,225 A | 7/1998 | Wigler et al. |
| 5,807,715 A | 9/1998 | Morrison et al. |
| 5,814,318 A | 9/1998 | Lonberg et al. |
| 5,821,047 A | 10/1998 | Garrard et al. |
| 5,837,242 A | 11/1998 | Holliger et al. |
| 5,840,674 A | 11/1998 | Yatvin et al. |
| 5,860,957 A | 1/1999 | Jacobsen et al. |
| 5,869,046 A | 2/1999 | Presta et al. |
| 5,869,620 A | 2/1999 | Whitlow et al. |
| 5,885,793 A | 3/1999 | Griffiths et al. |
| 5,900,252 A | 5/1999 | Calanchi et al. |
| 5,939,598 A | 8/1999 | Kucherlapati et al. |
| 5,948,433 A | 9/1999 | Burton et al. |
| 5,965,726 A | 10/1999 | Pavlakis et al. |
| 5,969,108 A | 10/1999 | McCafferty et al. |
| 5,972,366 A | 10/1999 | Haynes et al. |
| 5,983,134 A | 11/1999 | Ostrow |

(Continued)

FOREIGN PATENT DOCUMENTS

| EP | 0239400 A2 | 9/1987 |
| EP | 0519596 A1 | 12/1992 |

(Continued)

OTHER PUBLICATIONS

Colman et al., iResearch in Immunology (145(1):33-36, 1994.*
Abaza et al., Journal of Protein Chemistry (11(5):433-444, 1992.*
Lederman et al Molecular Immunology (28:1171-1181, 1991.*
Lin et al ., PNAS (77:3211-3214, 1980.*
Wang et al. (JBC 276:49213-49220.*
Lerner Nature 1982; 299:592-596.*
Edwards et al., JMB 2003, v.334, pp. 103-118.*
Lloyd et al., 2009, Protein Engineering, v.22, pp. 159-168.*
U.S. Appl. No. 15/730,249 / 2018/0127499 / U.S. Pat. No. 10,844,119, filed Oct. 11, 2017 / May 10, 2018 / Nov. 24, 2020, Nicholas Stuart Wilson.
U.S. Appl. No. 16/989,369 / 2020/0362037 / U.S. Pat. No. 10,882,908, filed Aug. 10, 2020 / Nov. 19, 2020 / Jan. 5, 2021, Nicholas Stuart Wilson.

(Continued)

Primary Examiner — Michail A Belyavskyi
(74) Attorney, Agent, or Firm — Dechert LLP; Andrew T. Wilkins

(57) ABSTRACT

The instant disclosure provides antibodies that specifically bind to LAG-3 (e.g., human LAG-3) and antagonize LAG-3 function. Also provided are pharmaceutical compositions comprising these antibodies, nucleic acids encoding these antibodies, expression vectors and host cells for making these antibodies, and methods of treating a subject using these antibodies.

15 Claims, 16 Drawing Sheets

Specification includes a Sequence Listing.

(56) References Cited

U.S. PATENT DOCUMENTS

| | | |
|---|---|---|
| 5,985,307 A | 11/1999 | Hanson et al. |
| 5,985,317 A | 11/1999 | Venkateshwaran et al. |
| 5,989,830 A | 11/1999 | Davis et al. |
| 6,004,534 A | 12/1999 | Langer et al. |
| 6,005,079 A | 12/1999 | Casterman et al. |
| 6,010,715 A | 1/2000 | Wick et al. |
| 6,024,975 A | 2/2000 | D'Angelo et al. |
| 6,039,975 A | 3/2000 | Shah et al. |
| 6,048,736 A | 4/2000 | Kosak |
| 6,060,082 A | 5/2000 | Chen et al. |
| 6,071,495 A | 6/2000 | Unger et al. |
| 6,075,181 A | 6/2000 | Kucherlapati et al. |
| 6,120,751 A | 9/2000 | Unger |
| 6,121,022 A | 9/2000 | Presta et al. |
| 6,131,570 A | 10/2000 | Schuster et al. |
| 6,132,992 A | 10/2000 | Ledbetter et al. |
| 6,139,865 A | 10/2000 | Friend et al. |
| 6,143,273 A | 11/2000 | Faure et al. |
| 6,150,184 A | 11/2000 | Evans et al. |
| 6,165,745 A | 12/2000 | Ward et al. |
| 6,167,301 A | 12/2000 | Flower et al. |
| 6,174,666 B1 | 1/2001 | Pavlakis et al. |
| 6,194,551 B1 | 2/2001 | Idusogie et al. |
| 6,197,524 B1 | 3/2001 | Romagnani |
| 6,253,872 B1 | 7/2001 | Neumann |
| 6,256,533 B1 | 7/2001 | Yuzhakov et al. |
| 6,261,595 B1 | 7/2001 | Stanley et al. |
| 6,267,983 B1 | 7/2001 | Fujii et al. |
| 6,271,359 B1 | 8/2001 | Norris et al. |
| 6,274,552 B1 | 8/2001 | Tamarkin et al. |
| 6,277,375 B1 | 8/2001 | Ward |
| 6,291,664 B1 | 9/2001 | Pavlakis et al. |
| 6,316,652 B1 | 11/2001 | Steliou |
| 6,331,415 B1 | 12/2001 | Cabilly et al. |
| 6,383,492 B1 | 5/2002 | Srivastava et al. |
| 6,391,306 B1 | 5/2002 | Srivastava et al. |
| 6,403,095 B1 | 6/2002 | Srivastava et al. |
| 6,407,213 B1 | 6/2002 | Carter et al. |
| 6,410,026 B1 | 6/2002 | Srivastava |
| 6,414,132 B1 | 7/2002 | Pavlakis et al. |
| 6,436,404 B1 | 8/2002 | Srivastava et al. |
| 6,447,780 B1 | 9/2002 | Srivastava et al. |
| 6,447,781 B1 | 9/2002 | Srivastava |
| 6,610,659 B1 | 8/2003 | Pramod |
| 6,645,495 B1 | 11/2003 | Kensil et al. |
| 6,737,056 B1 | 5/2004 | Presta |
| 6,794,498 B2 | 9/2004 | Pavlakis et al. |
| 6,808,710 B1 | 10/2004 | Wood et al. |
| 6,984,720 B1 | 1/2006 | Korman et al. |
| 7,029,678 B2 | 4/2006 | Momin et al. |
| 7,034,121 B2 | 4/2006 | Carreno et al. |
| 7,183,076 B2 | 2/2007 | Arathoon et al. |
| 7,332,582 B2 | 2/2008 | Hardy et al. |
| 7,411,057 B2 | 8/2008 | Hanson et al. |
| 7,488,802 B2 | 2/2009 | Collins et al. |
| 7,658,921 B2 | 2/2010 | Dall'Acqua et al. |
| 7,709,226 B2 | 5/2010 | Foote |
| 7,858,589 B2 | 12/2010 | Kensil |
| 7,943,743 B2 | 5/2011 | Korman et al. |
| 7,951,917 B1 | 5/2011 | Arathoon et al. |
| 7,972,993 B2 | 7/2011 | Slootstra et al. |
| 8,088,449 B2 | 1/2012 | Bailey et al. |
| 8,114,845 B2 | 2/2012 | Langermann et al. |
| 8,168,179 B2 | 5/2012 | Honjo et al. |
| 8,168,757 B2 | 5/2012 | Finnefrock et al. |
| 8,217,149 B2 | 7/2012 | Irving et al. |
| 8,227,577 B2 | 7/2012 | Klein et al. |
| 8,354,509 B2 | 1/2013 | Carven et al. |
| 8,354,847 B2 | 1/2013 | Robinson |
| 8,551,481 B2 | 10/2013 | Pardoll et al. |
| 8,552,154 B2 | 10/2013 | Freeman et al. |
| 8,586,713 B2 | 11/2013 | Davis et al. |
| 8,591,886 B2 | 11/2013 | Ponath et al. |
| 8,686,119 B2 | 4/2014 | Rotem-Yehudar et al. |
| 8,697,845 B2 | 4/2014 | Ward et al. |
| 8,735,553 B1 | 5/2014 | Li et al. |
| 8,747,847 B2 | 6/2014 | Rotem-Yehudar et al. |
| 8,779,105 B2 | 7/2014 | Korman et al. |
| 8,779,108 B2 | 7/2014 | Queva et al. |
| 8,927,697 B2 | 1/2015 | Davis et al. |
| 8,981,063 B2 | 3/2015 | Chen |
| 8,993,731 B2 | 3/2015 | Tyson |
| 9,005,629 B2 | 4/2015 | Pardoll et al. |
| 9,074,000 B2 | 7/2015 | Scheinberg et al. |
| 9,102,727 B2 | 8/2015 | Freeman et al. |
| 9,132,281 B2 | 9/2015 | Zeng et al. |
| 9,175,082 B2 | 11/2015 | Zhou et al. |
| 9,205,148 B2 | 12/2015 | Langermann et al. |
| 9,244,059 B2 | 1/2016 | Triebel et al. |
| 9,425,591 B2 | 8/2016 | Sharma et al. |
| 9,505,839 B2 | 11/2016 | Lonberg et al. |
| 9,515,982 B2 | 12/2016 | Belghoul |
| 9,850,306 B2 | 12/2017 | Bedi et al. |
| 9,902,772 B2 | 2/2018 | Zhou et al. |
| 9,908,936 B2 | 3/2018 | Triebel et al. |
| 10,081,681 B2 | 9/2018 | Alan et al. |
| 10,144,778 B2 | 12/2018 | Eisenbach-Schwartz et al. |
| 10,160,806 B2 | 12/2018 | Ezio et al. |
| 10,188,730 B2 | 1/2019 | Linda et al. |
| 10,844,119 B2 | 11/2020 | Wilson et al. |
| 10,882,908 B2 | 1/2021 | Wilson et al. |
| 2003/0232323 A1 | 12/2003 | Freeman et al. |
| 2004/0014194 A1 | 1/2004 | Beyer et al. |
| 2005/0042664 A1 | 2/2005 | Wu et al. |
| 2005/0048549 A1 | 3/2005 | Cao et al. |
| 2007/0099240 A1 | 5/2007 | Puijk et al. |
| 2008/0139407 A1 | 6/2008 | Slootstra et al. |
| 2009/0123477 A1 | 5/2009 | Hanke et al. |
| 2009/0304679 A1 | 12/2009 | Weidanz |
| 2010/0203056 A1 | 8/2010 | Irving et al. |
| 2011/0150892 A1 | 6/2011 | Thudium et al. |
| 2013/0202623 A1 | 8/2013 | Chomont et al. |
| 2013/0267688 A1 | 10/2013 | Chin et al. |
| 2013/0291136 A1 | 10/2013 | Freeman et al. |
| 2013/0323249 A1 | 12/2013 | Zhou et al. |
| 2014/0044738 A1 | 2/2014 | Langermann et al. |
| 2014/0093511 A1 | 4/2014 | Lonberg et al. |
| 2014/0105914 A1 | 4/2014 | Jones et al. |
| 2014/0134191 A1 | 5/2014 | Weidanz et al. |
| 2014/0286935 A1 | 9/2014 | Hamblin et al. |
| 2014/0341917 A1 | 11/2014 | Nastri et al. |
| 2014/0356363 A1 | 12/2014 | Zhou et al. |
| 2015/0174268 A1 | 6/2015 | Li et al. |
| 2015/0202291 A1 | 7/2015 | Bosch et al. |
| 2015/0203580 A1 | 7/2015 | Papadopoulos et al. |
| 2015/0225483 A1 | 8/2015 | Lo |
| 2015/0322119 A1 | 11/2015 | Engelhardt et al. |
| 2015/0346208 A1 | 12/2015 | Couto et al. |
| 2015/0355184 A1 | 12/2015 | Pierce et al. |
| 2016/0075783 A1 | 3/2016 | King et al. |
| 2016/0145355 A1 | 5/2016 | Saha et al. |
| 2016/0159905 A1 | 6/2016 | Abdiche et al. |
| 2016/0185870 A1 | 6/2016 | Van Eenennaam et al. |
| 2016/0193239 A1 | 7/2016 | Baylin et al. |
| 2016/0222121 A1 | 8/2016 | Johnson et al. |
| 2016/0355589 A1 | 12/2016 | Williams et al. |
| 2016/0376365 A1 | 12/2016 | Gurney et al. |
| 2017/0007698 A1 | 1/2017 | Kim et al. |
| 2017/0056391 A1 | 3/2017 | Li |
| 2017/0101472 A1 | 4/2017 | Ullman et al. |
| 2017/0106048 A1 | 4/2017 | Kunz et al. |
| 2017/0137517 A1 | 5/2017 | Bowman et al. |
| 2017/0143780 A1 | 5/2017 | Zitvogel et al. |
| 2017/0145099 A1 | 5/2017 | Ito et al. |
| 2017/0165230 A1 | 6/2017 | Rudd et al. |
| 2017/0184604 A1 | 6/2017 | Lee et al. |
| 2017/0209574 A1 | 7/2017 | Cao et al. |
| 2017/0216403 A1 | 8/2017 | Wittrup et al. |
| 2017/0239338 A1 | 8/2017 | Szalay et al. |
| 2017/0247459 A1 | 8/2017 | Cannarile et al. |
| 2017/0275353 A1 | 9/2017 | Sheng et al. |
| 2017/0281569 A1 | 10/2017 | Udono et al. |
| 2017/0281764 A1 | 10/2017 | Tso et al. |
| 2017/0296659 A1 | 10/2017 | Lebwohl et al. |

(56) References Cited

U.S. PATENT DOCUMENTS

| | | | |
|---|---|---|---|
| 2017/0313775 A1 | 11/2017 | Diaz et al. |
| 2017/0320950 A1 | 11/2017 | Snyder et al. |
| 2017/0334995 A1 | 11/2017 | Zettl et al. |
| 2017/0335281 A1 | 11/2017 | Loew et al. |
| 2017/0340733 A1 | 11/2017 | Cao |
| 2017/0355774 A1 | 12/2017 | Delfino et al. |
| 2017/0360932 A1 | 12/2017 | Parry |
| 2018/0015161 A1 | 1/2018 | Weiner et al. |
| 2018/0021378 A1 | 1/2018 | Kang et al. |
| 2018/0021407 A1 | 1/2018 | Gurney |
| 2018/0028626 A1 | 2/2018 | Slos et al. |
| 2018/0066053 A1 | 3/2018 | Keler et al. |
| 2018/0186878 A1 | 7/2018 | Rosenthal |
| 2018/0207212 A1 | 7/2018 | Conner |
| 2018/0214583 A1 | 8/2018 | Scholz |
| 2018/0221508 A1 | 8/2018 | Kadiyala et al. |
| 2018/0230431 A1 | 8/2018 | Bi et al. |
| 2018/0244773 A1 | 8/2018 | Gutierrez et al. |
| 2018/0250352 A1 | 9/2018 | Conner |
| 2018/0318365 A1 | 11/2018 | Yeung et al. |
| 2018/0326058 A1 | 11/2018 | Tsunenari et al. |
| 2018/0340025 A1 | 11/2018 | Dranoff et al. |
| 2018/0353524 A1 | 12/2018 | Gardai et al. |
| 2018/0355039 A1 | 12/2018 | Freeman et al. |
| 2018/0369375 A1 | 12/2018 | De Waal Malefyt et al. |
| 2018/0371083 A1 | 12/2018 | Williams et al. |
| 2019/0010231 A1 | 1/2019 | Rothe et al. |
| 2019/0015507 A1 | 1/2019 | Xu et al. |
| 2019/0016800 A1 | 1/2019 | Kang et al. |
| 2019/0023804 A1 | 1/2019 | Onik et al. |
| 2019/0031757 A1 | 1/2019 | Levade et al. |
| 2019/0038671 A1 | 2/2019 | Fan et al. |
| 2019/0038763 A1 | 2/2019 | Levade et al. |
| 2019/0040136 A1 | 2/2019 | Wang et al. |

FOREIGN PATENT DOCUMENTS

| | | |
|---|---|---|
| EP | 0592106 A1 | 4/1994 |
| EP | 1897548 A1 | 3/2008 |
| EP | 3010340 A2 | 4/2016 |
| EP | 3192805 A1 | 7/2017 |
| EP | 3226900 A1 | 10/2017 |
| WO | WO-1986005807 A1 | 10/1986 |
| WO | WO-1989001036 A1 | 2/1989 |
| WO | WO-1990002809 A1 | 3/1990 |
| WO | WO-1991009967 A1 | 7/1991 |
| WO | WO-1991010737 A1 | 7/1991 |
| WO | WO-1991010741 A1 | 7/1991 |
| WO | WO-1992001047 A1 | 1/1992 |
| WO | WO-1992018619 A1 | 10/1992 |
| WO | WO-1992022324 A1 | 12/1992 |
| WO | WO-1993011236 A1 | 6/1993 |
| WO | WO-1993017105 A1 | 9/1993 |
| WO | WO-1994004678 A1 | 3/1994 |
| WO | WO-1994025591 A1 | 11/1994 |
| WO | WO-1994/029351 A2 | 12/1994 |
| WO | WO-1995015982 A2 | 6/1995 |
| WO | WO-1995020401 A1 | 8/1995 |
| WO | WO-1996033735 A1 | 10/1996 |
| WO | WO-1996034096 A1 | 10/1996 |
| WO | WO-1997003695 A1 | 2/1997 |
| WO | WO-1997013844 A1 | 4/1997 |
| WO | WO-1997/034631 A1 | 9/1997 |
| WO | WO-1998016654 A1 | 4/1998 |
| WO | WO-1998023289 A1 | 6/1998 |
| WO | WO-1998024893 A2 | 6/1998 |
| WO | WO-1998046645 A2 | 10/1998 |
| WO | WO-1998050433 A2 | 11/1998 |
| WO | WO-2000042072 A2 | 7/2000 |
| WO | WO-2001044301 A1 | 6/2001 |
| WO | WO-2002/060919 A2 | 8/2002 |
| WO | WO-2008132601 A1 | 11/2008 |
| WO | WO-2010005958 A2 | 1/2010 |
| WO | WO-2010019570 A2 | 2/2010 |
| WO | 2010059654 A1 | 5/2010 |
| WO | WO-2013033091 A1 | 3/2013 |
| WO | WO-2014022758 A1 | 2/2014 |
| WO | WO-2014055897 A2 | 4/2014 |
| WO | WO-2014100079 A1 | 6/2014 |
| WO | WO-2014108483 A1 | 7/2014 |
| WO | WO-2014179664 A2 | 11/2014 |
| WO | WO-2014206107 A1 | 12/2014 |
| WO | WO-2014207064 A1 | 12/2014 |
| WO | WO-2014209804 A1 | 12/2014 |
| WO | WO-2015019284 A2 | 2/2015 |
| WO | WO-2015036394 A1 | 3/2015 |
| WO | WO-2015058573 A1 | 4/2015 |
| WO | WO-2015061668 A1 | 4/2015 |
| WO | WO-2015061752 A1 | 4/2015 |
| WO | WO-2015085847 A1 | 6/2015 |
| WO | WO-2015109124 A2 | 7/2015 |
| WO | WO-2015125652 A1 | 8/2015 |
| WO | WO-2015131176 A1 | 9/2015 |
| WO | WO-2015174439 A1 | 11/2015 |
| WO | WO-2015195163 A1 | 12/2015 |
| WO | WO-2015200119 A1 | 12/2015 |
| WO | WO-2016000619 A1 | 1/2016 |
| WO | WO-2016015675 A1 | 2/2016 |
| WO | WO-2016015685 A1 | 2/2016 |
| WO | WO-2016020538 A1 | 2/2016 |
| WO | WO-2016020856 A2 | 2/2016 |
| WO | WO-2016028672 A1 | 2/2016 |
| WO | WO-2016030350 A1 | 3/2016 |
| WO | WO-2016057898 A1 | 4/2016 |
| WO | WO-2016073770 A1 | 5/2016 |
| WO | WO-2016081746 A2 | 5/2016 |
| WO | WO-2016106302 A1 | 6/2016 |
| WO | WO-2016126858 A2 | 8/2016 |
| WO | WO-2016168361 A1 | 10/2016 |
| WO | WO-2016180781 A1 | 11/2016 |
| WO | WO-2016193680 A1 | 12/2016 |
| WO | WO-2016197204 A1 | 12/2016 |
| WO | WO-2016200782 A1 | 12/2016 |
| WO | WO-2017037203 A1 | 3/2017 |
| WO | WO-2017053748 A2 | 3/2017 |
| WO | WO-2017059095 A1 | 4/2017 |
| WO | WO-2017068186 A1 | 4/2017 |
| WO | WO-2017087547 A1 | 5/2017 |
| WO | WO-2017087901 A2 | 5/2017 |
| WO | WO-2017091611 A1 | 6/2017 |
| WO | WO-2017106278 A1 | 6/2017 |
| WO | WO-2017149150 A1 | 9/2017 |
| WO | WO-2017152085 A1 | 9/2017 |
| WO | WO-2017156349 A1 | 9/2017 |
| WO | WO-2017157964 A1 | 9/2017 |
| WO | WO-2017160717 A2 | 9/2017 |
| WO | WO-2017165732 A1 | 9/2017 |
| WO | WO-2017174331 A1 | 10/2017 |
| WO | WO-2017181139 A2 | 10/2017 |
| WO | WO-2017193094 A1 | 11/2017 |
| WO | WO-2017193098 A1 | 11/2017 |
| WO | WO-2017201502 A1 | 11/2017 |
| WO | WO-2017205014 A1 | 11/2017 |
| WO | WO-2017207628 A1 | 12/2017 |
| WO | WO-2017219995 A1 | 12/2017 |
| WO | WO-2017220555 A1 | 12/2017 |
| WO | WO-2017223422 A1 | 12/2017 |
| WO | WO-2018013534 A1 | 1/2018 |
| WO | WO-2018045110 A1 | 3/2018 |
| WO | WO-2018053242 A1 | 3/2018 |
| WO | WO-2018058111 A1 | 3/2018 |
| WO | WO-2018069500 A2 | 4/2018 |
| WO | WO-2018071500 A1 | 4/2018 |
| WO | WO-2018129553 A1 | 7/2018 |
| WO | WO-2018129559 A1 | 7/2018 |
| WO | WO-2018137598 A1 | 8/2018 |
| WO | WO-2018148378 A1 | 8/2018 |
| WO | WO-2018152687 A1 | 8/2018 |
| WO | WO-2018156494 A1 | 8/2018 |
| WO | WO-2018160671 A1 | 9/2018 |
| WO | WO-2018160754 A2 | 9/2018 |
| WO | WO-2018167320 A1 | 9/2018 |
| WO | WO-2018185046 A1 | 10/2018 |
| WO | WO-2018185135 A1 | 10/2018 |

(56) References Cited

FOREIGN PATENT DOCUMENTS

| | | |
|---|---|---|
| WO | WO-2018185232 A1 | 10/2018 |
| WO | WO-2018186924 A1 | 10/2018 |
| WO | WO-2018195552 A1 | 10/2018 |
| WO | WO-2018204374 A1 | 11/2018 |
| WO | WO-2018204760 A1 | 11/2018 |
| WO | WO-2018208868 A1 | 11/2018 |
| WO | WO-2018218056 A1 | 11/2018 |
| WO | WO-2018219956 A1 | 12/2018 |
| WO | WO-2018222711 A2 | 12/2018 |
| WO | WO-2018222718 A1 | 12/2018 |
| WO | WO-2018222722 A2 | 12/2018 |
| WO | WO-2018223002 A1 | 12/2018 |
| WO | WO-2018223004 A1 | 12/2018 |
| WO | WO-2018223182 A1 | 12/2018 |
| WO | WO-2018226336 A1 | 12/2018 |
| WO | WO-2018226985 A2 | 12/2018 |
| WO | WO-2018232195 A1 | 12/2018 |
| WO | WO-2018234367 A1 | 12/2018 |
| WO | WO-2018237173 A1 | 12/2018 |
| WO | WO-2018237326 A1 | 12/2018 |
| WO | WO-2019003164 A1 | 1/2019 |
| WO | WO-2019008386 A1 | 1/2019 |
| WO | WO-2019009728 A1 | 1/2019 |
| WO | WO-2019014665 A1 | 1/2019 |
| WO | WO-2019018730 A1 | 1/2019 |
| WO | WO-2019020593 A1 | 1/2019 |
| WO | WO-2019023525 A1 | 1/2019 |

OTHER PUBLICATIONS

U.S. Appl. No. 17/078,602 / 2021/0054074 / N/A, filed Oct. 23, 2020 / Feb. 25, 2021 / N/A, Nicholas Stuart Wilson.
Agenus, "Agenus IR Deck," Jan. 2017.
Anderson et al., "Lag-3, Tim-3, and TIGIT: Co-inhibitory Receptors with Specialized Functions in Immune Regulation," Immunity. May 17, 2016;44(5):989-1004.
Baixeras et al., "Characterization of the lymphocyte activation gene 3-encoded protein. A new ligand for human leukocyte antigen class II antigens," J Exp Med. 1992;176(2):327-37.
Berman et al., "The development of immunomodulatory monoclonal antibodies as a new therapeutic modality for cancer: the Bristol-Myers Squibb experience," Pharmacol Ther. Apr. 2015;148:132-53.
Blackburn et al., "Coregulation of CD8+ T cell exhaustion by multiple inhibitory receptors during chronic viral infection," Nat Immunol. Jan. 2009;10(1):29-37.
Brignone et al., "First-line chemoimmunotherapy in metastatic breast carcinoma: combination of paclitaxel and IMP321 (LAG-3Ig) enhances immune responses and antitumor activity," J Transl Med. Jul. 23, 2010;8:71.
Brignone et al., "A phase I pharmacokinetic and biological correlative study of IMP321, a novel MHC class II agonist, in patients with advanced renal cell carcinoma," Clin Cancer Res. Oct. 1, 2009;15(19):6225-31.
Butler et al., "Therapeutic PD-L1 and LAG-3 blockade rapidly clears established blood-stage Plasmodium infection," Nat Immunol. Feb. 2012;13(2):188-95.
Caldas et al., "Design and synthesis of germline-based hemi-humanized single-chain Fv against the CD18 surface antigen," Protein Eng. May 2000;13(5):353-60.
Camisaschi et al., "LAG-3 expression defines a subset of CD4(+)CD25(high)Foxp3(+) regulatory T cells that are expanded at tumor sites," J Immunol. Jun. 1, 2010;184(11):6545-51.
Champe et al., "Monoclonal antibodies that block the activity of leukocyte function-associated antigen 1 recognize three discrete epitopes in the inserted domain of CD11a," J Biol Chem. Jan. 20, 1995;270(3):1388-94.
Dall'Acqua et al., "Properties of human IgG1s engineered for enhanced binding to the neonatal Fc receptor (FcRn)," J Biol Chem. Aug. 18, 2006;281(33):23514-24.

Demeure et al., "T Lymphocytes infiltrating various tumour types express the MHC class II ligand lymphocyte activation gene-3 (LAG-3): role of LAG-3/MHC class II interactions in cell-cell contacts," Eur J Cancer. Sep. 2001;37(13):1709-18.
Di Domizio et al., "Plasmacytoid dendritic cells in melanoma: can we revert bad into good?" J Invest Dermatol. Jul. 2014;134(7):1797-1800.
Drake, "Combined Immune Checkpoint Blockade," Semin Oncol. Aug. 2015;42(4):656-62.
Edwards et al., "The remarkable flexibility of the human antibody repertoire; isolation of over one thousand different antibodies to a single protein, BLyS," J Mol Biol. Nov. 14, 2003;334(1):103-18.
Fehlings et al., "Checkpoint blockade immunotherapy reshapes the high-dimensional phenotypic heterogeneity of murine intratumoural neoantigen-specific CD8+ T cells," Nat Commun. Sep. 15, 2017;8(1):562.
Ferrara et al., "Recombinant renewable polyclonal antibodies," MAbs. 2015;7(1):32-41.
Freeman and Sharpe, "A new therapeutic strategy for malaria: targeting T cell exhaustion," Nat Immunol. Jan. 19, 2012;13(2):113-5.
Gagliani et al., "Coexpression of CD49b and LAG-3 identifies human and mouse T regulatory type 1 cells," Nat Med. Jun. 2013;19(6):739-46.
Gandhi et al., "Expression of LAG-3 by tumor-infiltrating lymphocytes is coincident with the suppression of latent membrane antigen-specific CD8+ T-cell function in Hodgkin lymphoma patients," Blood. Oct. 1, 2006;108(7):2280-9.
Giraldo et al., "Orchestration and Prognostic Significance of Immune Checkpoints in the Microenvironment of Primary and Metastatic Renal Cell Cancer," Clin Cancer Res. 2015, 21(13):3031-3040.
Gobert et al., "Regulatory T cells recruited through CCL22/CCR4 are selectively activated in lymphoid infiltrates surrounding primary breast tumors and lead to an adverse clinical outcome," Cancer Res. Mar. 1, 2009;69(5):2000-9.
Goding et al., "Combination of adoptive cell transfer, anti-PD-L1 and anti-LAG-3 antibodies for the treatment of recurrent tumors," Oncoimmunology. May 20, 2013;2(8):e25050.
Gombos et al., "Characterization of the anti-CTLA-4 antibody AGEN1884, including toxicology and pharmacology assessments in non-human primates," SITC Annual Meeting. Nov. 8-12, 2017;P325.
Gros et al., "PD-1 identifies the patient-specific CD8? tumor-reactive repertoire infiltrating human tumors," J Clin Invest. May 2014;124(5):2246-59.
Hassan and Mourad, "An unexpected role for MHC class II," Nat Immunol. May 2011;12(5):375-6.
Haudebourg et al., "Depletion of LAG-3 positive cells in cardiac allograft reveals their role in rejection and tolerance," Transplantation. Dec. 15, 2007;84(11):1500-6.
Huang et al., "Role of LAG-3 in regulatory T cells," Immunity. Oct. 2004;21(4):503-13.
Huard et al., "Characterization of the major histocompatibility complex class II binding site on LAG-3 protein," Proc Natl Acad Sci U S A. May 27, 1997;94(11):5744-9.
"Human heat shock protein (hsp 70) gene, complete cds," GenBank Accession No. M11717. Nov. 8, 1994: https://www.ncbi.nlm.nih.gov/nuccore/184416/.
Agenus, "Integrated Immunotherapy: Enabling Best-in-Class I-O Combinations," Feb. 2017.
PCT International Search Report and Written Opinion from PCT/US2017/056078, dated Dec. 13, 2017.
Jiang et al., "T-cell exhaustion in the tumor microenvironment," Cell Death and Disease 2015 e1792; doi:10.1038/cddis.2015.162.
Jing et al., "Combined immune checkpoint protein blockade and low dose whole body irradiation as immunotherapy for myeloma," J Immunother Cancer. Jan. 20, 2015;3(1):2.
Jun et al., "Generation of antagonistic anti-TIM-3 and anti-LAG-3 monoclonal antibodies for potential novel immunotherapy combinations," Cancer Res. Oct. 1, 2014;74(19 suppl):LB-266.
Kisielow et al., "Expression of lymphocyte activation gene 3 (LAG-3) on B cells is induced by T cells," Eur J Immunol. Jul. 2005;35(7):2081-8.

(56) References Cited

OTHER PUBLICATIONS

Kotaskova et al., "High expression of lymphocyte-activation gene 3 (LAG3) in chronic lymphocytic leukemia cells is associated with unmutated immunoglobulin variable heavy chain region (IGHV) gene and reduced treatment-free survival," J Mol Diagn. May 2010;12(3):328-34.
Koyama et al., "Adaptive resistance to therapeutic PD-1 blockade is associated with upregulation of alternative immune checkpoints," Nat Commun. Feb. 17, 2016;7:10501.
Li et al., "Metalloproteases regulate T-cell proliferation and effector function via LAG-3," EMBO J. Jan. 24, 2007;26(2):494-504.
Lloyd et al., "Modelling the human immune response: performance of a 1011 human antibody repertoire against a broad panel of therapeutically relevant antigens," Protein Eng Des Sel. Mar. 2009;22(3):159-68.
Maçon-Lemaître and Triebel, "The negative regulatory function of the lymphocyte-activation gene-3 co-receptor (CD223) on human T cells," Immunology. Jun. 2005; 115(2):170-8.
Mataraza et al., "Checkpoint Inhibitors in Combination: Novartis Enters the Clinic," Advances in Immuno-oncology Congress. 2016.
Mataraza et al., "Coordinating Immune Checkpoint Blockade for Cancer Immunotherapy in Combination," Immune Oncology, NIBR. Mar. 25, 2015.
Matsuzaki et al., "Tumor-infiltrating NY-ESO-1-specific CD8+ T cells are negatively regulated by LAG-3 and PD-1 in human ovarian cancer," Proc Natl Acad Sci U S A. Apr. 27, 2010;107(17):7875-80.
Le Mercier et al., "Beyond CTLA-4 and PD-1, the Generation Z of Negative Checkpoint Regulators," Front Immunol. Aug. 21, 2015;6:418.
Nguyen and Ohashi, "Clinical blockade of PD1 and LAG3—potential mechanisms of action," Nat Rev Immunol. Jan. 2015;15(1):45-56.
Nirschl and Drake, "Molecular pathways: coexpression of immune checkpoint molecules: signaling pathways and implications for cancer immunotherapy," Clin Cancer Res. Sep. 15, 2013;19(18):4917-24.
Nuttall et al., "Immunoglobulin VH domains and beyond: design and selection of single-domain binding and targeting reagents," Curr Pharm Biotechnol. Nov. 2000;1(3):253-63.
Okazaki et al., "PD-1 and LAG-3 inhibitory co-receptors act synergistically to prevent autoimmunity in mice," J Exp Med. Feb. 14, 2011;208(2):395-407.
Park et al., "Tumor-infiltrating regulatory T cells delineated by upregulation of PD-1 and inhibitory receptors," Cell Immunol. Jul.-Aug. 2012;278(1-2):76-83.
Petersson et al., "Crystal structure of a SEA variant in complex with MHC class II reveals the ability of SEA to crosslink MHC molecules," Structure. Dec. 2002;10(12):1619-26.
Poirier et al., "Antibody-mediated depletion of lymphocyte-activation gene-3 (LAG-3(+) )-activated T lymphocytes prevents delayed-type hypersensitivity in non-human primates," Clin Exp Immunol. May 2011;164(2):265-74.
Postow et al., "Nivolumab and ipilimumab versus ipilimumab in untreated melanoma," N Engl J Med. May 21, 2015;372(21):2006-17.
Retter et al., "VBASE2, an integrative V gene database," Nucleic Acids Res. Jan. 1, 2005;33(Database issue):D671-4.
Roche and Furuta, "The ins and outs of MHC class II-mediated antigen processing and presentation," Nat Rev Immunol. Apr. 2015;15(4):203-16.
Savitsky et al., "Abstract 3819: INCAGN02385 is an antagonist antibody targeting the co-inhibitory receptor LAG-3 for the treatment of human malignancies," Cancer Res. 2018;78(13 suppl):3819.
Schmitz-Winnenthal et al., "High frequencies of functional tumor-reactive T cells in bone marrow and blood of pancreatic cancer patients," Cancer Res. Nov. 1, 2005;65(21):10079-87.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem. Mar. 2, 2001;276(9):6591-604.
Shinmoto et al., "Generation of mouse-human hybridomas secreting antibodies against peanut allergen Ara h1," Cytotechnology. Sep. 2004;46(1):19-23.
Sledzinska et al., "Negative immune checkpoints on T lymphocytes and their relevance to cancer immunotherapy," Mol Oncol. Dec. 2015;9(10):1936-65.
Smith et al., "Mouse model recapitulating human Fc? receptor structural and functional diversity," Proc Natl Acad Sci U S A. Apr. 17, 2012;109(16):6181-6.
Triebel et al., "LAG-3, a novel lymphocyte activation gene closely related to CD4," J Exp Med. May 1, 1990;171(5):1393-405.
Wilson et al., "An Fc(gamma) receptor-dependent mechanism drives antibody-mediated target-receptor signaling in cancer cells," Cancer Cell. Jan. 18, 2011;19(1):101-13.
Woo et al., "Immune inhibitory molecules LAG-3 and PD-1 synergistically regulate T-cell function to promote tumoral immune escape," Cancer Res. Feb. 15, 2012;72(4):917-27.
Woo et al., "Differential subcellular localization of the regulatory T-cell protein LAG-3 and the coreceptor CD4," Eur J Immunol. Jun. 2010;40(6):1768-77.
Workman et al., "Phenotypic analysis of the murine CD4-related glycoprotein, CD223 (LAG-3)," Eur J Immunol. Aug. 2002;32(8):2255-63.
Workman and Vignali, "Negative regulation of T cell homeostasis by lymphocyte activation gene-3 (CD223)," J Immunol. Jan. 15, 2005;174(2):688-95.
Workman et al., "Cutting edge: molecular analysis of the negative regulatory function of lymphocyte activation gene-3," J Immunol. Nov. 15, 2002;169(10):5392-5.
Workman et al., "LAG-3 regulates plasmacytoid dendritic cell homeostasis," J Immunol. Feb. 15, 2009;182(4):1885-91.
Rudikoff et al. "Single amino acid substitution altering antigen-binding specificity." Proc. Natl. Acad. Sci. USA. 1982;79:6:1979-1983.

* cited by examiner

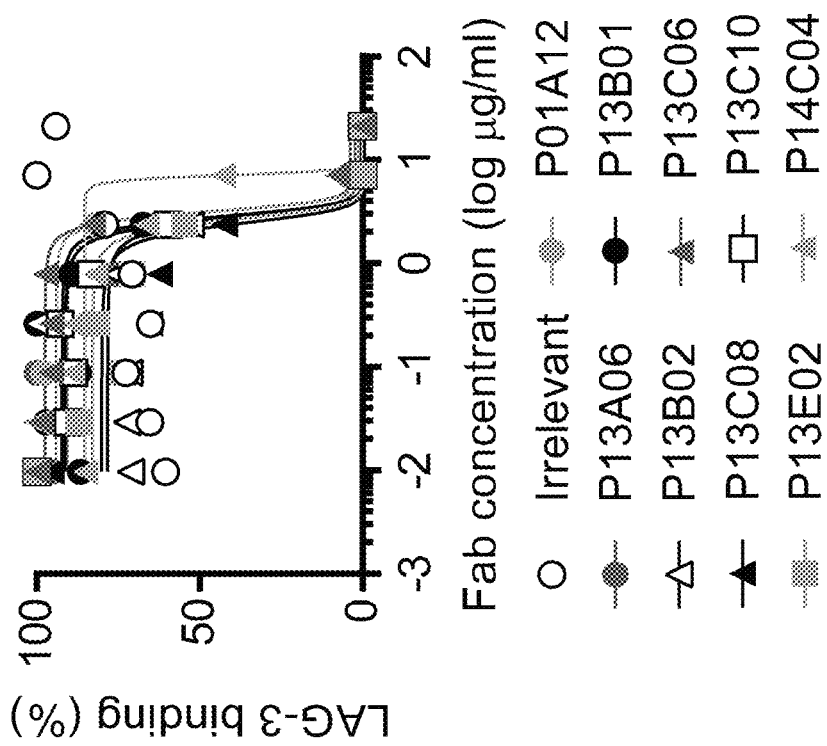
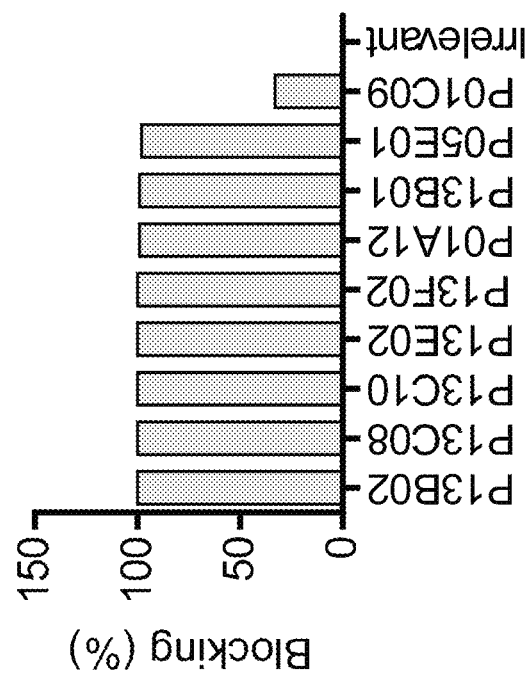
Figure 2A
Figure 2B

Figure 5B

```
              10        20        30        40        50        60
              |         |         |         |         |         |
L0        EIVLTQSPGTLSLSPGERATLSCSVSSSISSSNLHWYQQKPGQAPRLLIYGTSNLASGIP
L1        .L..........................................................
L2        .L............................F.............................
L3        .L.................T..........F....W.........V...............
L4        .L..ALMAA..KV.IT..............F..S..W.........V...............
P13B02 VL .L.........................F..S.TS.K.W........V...............
IGKV3-20*01 ...............RA.Q.V...Y.A.................A.SR.T...
IGKJ1*01  ------------------------------------------------------------

70        80        90        100
              |         |         |         |
L0        DRFSGSGSGTDFTLTISRLEPEDFAVYYCQQWSSYPFTFGQGTKVEIK    (SEQ ID NO: 73)
L1        ...SY..........................................    (SEQ ID NO: 74)
L2        ...SY..........................................    (SEQ ID NO: 75)
L3        ...SY..........................................    (SEQ ID NO: 76)
L4        ...SY..........................................    (SEQ ID NO: 77)
P13B02 VL V..SYS....SM.A..A.T..........S..L...............    (SEQ ID NO: 16)
IGKV3-20*01 ..................YG.S.-------------------------   (SEQ ID NO: 160)
IGKJ1*01  -----------------------------W..................    (SEQ ID NO: 201)
```

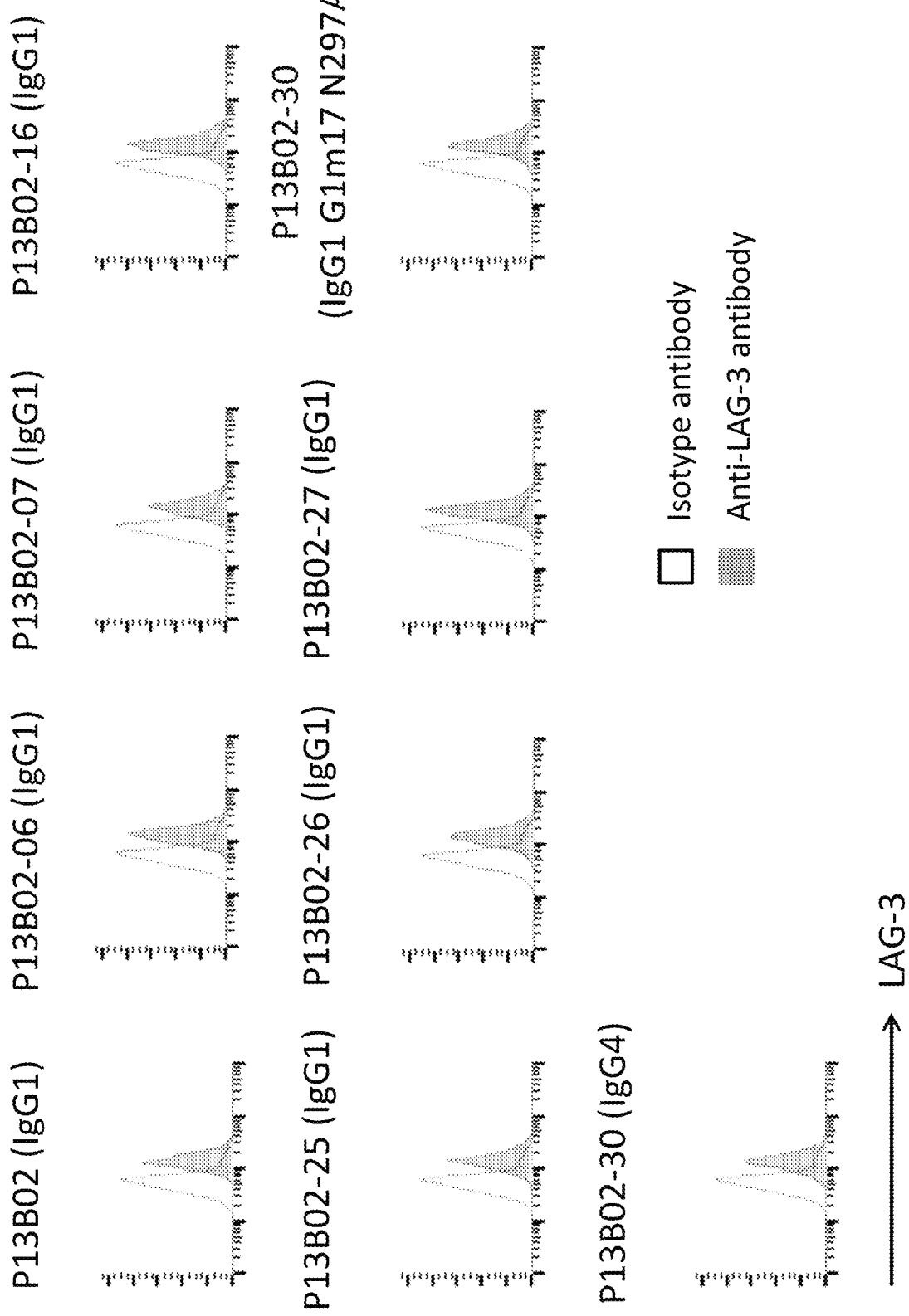

SEQUENCE LISTING

```
<160> NUMBER OF SEQ ID NOS: 228

<210> SEQ ID NO 1
<211> LENGTH: 120
<212> TYPE: PRT
<213> ORGANISM: Artificial Sequence
```

```
-continued

<220> FEATURE:
<223> OTHER INFORMATION: Description of Artificial Sequence: Synthetic
      polypeptide

<400> SEQUENCE: 1

Gln Val Gln Leu Lys Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met Tyr Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Leu
    50                  55                  60

Gln Gly Lys Ala Thr Ile Thr Ala Asp Thr Ser Ser Asn Thr Val Tyr
65                  70                  75                  80

Leu Gln Leu Ser Ser Leu Thr Ser Glu Asp Thr Ala Val Phe Tyr Cys
                85                  90                  95

Val Ile Tyr Ser Tyr Arg Tyr Asp Val Gly Gly Phe Asp Tyr Trp Gly
            100                 105                 110

Gln Gly Thr Thr Leu Thr Val Ser
        115                 120

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Tyr Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Phe Thr Phe Gly Ser Gly Thr Lys Leu Glu Ile Lys
            100                 105

<210> SEQ ID NO 3
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Val Gln Leu Val Glu Ser Gly Ala Glu Leu Val Lys Pro Gly Ala
1               5                   10                  15

Ser Val Lys Leu Ser Cys Thr Ala Ser Gly Phe Thr Ile Lys Asp Thr
            20                  25                  30
```

```
Tyr Ile His Trp Val Lys Gln Arg Pro Glu Gln Gly Leu Glu Trp Ile
            35                  40                  45

Gly Glu Ile Asp Pro Ala Asn Gly Asn Thr Lys Tyr Asp Pro Lys Phe
 50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Ala Thr Tyr Tyr Tyr Arg Tyr Asp Val Gly Gly Phe Asp Tyr Trp Gly
            100                 105                 110

Gln Gly Thr Thr Leu Thr Val Ser
            115                 120

<210> SEQ ID NO 4
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Val Leu Thr Gln Ser Pro Ala Leu Met Ala Ala Ser Pro Gly
 1               5                  10                  15

Glu Lys Val Thr Ile Thr Cys Ser Val Ser Ser Ile Ser Ser Ser
            20                  25                  30

Asn Leu His Trp Phe Gln Gln Lys Ser Gly Thr Ser Pro Lys Leu Trp
            35                  40                  45

Ile Tyr Gly Thr Ser Asn Leu Ala Ser Gly Val Pro Val Arg Phe Ser
 50                  55                  60

Gly Ser Gly Ser Gly Thr Ser Tyr Ser Leu Thr Ile Ser Asn Met Glu
 65                  70                  75                  80

Ala Glu Asp Ala Ala Thr Tyr Tyr Cys Gln Gln Trp Asn Ser Tyr Pro
                 85                  90                  95

Leu Thr Phe Gly Ala Gly Thr Lys Leu Glu Leu Lys
            100                 105

<210> SEQ ID NO 5
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Thr
            20                  25                  30

Tyr Met Tyr Trp Val Lys Gln Arg Pro Glu Gln Gly Leu Asp Trp Ile
            35                  40                  45

Gly Arg Ile Asp Pro Ala Asn Gly Asn Thr Lys Phe Asp Pro Lys Phe
 50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95
```

```
Ser Thr Tyr Tyr Tyr Arg Tyr Asp Val Gly Gly Phe Asp Tyr Trp Gly
                100                 105                 110

Gln Gly Thr Thr Leu Thr Val Ser
        115                 120

<210> SEQ ID NO 6
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Tyr Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Phe Thr Phe Gly Ser Gly Thr Lys Leu Glu Ile Lys
            100                 105

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile Tyr Trp Val Lys Gln Arg Pro Glu Arg Gly Leu Glu Trp Ile
        35                  40                  45

Gly Arg Ile Asp Pro Ala Asn Gly Asn Thr Lys Phe Asp Pro Lys Phe
    50                  55                  60

Gln Gly Thr Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Thr Tyr Phe Tyr Arg Tyr Asp Val Gly Gly Phe Asp Tyr Trp Gly
            100                 105                 110

Gln Gly Thr Thr Leu Thr Val Ser
        115                 120

<210> SEQ ID NO 8
<211> LENGTH: 108
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 8

Glu Asn Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Tyr Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Phe Thr Phe Gly Ser Gly Thr Lys Leu Glu Ile Lys
            100                 105

<210> SEQ ID NO 9
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Gln Ser Gly Ala Glu Leu Val Lys Pro Gly Ala
1               5                   10                  15

Ser Val Glu Leu Ser Cys Thr Ala Ser Gly Phe Asn Ile Arg Asp Thr
            20                  25                  30

Tyr Met Tyr Trp Val Lys Gln Arg Pro Glu Gln Gly Leu Glu Trp Ile
        35                  40                  45

Gly Arg Ile Asp Pro Ala Asn Gly Asn Thr Lys Phe Asp Pro Lys Phe
    50                  55                  60

Gln Asp Arg Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Thr Tyr Phe Tyr Arg Tyr Asp Val Gly Gly Phe Asp Tyr Trp Gly
            100                 105                 110

Gln Gly Thr Thr Leu Thr Val Ser
        115                 120

<210> SEQ ID NO 10
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Asn Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Phe Gln Gln Lys Ser Gly Thr Ser Pro Lys Leu Trp 35                  40                  45

Ile Tyr Gly Thr Ser Asn Leu Ala Ser Gly Val Pro Val Arg Phe Ser
         50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                 85                  90                  95

Phe Thr Phe Gly Ser Gly Thr Lys Leu Glu Ile Lys
            100                 105

<210> SEQ ID NO 11
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Lys Gln Ser Gly Ala Glu Leu Val Lys Pro Gly Ala
1               5                   10                  15

Ser Val Lys Leu Ser Cys Thr Ala Ser Gly Phe Asn Ile Lys Asp Asn
            20                  25                  30

Tyr Ile His Trp Val Lys Gln Arg Pro Glu Gln Gly Leu Glu Trp Ile
        35                  40                  45

Gly Ser Ile Asp Pro Ala Asn Gly Asn Thr Lys Tyr Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Tyr Phe Tyr Arg Tyr Asp Val Gly Gly Phe Asp Tyr Trp Gly
            100                 105                 110

Gln Gly Thr Thr Leu Thr Val Ser
        115                 120

<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Val Val Met Thr Gln Thr Pro Ala Leu Met Ala Ala Ser Pro Gly
1               5                   10                  15

Glu Lys Val Thr Ile Thr Cys Ser Val Ser Ser Ile Ser Ser Ser
            20                  25                  30

Asn Leu His Trp Phe Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Phe Thr Phe Gly Ser Gly Thr Lys Leu Glu Ile Lys

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 13

```
Gln Val Gln Leu Gln Gln Pro Gly Ala Glu Leu Val Lys Pro Gly Ala
1               5                   10                  15

Ser Val Lys Leu Ser Cys Thr Val Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Glu Ile Asp Pro Ala Asn Gly Asn Ser Lys Tyr Ala Pro Arg Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Thr Tyr Tyr Tyr Arg Tyr Asp Val Gly Gly Phe Asp Tyr Trp Gly
            100                 105                 110

Gln Gly Thr Thr Leu Thr Val Ser
        115                 120
```

<210> SEQ ID NO 14
<211> LENGTH: 120
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 14

```
Gln Val Gln Leu Gln Gln Pro Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Asp Trp Val
        35                  40                  45

Gly Glu Ile Asp Pro Ala Asn Gly His Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Thr Tyr Tyr Tyr Arg Tyr Asp Val Gly Gly Phe Asp Tyr Trp Gly
            100                 105                 110

Gln Gly Thr Thr Leu Thr Val Ser
        115                 120
```

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Gln Val Gln Met Lys Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Glu Ile Asp Pro Ala Asn Asp Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Thr Tyr Tyr Tyr Arg Tyr Asp Val Gly Gly Phe Asp Tyr Trp Gly
            100                 105                 110

Gln Gly Thr Thr Leu Thr Val Ser
        115                 120

<210> SEQ ID NO 16
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Ile Leu Leu Thr Gln Ser Pro Ala Leu Met Ala Ala Ser Pro Gly
1               5                   10                  15

Glu Lys Val Thr Ile Thr Cys Ser Val Ser Ser Ile Ser Ser Ser
            20                  25                  30

Asn Leu His Trp Phe Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Phe Thr Phe Gly Ser Gly Thr Lys Leu Glu Ile Lys
            100                 105

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Lys Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met Tyr Trp Val Lys Gln Arg Pro Glu Gln Gly Leu Glu Trp Ile
        35                  40                  45

```
Gly Arg Ile Asp Pro Ala Asn Gly Asn Thr Lys Tyr Asp Pro Lys Phe
        50                  55                  60

Gln Gly Lys Ala Thr Ile Thr Ala Asp Thr Ser Ser Asn Thr Val Tyr
 65                  70                  75                  80

Leu Gln Leu Ser Ser Leu Thr Ser Glu Asp Thr Ala Val Phe Tyr Cys
                85                  90                  95

Val Ile Tyr Ser Tyr Arg Tyr Asp Val Gly Gly Phe Asp Tyr Trp Gly
                100                 105                 110

Gln Gly Thr Thr Leu Thr Val Ser
                115                 120

<210> SEQ ID NO 18
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Asn Val Leu Thr Gln Ser Pro Ala Leu Met Ala Ala Ser Pro Gly
 1               5                  10                  15

Glu Lys Val Thr Ile Thr Cys Ser Val Ser Ser Ser Ile Ser Ser Ser
                20                  25                  30

Asn Leu His Trp Tyr Gln Gln Lys Ser Gly Thr Ser Pro Lys Leu Trp
            35                  40                  45

Ile Tyr Gly Thr Ser Asn Leu Ala Ser Gly Val Pro Val Arg Phe Ser
        50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys Gln Gln Trp Ser Ser Tyr Pro
                85                  90                  95

His Thr Phe Gly Gly Gly Thr Lys Leu Glu Ile Lys
                100                 105

<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Gln Pro Gly Ala Glu Leu Val Lys Pro Gly Ala
 1               5                  10                  15

Ser Val Lys Leu Ser Cys Thr Ala Ser Gly Phe Asn Ile Lys Asp Thr
                20                  25                  30

Tyr Met Tyr Trp Val Lys Gln Arg Pro Glu Gln Gly Leu Asp Trp Ile
            35                  40                  45

Gly Arg Ile Asp Pro Ala Asn Gly Asn Thr His Phe Asp Pro Lys Phe
        50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                85                  90                  95

Ser Thr Tyr Phe Tyr Arg Tyr Asp Val Gly Gly Phe Asp Tyr Trp Gly
                100                 105                 110
```

```
Gln Gly Thr Thr Leu Thr Val Ser
        115                 120

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Gln Gln Pro Gly Ala Glu Leu Val Lys Pro Gly Ala
1               5                   10                  15

Ser Val Glu Leu Ser Cys Thr Ala Ser Gly Phe Asn Ile Arg Asp Thr
            20                  25                  30

Tyr Met Tyr Trp Val Lys Gln Arg Pro Glu Gln Gly Leu Glu Trp Ile
        35                  40                  45

Gly Arg Ile Asp Pro Ala Asn Gly Asn Thr Lys Phe Asp Pro Lys Phe
    50                  55                  60

Gln Asp Arg Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Thr Tyr Phe Tyr Arg Tyr Asp Val Gly Phe Asp Tyr Trp Gly
            100                 105                 110

Gln Gly Thr Thr Leu Thr Val Ser
        115                 120

<210> SEQ ID NO 21
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Phe Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Phe Thr Phe Gly Ser Gly Thr Lys Leu Glu Ile Lys
            100                 105

<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 22

Gln Val Gln Leu Lys Gln Ser Gly Ala Glu Leu Val Lys Pro Gly Ala
1               5                   10                  15

Ser Val Glu Leu Ser Cys Thr Ala Ser Gly Phe Asn Ile Arg Asp Thr
            20                  25                  30

Tyr Met Tyr Trp Val Lys Gln Arg Pro Glu Gln Gly Leu Glu Trp Ile
        35                  40                  45

Gly Arg Ile Asp Pro Ala Asn Gly Asn Thr Lys Phe Asp Pro Lys Phe
50                  55                  60

Gln Asp Arg Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Thr Tyr Phe Tyr Arg Tyr Asp Val Gly Gly Phe Asp Tyr Trp Gly
            100                 105                 110

Gln Gly Thr Thr Leu Thr Val Ser
            115                 120

<210> SEQ ID NO 23
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Asn Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Thr Leu His Trp Phe Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Trp Thr Phe Gly Gly Gly Thr Lys Leu Glu Ile Lys
            100                 105

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

```
Gly Glu Ile Asp Pro Ala Asn Gly Asn Thr Lys Tyr Asp Pro Lys Phe
 50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Ala Thr Tyr Tyr Tyr Arg Tyr Asp Val Gly Gly Phe Asp Tyr Trp Gly
                100                 105                 110

Gln Gly Thr Thr Leu Thr Val Ser
        115                 120

<210> SEQ ID NO 25
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Val Val Met Thr Gln Thr Pro Ala Leu Met Ala Ala Ser Pro Gly
 1               5                  10                  15

Glu Lys Val Thr Ile Thr Cys Ser Val Ser Ser Ser Ile Ser Ser Ser
                 20                  25                  30

Asn Leu His Trp Tyr Gln Gln Lys Ser Gly Thr Ser Pro Lys Leu Trp
             35                  40                  45

Ile Tyr Gly Thr Ser Asn Leu Ala Ser Gly Val Pro Val Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys Gln Gln Trp Ser Ser Tyr Pro
                 85                  90                  95

Phe Thr Phe Gly Ser Gly Thr Lys Leu Glu Ile Lys
                100                 105

<210> SEQ ID NO 26
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Asn Val Leu Thr Gln Ser Pro Ala Leu Met Ala Ala Ser Pro Gly
 1               5                  10                  15

Glu Lys Val Thr Ile Thr Cys Ser Val Ser Ser Ser Ile Ser Ser Ser
                 20                  25                  30

Asn Leu His Trp Tyr Gln Gln Lys Ser Gly Thr Ser Pro Lys Leu Trp
             35                  40                  45

Ile Tyr Gly Thr Ser Asn Leu Ala Ser Gly Val Pro Val Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys Gln Gln Trp Ser Ser Tyr Pro
                 85                  90                  95

Leu Thr Phe Gly Ala Gly Thr Lys Leu Glu Leu Lys
                100                 105
```

```
<210> SEQ ID NO 27
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Gln Gln Pro Gly Ala Glu Leu Val Lys Pro Gly Ala
1               5                   10                  15

Ser Val Glu Leu Ser Cys Thr Ala Ser Gly Phe Asn Ile Arg Asp Thr
            20                  25                  30

Tyr Met Tyr Trp Val Lys Gln Arg Pro Glu Gln Gly Leu Glu Trp Ile
        35                  40                  45

Gly Arg Ile Asp Pro Ala Asn Gly Asn Thr Lys Phe Asp Pro Lys Phe
    50                  55                  60

Gln Asp Arg Ala Thr Met Thr Ala Asp Thr Ser Ser Asn Thr Ala Tyr
65                  70                  75                  80

Leu Gln Leu Ser Ser Leu Thr Ser Ala Asp Thr Ala Val Tyr Tyr Cys
                85                  90                  95

Thr Thr Tyr Phe Tyr Arg Tyr Asp Val Gly Gly Phe Asp Tyr Trp Gly
            100                 105                 110

Gln Gly Thr Thr Leu Thr Val Ser
        115                 120

<210> SEQ ID NO 28
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Tyr Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Asn Met Glu
65                  70                  75                  80

Ala Glu Asp Ala Ala Thr Tyr Tyr Cys Gln Gln Trp Ser Ser Tyr Pro
                85                  90                  95

Phe Thr Phe Gly Ser Gly Thr Lys Leu Glu Ile Lys
            100                 105

<210> SEQ ID NO 29
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Gln Pro Gly Ala Glu Leu Val Lys Pro Gly Ala
```

```
                1               5                   10                  15
Ser Val Lys Leu Ser Cys Thr Ala Ser Gly Phe Asn Ile Lys Asp Asn
                20                  25                  30

Tyr Ile His Trp Val Lys Gln Arg Pro Glu Gln Gly Leu Glu Trp Ile
                35                  40                  45

Gly Ser Ile Asp Pro Ala Asn Gly Asn Thr Lys Tyr Asp Pro Lys Phe
            50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Ser Tyr Phe Tyr Arg Tyr Asp Val Gly Gly Phe Asp Tyr Trp Gly
                100                 105                 110

Gln Gly Thr Thr Leu Thr Val Ser
                115                 120
```

<210> SEQ ID NO 30
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
                20                  25                  30

Asn Leu His Trp Tyr Gln Gln Lys Ser Gly Thr Ser Pro Lys Leu Trp
                35                  40                  45

Ile Tyr Gly Thr Ser Asn Leu Ala Ser Gly Val Pro Val Arg Phe Ser
            50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

His Thr Phe Gly Gly Gly Thr Lys Leu Glu Ile Lys
                100                 105
```

<210> SEQ ID NO 31
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Gln Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Asn
                20                  25                  30

Tyr Ile His Trp Val Lys Gln Arg Pro Glu Gln Gly Leu Glu Trp Ile
                35                  40                  45

Gly Ser Ile Asp Pro Ala Asn Gly Asn Thr Lys Tyr Asp Pro Lys Phe
            50                  55                  60

Gln Gly Lys Ala Ser Ile Thr Ala Asp Thr Ser Ser Asn Thr Ala Tyr
```

```
                 65                  70                  75                  80
Leu Gln Leu Ser Ser Leu Thr Ser Glu Gly Thr Ala Val Tyr Tyr Cys
                    85                  90                  95

Ala Ser Tyr Phe Tyr Arg Tyr Asp Val Gly Gly Phe Asp Tyr Trp Gly
               100                 105                 110

Gln Gly Thr Thr Leu Thr Val Ser
           115                 120

<210> SEQ ID NO 32
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Ile Val Leu Thr Gln Ser Pro Ala Leu Met Ala Ala Ser Pro Gly
1               5                  10                  15

Glu Lys Val Thr Ile Thr Cys Ser Val Ser Ser Ser Ile Ser Ser Ser
                20                  25                  30

Asn Leu His Trp Phe Gln Gln Lys Ser Gly Thr Ser Pro Lys Leu Trp
            35                  40                  45

Ile Tyr Gly Thr Ser Asn Leu Ala Ser Gly Val Pro Val Arg Phe Ser
50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Phe Thr Phe Gly Ser Gly Thr Lys Leu Glu Ile Lys
               100                 105

<210> SEQ ID NO 33
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Gln Gln Ser Gly Ala Glu Leu Val Lys Pro Gly Ala
1               5                  10                  15

Ser Val Glu Leu Ser Cys Thr Ala Ser Gly Phe Asn Ile Arg Asp Thr
                20                  25                  30

Tyr Met Tyr Trp Val Lys Gln Arg Pro Glu Gln Gly Leu Glu Trp Ile
            35                  40                  45

Gly Arg Ile Asp Pro Ala Asn Gly Asn Thr Lys Phe Asp Pro Lys Phe
50                  55                  60

Gln Asp Arg Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Thr Tyr Phe Tyr Arg Tyr Asp Val Gly Gly Phe Asp Tyr Trp Gly
               100                 105                 110

Gln Gly Thr Thr Leu Thr Val Ser
           115                 120
```

```
<210> SEQ ID NO 34
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Ile Val Leu Thr Gln Ser Pro Ala Leu Met Ala Ala Ser Pro Gly
1               5                   10                  15

Glu Lys Val Thr Ile Thr Cys Ser Val Ser Ser Ile Ser Ser Ser
            20                  25                  30

Asn Leu His Trp Tyr Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Phe Thr Phe Gly Ser Gly Thr Lys Leu Glu Ile Lys
            100                 105

<210> SEQ ID NO 35
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Gln Pro Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Glu Ile Asp Pro Ala Asn Asp Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Thr Tyr Tyr Tyr Arg Tyr Asp Val Gly Gly Phe Asp Tyr Trp Gly
            100                 105                 110

Gln Gly Thr Thr Leu Thr Val Ser
            115                 120

<210> SEQ ID NO 36
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Gln Gln Ser Gly Ala Glu Leu Val Lys Pro Gly Ala
1               5                   10                  15
```

```
Ser Val Lys Leu Ser Cys Thr Ala Ser Gly Phe Asn Ile Lys Asp Asn
             20                  25                  30

Tyr Met Asp Trp Val Lys Gln Arg Pro Glu Gln Gly Leu Glu Trp Ile
         35                  40                  45

Gly Lys Ile Asp Pro Ala Asn Gly Asn Thr Lys Tyr Asp Pro Lys Phe
 50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                 85                  90                  95

Ala Thr Tyr Tyr Tyr Arg Tyr Asp Val Gly Gly Phe Asp Tyr Trp Gly
            100                 105                 110

Gln Gly Thr Thr Leu Thr Val Ser
        115                 120

<210> SEQ ID NO 37
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Val Leu Thr Gln Ser Pro Ala Leu Met Ala Ala Ser Pro Gly
1               5                  10                  15

Glu Lys Val Thr Ile Thr Cys Ser Val Ser Ser Ser Ile Ser Ser Ser
             20                  25                  30

Asn Leu His Trp Phe Gln Gln Lys Ser Gly Thr Pro Pro Lys Leu Trp
         35                  40                  45

Ile Tyr Gly Thr Ser Asn Leu Ala Ser Gly Val Pro Val Arg Phe Ser
 50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                 85                  90                  95

Phe Thr Phe Gly Ser Gly Thr Lys Leu Glu Ile Lys
            100                 105

<210> SEQ ID NO 38
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Lys Glu Ser Gly Ala Glu Leu Val Lys Pro Gly Ala
1               5                  10                  15

Ser Val Glu Leu Ser Cys Thr Ala Ser Gly Phe Asn Ile Arg Asp Thr
             20                  25                  30

Tyr Met Tyr Trp Val Lys Gln Arg Pro Glu Gln Gly Leu Glu Trp Ile
         35                  40                  45

Gly Arg Ile Asp Pro Ala Asn Gly Asn Thr Lys Phe Asp Pro Lys Phe
 50                  55                  60

Gln Asp Arg Ala Thr Met Thr Ala Asp Thr Ser Ser Asn Thr Ala Tyr
65                  70                  75                  80
```

```
Leu Gln Leu Ser Ser Leu Thr Ser Glu Asp Thr Ala Val Tyr Tyr Cys
                85                  90                  95

Thr Thr Tyr Phe Tyr Arg Tyr Asp Val Gly Gly Phe Asp Tyr Trp Gly
            100                 105                 110

Gln Gly Thr Thr Leu Thr Val Ser
        115                 120

<210> SEQ ID NO 39
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Met Lys Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Gly Gln Gly Leu Glu Trp Ile
        35                  40                  45

Gly Glu Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Thr Tyr Tyr Tyr Arg Tyr Asp Val Gly Gly Phe Asp Tyr Trp Gly
            100                 105                 110

Gln Gly Thr Thr Leu Thr Val Ser
        115                 120

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu Tyr Trp Phe Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Phe Thr Phe Gly Ser Gly Thr Lys Leu Glu Ile Lys
            100                 105

<210> SEQ ID NO 41
```

<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Ile Leu Leu Thr Gln Ser Pro Ala Leu Met Ala Ala Ser Pro Gly
1               5                   10                  15

Glu Lys Val Thr Ile Thr Cys Ser Val Ser Ser Ile Ser Ser Ser
            20                  25                  30

Asn Leu His Trp Tyr Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Phe Thr Phe Gly Ser Gly Thr Lys Leu Glu Ile Lys
            100                 105

<210> SEQ ID NO 42
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Gln Gln Pro Gly Ala Glu Leu Val Lys Pro Gly Ala
1               5                   10                  15

Ser Val Lys Leu Ser Cys Thr Ala Ser Gly Phe Asn Ile Lys Asp Asn
            20                  25                  30

Tyr Met Asp Trp Val Lys Gln Arg Pro Glu Gln Gly Leu Glu Trp Ile
        35                  40                  45

Gly Lys Ile Asp Pro Ala Asn Gly Asn Thr Lys Tyr Asp Pro Lys Phe
50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Thr Tyr Tyr Tyr Arg Tyr Asp Val Gly Phe Asp Tyr Trp Gly
            100                 105                 110

Gln Gly Thr Thr Leu Thr Val Ser
        115                 120

<210> SEQ ID NO 43
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Ile Val Leu Thr Gln Ser Pro Ala Leu Met Ala Ala Ser Pro Gly
1               5                   10                  15

Glu Lys Val Thr Ile Thr Cys Ser Val Ser Ser Ile Ser Ser Ser
            20                  25                  30

Asn Leu His Trp Phe Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Phe Thr Phe Gly Ser Gly Thr Lys Leu Glu Ile Lys
            100                 105

<210> SEQ ID NO 44
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Asn Val Leu Thr Gln Ser Pro Ala Leu Met Ala Ala Ser Pro Gly
1               5                   10                  15

Glu Lys Val Thr Ile Thr Cys Ser Val Ser Ser Ile Ser Ser Ser
            20                  25                  30

Asn Leu His Trp Tyr Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Thr Tyr Pro
                85                  90                  95

Phe Thr Phe Gly Ser Gly Thr Lys Leu Glu Ile Lys
            100                 105

<210> SEQ ID NO 45
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Met Lys Gln Ser Gly Ala Glu Leu Val Lys Pro Gly Ala
1               5                   10                  15

Ser Val Lys Leu Ser Cys Thr Ala Ser Gly Phe Asn Ile Lys Asp Asn
            20                  25                  30

Tyr Ile His Trp Val Lys Gln Arg Pro Glu Gln Gly Leu Glu Trp Ile
        35                  40                  45

Gly Ser Ile Asp Pro Ala Asn Gly Asn Thr Lys Tyr Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

```
Ala Ser Tyr Phe Tyr Arg Tyr Asp Val Gly Gly Phe Asp Tyr Trp Gly
            100                 105                 110

Gln Gly Thr Thr Leu Thr Val Ser
        115                 120

<210> SEQ ID NO 46
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Gln Gln Pro Gly Ala Glu Leu Val Lys Pro Gly Ala
1               5                   10                  15

Ser Val Glu Leu Ser Cys Thr Ala Ser Gly Phe Asn Ile Arg Asp Thr
            20                  25                  30

Tyr Met Tyr Trp Val Lys Gln Arg Pro Glu Gln Gly Leu Gly Trp Ile
        35                  40                  45

Gly Arg Ile Asp Pro Ala Asn Gly Asn Thr Lys Phe Asp Pro Lys Phe
    50                  55                  60

Gln Asp Arg Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Thr Tyr Phe Tyr Arg Tyr Asp Val Gly Gly Phe Asp Tyr Trp Gly
            100                 105                 110

Gln Gly Thr Thr Leu Thr Val Ser
        115                 120

<210> SEQ ID NO 47
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ile Ser Ser Ser
            20                  25                  30

Asn Leu His Trp Phe Arg Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Phe Thr Phe Gly Ser Gly Thr Lys Leu Glu Ile Lys
            100                 105

<210> SEQ ID NO 48
<211> LENGTH: 120
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 48

Glu Val Lys Leu Met Glu Ser Gly Ala Glu Leu Val Lys Pro Gly Ala
1               5                   10                  15

Ser Ala Glu Leu Ser Cys Thr Ala Ser Gly Phe Asn Ile Arg Asp Thr
            20                  25                  30

Tyr Met Tyr Trp Val Lys Gln Arg Pro Glu Gln Gly Leu Glu Trp Ile
        35                  40                  45

Gly Arg Ile Asp Pro Ala Asn Gly Asn Thr Lys Phe Asp Pro Lys Phe
50                  55                  60

Gln Asp Arg Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Thr Tyr Phe Tyr Arg Tyr Asp Val Gly Phe Asp Tyr Trp Gly
            100                 105                 110

Gln Gly Thr Thr Leu Thr Val Ser
        115                 120

<210> SEQ ID NO 49
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Asn Val Leu Thr Gln Ser Pro Ala Leu Met Ala Ala Ser Pro Gly
1               5                   10                  15

Glu Lys Val Thr Ile Thr Cys Ser Val Ser Ser Gly Ile Ser Ser Ser
            20                  25                  30

Asn Leu His Trp Tyr Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Arg Tyr Pro
                85                  90                  95

Trp Thr Phe Gly Gly Gly Thr Lys Leu Glu Ile Lys
            100                 105

<210> SEQ ID NO 50
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ile Ser Ser Ser
            20                  25                  30

Asn Leu His Trp Tyr Gln Gln Lys Ser Gly Thr Ser Pro Lys Leu Trp

```
                35                  40                  45
Ile Tyr Gly Thr Ser Asn Leu Ala Ser Gly Val Pro Val Arg Phe Ser
         50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys Gln Gln Trp Ser Ser Tyr Pro
                 85                  90                  95

Leu Thr Phe Gly Ala Gly Thr Lys Leu Glu Leu Lys
            100                 105

<210> SEQ ID NO 51
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Thr
             20                  25                  30

Tyr Met Tyr Trp Val Lys Gln Arg Pro Glu Gln Gly Leu Asp Trp Ile
         35                  40                  45

Gly Arg Ile Asp Pro Ala Asn Gly Asn Thr His Phe Asp Pro Lys Phe
     50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Ser Thr Tyr Phe Tyr Arg Tyr Asp Val Gly Gly Phe Asp Tyr Trp Gly
            100                 105                 110

Gln Gly Thr Thr Leu Thr Val Ser
            115                 120

<210> SEQ ID NO 52
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Ile Leu Leu Thr Gln Ser Pro Ala Leu Met Ala Ala Ser Pro Gly
 1               5                  10                  15

Glu Lys Val Thr Ile Thr Cys Ser Val Ser Ser Ser Ile Ser Ser Ser
             20                  25                  30

Asn Leu His Trp Tyr Gln Gln Lys Ser Gly Thr Ser Pro Lys Leu Trp
         35                  40                  45

Ile Tyr Gly Thr Ser Asn Leu Ala Ser Gly Val Pro Val Arg Phe Ser
     50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys Gln Gln Trp Ser Ser Tyr Pro
                 85                  90                  95

Leu Thr Phe Gly Ala Gly Thr Lys Leu Glu Leu Lys
```

<210> SEQ ID NO 53
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Gln Gln Pro Gly Ala Glu Leu Val Lys Pro Gly Ala
1               5                   10                  15

Ser Val Lys Leu Ser Cys Thr Ala Ser Gly Phe Asn Ile Lys Asp Asn
            20                  25                  30

Tyr Ile His Trp Val Lys Gln Arg Pro Glu Gln Gly Leu Glu Trp Ile
        35                  40                  45

Gly Ser Ile Asp Pro Ala Asn Gly Asn Thr Lys Tyr Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Thr Val Tyr Tyr Cys
                85                  90                  95

Ala Ser Tyr Phe Tyr Arg Tyr Asp Val Gly Gly Phe Asp Tyr Trp Gly
            100                 105                 110

Gln Gly Thr Thr Leu Thr Val Ser
        115                 120

<210> SEQ ID NO 54
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Met Lys Gln Ser Gly Ala Glu Leu Val Lys Pro Gly Ala
1               5                   10                  15

Ser Val Glu Leu Ser Cys Thr Ala Ser Gly Phe Asn Ile Thr Asp Thr
            20                  25                  30

Tyr Met Tyr Trp Val Lys Gln Arg Pro Glu Gln Gly Leu Glu Trp Ile
        35                  40                  45

Gly Arg Ile Asp Pro Ala Asn Gly Asn Thr Lys Phe Asp Pro Lys Phe
    50                  55                  60

Gln Asp Arg Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Thr Tyr Phe Asp Lys Tyr Asp Val Gly Gly Cys Asp Tyr Trp Gly
            100                 105                 110

Gln Gly Thr Thr Leu Thr Val Ser
        115                 120

<210> SEQ ID NO 55
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ile Ser Ser Ser
            20                  25                  30

Asn Leu Tyr Trp Phe Gln His Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Asp
65                  70                  75                  80

Ala Glu Asn Ala Ala Thr Tyr Tyr Cys Gln Gln Trp Arg Ser Tyr Pro
                85                  90                  95

Phe Thr Phe Gly Ser Gly Thr Lys Leu Glu Ile Lys
            100                 105

<210> SEQ ID NO 56
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Arg Tyr Asp Val Gly Gly Phe Asp Tyr Trp Gly
            100                 105                 110

Gln Gly Thr Leu Val Thr Val Ser Ser
        115                 120

<210> SEQ ID NO 57
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

```
Gly Glu Ile Asp Pro Ala Asn Asp Asn Thr Lys Tyr Asp Pro Lys Phe
            50                  55                  60

Gln Gly Arg Val Thr Ile Thr Ala Asp Thr Ser Ser Thr Val Tyr
 65                  70                  75                  80

Met Glu Leu Ser Ser Leu Arg Ser Glu Asp Thr Ala Val Tyr Tyr Cys
                85                  90                  95

Ala Thr Tyr Tyr Tyr Arg Tyr Asp Val Gly Gly Phe Asp Tyr Trp Gly
                    100                 105                 110

Gln Gly Thr Leu Val Thr Val Ser Ser
            115                 120
```

<210> SEQ ID NO 58
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Lys Asp Thr
                20                  25                  30

Tyr Ile His Trp Val Arg Gln Ala Pro Gly Gln Gly Leu Glu Trp Met
            35                  40                  45

Gly Glu Ile Asp Pro Ala Asn Asp Asn Thr Lys Tyr Asp Pro Lys Phe
        50                  55                  60

Gln Gly Arg Val Thr Ile Thr Ala Asp Thr Ser Ser Asn Thr Val Tyr
 65                  70                  75                  80

Met Glu Leu Ser Ser Leu Arg Ser Glu Asp Thr Ala Val Tyr Tyr Cys
                85                  90                  95

Ala Thr Tyr Tyr Tyr Arg Tyr Asp Val Gly Gly Phe Asp Tyr Trp Gly
                    100                 105                 110

Gln Gly Thr Leu Val Thr Val Ser Ser
            115                 120
```

<210> SEQ ID NO 59
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Gln Val Gln Met Lys Gln Ser Gly Ala Glu Val Lys Lys Pro Gly Ala
 1               5                  10                  15

Ser Val Lys Val Ser Cys Thr Ala Ser Gly Phe Asn Ile Lys Asp Thr
                20                  25                  30

Tyr Ile His Trp Val Arg Gln Ala Pro Gly Gln Gly Leu Glu Trp Met
            35                  40                  45

Gly Glu Ile Asp Pro Ala Asn Asp Asn Thr Lys Tyr Asp Pro Lys Phe
        50                  55                  60

Gln Gly Arg Val Thr Ile Thr Ala Asp Thr Ser Ser Asn Thr Val Tyr
 65                  70                  75                  80

Met Glu Leu Ser Ser Leu Arg Ser Glu Asp Thr Ala Val Tyr Tyr Cys
                85                  90                  95
```

```
Ala Thr Tyr Tyr Tyr Arg Tyr Asp Val Gly Gly Phe Asp Tyr Trp Gly
                100                 105                 110

Gln Gly Thr Leu Val Thr Val Ser Ser
        115                 120

<210> SEQ ID NO 60
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Met Lys Gln Ser Gly Ala Glu Val Val Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Gly Leu Glu Trp Ile
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Ser Asn Thr Val Tyr
65                  70                  75                  80

Leu Gln Leu Ser Ser Leu Arg Ser Glu Asp Thr Ala Val Tyr Tyr Cys
                85                  90                  95

Ala Thr Tyr Tyr Tyr Arg Tyr Asp Val Gly Gly Phe Asp Tyr Trp Gly
                100                 105                 110

Gln Gly Thr Leu Val Thr Val Ser Ser
        115                 120

<210> SEQ ID NO 61
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Met Lys Gln Ser Gly Ala Glu Val Val Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Gly Leu Glu Trp Ile
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Ser Asn Thr Val Tyr
65                  70                  75                  80

Leu Gln Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
                100                 105                 110

Gln Gly Thr Leu Val Thr Val Ser Ser
        115                 120

<210> SEQ ID NO 62
```

<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Met Lys Gln Ser Gly Ala Glu Val Val Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Gly Leu Glu Trp Ile
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Ser Asn Thr Val Tyr
65                  70                  75                  80

Leu Gln Leu Ser Ser Leu Arg Ser Glu Asp Thr Ala Val Tyr Tyr Cys
                85                  90                  95

Ala Thr Tyr Tyr Arg Tyr Glu Val Gly Gly Phe Asp Tyr Trp Gly
            100                 105                 110

Gln Gly Thr Leu Val Thr Val Ser Ser
        115                 120

<210> SEQ ID NO 63
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Lys Tyr Asp Val Gly Gly Phe Asp Tyr Trp Gly
            100                 105                 110

Gln Gly Thr Leu Val Thr Val Ser Ser
        115                 120

<210> SEQ ID NO 64
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
                100                 105                 110

Gln Gly Thr Leu Val Thr Val Ser Ser
            115                 120

<210> SEQ ID NO 65
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Met Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
                100                 105                 110

Gln Gly Thr Leu Val Thr Val Ser Ser
            115                 120

<210> SEQ ID NO 66
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Met Val Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45
```

Gly Glu Ile Asp Pro Ala Asn Asp Asn Thr Lys Tyr Asp Pro Lys Phe
            50                   55                  60

Gln Gly Arg Val Thr Ile Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
                100                 105                 110

Gln Gly Thr Leu Val Thr Val Ser Ser
        115                 120

<210> SEQ ID NO 67
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Met Lys Gln Ser Gly Ala Glu Val Lys Lys Pro Gly Ala
 1               5                  10                  15

Ser Val Lys Val Ser Cys Lys Ala Ser Gly Phe Asn Ile Lys Asp Thr
                20                  25                  30

Tyr Ile His Trp Val Arg Gln Ala Pro Gly Gln Gly Leu Glu Trp Met
            35                  40                  45

Gly Glu Ile Asp Pro Ala Asn Asp Asn Thr Lys Tyr Asp Pro Lys Phe
        50                  55                  60

Gln Gly Arg Val Thr Ile Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
                100                 105                 110

Gln Gly Thr Leu Val Thr Val Ser Ser
        115                 120

<210> SEQ ID NO 68
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Gln Met Lys Gln Ser Gly Ala Glu Val Lys Lys Pro Gly Ala
 1               5                  10                  15

Ser Val Lys Val Ser Cys Thr Ala Ser Gly Phe Asn Ile Lys Asp Thr
                20                  25                  30

Tyr Ile His Trp Val Arg Gln Ala Pro Gly Gln Gly Leu Glu Trp Met
            35                  40                  45

Gly Glu Ile Asp Pro Ala Asn Asp Asn Thr Lys Tyr Asp Pro Lys Phe
        50                  55                  60

Gln Gly Arg Val Thr Ile Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

```
Ala Thr Tyr Tyr Tyr Lys Tyr Asp Val Gly Gly Phe Asp Tyr Trp Gly
            100                 105                 110

Gln Gly Thr Leu Val Thr Val Ser Ser
        115                 120

<210> SEQ ID NO 69
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Lys Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
            100                 105                 110

Gln Gly Thr Leu Val Thr Val Ser Ser
        115                 120

<210> SEQ ID NO 70
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Val Gln Leu Lys Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
            100                 105                 110

Gln Gly Thr Leu Val Thr Val Ser Ser
        115                 120

<210> SEQ ID NO 71
<211> LENGTH: 121
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Ser Asn Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
            100                 105                 110

Gln Gly Thr Leu Val Thr Val Ser Ser
        115                 120

<210> SEQ ID NO 72
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Met Lys Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Ser Asn Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
            100                 105                 110

Gln Gly Thr Leu Val Thr Val Ser Ser
        115                 120

<210> SEQ ID NO 73
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Ile Val Leu Thr Gln Ser Pro Gly Thr Leu Ser Leu Ser Pro Gly

Glu Arg Ala Thr Leu Ser Cys Ser Val Ser Ser Ile Ser Ser
            20                  25                  30

Asn Leu His Trp Tyr Gln Gln Lys Pro Gly Gln Ala Pro Arg Leu Leu
        35                  40                  45

Ile Tyr Gly Thr Ser Asn Leu Ala Ser Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Trp Ser Ser Tyr Pro
                85                  90                  95

Phe Thr Phe Gly Gln Gly Thr Lys Val Glu Ile Lys
            100                 105

<210> SEQ ID NO 74
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Ile Val Leu Thr Gln Ser Pro Gly Thr Leu Ser Leu Ser Pro Gly
1               5                   10                  15

Glu Arg Ala Thr Leu Ser Cys Ser Val Ser Ser Ile Ser Ser
            20                  25                  30

Asn Leu His Trp Tyr Gln Gln Lys Pro Gly Gln Ala Pro Arg Leu Leu
        35                  40                  45

Ile Tyr Gly Thr Ser Asn Leu Ala Ser Gly Ile Pro Asp Arg Phe Ser
50                  55                  60

Gly Ser Gly Ser Gly Thr Ser Tyr Thr Leu Thr Ile Ser Arg Leu Glu
65                  70                  75                  80

Pro Glu Asp Phe Ala Val Tyr Tyr Cys Gln Gln Trp Ser Ser Tyr Pro
                85                  90                  95

Phe Thr Phe Gly Gln Gly Thr Lys Val Glu Ile Lys
            100                 105

<210> SEQ ID NO 75
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Ile Leu Leu Thr Gln Ser Pro Gly Thr Leu Ser Leu Ser Pro Gly
1               5                   10                  15

Glu Arg Ala Thr Leu Ser Cys Ser Val Ser Ser Ile Ser Ser
            20                  25                  30

Asn Leu His Trp Phe Gln Gln Lys Pro Gly Gln Ala Pro Arg Leu Leu
        35                  40                  45

Ile Tyr Gly Thr Ser Asn Leu Ala Ser Gly Ile Pro Asp Arg Phe Ser
50                  55                  60

Gly Ser Gly Ser Gly Thr Ser Tyr Thr Leu Thr Ile Ser Arg Leu Glu
65                  70                  75                  80

Pro Glu Asp Phe Ala Val Tyr Tyr Cys Gln Gln Trp Ser Ser Tyr Pro

Phe Thr Phe Gly Gln Gly Thr Lys Val Glu Ile Lys
            100                 105

<210> SEQ ID NO 76
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Ile Leu Leu Thr Gln Ser Pro Gly Thr Leu Ser Leu Ser Pro Gly
1               5                   10                  15

Glu Arg Ala Thr Leu Ser Cys Ser Val Ser Ser Ser Ile Ser Ser Ser
            20                  25                  30

Asn Leu His Trp Phe Gln Gln Lys Pro Gly Gln Ala Pro Arg Leu Trp
        35                  40                  45

Ile Tyr Gly Thr Ser Asn Leu Ala Ser Gly Val Pro Asp Arg Phe Ser
    50                  55                  60

Gly Ser Gly Ser Gly Thr Ser Tyr Thr Leu Thr Ile Ser Arg Leu Glu
65                  70                  75                  80

Pro Glu Asp Phe Ala Val Tyr Tyr Cys Gln Gln Trp Ser Ser Tyr Pro
                85                  90                  95

Phe Thr Phe Gly Gln Gly Thr Lys Val Glu Ile Lys
            100                 105

<210> SEQ ID NO 77
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Ile Leu Leu Thr Gln Ser Pro Gly Thr Leu Ser Leu Ser Pro Gly
1               5                   10                  15

Glu Arg Ala Thr Leu Thr Cys Ser Val Ser Ser Ser Ile Ser Ser Ser
            20                  25                  30

Asn Leu His Trp Phe Gln Gln Lys Pro Gly Gln Ser Pro Arg Leu Trp
        35                  40                  45

Ile Tyr Gly Thr Ser Asn Leu Ala Ser Gly Val Pro Asp Arg Phe Ser
    50                  55                  60

Gly Ser Gly Ser Gly Thr Ser Tyr Thr Leu Thr Ile Ser Arg Leu Glu
65                  70                  75                  80

Pro Glu Asp Phe Ala Val Tyr Tyr Cys Gln Gln Trp Ser Ser Tyr Pro
                85                  90                  95

Phe Thr Phe Gly Gln Gly Thr Lys Val Glu Ile Lys
            100                 105

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

```
Asp Thr Tyr Met Tyr
1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Thr Tyr Ile His
1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Thr Tyr Ile Tyr
1               5

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp Asn Tyr Ile His
1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Asn Tyr Met Asp
1               5

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Ile Asp Pro Ala Asn Gly Asn Thr Lys Tyr Asp Pro Lys Leu Gln
1               5                   10                  15

Gly

<210> SEQ ID NO 84
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Ile Asp Pro Ala Asn Gly Asn Thr Lys Tyr Asp Pro Lys Phe Gln
1               5                   10                  15

Gly

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Ile Asp Pro Ala Asn Gly Asn Thr Lys Phe Asp Pro Lys Phe Gln
1               5                   10                  15

Gly

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Ile Asp Pro Ala Asn Gly Asn Thr Lys Phe Asp Pro Lys Phe Gln
1               5                   10                  15

Asp

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Ile Asp Pro Ala Asn Gly Asn Thr Lys Tyr Asp Pro Lys Phe Gln
1               5                   10                  15

Gly

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Glu Ile Asp Pro Ala Asn Gly Asn Ser Lys Tyr Ala Pro Arg Phe Gln
1               5                   10                  15

Gly

<210> SEQ ID NO 89
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Glu Ile Asp Pro Ala Asn Gly His Thr Lys Tyr Asp Pro Lys Phe Gln
1               5                   10                  15
Gly

<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Glu Ile Asp Pro Ala Asn Asp Asn Thr Lys Tyr Asp Pro Lys Phe Gln
1               5                   10                  15
Gly

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Ile Asp Pro Ala Asn Gly Asn Thr Lys Tyr Asp Pro Lys Phe Gln
1               5                   10                  15
Gly

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Ile Asp Pro Ala Asn Gly Asn Thr His Phe Asp Pro Lys Phe Gln
1               5                   10                  15
Gly

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Ile Asp Pro Ala Asn Gly Asn Thr Lys Tyr Asp Pro Lys Phe Gln
1               5                   10                  15
Gly
```

```
<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Tyr Ser Tyr Arg Tyr Asp Val Gly Gly Phe Asp Tyr
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Tyr Tyr Tyr Arg Tyr Asp Val Gly Gly Phe Asp Tyr
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Phe Tyr Arg Tyr Asp Val Gly Gly Phe Asp Tyr
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Tyr Phe Asp Lys Tyr Asp Val Gly Gly Cys Asp Tyr
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Tyr Tyr Tyr Lys Tyr Asp Val Gly Gly Phe Asp Tyr
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99
```

```
Tyr Tyr Tyr Arg Tyr Glu Val Gly Gly Phe Asp Tyr
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Val Ser Ser Ser Ile Ser Ser Ser Asn Leu His
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Val Ser Ser Ser Ile Ser Ser Ser Thr Leu His
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Val Ser Ser Ser Ile Ser Ser Ser Asn Leu Tyr
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Val Ser Ser Gly Ile Ser Ser Asn Leu His
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Thr Ser Asn Leu Ala Ser
1               5

<210> SEQ ID NO 105
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 105

Gln Gln Trp Ser Ser Tyr Pro Phe Thr
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Gln Trp Asn Ser Tyr Pro Leu Thr
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Gln Trp Ser Ser Tyr Pro His Thr
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gln Gln Trp Ser Ser Tyr Pro Trp Thr
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Gln Trp Ser Ser Tyr Pro Leu Thr
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Gln Trp Ser Thr Tyr Pro Phe Thr
1               5
```

```
<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Gln Trp Ser Arg Tyr Pro Trp Thr
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Gln Trp Arg Ser Tyr Pro Phe Thr
1               5

<210> SEQ ID NO 113
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys
            20                  25                  30

<210> SEQ ID NO 114
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Val Gln Met Lys Gln Ser Gly Ala Glu Val Lys Lys Pro Gly Ala
1               5                   10                  15

Ser Val Lys Val Ser Cys Thr Ala Ser Gly Phe Asn Ile Lys
            20                  25                  30

<210> SEQ ID NO 115
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Val Gln Met Lys Gln Ser Gly Ala Glu Val Val Lys Pro Gly Ala
1               5                   10                  15

Ser Val Lys Val Ser Cys Thr Ala Ser Gly Phe Asn Ile Lys
            20                  25                  30
```

<210> SEQ ID NO 116
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys
            20                  25                  30

<210> SEQ ID NO 117
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Gln Met Val Gln Ser Gly Ala Glu Val Lys Lys Pro Gly Ala
1               5                   10                  15

Ser Val Lys Val Ser Cys Lys Ala Ser Gly Phe Asn Ile Lys
            20                  25                  30

<210> SEQ ID NO 118
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Val Gln Met Val Gln Ser Gly Ala Glu Val Lys Lys Pro Gly Ala
1               5                   10                  15

Ser Val Lys Val Ser Cys Thr Ala Ser Gly Phe Asn Ile Lys
            20                  25                  30

<210> SEQ ID NO 119
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Val Gln Met Lys Gln Ser Gly Ala Glu Val Lys Lys Pro Gly Ala
1               5                   10                  15

Ser Val Lys Val Ser Cys Lys Ala Ser Gly Phe Asn Ile Lys
            20                  25                  30

<210> SEQ ID NO 120
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Lys Gln Ser Gly Ala Glu Val Lys Lys Pro Gly Ala
1               5                   10                  15

Ser Val Lys Val Ser Cys Lys Ala Ser Gly Phe Asn Ile Lys
            20                  25                  30

<210> SEQ ID NO 121
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Val Gln Leu Lys Gln Ser Gly Ala Glu Val Lys Lys Pro Gly Ala
1               5                   10                  15

Ser Val Lys Val Ser Cys Thr Ala Ser Gly Phe Asn Ile Lys
            20                  25                  30

<210> SEQ ID NO 122
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Trp Val Arg Gln Ala Pro Gly Gln Gly Leu Glu Trp Met Gly
1               5                   10

<210> SEQ ID NO 123
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Trp Val Arg Gln Ala Pro Gly Gln Gly Leu Glu Trp Ile Gly
1               5                   10

<210> SEQ ID NO 124
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 125
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

```
Arg Val Thr Ile Thr Ala Asp Thr Ser Thr Ser Val Tyr Met Glu
1               5                   10                  15

Leu Ser Ser Leu Arg Ser Glu Asp Thr Ala Val Tyr Tyr Cys Ala Thr
            20                  25                  30
```

<210> SEQ ID NO 126
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Arg Val Thr Ile Thr Ala Asp Thr Ser Ser Asn Thr Val Tyr Met Glu
1               5                   10                  15

Leu Ser Ser Leu Arg Ser Glu Asp Thr Ala Val Tyr Tyr Cys Ala Thr
            20                  25                  30
```

<210> SEQ ID NO 127
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Arg Val Thr Ile Thr Ala Asp Thr Ser Ser Asn Thr Val Tyr Leu Gln
1               5                   10                  15

Leu Ser Ser Leu Arg Ser Glu Asp Thr Ala Val Tyr Tyr Cys Ala Thr
            20                  25                  30
```

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

```
Trp Gly Gln Gly Thr Leu Val Thr Val Ser Ser
1               5                   10
```

<210> SEQ ID NO 129
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

```
Glu Ile Val Leu Thr Gln Ser Pro Gly Thr Leu Ser Leu Ser Pro Gly
1               5                   10                  15

Glu Arg Ala Thr Leu Ser Cys
            20
```

<210> SEQ ID NO 130
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Glu Ile Leu Leu Thr Gln Ser Pro Gly Thr Leu Ser Leu Ser Pro Gly
1               5                   10                  15

Glu Arg Ala Thr Leu Ser Cys
            20

<210> SEQ ID NO 131
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Glu Ile Leu Leu Thr Gln Ser Pro Gly Thr Leu Ser Leu Ser Pro Gly
1               5                   10                  15

Glu Arg Ala Thr Leu Thr Cys
            20

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Trp Tyr Gln Gln Lys Pro Gly Gln Ala Pro Arg Leu Leu Ile Tyr
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Trp Phe Gln Gln Lys Pro Gly Gln Ala Pro Arg Leu Leu Ile Tyr
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Trp Phe Gln Gln Lys Pro Gly Gln Ala Pro Arg Leu Trp Ile Tyr
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

```
Trp Phe Gln Gln Lys Pro Gly Gln Ser Pro Arg Leu Trp Ile Tyr
1               5                   10                  15
```

<210> SEQ ID NO 136
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

```
Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30
```

<210> SEQ ID NO 137
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

```
Gly Ile Pro Asp Arg Phe Ser Gly Ser Gly Ser Gly Thr Ser Tyr Thr
1               5                   10                  15

Leu Thr Ile Ser Arg Leu Glu Pro Glu Asp Phe Ala Val Tyr Tyr Cys
            20                  25                  30
```

<210> SEQ ID NO 138
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Gly Val Pro Asp Arg Phe Ser Gly Ser Gly Ser Gly Thr Ser Tyr Thr
1               5                   10                  15

Leu Thr Ile Ser Arg Leu Glu Pro Glu Asp Phe Ala Val Tyr Tyr Cys
            20                  25                  30
```

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

```
Phe Gly Gln Gly Thr Lys Val Glu Ile Lys
1               5                   10
```

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)

```
<223> OTHER INFORMATION: T or N
<220> FEATURE:
<221> NAME/KEY: MOD_RES
<222> LOCATION: (4)..(4)
<223> OTHER INFORMATION: I or M
<220> FEATURE:
<221> NAME/KEY: MOD_RES
<222> LOCATION: (5)..(5)
<223> OTHER INFORMATION: H, Y or D

<400> SEQUENCE: 140

Asp Xaa Tyr Xaa Xaa
1               5

<210> SEQ ID NO 141
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: T or N
<220> FEATURE:
<221> NAME/KEY: MOD_RES
<222> LOCATION: (4)..(4)
<223> OTHER INFORMATION: I or M
<220> FEATURE:
<221> NAME/KEY: MOD_RES
<222> LOCATION: (5)..(5)
<223> OTHER INFORMATION: H or Y

<400> SEQUENCE: 141

Asp Xaa Tyr Xaa Xaa
1               5

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: E, R, S or K
<220> FEATURE:
<221> NAME/KEY: MOD_RES
<222> LOCATION: (7)..(7)
<223> OTHER INFORMATION: D or G
<220> FEATURE:
<221> NAME/KEY: MOD_RES
<222> LOCATION: (8)..(8)
<223> OTHER INFORMATION: N or H
<220> FEATURE:
<221> NAME/KEY: MOD_RES
<222> LOCATION: (9)..(9)
<223> OTHER INFORMATION: T or S
<220> FEATURE:
<221> NAME/KEY: MOD_RES
<222> LOCATION: (10)..(10)
<223> OTHER INFORMATION: K or H
<220> FEATURE:
<221> NAME/KEY: MOD_RES
<222> LOCATION: (11)..(11)
<223> OTHER INFORMATION: Y or F
<220> FEATURE:
<221> NAME/KEY: MOD_RES
<222> LOCATION: (12)..(12)
<223> OTHER INFORMATION: D or A
<220> FEATURE:
<221> NAME/KEY: MOD_RES
```

```
<222> LOCATION: (14)..(14)
<223> OTHER INFORMATION: K or R
<220> FEATURE:
<221> NAME/KEY: MOD_RES
<222> LOCATION: (15)..(15)
<223> OTHER INFORMATION: F or L
<220> FEATURE:
<221> NAME/KEY: MOD_RES
<222> LOCATION: (17)..(17)
<223> OTHER INFORMATION: G or D

<400> SEQUENCE: 142

Xaa Ile Asp Pro Ala Asn Xaa Xaa Xaa Xaa Xaa Xaa Pro Xaa Xaa Gln
1               5                   10                  15

Xaa

<210> SEQ ID NO 143
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: E, R or S
<220> FEATURE:
<221> NAME/KEY: MOD_RES
<222> LOCATION: (7)..(7)
<223> OTHER INFORMATION: D or G
<220> FEATURE:
<221> NAME/KEY: MOD_RES
<222> LOCATION: (8)..(8)
<223> OTHER INFORMATION: N or H
<220> FEATURE:
<221> NAME/KEY: MOD_RES
<222> LOCATION: (9)..(9)
<223> OTHER INFORMATION: T or S
<220> FEATURE:
<221> NAME/KEY: MOD_RES
<222> LOCATION: (11)..(11)
<223> OTHER INFORMATION: Y or F
<220> FEATURE:
<221> NAME/KEY: MOD_RES
<222> LOCATION: (12)..(12)
<223> OTHER INFORMATION: D or A
<220> FEATURE:
<221> NAME/KEY: MOD_RES
<222> LOCATION: (14)..(14)
<223> OTHER INFORMATION: K or R
<220> FEATURE:
<221> NAME/KEY: MOD_RES
<222> LOCATION: (17)..(17)
<223> OTHER INFORMATION: G or D

<400> SEQUENCE: 143

Xaa Ile Asp Pro Ala Asn Xaa Xaa Xaa Lys Xaa Xaa Pro Xaa Phe Gln
1               5                   10                  15

Xaa

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Y, F or S
<220> FEATURE:
```

<221> NAME/KEY: MOD_RES
<222> LOCATION: (3)..(3)
<223> OTHER INFORMATION: Y or D
<220> FEATURE:
<221> NAME/KEY: MOD_RES
<222> LOCATION: (4)..(4)
<223> OTHER INFORMATION: K or R
<220> FEATURE:
<221> NAME/KEY: MOD_RES
<222> LOCATION: (6)..(6)
<223> OTHER INFORMATION: D or E
<220> FEATURE:
<221> NAME/KEY: MOD_RES
<222> LOCATION: (10)..(10)
<223> OTHER INFORMATION: F or C

<400> SEQUENCE: 144

Tyr Xaa Xaa Xaa Tyr Xaa Val Gly Gly Xaa Asp Tyr
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Y, F or S
<220> FEATURE:
<221> NAME/KEY: MOD_RES
<222> LOCATION: (3)..(3)
<223> OTHER INFORMATION: Y or D
<220> FEATURE:
<221> NAME/KEY: MOD_RES
<222> LOCATION: (4)..(4)
<223> OTHER INFORMATION: K or R
<220> FEATURE:
<221> NAME/KEY: MOD_RES
<222> LOCATION: (10)..(10)
<223> OTHER INFORMATION: F or C

<400> SEQUENCE: 145

Tyr Xaa Xaa Xaa Tyr Asp Val Gly Gly Xaa Asp Tyr
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: K or R
<220> FEATURE:
<221> NAME/KEY: MOD_RES
<222> LOCATION: (6)..(6)
<223> OTHER INFORMATION: D or E

<400> SEQUENCE: 146

Tyr Tyr Tyr Xaa Tyr Xaa Val Gly Gly Phe Asp Tyr
1               5                   10

<210> SEQ ID NO 147
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: S or G
<220> FEATURE:
<221> NAME/KEY: MOD_RES
<222> LOCATION: (10)..(10)
<223> OTHER INFORMATION: N or T
<220> FEATURE:
<221> NAME/KEY: MOD_RES
<222> LOCATION: (12)..(12)
<223> OTHER INFORMATION: H or Y

<400> SEQUENCE: 147

Ser Val Ser Ser Xaa Ile Ser Ser Ser Xaa Leu Xaa
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: H or Y

<400> SEQUENCE: 148

Ser Val Ser Ser Ser Ile Ser Ser Ser Asn Leu Xaa
1               5                   10

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: S, N or R
<220> FEATURE:
<221> NAME/KEY: MOD_RES
<222> LOCATION: (5)..(5)
<223> OTHER INFORMATION: S, T or R
<220> FEATURE:
<221> NAME/KEY: MOD_RES
<222> LOCATION: (8)..(8)
<223> OTHER INFORMATION: F, L, H or W

<400> SEQUENCE: 149

Gln Gln Trp Xaa Xaa Tyr Pro Xaa Thr
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: S, N or R
<220> FEATURE:
<221> NAME/KEY: MOD_RES
<222> LOCATION: (8)..(8)
```

<223> OTHER INFORMATION: F, L or H

<400> SEQUENCE: 150

Gln Gln Trp Xaa Ser Tyr Pro Xaa Thr
1               5

<210> SEQ ID NO 151
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: M or L
<220> FEATURE:
<221> NAME/KEY: MOD_RES
<222> LOCATION: (5)..(5)
<223> OTHER INFORMATION: V or K
<220> FEATURE:
<221> NAME/KEY: MOD_RES
<222> LOCATION: (12)..(12)
<223> OTHER INFORMATION: K or V
<220> FEATURE:
<221> NAME/KEY: MOD_RES
<222> LOCATION: (48)..(48)
<223> OTHER INFORMATION: M or I
<220> FEATURE:
<221> NAME/KEY: MOD_RES
<222> LOCATION: (70)..(70)
<223> OTHER INFORMATION: I or M
<220> FEATURE:
<221> NAME/KEY: MOD_RES
<222> LOCATION: (72)..(72)
<223> OTHER INFORMATION: A or R
<220> FEATURE:
<221> NAME/KEY: MOD_RES
<222> LOCATION: (76)..(76)
<223> OTHER INFORMATION: T or S
<220> FEATURE:
<221> NAME/KEY: MOD_RES
<222> LOCATION: (77)..(77)
<223> OTHER INFORMATION: S or N
<220> FEATURE:
<221> NAME/KEY: MOD_RES
<222> LOCATION: (81)..(81)
<223> OTHER INFORMATION: M or L
<220> FEATURE:
<221> NAME/KEY: MOD_RES
<222> LOCATION: (82)..(82)
<223> OTHER INFORMATION: E or Q
<220> FEATURE:
<221> NAME/KEY: MOD_RES
<222> LOCATION: (98)..(98)
<223> OTHER INFORMATION: T or R
<220> FEATURE:
<221> NAME/KEY: MOD_RES
<222> LOCATION: (102)..(102)
<223> OTHER INFORMATION: K or R
<220> FEATURE:
<221> NAME/KEY: MOD_RES
<222> LOCATION: (104)..(104)
<223> OTHER INFORMATION: D or E

<400> SEQUENCE: 151

Gln Val Gln Xaa Xaa Gln Ser Gly Ala Glu Val Xaa Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Xaa
        35                  40                  45

```
Gly Glu Ile Asp Pro Ala Asn Asp Asn Thr Lys Tyr Asp Pro Lys Phe
     50                  55                  60

Gln Gly Arg Val Thr Xaa Thr Xaa Asp Thr Ser Xaa Xaa Thr Val Tyr
 65                  70                  75                  80

Xaa Xaa Leu Ser Ser Leu Arg Ser Glu Asp Thr Ala Val Tyr Tyr Cys
                 85                  90                  95

Ala Xaa Tyr Tyr Tyr Xaa Tyr Xaa Val Gly Gly Phe Asp Tyr Trp Gly
            100                 105                 110

Gln Gly Thr Leu Val Thr Val Ser Ser
            115                 120
```

<210> SEQ ID NO 152
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: V or L
<220> FEATURE:
<221> NAME/KEY: MOD_RES
<222> LOCATION: (22)..(22)
<223> OTHER INFORMATION: S or T
<220> FEATURE:
<221> NAME/KEY: MOD_RES
<222> LOCATION: (37)..(37)
<223> OTHER INFORMATION: Y or F
<220> FEATURE:
<221> NAME/KEY: MOD_RES
<222> LOCATION: (44)..(44)
<223> OTHER INFORMATION: A or S
<220> FEATURE:
<221> NAME/KEY: MOD_RES
<222> LOCATION: (48)..(48)
<223> OTHER INFORMATION: L or W
<220> FEATURE:
<221> NAME/KEY: MOD_RES
<222> LOCATION: (59)..(59)
<223> OTHER INFORMATION: I or V
<220> FEATURE:
<221> NAME/KEY: MOD_RES
<222> LOCATION: (71)..(71)
<223> OTHER INFORMATION: D or S
<220> FEATURE:
<221> NAME/KEY: MOD_RES
<222> LOCATION: (72)..(72)
<223> OTHER INFORMATION: F or Y

<400> SEQUENCE: 152

```
Glu Ile Xaa Leu Thr Gln Ser Pro Gly Thr Leu Ser Leu Ser Pro Gly
 1               5                  10                  15

Glu Arg Ala Thr Leu Xaa Cys Ser Val Ser Ser Ser Ile Ser Ser Ser
            20                  25                  30

Asn Leu His Trp Xaa Gln Gln Lys Pro Gly Gln Xaa Pro Arg Leu Xaa
             35                  40                  45

Ile Tyr Gly Thr Ser Asn Leu Ala Ser Gly Xaa Pro Asp Arg Phe Ser
     50                  55                  60

Gly Ser Gly Ser Gly Thr Xaa Xaa Thr Leu Thr Ile Ser Arg Leu Glu
 65                  70                  75                  80

Pro Glu Asp Phe Ala Val Tyr Tyr Cys Gln Gln Trp Ser Ser Tyr Pro
                 85                  90                  95

Phe Thr Phe Gly Gln Gly Thr Lys Val Glu Ile Lys
            100                 105
```

<210> SEQ ID NO 153
<211> LENGTH: 98
<212> TYPE: PRT
<213> ORGANISM: Homo sapiens

<400> SEQUENCE: 153

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 154
<211> LENGTH: 98
<212> TYPE: PRT
<213> ORGANISM: Homo sapiens

<400> SEQUENCE: 154

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr
```

<210> SEQ ID NO 155
<211> LENGTH: 98
<212> TYPE: PRT
<213> ORGANISM: Homo sapiens

<400> SEQUENCE: 155

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80
```

```
Met Glu Leu Ser Ser Leu Arg Ser Glu Asp Thr Ala Val Tyr Tyr Cys
            85                  90                  95

Ala Arg

<210> SEQ ID NO 156
<211> LENGTH: 98
<212> TYPE: PRT
<213> ORGANISM: Homo sapiens

<400> SEQUENCE: 156

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Ala Thr

<210> SEQ ID NO 157
<211> LENGTH: 98
<212> TYPE: PRT
<213> ORGANISM: Homo sapiens

<400> SEQUENCE: 157

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
            85                  90                  95

Ala Arg

<210> SEQ ID NO 158
<211> LENGTH: 98
<212> TYPE: PRT
<213> ORGANISM: Homo sapiens

<400> SEQUENCE: 158

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
            20                  25                  30

Tyr Leu His Trp Val Arg Gln Ala Pro Gly Gln Ala Leu Glu Trp Met
        35                  40                  45

Gly Trp Ile Thr Pro Phe Asn Gly Asn Thr Asn Tyr Ala Gln Lys Phe
```

```
                50                  55                  60
Gln Asp Arg Val Thr Ile Thr Arg Asp Arg Ser Met Ser Thr Ala Tyr
 65                  70                  75                  80

Met Glu Leu Ser Ser Leu Arg Ser Glu Asp Thr Ala Met Tyr Tyr Cys
                 85                  90                  95

Ala Arg

<210> SEQ ID NO 159
<211> LENGTH: 98
<212> TYPE: PRT
<213> ORGANISM: Homo sapiens

<400> SEQUENCE: 159

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg

<210> SEQ ID NO 160
<211> LENGTH: 96
<212> TYPE: PRT
<213> ORGANISM: Homo sapiens

<400> SEQUENCE: 160

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

<210> SEQ ID NO 161
<211> LENGTH: 95
<212> TYPE: PRT
<213> ORGANISM: Homo sapiens

<400> SEQUENCE: 161

Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Ser Asn
                 20                  25                  30

Leu Ala Trp Tyr Gln Gln Lys Pro Gly Gln Ala Pro Arg Leu Leu Ile
```

```
                35                  40                  45
Tyr Gly Ala Ser Thr Arg Ala Thr Gly Ile Pro Ala Arg Phe Ser Gly
        50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn Asn Trp Pro
                85                  90                  95
```

<210> SEQ ID NO 162
<211> LENGTH: 96
<212> TYPE: PRT
<213> ORGANISM: Homo sapiens

<400> SEQUENCE: 162

```
Glu Ile Val Leu Thr Gln Ser Pro Ala Thr Leu Ser Leu Ser Pro Gly
1               5                   10                  15
Glu Arg Ala Thr Leu Ser Cys Gly Ala Ser Gln Ser Val Ser Ser
                20                  25                  30
Tyr Leu Ala Trp Tyr Gln Gln Lys Pro Gly Leu Ala Pro Arg Leu Leu
            35                  40                  45
Ile Tyr Asp Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Pro
                85                  90                  95
```

<210> SEQ ID NO 163
<211> LENGTH: 97
<212> TYPE: PRT
<213> ORGANISM: Homo sapiens

<400> SEQUENCE: 163

```
Glu Ile Val Met Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser
                20                  25                  30
Tyr Leu Ser Trp Tyr Gln Gln Lys Pro Gly Gln Ala Pro Arg Leu Leu
            35                  40                  45
Ile Tyr Gly Ala Ser Thr Arg Ala Thr Gly Ile Pro Ala Arg Phe Ser
        50                  55                  60
Gly Ser Gly Ser Gly Thr Asp Phe Thr Leu Thr Ile Ser Ser Leu Gln
65                  70                  75                  80
Pro Glu Asp Phe Ala Val Tyr Tyr Cys Gln Gln Asp Tyr Asn Leu Pro
                85                  90                  95
Pro
```

<210> SEQ ID NO 164
<211> LENGTH: 95
<212> TYPE: PRT
<213> ORGANISM: Homo sapiens

<400> SEQUENCE: 164

```
Asp Ile Gln Leu Thr Gln Ser Pro Ser Phe Leu Ser Ala Ser Val Gly
1               5                   10                  15
Asp Arg Val Thr Ile Thr Cys Arg Ala Ser Gln Gly Ile Ser Ser Tyr
                20                  25                  30
```

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro
                85                  90                  95

<210> SEQ ID NO 165
<211> LENGTH: 95
<212> TYPE: PRT
<213> ORGANISM: Homo sapiens

<400> SEQUENCE: 165

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro
                85                  90                  95

<210> SEQ ID NO 166
<211> LENGTH: 525
<212> TYPE: PRT
<213> ORGANISM: Homo sapiens

<400> SEQUENCE: 166

Met Trp Glu Ala Gln Phe Leu Gly Leu Leu Phe Leu Gln Pro Leu Trp
 1               5                  10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
 50                  55                  60

His Gln Pro Asp Ser Gly Pro Pro Ala Ala Ala Pro Gly His Pro Leu
 65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
                100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
        130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
                260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
                340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
        370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
                500                 505                 510

Glu Pro Glu Pro Glu Pro Glu Pro Glu Gln Leu
            515                 520                 525

<210> SEQ ID NO 167
<211> LENGTH: 497
<212> TYPE: PRT
<213> ORGANISM: Homo sapiens

<400> SEQUENCE: 167

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

```
Val Thr Trp Gln His Gln Pro Asp Ser Gly Pro Ala Ala Pro
        35                  40                  45

Gly His Pro Leu Ala Pro Gly Pro His Pro Ala Ala Pro Ser Ser Trp
        50                  55                  60

Gly Pro Arg Pro Arg Arg Tyr Thr Val Leu Ser Val Gly Pro Gly Gly
 65                  70                  75                  80

Leu Arg Ser Gly Arg Leu Pro Leu Gln Pro Arg Val Gln Leu Asp Glu
                 85                  90                  95

Arg Gly Arg Gln Arg Gly Asp Phe Ser Leu Trp Leu Arg Pro Ala Arg
                100                 105                 110

Arg Ala Asp Ala Gly Glu Tyr Arg Ala Val His Leu Arg Asp Arg
            115                 120                 125

Ala Leu Ser Cys Arg Leu Arg Leu Gly Gln Ala Ser Met Thr
        130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
                180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
        210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
                260                 265                 270

Pro Gly Gly Gly Pro Asp Leu Leu Val Thr Gly Asp Asn Gly Asp Phe
            275                 280                 285

Thr Leu Arg Leu Glu Asp Val Ser Gln Ala Gln Ala Gly Thr Tyr Thr
        290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
        355                 360                 365

Trp Leu Glu Ala Gln Glu Ala Gln Leu Leu Ser Gln Pro Trp Gln Cys
    370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
                405                 410                 415

Leu Pro Ala Gly His Leu Leu Phe Leu Ile Leu Gly Val Leu Ser
            420                 425                 430

Leu Leu Leu Leu Val Thr Gly Ala Phe Gly Phe His Leu Trp Arg Arg
        435                 440                 445
```

-continued

```
Gln Trp Arg Pro Arg Arg Phe Ser Ala Leu Glu Gln Gly Ile His Pro
    450                 455                 460
Pro Gln Ala Gln Ser Lys Ile Glu Glu Leu Glu Gln Glu Pro Glu Pro
465                 470                 475                 480
Glu Pro Glu Pro Glu Pro Glu Pro Glu Pro Glu Pro Glu Pro Glu Gln
                485                 490                 495
Leu

<210> SEQ ID NO 168
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gln Val Gln Met Val Gln Ser Gly Ala Glu Val Lys Lys Pro Gly Ala
1               5                   10                  15
Ser Val Lys Val Ser Cys Lys Ala Ser Gly Phe Asn Ile Lys Asp Thr
                20                  25                  30
Tyr Ile His Trp Val Arg Gln Ala Pro Gly Gln Gly Leu Glu Trp Met
            35                  40                  45
Gly Glu Ile Asp Pro Ala Asn Asp Asn Thr Lys Tyr Asp Pro Lys Phe
        50                  55                  60
Gln Gly Arg Val Thr Ile Thr Ala Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Thr Tyr Tyr Tyr Lys Tyr Asp Val Gly Gly Phe Tyr Trp Gly
                100                 105                 110
Gln Gly Thr Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 169
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gln Val Gln Met Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Phe Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Ala Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly
    450

<210> SEQ ID NO 170
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Val Gln Met Val Gln Ser Gly Ala Glu Val Lys Lys Pro Gly Ala
1               5                   10                  15
Ser Val Lys Val Ser Cys Lys Ala Ser Gly Phe Asn Ile Lys Asp Thr
            20                  25                  30
Tyr Ile His Trp Val Arg Gln Ala Pro Gly Gln Gly Leu Glu Trp Met
        35                  40                  45
Gly Glu Ile Asp Pro Ala Asn Asp Asn Thr Lys Tyr Asp Pro Lys Phe
    50                  55                  60
Gln Gly Arg Val Thr Ile Thr Ala Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Thr Tyr Tyr Tyr Lys Tyr Asp Val Gly Gly Phe Asp Tyr Trp Gly
```

```
            100                 105                 110
Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 171
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Val Gln Leu Val Gln Ser Gly Ala Glu Val Lys Lys Pro Gly Ala
1               5                   10                  15
```

-continued

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Arg Tyr Asp Val Gly Gly Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser

Pro Gly
    450

<210> SEQ ID NO 172
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Arg Tyr Asp Val Gly Phe Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

```
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly
    450

<210> SEQ ID NO 173
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Gln Val Gln Leu Val Gln Ser Gly Ala Glu Val Lys Lys Pro Gly Ala
1               5                   10                  15
Ser Val Lys Val Ser Cys Lys Ala Ser Gly Phe Asn Ile Lys Asp Thr
            20                  25                  30
Tyr Ile His Trp Val Arg Gln Ala Pro Gly Gln Gly Leu Glu Trp Met
        35                  40                  45
Gly Glu Ile Asp Pro Ala Asn Asp Asn Thr Lys Tyr Asp Pro Lys Phe
    50                  55                  60
Gln Gly Arg Val Thr Ile Thr Ala Asp Thr Ser Ser Asn Thr Val Tyr
65                  70                  75                  80
Met Glu Leu Ser Ser Leu Arg Ser Glu Asp Thr Ala Val Tyr Tyr Cys
                85                  90                  95
Ala Thr Tyr Tyr Tyr Arg Tyr Asp Val Gly Gly Phe Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
```

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 174
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gln Val Gln Met Lys Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Ser Asn Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Arg Tyr Asp Val Gly Gly Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
```

```
                130             135             140
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Ala Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 175
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Val Gln Met Lys Gln Ser Gly Ala Glu Val Val Lys Pro Gly Ala
1               5                   10                  15

Ser Val Lys Val Ser Cys Thr Ala Ser Gly Phe Asn Ile Lys Asp Thr
            20                  25                  30
```

```
Tyr Ile His Trp Val Arg Gln Ala Pro Gly Gln Gly Leu Glu Trp Ile
             35                  40                  45
Gly Glu Ile Asp Pro Ala Asn Asp Asn Thr Lys Tyr Asp Pro Lys Phe
 50                  55                  60
Gln Gly Arg Val Thr Ile Thr Ala Asp Thr Ser Ser Asn Thr Val Tyr
 65                  70                  75                  80
Leu Gln Leu Ser Ser Leu Arg Ser Glu Asp Thr Ala Val Tyr Tyr Cys
                 85                  90                  95
Ala Thr Tyr Tyr Tyr Arg Tyr Asp Val Gly Gly Phe Asp Tyr Trp Gly
             100                 105                 110
Gln Gly Thr Leu Val Thr Val Ser Ser Ala Ser Thr Lys Gly Pro Ser
             115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
             165                 170                 175
Val Leu Gln Ser Ser Gly Leu Tyr Ser Leu Ser Ser Val Val Thr Val
             180                 185                 190
Pro Ser Ser Ser Leu Gly Thr Gln Thr Tyr Ile Cys Asn Val Asn His
             195                 200                 205
Lys Pro Ser Asn Thr Lys Val Asp Lys Arg Val Glu Pro Lys Ser Cys
             210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
             245                 250                 255
Ile Ser Arg Thr Pro Glu Val Thr Cys Val Val Val Asp Val Ser His
             260                 265                 270
Glu Asp Pro Glu Val Lys Phe Asn Trp Tyr Val Asp Gly Val Glu Val
             275                 280                 285
His Asn Ala Lys Thr Lys Pro Arg Glu Glu Gln Tyr Ala Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
             325                 330                 335
Glu Lys Thr Ile Ser Lys Ala Lys Gly Gln Pro Arg Glu Pro Gln Val
             340                 345                 350
Tyr Thr Leu Pro Pro Ser Arg Glu Glu Met Thr Lys Asn Gln Val Ser
             355                 360                 365
Leu Thr Cys Leu Val Lys Gly Phe Tyr Pro Ser Asp Ile Ala Val Glu
             370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
             405                 410                 415
Asp Lys Ser Arg Trp Gln Gln Gly Asn Val Phe Ser Cys Ser Val Met
             420                 425                 430
His Glu Ala Leu His Asn His Tyr Thr Gln Lys Ser Leu Ser Leu Ser
             435                 440                 445

Pro Gly
```

<210> SEQ ID NO 176
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gln Val Gln Met Lys Gln Ser Gly Ala Glu Val Val Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Gly Leu Glu Trp Ile
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Ser Asn Thr Val Tyr
65                  70                  75                  80

Leu Gln Leu Ser Ser Leu Arg Ser Glu Asp Thr Ala Val Tyr Tyr Cys
                85                  90                  95

Ala Thr Tyr Tyr Lys Tyr Asp Val Gly Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

```
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly
    450

<210> SEQ ID NO 177
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gln Val Gln Met Lys Gln Ser Gly Ala Glu Val Val Lys Pro Gly Ala
1               5                   10                  15
Ser Val Lys Val Ser Cys Thr Ala Ser Gly Phe Asn Ile Lys Asp Thr
            20                  25                  30
Tyr Ile His Trp Val Arg Gln Ala Pro Gly Gln Gly Leu Glu Trp Ile
        35                  40                  45
Gly Glu Ile Asp Pro Ala Asn Asp Asn Thr Lys Tyr Asp Pro Lys Phe
    50                  55                  60
Gln Gly Arg Val Thr Ile Thr Ala Asp Thr Ser Ser Asn Thr Val Tyr
65                  70                  75                  80
Leu Gln Leu Ser Ser Leu Arg Ser Glu Asp Thr Ala Val Tyr Tyr Cys
                85                  90                  95
Ala Thr Tyr Tyr Tyr Arg Tyr Glu Val Gly Gly Phe Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
```

-continued

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 178
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
```

```
                145                 150                 155                 160
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Ala Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
    450

<210> SEQ ID NO 179
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
                20                  25                  30

Tyr Ile His Trp Val Arg Gln Ala Pro Gly Gln Gly Leu Glu Trp Met
            35                  40                  45
```

```
Gly Glu Ile Asp Pro Ala Asn Asp Asn Thr Lys Tyr Asp Pro Lys Phe
    50                  55                  60
Gln Gly Arg Val Thr Ile Thr Ala Asp Thr Ser Thr Ser Thr Val Tyr
 65              70                  75                  80
Met Glu Leu Ser Ser Leu Arg Ser Glu Asp Thr Ala Val Tyr Tyr Cys
                85                  90                  95
Ala Thr Tyr Tyr Tyr Lys Tyr Asp Val Gly Phe Asp Tyr Trp Gly
            100                 105                 110
Gln Gly Thr Leu Val Thr Val Ser Ala Ser Thr Lys Gly Pro Ser
            115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Arg Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Ala Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly
450
```

```
<210> SEQ ID NO 180
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gln Val Gln Met Val Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365
```

Leu Thr Cys Leu Val Lys Gly Phe Tyr Pro Ser Asp Ile Ala Val Glu
    370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly
    450

<210> SEQ ID NO 181
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gln Val Gln Met Lys Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

Tyr Ile His Trp Val Arg Gln Ala Pro Gly Gln Gly Leu Glu Trp Met
            35                  40                  45

Gly Glu Ile Asp Pro Ala Asn Asp Asn Thr Lys Tyr Asp Pro Lys Phe
50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

```
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Ala Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 182
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gln Val Gln Met Lys Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
```

```
                165                 170                 175
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 183
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gln Val Gln Leu Lys Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60
```

Gln Gly Arg Val Thr Ile Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
             85                  90                  95

Ala Thr Tyr Tyr Tyr Lys Tyr Asp Val Gly Phe Asp Tyr Trp Gly
        100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 184
<211> LENGTH: 450
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 184

```
Gln Val Gln Leu Lys Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
        435                 440                 445

Pro Gly
    450

<210> SEQ ID NO 185
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Ser Asn Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

```
His Asn Ala Lys Thr Lys Pro Arg Glu Glu Gln Tyr Ala Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 186
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Gln Val Gln Met Lys Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Ser Asn Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

```
            180                 185                 190
Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 187
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Glu Ile Val Leu Thr Gln Ser Pro Gly Thr Leu Ser Leu Ser Pro Gly
1               5                   10                  15

Glu Arg Ala Thr Leu Ser Cys Ser Val Ser Ser Ser Ile Ser Ser Ser
            20                  25                  30

Asn Leu His Trp Tyr Gln Gln Lys Pro Gly Gln Ala Pro Arg Leu Leu
        35                  40                  45

Ile Tyr Gly Thr Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Trp Ser Ser Tyr Pro
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 188
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Glu Ile Val Leu Thr Gln Ser Pro Gly Thr Leu Ser Leu Ser Pro Gly
1               5                   10                  15

Glu Arg Ala Thr Leu Ser Cys Ser Val Ser Ser Ser Ile Ser Ser Ser
            20                  25                  30

Asn Leu His Trp Tyr Gln Gln Lys Pro Gly Gln Ala Pro Arg Leu Leu
        35                  40                  45

Ile Tyr Gly Thr Ser Asn Leu Ala Ser Gly Ile Pro Asp Arg Phe Ser
50                  55                  60

Gly Ser Gly Ser Gly Thr Ser Tyr Thr Leu Thr Ile Ser Arg Leu Glu
65                  70                  75                  80

Pro Glu Asp Phe Ala Val Tyr Tyr Cys Gln Gln Trp Ser Ser Tyr Pro
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215
```

<210> SEQ ID NO 189
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

```
Glu Ile Leu Leu Thr Gln Ser Pro Gly Thr Leu Ser Leu Ser Pro Gly
1               5                   10                  15

Glu Arg Ala Thr Leu Ser Cys Ser Val Ser Ser Ile Ser Ser Ser
            20                  25                  30

Asn Leu His Trp Phe Gln Gln Lys Pro Gly Gln Ala Pro Arg Leu Leu
        35                  40                  45

Ile Tyr Gly Thr Ser Asn Leu Ala Ser Gly Ile Pro Asp Arg Phe Ser
    50                  55                  60

Gly Ser Gly Ser Gly Thr Ser Tyr Thr Leu Thr Ile Ser Arg Leu Glu
65                  70                  75                  80

Pro Glu Asp Phe Ala Val Tyr Tyr Cys Gln Gln Trp Ser Ser Tyr Pro
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 190
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

```
Glu Ile Leu Leu Thr Gln Ser Pro Gly Thr Leu Ser Leu Ser Pro Gly
1               5                   10                  15

Glu Arg Ala Thr Leu Ser Cys Ser Val Ser Ser Ile Ser Ser Ser
            20                  25                  30

Asn Leu His Trp Phe Gln Gln Lys Pro Gly Gln Ala Pro Arg Leu Trp
        35                  40                  45

Ile Tyr Gly Thr Ser Asn Leu Ala Ser Gly Val Pro Asp Arg Phe Ser
    50                  55                  60

Gly Ser Gly Ser Gly Thr Ser Tyr Thr Leu Thr Ile Ser Arg Leu Glu
65                  70                  75                  80
```

Pro Glu Asp Phe Ala Val Tyr Tyr Cys Gln Gln Trp Ser Ser Tyr Pro
            85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 191
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Glu Ile Leu Leu Thr Gln Ser Pro Gly Thr Leu Ser Leu Ser Pro Gly
1               5                   10                  15

Glu Arg Ala Thr Leu Thr Cys Ser Val Ser Ser Ser Ile Ser Ser Ser
            20                  25                  30

Asn Leu His Trp Phe Gln Gln Lys Pro Gly Gln Ser Pro Arg Leu Trp
            35                  40                  45

Ile Tyr Gly Thr Ser Asn Leu Ala Ser Gly Val Pro Asp Arg Phe Ser
50                  55                  60

Gly Ser Gly Ser Gly Thr Ser Tyr Thr Leu Thr Ile Ser Arg Leu Glu
65                  70                  75                  80

Pro Glu Asp Phe Ala Val Tyr Tyr Cys Gln Gln Trp Ser Ser Tyr Pro
            85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys

```
                210                 215

<210> SEQ ID NO 192
<211> LENGTH: 329
<212> TYPE: PRT
<213> ORGANISM: Homo sapiens

<400> SEQUENCE: 192

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 193
<211> LENGTH: 330
<212> TYPE: PRT
<213> ORGANISM: Homo sapiens
```

<400> SEQUENCE: 193

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 194
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 195
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 196
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr

```
               65                  70                  75                  80
Tyr Thr Cys Asn Val Asp His Lys Pro Ser Asn Thr Lys Val Asp Lys
                    85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 197
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95
```

```
Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 198
<211> LENGTH: 107
<212> TYPE: PRT
<213> ORGANISM: Homo sapiens

<400> SEQUENCE: 198

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 199
<211> LENGTH: 30
<212> TYPE: PRT
<213> ORGANISM: Homo sapiens
```

```
<400> SEQUENCE: 199

Gly Pro Pro Ala Ala Pro Gly His Pro Leu Ala Pro Gly Pro His
1               5                   10                  15

Pro Ala Ala Pro Ser Ser Trp Gly Pro Arg Pro Arg Arg Tyr
            20                  25                  30

<210> SEQ ID NO 200
<211> LENGTH: 17
<212> TYPE: PRT
<213> ORGANISM: Homo sapiens

<400> SEQUENCE: 200

Ala Glu Tyr Phe Gln His Trp Gly Gln Gly Thr Leu Val Thr Val Ser
1               5                   10                  15

Ser

<210> SEQ ID NO 201
<211> LENGTH: 12
<212> TYPE: PRT
<213> ORGANISM: Homo sapiens

<400> SEQUENCE: 201

Trp Thr Phe Gly Gln Gly Thr Lys Val Glu Ile Lys
1               5                   10

<210> SEQ ID NO 202
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 203
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Thr Ser Ser
                85                  90                  95
```

```
Ser Thr Arg Val Phe Gly Thr Gly Thr Lys Val Thr Val Leu Gln Pro
            100                 105                 110

Lys Ala Asn Pro Thr Val Thr Leu Phe Pro Pro Ser Glu Glu Leu
        115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Gly Ser Pro Val Lys Ala
145                 150                 155                 160

Gly Val Glu Thr Thr Lys Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 204
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
```

```
                225                 230                 235                 240
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly
    450

<210> SEQ ID NO 205
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125
```

```
Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 206
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 207
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

Ala Cys Glu Val Thr His Gln Gly Leu Ser Ser Pro Val Thr Lys Ser
            195                 200                 205

Phe Asn Arg Gly Glu Cys
            210

<210> SEQ ID NO 208
<211> LENGTH: 329
<212> TYPE: PRT
<213> ORGANISM: Homo sapiens

<400> SEQUENCE: 208

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

```
<210> SEQ ID NO 209
<211> LENGTH: 330
<212> TYPE: PRT
<213> ORGANISM: Homo sapiens

<400> SEQUENCE: 209

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 210
<211> LENGTH: 503
<212> TYPE: PRT
<213> ORGANISM: Homo sapiens

<400> SEQUENCE: 210
```

```
Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
            35                  40              45

Pro Pro Ala Ala Ala Pro Gly His Pro Leu Ala Pro Gly Pro His Pro
50                      55                  60

Ala Ala Pro Ser Ser Trp Gly Pro Arg Pro Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
            115                 120                 125

Val His Leu Arg Asp Arg Ala Leu Ser Cys Arg Leu Arg Leu Arg Leu
        130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Gly Pro Asp Leu Leu Val Thr
        275                 280                 285

Gly Asp Asn Gly Asp Phe Thr Leu Arg Leu Glu Asp Val Ser Gln Ala
290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
            340                 345                 350

Ser Gly Gln Glu Arg Phe Val Trp Ser Ser Leu Asp Thr Pro Ser Gln
        355                 360                 365

Arg Ser Phe Ser Gly Pro Trp Leu Glu Ala Gln Glu Ala Gln Leu Leu
370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu Leu Leu Phe Leu
```

```
            420                 425                 430
Ile Leu Gly Val Leu Ser Leu Leu Leu Val Thr Gly Ala Phe Gly
        435                 440                 445
Phe His Leu Trp Arg Arg Gln Trp Arg Pro Arg Arg Phe Ser Ala Leu
    450                 455                 460
Glu Gln Gly Ile His Pro Pro Gln Ala Gln Ser Lys Ile Glu Glu Leu
465                 470                 475                 480
Glu Gln Glu Pro Glu Pro Glu Pro Glu Pro Glu Pro Glu Pro Glu Pro
                485                 490                 495
Glu Pro Glu Pro Glu Gln Leu
                500
```

<210> SEQ ID NO 211
<211> LENGTH: 7
<212> TYPE: PRT
<213> ORGANISM: Homo sapiens

<400> SEQUENCE: 211

```
Pro Thr Ile Pro Leu Gln Asp
1               5
```

<210> SEQ ID NO 212
<211> LENGTH: 8
<212> TYPE: PRT
<213> ORGANISM: Homo sapiens

<400> SEQUENCE: 212

```
Ser Pro Thr Ile Pro Leu Gln Asp
1               5
```

<210> SEQ ID NO 213
<211> LENGTH: 9
<212> TYPE: PRT
<213> ORGANISM: Homo sapiens

<400> SEQUENCE: 213

```
Ser Pro Thr Ile Pro Leu Gln Asp Leu
1               5
```

<210> SEQ ID NO 214
<211> LENGTH: 10
<212> TYPE: PRT
<213> ORGANISM: Homo sapiens

<400> SEQUENCE: 214

```
Ser Pro Thr Ile Pro Leu Gln Asp Leu Ser
1               5                   10
```

<210> SEQ ID NO 215
<211> LENGTH: 11
<212> TYPE: PRT
<213> ORGANISM: Homo sapiens

<400> SEQUENCE: 215

```
Ser Pro Thr Ile Pro Leu Gln Asp Leu Ser Leu
1               5                   10
```

<210> SEQ ID NO 216
<211> LENGTH: 12
<212> TYPE: PRT
<213> ORGANISM: Homo sapiens

<400> SEQUENCE: 216

Ser Pro Thr Ile Pro Leu Gln Asp Leu Ser Leu Leu
1               5                   10

<210> SEQ ID NO 217
<211> LENGTH: 428
<212> TYPE: PRT
<213> ORGANISM: Homo sapiens

<400> SEQUENCE: 217

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
                20                  25                  30

Leu Leu Arg Arg Ala Gly Val Thr Trp Gln His Gln Pro Asp Ser Gly
            35                  40                  45

Pro Pro Ala Ala Ala Pro Gly His Pro Leu Ala Pro Gly Pro His Pro
        50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
                100                 105                 110

Trp Leu Arg Pro Ala Arg Arg Ala Asp Ala Gly Glu Tyr Arg Ala Ala
            115                 120                 125

Val His Leu Arg Asp Arg Ala Leu Ser Cys Arg Leu Arg Leu Arg Leu
130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
                180                 185                 190

Glu Ser Pro His His His Leu Ala Glu Ser Phe Leu Phe Leu Pro Gln
            195                 200                 205

Val Ser Pro Met Asp Ser Gly Pro Trp Gly Cys Ile Leu Thr Tyr Arg
210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
                260                 265                 270

Thr Ala Lys Trp Thr Pro Pro Gly Gly Gly Pro Asp Leu Leu Val Thr
            275                 280                 285

Gly Asp Asn Gly Asp Phe Thr Leu Arg Leu Glu Asp Val Ser Gln Ala
290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
                340                 345                 350

Ser Gly Gln Glu Arg Phe Val Trp Ser Ser Leu Asp Thr Pro Ser Gln

```
                355                 360                 365
Arg Ser Phe Ser Gly Pro Trp Leu Glu Ala Gln Glu Ala Gln Leu Leu
    370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu
            420                 425

<210> SEQ ID NO 218
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: M or L
<220> FEATURE:
<221> NAME/KEY: MOD_RES
<222> LOCATION: (5)..(5)
<223> OTHER INFORMATION: V or K
<220> FEATURE:
<221> NAME/KEY: MOD_RES
<222> LOCATION: (12)..(12)
<223> OTHER INFORMATION: K or V
<220> FEATURE:
<221> NAME/KEY: MOD_RES
<222> LOCATION: (23)..(23)
<223> OTHER INFORMATION: K or T
<220> FEATURE:
<221> NAME/KEY: MOD_RES
<222> LOCATION: (48)..(48)
<223> OTHER INFORMATION: M or I
<220> FEATURE:
<221> NAME/KEY: MOD_RES
<222> LOCATION: (70)..(70)
<223> OTHER INFORMATION: I or M
<220> FEATURE:
<221> NAME/KEY: MOD_RES
<222> LOCATION: (72)..(72)
<223> OTHER INFORMATION: A or R
<220> FEATURE:
<221> NAME/KEY: MOD_RES
<222> LOCATION: (76)..(76)
<223> OTHER INFORMATION: T or S
<220> FEATURE:
<221> NAME/KEY: MOD_RES
<222> LOCATION: (77)..(77)
<223> OTHER INFORMATION: S or N
<220> FEATURE:
<221> NAME/KEY: MOD_RES
<222> LOCATION: (81)..(81)
<223> OTHER INFORMATION: M or L
<220> FEATURE:
<221> NAME/KEY: MOD_RES
<222> LOCATION: (82)..(82)
<223> OTHER INFORMATION: E or Q
<220> FEATURE:
<221> NAME/KEY: MOD_RES
<222> LOCATION: (98)..(98)
<223> OTHER INFORMATION: T or R
<220> FEATURE:
<221> NAME/KEY: MOD_RES
<222> LOCATION: (102)..(102)
<223> OTHER INFORMATION: K or R
<220> FEATURE:
<221> NAME/KEY: MOD_RES
<222> LOCATION: (104)..(104)
<223> OTHER INFORMATION: D or E
```

<400> SEQUENCE: 218

Gln Val Gln Xaa Xaa Gln Ser Gly Ala Glu Val Xaa Lys Pro Gly Ala
1               5                   10                  15

Ser Val Lys Val Ser Cys Xaa Ala Ser Gly Phe Asn Ile Lys Asp Thr
            20                  25                  30

Tyr Ile His Trp Val Arg Gln Ala Pro Gly Gln Gly Leu Glu Trp Xaa
        35                  40                  45

Gly Glu Ile Asp Pro Ala Asn Asp Asn Thr Lys Tyr Asp Pro Lys Phe
    50                  55                  60

Gln Gly Arg Val Thr Xaa Thr Xaa Asp Thr Ser Xaa Xaa Thr Val Tyr
65                  70                  75                  80

Xaa Xaa Leu Ser Ser Leu Arg Ser Glu Asp Thr Ala Val Tyr Tyr Cys
                85                  90                  95

Ala Xaa Tyr Tyr Tyr Xaa Tyr Xaa Val Gly Gly Phe Asp Tyr Trp Gly
            100                 105                 110

Gln Gly Thr Leu Val Thr Val Ser Ser
            115                 120

<210> SEQ ID NO 219
<211> LENGTH: 107
<212> TYPE: PRT
<213> ORGANISM: Homo sapiens

<400> SEQUENCE: 219

Gly Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 220
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Q or pE (pyroglutamate)

<400> SEQUENCE: 220

Xaa Val Gln Met Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

```
Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Phe Asp Tyr Trp Gly
                100                 105                 110

Gln Gly Thr Leu Val Thr Val Ser Ser
            115                 120

<210> SEQ ID NO 221
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: E or pE (pyroglutamate)

<400> SEQUENCE: 221

Xaa Ile Val Leu Thr Gln Ser Pro Gly Thr Leu Ser Leu Ser Pro Gly
1               5                   10                  15

Glu Arg Ala Thr Leu Ser Cys Ser Val Ser Ser Ser Ile Ser Ser Ser
                20                  25                  30

Asn Leu His Trp Tyr Gln Gln Lys Pro Gly Gln Ala Pro Arg Leu Leu
            35                  40                  45

Ile Tyr Gly Thr Ser Asn Leu Ala Ser Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Trp Ser Ser Tyr Pro
                85                  90                  95

Phe Thr Phe Gly Gln Gly Thr Lys Val Glu Ile Lys
            100                 105

<210> SEQ ID NO 222
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Q or pE (pyroglutamate)
<220> FEATURE:
<221> NAME/KEY: MOD_RES
<222> LOCATION: (4)..(4)
<223> OTHER INFORMATION: M or L
<220> FEATURE:
<221> NAME/KEY: MOD_RES
<222> LOCATION: (5)..(5)
<223> OTHER INFORMATION: V or K
<220> FEATURE:
<221> NAME/KEY: MOD_RES
<222> LOCATION: (12)..(12)
<223> OTHER INFORMATION: K or V
<220> FEATURE:
<221> NAME/KEY: MOD_RES
<222> LOCATION: (48)..(48)
<223> OTHER INFORMATION: M or I
```

```
<220> FEATURE:
<221> NAME/KEY: MOD_RES
<222> LOCATION: (70)..(70)
<223> OTHER INFORMATION: I or M
<220> FEATURE:
<221> NAME/KEY: MOD_RES
<222> LOCATION: (72)..(72)
<223> OTHER INFORMATION: A or R
<220> FEATURE:
<221> NAME/KEY: MOD_RES
<222> LOCATION: (76)..(76)
<223> OTHER INFORMATION: T or S
<220> FEATURE:
<221> NAME/KEY: MOD_RES
<222> LOCATION: (77)..(77)
<223> OTHER INFORMATION: S or N
<220> FEATURE:
<221> NAME/KEY: MOD_RES
<222> LOCATION: (81)..(81)
<223> OTHER INFORMATION: M or L
<220> FEATURE:
<221> NAME/KEY: MOD_RES
<222> LOCATION: (82)..(82)
<223> OTHER INFORMATION: E or Q
<220> FEATURE:
<221> NAME/KEY: MOD_RES
<222> LOCATION: (98)..(98)
<223> OTHER INFORMATION: T or R
<220> FEATURE:
<221> NAME/KEY: MOD_RES
<222> LOCATION: (102)..(102)
<223> OTHER INFORMATION: K or R
<220> FEATURE:
<221> NAME/KEY: MOD_RES
<222> LOCATION: (104)..(104)
<223> OTHER INFORMATION: D or E

<400> SEQUENCE: 222

Xaa Val Gln Xaa Xaa Gln Ser Gly Ala Glu Val Xaa Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Xaa
        35                  40                  45

Gly Glu Ile Asp Pro Ala Asn Asp Asn Thr Lys Tyr Asp Pro Lys Phe
    50                  55                  60

Gln Gly Arg Val Thr Xaa Thr Xaa Asp Thr Ser Xaa Xaa Thr Val Tyr
65                  70                  75                  80

Xaa Xaa Leu Ser Ser Leu Arg Ser Glu Asp Thr Ala Val Tyr Tyr Cys
                85                  90                  95

Ala Xaa Tyr Tyr Tyr Xaa Tyr Xaa Val Gly Gly Phe Asp Tyr Trp Gly
            100                 105                 110

Gln Gly Thr Leu Val Thr Val Ser Ser
        115                 120

<210> SEQ ID NO 223
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Q or pE (pyroglutamate)
<220> FEATURE:
<221> NAME/KEY: MOD_RES
<222> LOCATION: (4)..(4)
<223> OTHER INFORMATION: M or L
```

```
<220> FEATURE:
<221> NAME/KEY: MOD_RES
<222> LOCATION: (5)..(5)
<223> OTHER INFORMATION: V or K
<220> FEATURE:
<221> NAME/KEY: MOD_RES
<222> LOCATION: (12)..(12)
<223> OTHER INFORMATION: K or V
<220> FEATURE:
<221> NAME/KEY: MOD_RES
<222> LOCATION: (23)..(23)
<223> OTHER INFORMATION: K or T
<220> FEATURE:
<221> NAME/KEY: MOD_RES
<222> LOCATION: (48)..(48)
<223> OTHER INFORMATION: M or I
<220> FEATURE:
<221> NAME/KEY: MOD_RES
<222> LOCATION: (70)..(70)
<223> OTHER INFORMATION: I or M
<220> FEATURE:
<221> NAME/KEY: MOD_RES
<222> LOCATION: (72)..(72)
<223> OTHER INFORMATION: A or R
<220> FEATURE:
<221> NAME/KEY: MOD_RES
<222> LOCATION: (76)..(76)
<223> OTHER INFORMATION: T or S
<220> FEATURE:
<221> NAME/KEY: MOD_RES
<222> LOCATION: (77)..(77)
<223> OTHER INFORMATION: S or N
<220> FEATURE:
<221> NAME/KEY: MOD_RES
<222> LOCATION: (81)..(81)
<223> OTHER INFORMATION: M or L
<220> FEATURE:
<221> NAME/KEY: MOD_RES
<222> LOCATION: (82)..(82)
<223> OTHER INFORMATION: E or Q
<220> FEATURE:
<221> NAME/KEY: MOD_RES
<222> LOCATION: (98)..(98)
<223> OTHER INFORMATION: T or R
<220> FEATURE:
<221> NAME/KEY: MOD_RES
<222> LOCATION: (102)..(102)
<223> OTHER INFORMATION: K or R
<220> FEATURE:
<221> NAME/KEY: MOD_RES
<222> LOCATION: (104)..(104)
<223> OTHER INFORMATION: D or E

<400> SEQUENCE: 223

Xaa Val Gln Xaa Xaa Gln Ser Gly Ala Glu Val Xaa Lys Pro Gly Ala
1               5                   10                  15

Ser Val Lys Val Ser Cys Xaa Ala Ser Gly Phe Asn Ile Lys Asp Thr
            20                  25                  30

Tyr Ile His Trp Val Arg Gln Ala Pro Gly Gln Gly Leu Glu Trp Xaa
        35                  40                  45

Gly Glu Ile Asp Pro Ala Asn Asp Asn Thr Lys Tyr Asp Pro Lys Phe
    50                  55                  60

Gln Gly Arg Val Thr Xaa Thr Xaa Asp Thr Ser Xaa Xaa Thr Val Tyr
65                  70                  75                  80

Xaa Xaa Leu Ser Ser Leu Arg Ser Glu Asp Thr Ala Val Tyr Tyr Cys
            85                  90                  95

Ala Xaa Tyr Tyr Tyr Xaa Tyr Xaa Val Gly Gly Phe Asp Tyr Trp Gly
        100                 105                 110

Gln Gly Thr Leu Val Thr Val Ser Ser
        115                 120
```

<210> SEQ ID NO 224
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (1)..(1)
<223> OTHER INFORMATION: E or pE (pyroglutamate)
<220> FEATURE:
<221> NAME/KEY: MOD_RES
<222> LOCATION: (3)..(3)
<223> OTHER INFORMATION: V or L
<220> FEATURE:
<221> NAME/KEY: MOD_RES
<222> LOCATION: (22)..(22)
<223> OTHER INFORMATION: S or T
<220> FEATURE:
<221> NAME/KEY: MOD_RES
<222> LOCATION: (37)..(37)
<223> OTHER INFORMATION: Y or F
<220> FEATURE:
<221> NAME/KEY: MOD_RES
<222> LOCATION: (44)..(44)
<223> OTHER INFORMATION: A or S
<220> FEATURE:
<221> NAME/KEY: MOD_RES
<222> LOCATION: (48)..(48)
<223> OTHER INFORMATION: L or W
<220> FEATURE:
<221> NAME/KEY: MOD_RES
<222> LOCATION: (59)..(59)
<223> OTHER INFORMATION: I or V
<220> FEATURE:
<221> NAME/KEY: MOD_RES
<222> LOCATION: (71)..(71)
<223> OTHER INFORMATION: D or S
<220> FEATURE:
<221> NAME/KEY: MOD_RES
<222> LOCATION: (72)..(72)
<223> OTHER INFORMATION: F or Y

<400> SEQUENCE: 224

Xaa Ile Xaa Leu Thr Gln Ser Pro Gly Thr Leu Ser Leu Ser Pro Gly
1               5                   10                  15

Glu Arg Ala Thr Leu Xaa Cys Ser Val Ser Ser Ile Ser Ser Ser
            20                  25                  30

Asn Leu His Trp Xaa Gln Gln Lys Pro Gly Gln Xaa Pro Arg Leu Xaa
        35                  40                  45

Ile Tyr Gly Thr Ser Asn Leu Ala Ser Gly Xaa Pro Asp Arg Phe Ser
    50                  55                  60

Gly Ser Gly Ser Gly Thr Xaa Xaa Thr Leu Thr Ile Ser Arg Leu Glu
65                  70                  75                  80

Pro Glu Asp Phe Ala Val Tyr Tyr Cys Gln Gln Trp Ser Ser Tyr Pro
                85                  90                  95

Phe Thr Phe Gly Gln Gly Thr Lys Val Glu Ile Lys
            100                 105

<210> SEQ ID NO 225
<211> LENGTH: 450
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (1)..(1)

<223> OTHER INFORMATION: Q or pE (pyroglutamate)

<400> SEQUENCE: 225

```
Xaa Val Gln Met Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

-continued

```
Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 226
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Q or pE (pyroglutamate)

<400> SEQUENCE: 226

Xaa Val Gln Met Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
```

```
                275                 280                 285
His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 227
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Q or pE (pyroglutamate)

<400> SEQUENCE: 227

Xaa Val Gln Met Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Glu Ile Asp Pro Ala Asn Asp Asn Thr Lys Tyr Asp Pro Lys Phe
    50                  55                  60

Gln Gly Arg Val Thr Ile Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Tyr Tyr Tyr Lys Tyr Asp Val Gly Gly Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 228
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: E or pE (pyroglutamate)

<400> SEQUENCE: 228

Xaa Ile Val Leu Thr Gln Ser Pro Gly Thr Leu Ser Leu Ser Pro Gly
1               5                   10                  15

Glu Arg Ala Thr Leu Ser Cys Ser Val Ser Ser Ser Ile Ser Ser Ser
            20                  25                  30

Asn Leu His Trp Tyr Gln Gln Lys Pro Gly Gln Ala Pro Arg Leu Leu
        35                  40                  45
```

-continued

```
Ile Tyr Gly Thr Ser Asn Leu Ala Ser Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Trp Ser Ser Tyr Pro
                85                  90                  95
Phe Thr Phe Gly Gln Gly Thr Lys Val Glu Ile Lys Arg Thr Val Ala
                100                 105                 110
Ala Pro Ser Val Phe Ile Phe Pro Pro Ser Asp Glu Gln Leu Lys Ser
            115                 120                 125
Gly Thr Ala Ser Val Val Cys Leu Leu Asn Asn Phe Tyr Pro Arg Glu
130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
210                 215
```

ANTI-LAG-3 ANTIBODIES AND METHODS OF USE THEREOF

1. RELATED APPLICATIONS

This application is a continuation of U.S. patent application Ser. No. 16/989,369, filed Aug. 10, 2020, which is a continuation of U.S. patent application Ser. No. 15/730,249 (allowed), filed Oct. 11, 2017, which claims the benefit of U.S. Provisional Application Nos. 62/406,766, filed Oct. 11, 2016; and 62/420,280, filed Nov. 10, 2016, each of which is incorporated by reference herein in its entirety.

2. FIELD

The instant disclosure relates to antibodies that specifically bind to LAG-3 (e.g., human LAG-3) and methods of using the same.

3. BACKGROUND

Lymphocyte activation gene 3 (LAG-3), also known as CD223, is a type I membrane protein in the immunoglobulin (Ig) superfamily that is composed of four extracellular Ig domains and a cytoplasmic domain containing a conserved repeated EP motif and a single conserved KIEELE motif (Triebel et al, (1990) J Exp Med, 171: 1393-405; Workman et al., (2002) J Immunol, 169: 5392-5). LAG-3 is expressed on activated effector T lymphocytes (Teff), activated regulatory T lymphocytes (Treg), activated B lymphocytes, a subset of resting natural killer (NK) cells, and resting plasmacytoid dendritic cells (PDC) (Huang et al, (2004) Immunity, 21: 503-13; Workman et al, (2009) J Immunol, 182: 1885-91; Kisielow et al, (2005) Eur J Immunol, 35: 2081-8; Baixeras et al, (1992) J Exp Med, 176: 327-37; Workman et al, (2002) Eur J Immunol, 32: 2255-63). Under conditions of persistent antigenic exposure, such as in chronic pathogenic infections or within the tumor microenvironment (TME), LAG-3 expression is sustained on T regulatory type 1 cells (Tr1) and so-called exhausted antigen-specific T cells (Park et al, (2012) Cell Immunol, 278: 76-83; Gagliani et al, (2013) Nat Med, 19: 739-46; Blackburn et al, (2009) Nat Immunol, 10: 29-37).

LAG-3 functions to negatively regulate activated T cells. The ligand for LAG-3 is MHC class II, expressed on antigen presenting cells (APC) and activated T cells (Roche and Furuta (2015) Nat Rev Immunol, 15: 203-16). The interaction between LAG-3 and its ligand inhibits proliferation and cytokine secretion of CD4+ and CD8+ Teff cells (Macon-Lemaitre and Triebel (2005) Immunology, 115: 170-8; Huard et al, (1997) Proc Natl Acad Sci USA, 94: 5744-9). LAG-3 in Tregs and PDCs contributes to the negative regulation of T cell function (Huang et al, (2004) Immunity, 21: 503-13; Workman et al, (2009) J Immunol, 182: 1885-91). Consistent with its role in maintaining immune homeostasis, LAG-3 deficiency induced lethal myocarditis in mice also genetically deficient in PD-1 (Okazaki et al., (2011) J Exp Med, 208: 395-407). Furthermore, in vivo blockade with a monoclonal antibody against mouse LAG-3 in combination with PD-1 blockade synergized to potentiate anti-tumor immunity in syngeneic mouse tumor models (Woo et al, (2012) Cancer Res, 72: 917-27).

Given LAG-3's role in modulating immune responses, therapeutic agents designed to antagonize LAG-3 signaling hold great promise for the treatment of diseases that involve LAG-3-mediated immune suppression.

4. SUMMARY

The instant disclosure provides antibodies that specifically bind to LAG-3 (e.g., human LAG-3) and antagonize LAG-3 function, e.g., LAG-3-mediated immune suppression. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for increasing T cell activation in response to an antigen (e.g., a tumor antigen or an infectious disease antigen) and/or decreasing Treg-mediated immune suppression, and hence for treating cancer in a subject or treating or preventing an infectious disease in a subject.

Accordingly, in one aspect, the instant disclosure provides an antibody or isolated antibody comprising a heavy chain variable region comprising complementarity determining regions CDRH1, CDRH2 and CDRH3 and a light chain variable region comprising complementarity determining regions CDRL1, CDRL2 and CDRL3, wherein:
  (a) CDRH1 comprises the amino acid sequence of $DX_1YX_2X_3$ (SEQ ID NO: 140), wherein
    $X_1$ is T or N,
    $X_2$ is I or M, and
    $X_3$ is H, Y or D;
  (b) CDRH2 comprises the amino acid sequence of $X_1IDPANX_2X_3X_4X_5X_6X_7PX_8X_9QX_{10}$ (SEQ ID NO: 142), wherein
    $X_1$ is E, R, S, or K,
    $X_2$ is D or G,
    $X_3$ is N or H,
    $X_4$ is T or S,
    $X_5$ is K or H,
    $X_6$ is Y or F,
    $X_7$ is D or A,
    $X_8$ is K or R,
    $X_9$ is F or L, and
    $X_{10}$ is G or D;
  (c) CDRH3 comprises the amino acid sequence of $YX_1X_2X_3YX_4VGGX_5DY$ (SEQ ID NO: 144), wherein
    $X_1$ is Y, F, or S,
    $X_2$ is Y or D,
    $X_3$ is K or R,
    $X_4$ is D or E, and
    $X_5$ is F or C;
  (d) CDRL1 comprises the amino acid sequence of $SVSSX_1SSSX_2LX_3$ (SEQ ID NO: 147), wherein
    $X_1$ is S or G,
    $X_2$ is N or T, and
    $X_3$ is H or Y;
  (e) CDRL2 comprises the amino acid sequence of GTSNLAS (SEQ ID NO: 104); and
  (f) CDRL3 comprises the amino acid sequence of $QQWX_1X_2YPX_3T$ (SEQ ID NO: 149), wherein
    $X_1$ is S, N, or R,
    $X_2$ is S, T or R, and
    $X_3$ is F, L, H, or W.

In another aspect, the instant disclosure provides an antibody or isolated antibody that specifically binds to human LAG-3, the antibody comprising a heavy chain variable region comprising complementarity determining regions CDRH1, CDRH2 and CDRH3 and a light chain variable region comprising complementarity determining regions CDRL1, CDRL2 and CDRL3, wherein:
  (a) CDRH1 comprises the amino acid sequence of $DX_1YX_2X_3$ (SEQ ID NO: 140), wherein X₁ is T or N,
X₂ is I or M, and
X₃ is H, Y or D;
(b) CDRH2 comprises the amino acid sequence of X₁IDPANX₂X₃X₄X₅X₆X₇PX₈X₉QX₁₀ (SEQ ID NO: 142), wherein
X₁ is E, R, S, or K,
X₂ is D or G,
X₃ is N or H,
X₄ is T or S,
X₅ is K or H,
X₆ is Y or F,
X₇ is D or A,
X₈ is K or R,
X₉ is F or L, and
X₁₀ is G or D;
(c) CDRH3 comprises the amino acid sequence of YX₁X₂X₃YX₄VGGX₅DY (SEQ ID NO: 144), wherein
X₁ is Y, F, or S,
X₂ is Y or D,
X₃ is K or R,
X₄ is D or E, and
X₅ is F or C;
(d) CDRL1 comprises the amino acid sequence of SVSSX₁SSSX₂LX₃ (SEQ ID NO: 147), wherein
X₁ is S or G,
X₂ is N or T, and
X₃ is H or Y;
(e) CDRL2 comprises the amino acid sequence of GTSNLAS (SEQ ID NO: 104); and
(f) CDRL3 comprises the amino acid sequence of QQWX₁X₂YPX₃T (SEQ ID NO: 149), wherein
X₁ is S, N, or R,
X₂ is S, T or R, and
X₃ is F, L, H, or W.

In certain embodiments, CDRH1 comprises the amino acid sequence of DX₁YX₂X₃ (SEQ ID NO: 141), wherein: X₁ is T or N; X₂ is I or M; and X₃ is H or Y. In certain embodiments, CDRH2 comprises the amino acid sequence of X₁IDPANX₂X₃X₄KX₅X₆PX₇FQX₈ (SEQ ID NO: 143), wherein: X₁ is E, R, or S; X₂ is D or G; X₃ is N or H; X₄ is T or S; X₅ is Y or F; X₆ is D or A; X₇ is K or R; and X₈ is G or D. In certain embodiments, CDRH3 comprises the amino acid sequence of YX₁X₂X₃YDVGGX₄DY (SEQ ID NO: 145), wherein: X₁ is Y, F, or S; X₂ is Y or D; X₃ is K or R; and X₄ is F or C. In certain embodiments, CDRH3 comprises the amino acid sequence of YYYX₁YX₂VGGFDY (SEQ ID NO: 146), wherein: X₁ is K or R; and X₂ is D or E. In certain embodiments, CDRL1 comprises the amino acid sequence of SVSSSISSSNLX₁ (SEQ ID NO: 148), wherein: X₁ is H or Y. In certain embodiments, CDRL3 comprises the amino acid sequence of QQWX₁SYPX₁T (SEQ ID NO: 150), wherein: X₁ is S, N, or R; and X₂ is F, L, or H.

In certain embodiments:
(a) CDRH1 comprises the amino acid sequence of DTYIH (SEQ ID NO: 79);
(b) CDRH2 comprises the amino acid sequence of EIDPANDNTKYDPKFQG (SEQ ID NO: 90);
(c) CDRH3 comprises the amino acid sequence of YYYX₁YX₂VGGFDY (SEQ ID NO: 146), wherein: X₁ is K or R; and X₂ is D or E;
(d) CDRL1 comprises the amino acid sequence of SVSSSISSSNLH (SEQ ID NO: 100);
(e) CDRL2 comprises the amino acid sequence of GTSNLAS (SEQ ID NO: 104); and
(f) CDRL3 comprises the amino acid sequence of QQWSSYPFT (SEQ ID NO: 105).

In certain embodiments, CDRH1, CDRH2, and CDRH3 comprise the amino acid sequences set forth in SEQ ID NOs: 79, 90, and 98, respectively. In certain embodiments, the heavy chain variable region comprises an amino acid sequence that is at least 75%, 80%, 85%, 90%, 95%, 97%, 98%, or 99% identical to the amino acid sequence of SEQ ID NO: 65 or 220. In certain embodiments, the heavy chain variable region comprises an amino acid sequence that is at least 98% identical to the amino acid sequence of SEQ ID NO: 65 or 220. In certain embodiments, the heavy chain variable region comprises the amino acid sequence of SEQ ID NO: 220. In certain embodiments, the heavy chain variable region comprises the amino acid sequence of SEQ ID NO: 65. In certain embodiments, the heavy chain variable region comprises the amino acid sequence of SEQ ID NO: 220. In certain embodiments, the antibody comprises a heavy chain comprising the amino acid sequence of SEQ ID NO: 226. In certain embodiments, the antibody comprises a heavy chain comprising the amino acid sequence of SEQ ID NO: 169.

In certain embodiments, CDRL1, CDRL2, and CDRL3 comprise the amino acid sequences set forth in SEQ ID NOs: 100, 104, and 105, respectively. In certain embodiments, the light chain variable region comprises an amino acid sequence that is at least 75%, 80%, 85%, 90%, 95%, 97%, 98%, or 99% identical to the amino acid sequence of SEQ ID NO: 73 or 221. In certain embodiments, the light chain variable region comprises an amino acid sequence that is at least 98% identical to the amino acid sequence of SEQ ID NO: 73 or 221. In certain embodiments, the light chain variable region comprises the amino acid sequence of SEQ ID NO: 221. In certain embodiments, the light chain variable region comprises the amino acid sequence of SEQ ID NO: 73. In certain embodiments, the antibody comprises a light chain comprising the amino acid sequence of SEQ ID NO: 228. In certain embodiments, the antibody comprises a light chain comprising the amino acid sequence of SEQ ID NO: 187.

In certain embodiments, CDRH1 comprises an amino acid sequence selected from the group consisting of SEQ ID NOs: 78-82. In certain embodiments, CDRH2 comprises an amino acid sequence selected from the group consisting of SEQ ID NOs: 83-93. In certain embodiments, CDRH3 comprises an amino acid sequence selected from the group consisting of SEQ ID NOs: 94-99. In certain embodiments, CDRL1 comprises an amino acid sequence selected from the group consisting of SEQ ID NOs: 100-103. In certain embodiments, CDRL3 comprises an amino acid sequence selected from the group consisting of SEQ ID NOs: 105-112.

In certain embodiments, CDRH1, CDRH2 and CDRH3 comprise the CDRH1, CDRH2 and CDRH3 amino acid sequences, respectively, set forth in SEQ ID NOs: 78, 83, and 94; 78, 85, and 95; 78, 86, and 96; 78, 86, and 97; 78, 91, and 94; 78, 92, and 96; 79, 84, and 95; 79, 88, and 95; 79, 89, and 95; 79, 90, and 95; 79, 90, and 98; 79, 90, and 99; 80, 85, and 96; 81, 87, and 96; or, 82, 93, and 95.

In certain embodiments, CDRL1, CDRL2 and CDRL3 comprise the CDRL1, CDRL2 and CDRL3 amino acid sequences, respectively, set forth in SEQ ID NOs: 100, 104, and 105; 100, 104, and 106; 100, 104, and 107; 100, 104, and 109; 100, 104, and 110; 101, 104, and 108; 102, 104, and 105; 102, 104, and 112; or, 103, 104, and 111.

In certain embodiments, CDRH1, CDRH2, CDRH3, CDRL1, CDRL2, and CDRL3 comprise the amino acid sequences set forth in SEQ ID NOs: 78, 83, 94, 100, 104, and 105; 78, 85, 95, 100, 104, and 105; 78, 86, 96, 100, 104, and 105; 78, 86, 96, 100, 104, and 109; 78, 86, 96, 100, 104, and 110; 78, 86, 96, 101, 104, and 108; 78, 86, 96, 103, 104, and 111; 78, 86, 97, 102, 104, and 112; 78, 91, 94, 100, 104, and 107; 78, 92, 96, 100, 104, and 105; 78, 92, 96, 100, 104, and 109; 79, 84, 95, 100, 104, and 105; 79, 84, 95, 100, 104, and 106; 79, 84, 95, 102, 104, and 105; 79, 88, 95, 100, 104, and 105; 79, 89, 95, 100, 104, and 105; 79, 90, 95, 100, 104, and 105; 79, 90, 98, 100, 104, and 105; 79, 90, 99, 100, 104, and 105; 80, 85, 96, 100, 104, and 105; 81, 87, 96, 100, 104, and 105; 81, 87, 96, 100, 104, and 107; or, 82, 93, 95, 100, 104, and 105, respectively.

In another aspect, the instant disclosure provides an antibody or isolated antibody comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 79, 90, 95, 100, 104, and 105, respectively.

In another aspect, the instant disclosure provides an antibody or isolated antibody that specifically binds to human LAG-3, comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 79, 90, 95, 100, 104, and 105, respectively.

In another aspect, the instant disclosure provides an antibody or isolated antibody comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 79, 90, 98, 100, 104, and 105, respectively.

In another aspect, the instant disclosure provides an antibody or isolated antibody that specifically binds to human LAG-3, comprising a heavy chain variable region comprising complementarity determining regions CDRH1, CDRH2 and CDRH3, and a light chain variable region comprising complementarity determining regions CDRL1, CDRL2 and CDRL3, wherein CDRH1, CDRH2, CDRH3, CDRL1, CDRL2, and CDRL3 comprise the amino acid sequences set forth in SEQ ID NOs: 79, 90, 98, 100, 104, and 105, respectively.

In certain embodiments, the heavy chain variable region comprises an amino acid sequence that is at least 75%, 80%, 85%, 90%, 95%, 97%, 98%, or 99% identical to the amino acid sequence of SEQ ID NO: 65 or 220. In certain embodiments, the heavy chain variable region comprises an amino acid sequence that is at least 98% identical to the amino acid sequence of SEQ ID NO: 65 or 220. In certain embodiments, the heavy chain variable region comprises the amino acid sequence of SEQ ID NO: 220. In certain embodiments, the heavy chain variable region comprises the amino acid sequence of SEQ ID NO: 65. In certain embodiments, the antibody comprises a heavy chain comprising the amino acid sequence of SEQ ID NO: 226. In certain embodiments, the antibody comprises a heavy chain comprising the amino acid sequence of SEQ ID NO: 169.

In certain embodiments, the light chain variable region comprises an amino acid sequence that is at least 75%, 80%, 85%, 90%, 95%, 97%, 98%, or 99% identical to the amino acid sequence of SEQ ID NO: 73 or 221. In certain embodiments, the light chain variable region comprises an amino acid sequence that is at least 98% identical to the amino acid sequence of SEQ ID NO: 73 or 221. In certain embodiments, the light chain variable region comprises the amino acid sequence of SEQ ID NO: 221. In certain embodiments, the light chain variable region comprises the amino acid sequence of SEQ ID NO: 73. In certain embodiments, the antibody comprises a light chain comprising the amino acid sequence of SEQ ID NO: 228. In certain embodiments, the antibody comprises a light chain comprising the amino acid sequence of SEQ ID NO: 228. In certain embodiments, the antibody comprises a light chain comprising the amino acid sequence of SEQ ID NO: 187.

In certain embodiments, the heavy chain variable region comprises an amino acid sequence that is at least 75%, 80%, 85%, 90%, 95%, 97%, 98%, or 99% identical to the amino acid sequence of SEQ ID NO: 65 or 220, and the light chain variable region comprises an amino acid sequence that is at least 75%, 80%, 85%, 90%, 95%, 97%, 98%, or 99% identical to the amino acid sequence of SEQ ID NO: 73 or 221. In certain embodiments, the heavy chain variable region comprises an amino acid sequence that is at least 98% identical to the amino acid sequence of SEQ ID NO: 65 or 220, and the light chain variable region comprises an amino acid sequence that is at least 98% identical to the amino acid sequence of SEQ ID NO: 73 or 221. In certain embodiments, the heavy chain variable region comprises the amino acid sequence of SEQ ID NO: 220. In certain embodiments, the heavy chain variable region comprises the amino acid sequence of SEQ ID NO: 65. In certain embodiments, the light chain variable region comprises the amino acid sequence of SEQ ID NO: 73 or 221. In certain embodiments, the light chain variable region comprises the amino acid sequence of SEQ ID NO: 73.

In another aspect, the instant disclosure provides an isolated antibody that specifically binds to human LAG-3, comprising a heavy chain variable region comprising the amino acid sequence of SEQ ID NO: 65 or 220. In certain embodiments, the antibody comprises a light chain variable region comprising an amino acid sequence that is at least 75%, 80%, 85%, 90%, 95%, 97%, 98%, or 99% identical to the amino acid sequence of SEQ ID NO: 73 or 221. In certain embodiments, the antibody comprises a light chain variable region comprising an amino acid sequence that is at least 98% identical to the amino acid sequence of SEQ ID NO: 73 or 221.

In another aspect, the instant disclosure provides an isolated antibody that specifically binds to human LAG-3, comprising a light chain variable region comprising the amino acid sequence of SEQ ID NO: 73 or 221. In certain embodiments, the antibody comprises a heavy chain variable region comprising an amino acid sequence that is at least 75%, 80%, 85%, 90%, 95%, 97%, 98%, or 99% identical to the amino acid sequence of SEQ ID NO: 65 or 220. In certain embodiments, the antibody comprises a heavy chain variable region comprising an amino acid sequence that is at least 98% identical to the amino acid sequence of SEQ ID NO: 65 or 220.

In certain embodiments, the antibody comprises a heavy chain variable region comprising the framework regions of the heavy chain variable region sequence of SEQ ID NO: 151 or 222. In certain embodiments, the antibody comprises a heavy chain variable region comprising the amino acid sequence of SEQ ID NO: 151 or 222. In certain embodiments, the antibody comprises a heavy chain variable region comprising the framework regions of the heavy chain variable region sequence of SEQ ID NO: 218 or 223. In certain embodiments, the antibody comprises a heavy chain variable region comprising the amino acid sequence of SEQ ID NO: 218 or 223. In certain embodiments, the antibody comprises a heavy chain variable region comprising an amino acid sequence which is at least 75%, 80%, 85%, 90%, 95%, or 100% identical to an amino acid sequence selected from the group consisting of SEQ ID NOs: 56-72 and 220. In certain embodiments, the heavy chain variable region comprises an amino acid sequence selected from the group consisting of SEQ ID NOs: 56-72 and 220. In certain embodiments, the heavy chain variable region comprises the amino acid sequence of SEQ ID NO: 220. In certain embodiments, the heavy chain variable region comprises the amino acid sequence of SEQ ID NO: 65. In certain embodiments, the antibody comprises a heavy chain comprising an amino acid sequence selected from the group consisting of SEQ ID NOs: 168-186 and 225-227. In certain embodiments, the antibody comprises a heavy chain variable region having human derived framework regions. In certain embodiments, the antibody comprises a heavy chain variable framework region that is or is derived from an amino acid sequence encoded by a human gene, wherein said amino acid sequence is selected from the group consisting of IGHV1-46*01 (SEQ ID NO: 153), IGHV1-69-2*01 (SEQ ID NO: 154), IGHV1-3*01 (SEQ ID NO: 155), IGHV1-24*01 (SEQ ID NO: 156), IGHV1-2*01 (SEQ ID NO: 157), IGHV1-45*01 (SEQ ID NO: 158), and IGHV1-18*01 (SEQ ID NO: 159). In certain embodiments, the antibody comprises a heavy chain variable framework region that is derived from the amino acid sequence IGHV1-46*01 (SEQ ID NO: 153), wherein at least one amino acid in the amino acid sequence IGHV1-46*01 (SEQ ID NO: 153) is substituted with an amino acid in an analogous position in a corresponding non-human heavy chain variable framework region. In certain embodiments, the amino acid substitution is at an amino acid position selected from the group consisting of 4, 5, 12, 23, 27, 28, 29, 30, 48, 69, 71, 75, 76, 80, 81, and 94, wherein the amino acid position is indicated according to the Kabat numbering system. In certain embodiments, the amino acid substitution is selected from the group consisting of 4M, 5K, 12V, 23T, 27F, 28N, 29I, 30K, 48I, 69I, 71A, 75S, 76N, 80L, 81Q, and 94T, wherein the position of the amino acid substitution is indicated according to the Kabat numbering system. In certain embodiments, the amino acid substitution is at an amino acid position selected from the group consisting of 4, 27, 28, 29, 30, 69, 71, and 94, wherein the amino acid position is indicated according to the Kabat numbering system. In certain embodiments, the amino acid substitution is selected from the group consisting of 4M, 27F, 28N, 29I, 30K, 69I, 71A, and 94T, wherein the position of the amino acid substitution is indicated according to the Kabat numbering system.

In certain embodiments, the antibody comprises a light chain variable region comprising the framework regions of the light chain variable region sequence of SEQ ID NO: 152 or 224. In certain embodiments, the antibody comprises a light chain variable region comprising the amino acid sequence of SEQ ID NO: 152 or 224. In certain embodiments, the antibody comprises a light chain variable region comprising an amino acid sequence which is at least 75%, 80%, 85%, 90%, 95%, or 100% identical to an amino acid sequence selected from the group consisting of SEQ ID NOs: 73-77 and 221. In certain embodiments, the light chain variable region comprises an amino acid sequence selected from the group consisting of SEQ ID NOs: 73-77 and 221. In certain embodiments, the light chain variable region comprises the amino acid sequence of SEQ ID NO: 221. In certain embodiments, the light chain variable region comprises the amino acid sequence of SEQ ID NO: 73. In certain embodiments, the antibody comprises a light chain comprising an amino acid sequence selected from the group consisting of SEQ ID NOs: 187-191. In certain embodiments, the antibody comprises a light chain variable region having human derived framework regions. In certain embodiments, the antibody comprises a light chain variable framework region that is or is derived from an amino acid sequence encoded by a human gene, wherein said amino acid sequence is selected from the group consisting of IGKV3-20*01 (SEQ ID NO: 160), IGKV3D-15*01 (SEQ ID NO: 161), IGKV3-15*01 (SEQ ID NO: 161), IGKV3D-20*01 (SEQ ID NO: 162), IGKV3D-7*01 (SEQ ID NO: 163), IGKV1-9*01 (SEQ ID NO: 164), and IGKV3-11*01 (SEQ ID NO: 165). In certain embodiments, the antibody comprises a light chain variable framework region that is from the amino acid sequence IGKV3-20*01 (SEQ ID NO: 160). In certain embodiments, the antibody comprises a light chain variable framework region that is derived from the amino acid sequence IGKV3-20*01 (SEQ ID NO: 160), wherein at least one amino acid in the amino acid sequence IGKV3-20*01 (SEQ ID NO: 160) is substituted with an amino acid in an analogous position in a corresponding non-human light chain variable framework region. In certain embodiments, the amino acid substitution is at an amino acid position selected from the group consisting of 3, 22, 36, 43, 47, 58, 70, and 71, wherein the amino acid position is indicated according to the Kabat numbering system. In certain embodiments, the amino acid substitution is selected from the group consisting of 3L, 22T, 36F, 43S, 47W, 58V, 70S, and 71Y, wherein the position of the amino acid substitution is indicated according to the Kabat numbering system.

In another aspect, the instant disclosure provides an antibody or isolated antibody comprising a heavy chain variable region comprising an amino acid sequence selected from the group consisting of SEQ ID NOs: 56-72 and 220. In certain embodiments, the heavy chain variable region comprises the amino acid sequence of SEQ ID NO: 220. In certain embodiments, the heavy chain variable region comprises the amino acid sequence of SEQ ID NO: 65. In certain embodiments, the antibody comprises a heavy chain comprising an amino acid sequence selected from the group consisting of SEQ ID NOs: 168-186 and 225-227. In certain embodiments, the antibody comprises a heavy chain comprising the amino acid sequence of SEQ ID NO: 225. In certain embodiments, the antibody comprises a heavy chain comprising the amino acid sequence of SEQ ID NO: 168. In certain embodiments, the antibody comprises a heavy chain comprising the amino acid sequence of SEQ ID NO: 226. In certain embodiments, the antibody comprises a heavy chain comprising the amino acid sequence of SEQ ID NO: 169. In certain embodiments, the antibody comprises a heavy chain comprising the amino acid sequence of SEQ ID NO: 227. In certain embodiments, the antibody comprises a heavy chain comprising the amino acid sequence of SEQ ID NO: 170.

In another aspect, the instant disclosure provides an antibody or isolated antibody that specifically binds to human LAG-3, the antibody comprising a heavy chain variable region comprising an amino acid sequence selected from the group consisting of SEQ ID NOs: 56-72 and 220. In certain embodiments, the heavy chain variable region comprises the amino acid sequence of SEQ ID NO: 220. In certain embodiments, the heavy chain variable region comprises the amino acid sequence of SEQ ID NO: 65. In certain embodiments, the antibody comprises a heavy chain comprising an amino acid sequence selected from the group consisting of SEQ ID NOs: 168-186 and 225-227. In certain embodiments, the antibody comprises a heavy chain comprising the amino acid sequence of SEQ ID NO: 225. In certain embodiments, the antibody comprises a heavy chain comprising the amino acid sequence of SEQ ID NO: 168. In certain embodiments, the antibody comprises a heavy chain comprising the amino acid sequence of SEQ ID NO: 226. In certain embodiments, the antibody comprises a heavy chain comprising the amino acid sequence of SEQ ID NO: 169. In certain embodiments, the antibody comprises a heavy chain comprising the amino acid sequence of SEQ ID NO: 227. In certain embodiments, the antibody comprises a heavy chain comprising the amino acid sequence of SEQ ID NO: 170.

In another aspect, the instant disclosure provides an antibody or isolated antibody comprising a light chain variable region comprising an amino acid sequence selected from the group consisting of SEQ ID NOs: 73-77 and 221. In certain embodiments, the light chain variable region comprises the amino acid sequence of SEQ ID NO: 221. In certain embodiments, the light chain variable region comprises the amino acid sequence of SEQ ID NO: 73. In certain embodiments, the antibody comprises a light chain comprising an amino acid sequence selected from the group consisting of SEQ ID NOs: 187-191, and 228. In certain embodiments, the antibody comprises a light chain comprising the amino acid sequence of SEQ ID NO: 228. In certain embodiments, the antibody comprises a light chain comprising the amino acid sequence of SEQ ID NO: 187.

In another aspect, the instant disclosure provides an antibody or isolated antibody that specifically binds to human LAG-3, the antibody comprising a light chain variable region comprising an amino acid sequence selected from the group consisting of SEQ ID NOs: 73-77 and 221. In certain embodiments, the light chain variable region comprises the amino acid sequence of SEQ ID NO: 221. In certain embodiments, the light chain variable region comprises the amino acid sequence of SEQ ID NO: 73. In certain embodiments, the antibody comprises a light chain comprising an amino acid sequence selected from the group consisting of SEQ ID NOs: 187-191, and 228. In certain embodiments, the antibody comprises a light chain comprising the amino acid sequence of SEQ ID NO: 228. In certain embodiments, the antibody comprises a light chain comprising the amino acid sequence of SEQ ID NO: 187.

In another aspect, the instant disclosure provides an antibody or isolated antibody comprising a heavy chain variable region and a light chain variable region, wherein the heavy chain variable region and the light chain variable region, respectively, comprise the amino acid sequences set forth in SEQ ID NOs: 56 and 73; 56 and 74; 56 and 75; 56 and 76; 56 and 77; 57 and 73; 57 and 74; 57 and 75; 57 and 76; 57 and 77; 58 and 73; 58 and 74; 58 and 75; 58 and 76; 58 and 77; 59 and 73; 59 and 74; 59 and 75; 59 and 76; 59 and 77; 60 and 73; 60 and 74; 60 and 75; 60 and 76; 60 and 77; 61 and 77; 62 and 77; 63 and 73; 64 and 73; 65 and 73; 220 and 73; 65 and 221; 220 and 221; 66 and 73; 67 and 73; 68 and 73; 69 and 73; 70 and 73; 71 and 73; or 72 and 73. In certain embodiments, the heavy chain variable region and the light chain variable region, respectively, comprise the amino acid sequences set forth in SEQ ID NOs: 65 and 73. In certain embodiments, the heavy chain variable region and the light chain variable region, respectively, comprise the amino acid sequences set forth in SEQ ID NOs: 220 and 73; 65 and 221; or 220 and 221.

In another aspect, the instant disclosure provides an antibody or isolated antibody comprising a heavy chain variable region and a light chain variable region, wherein the amino acid sequences of the heavy chain variable region and the light chain variable region, respectively, consist of the amino acid sequences set forth in SEQ ID NOs: 56 and 73; 56 and 74; 56 and 75; 56 and 76; 56 and 77; 57 and 73; 57 and 74; 57 and 75; 57 and 76; 57 and 77; 58 and 73; 58 and 74; 58 and 75; 58 and 76; 58 and 77; 59 and 73; 59 and 74; 59 and 75; 59 and 76; 59 and 77; 60 and 73; 60 and 74; 60 and 75; 60 and 76; 60 and 77; 61 and 77; 62 and 77; 63 and 73; 64 and 73; 65 and 73; 220 and 73; 65 and 221; 220 and 221; 66 and 73; 67 and 73; 68 and 73; 69 and 73; 70 and 73; 71 and 73; or 72 and 73. In certain embodiments, the amino acid sequences of the heavy chain variable region and the light chain variable region, respectively, consist of the amino acid sequences set forth in SEQ ID NOs: 65 and 73. In certain embodiments, the amino acid sequences of the heavy chain variable region and the light chain variable region, respectively, consist of the amino acid sequences set forth in SEQ ID NOs: 220 and 73; 65 and 221; or 220 and 221.

In another aspect, the instant disclosure provides an antibody or isolated antibody that specifically binds to human LAG-3, the antibody comprising a heavy chain variable region and a light chain variable region, wherein the heavy chain variable region and the light chain variable region, respectively, comprise the amino acid sequences set forth in SEQ ID NOs: 56 and 73; 56 and 74; 56 and 75; 56 and 76; 56 and 77; 57 and 73; 57 and 74; 57 and 75; 57 and 76; 57 and 77; 58 and 73; 58 and 74; 58 and 75; 58 and 76; 58 and 77; 59 and 73; 59 and 74; 59 and 75; 59 and 76; 59 and 77; 60 and 73; 60 and 74; 60 and 75; 60 and 76; 60 and 77; 61 and 77; 62 and 77; 63 and 73; 64 and 73; 65 and 73; 220 and 73; 65 and 221; 220 and 221; 66 and 73; 67 and 73; 68 and 73; 69 and 73; 70 and 73; 71 and 73; or 72 and 73. In certain embodiments, the heavy chain variable region and the light chain variable region, respectively, comprise the amino acid sequences set forth in SEQ ID NOs: 65 and 73. In certain embodiments, the heavy chain variable region and the light chain variable region, respectively, comprise the amino acid sequences set forth in SEQ ID NOs: 220 and 73; 65 and 221; or 220 and 221.

In another aspect, the instant disclosure provides an antibody or isolated antibody that specifically binds to human LAG-3, the antibody comprising a heavy chain variable region and a light chain variable region, wherein the amino acid sequences of the heavy chain variable region and the light chain variable region, respectively, consist of the amino acid sequences set forth in SEQ ID NOs: 56 and 73; 56 and 74; 56 and 75; 56 and 76; 56 and 77; 57 and 73; 57 and 74; 57 and 75; 57 and 76; 57 and 77; 58 and 73; 58 and 74; 58 and 75; 58 and 76; 58 and 77; 59 and 73; 59 and 74; 59 and 75; 59 and 76; 59 and 77; 60 and 73; 60 and 74; 60 and 75; 60 and 76; 60 and 77; 61 and 77; 62 and 77; 63 and 73; 64 and 73; 65 and 73; 220 and 73; 65 and 221; 220 and 221; 66 and 73; 67 and 73; 68 and 73; 69 and 73; 70 and 73; 71 and 73; or 72 and 73. In certain embodiments, the amino acid sequences of the heavy chain variable region and the light chain variable region, respectively, consist of the amino acid sequences set forth in SEQ ID NOs: 65 and 73. In certain embodiments, the amino acid sequences of the heavy chain variable region and the light chain variable region, respectively, consist of the amino acid sequences set forth in SEQ ID NOs: 220 and 73; 65 and 221; or 220 and 221.

In certain embodiments of any one of the foregoing aspects where applicable, the X in SEQ ID NO: 220 is Q. In certain embodiments of any one of the foregoing aspects where applicable, the X in SEQ ID NO: 220 is pyroglutamate. In certain embodiments of any one of the foregoing aspects where applicable, the X in SEQ ID NO: 221 is E. In certain embodiments of any one of the foregoing aspects where applicable, the X in SEQ ID NO: 221 is pyroglutamate. In certain embodiments of any one of the foregoing aspects where applicable, the X in SEQ ID NO: 220 is Q, and the X in SEQ ID NO: 221 is E. In certain embodiments of any one of the foregoing aspects where applicable, the X in SEQ ID NO: 220 is Q, and the X in SEQ ID NO: 221 is pyroglutamate. In certain embodiments of any one of the foregoing aspects where applicable, the X in SEQ ID NO: 220 is pyroglutamate, and the X in SEQ ID NO: 221 is E. In certain embodiments of any one of the foregoing aspects where applicable, the X in SEQ ID NO: 220 is pyroglutamate, and the X in SEQ ID NO: 221 is pyroglutamate.

In another aspect, the instant disclosure provides an antibody or isolated antibody comprising a heavy chain comprising the amino acid sequence of SEQ ID NO: 168 or 225, and a light chain comprising the amino acid sequence of SEQ ID NO: 187 or 228.

In another aspect, the instant disclosure provides an antibody or isolated antibody comprising a heavy chain comprising the amino acid sequence of SEQ ID NO: 168, and a light chain comprising the amino acid sequence of SEQ ID NO: 187.

In another aspect, the instant disclosure provides an antibody or isolated antibody that specifically binds to human LAG-3, the antibody comprising a heavy chain comprising the amino acid sequence of SEQ ID NO: 168 or 225, and a light chain comprising the amino acid sequence of SEQ ID NO: 187 or 228.

In another aspect, the instant disclosure provides an antibody or isolated antibody that specifically binds to human LAG-3, the antibody comprising a heavy chain comprising the amino acid sequence of SEQ ID NO: 168, and a light chain comprising the amino acid sequence of SEQ ID NO: 187.

In another aspect, the instant disclosure provides an antibody or isolated antibody comprising a heavy chain comprising the amino acid sequence of SEQ ID NO: 169 or 226, and a light chain comprising the amino acid sequence of SEQ ID NO: 187 or 228.

In another aspect, the instant disclosure provides an antibody or isolated antibody comprising a heavy chain comprising the amino acid sequence of SEQ ID NO: 169, and a light chain comprising the amino acid sequence of SEQ ID NO: 187.

In another aspect, the instant disclosure provides an antibody or isolated antibody that specifically binds to human LAG-3, the antibody comprising a heavy chain comprising the amino acid sequence of SEQ ID NO: 169 or 226, and a light chain comprising the amino acid sequence of SEQ ID NO: 187 or 228.

In another aspect, the instant disclosure provides an antibody or isolated antibody that specifically binds to human LAG-3, the antibody comprising a heavy chain comprising the amino acid sequence of SEQ ID NO: 169, and a light chain comprising the amino acid sequence of SEQ ID NO: 187.

In another aspect, the instant disclosure provides an antibody or isolated antibody comprising a heavy chain comprising the amino acid sequence of SEQ ID NO: 170 or 227, and a light chain comprising the amino acid sequence of SEQ ID NO: 187 or 228.

In another aspect, the instant disclosure provides an antibody or isolated antibody comprising a heavy chain comprising the amino acid sequence of SEQ ID NO: 170, and a light chain comprising the amino acid sequence of SEQ ID NO: 187.

In another aspect, the instant disclosure provides an antibody or isolated antibody that specifically binds to human LAG-3, the antibody comprising a heavy chain comprising the amino acid sequence of SEQ ID NO: 170 or 227, and a light chain comprising the amino acid sequence of SEQ ID NO: 187 or 228.

In another aspect, the instant disclosure provides an antibody or isolated antibody that specifically binds to human LAG-3, the antibody comprising a heavy chain comprising the amino acid sequence of SEQ ID NO: 170, and a light chain comprising the amino acid sequence of SEQ ID NO: 187.

In another aspect, the instant disclosure provides an antibody or isolated antibody comprising a heavy chain and a light chain, wherein the amino acid sequence of the heavy chain consists of the amino acid sequence set forth in SEQ ID NO: 168 or 225, and the amino acid sequence of the light chain consists of the amino acid sequence set forth in SEQ ID NO: 187 or 228.

In another aspect, the instant disclosure provides an antibody or isolated antibody comprising a heavy chain and a light chain, wherein the amino acid sequences of the heavy chain and the light chain, respectively, consist of the amino acid sequences set forth in SEQ ID NOs: 168 and 187.

In another aspect, the instant disclosure provides an antibody or isolated antibody that specifically binds to human LAG-3, the antibody comprising a heavy chain and a light chain, wherein the amino acid sequence of the heavy chain consists of the amino acid sequence set forth in SEQ ID NO: 168 or 225, and the amino acid sequence of the light chain consists of the amino acid sequence set forth in SEQ ID NO: 187 or 228.

In another aspect, the instant disclosure provides an antibody or isolated antibody that specifically binds to human LAG-3, the antibody comprising a heavy chain and a light chain, wherein the amino acid sequences of the heavy chain and the light chain, respectively, consist of the amino acid sequences set forth in SEQ ID NOs: 168 and 187.

In another aspect, the instant disclosure provides an antibody or isolated antibody comprising a heavy chain and a light chain, wherein the amino acid sequence of the heavy chain consists of the amino acid sequence set forth in SEQ ID NO: 169 or 226, and the amino acid sequence of the light chain consists of the amino acid sequence set forth in SEQ ID NO: 187 or 228.

In another aspect, the instant disclosure provides an antibody or isolated antibody comprising a heavy chain and a light chain, wherein the amino acid sequences of the heavy chain and the light chain, respectively, consist of the amino acid sequences set forth in SEQ ID NOs: 169 and 187.

In another aspect, the instant disclosure provides an antibody or isolated antibody that specifically binds to human LAG-3, the antibody comprising a heavy chain and a light chain, wherein the amino acid sequence of the heavy chain consists of the amino acid sequence set forth in SEQ ID NO: 169 or 226, and the amino acid sequence of the light chain consists of the amino acid sequence set forth in SEQ ID NO: 187 or 228.

In another aspect, the instant disclosure provides an antibody or isolated antibody that specifically binds to human LAG-3, the antibody comprising a heavy chain and a light chain, wherein the amino acid sequences of the heavy chain and the light chain, respectively, consist of the amino acid sequences set forth in SEQ ID NOs: 169 and 187.

In another aspect, the instant disclosure provides an antibody or isolated antibody comprising a heavy chain and a light chain, wherein the amino acid sequence of the heavy chain consists of the amino acid sequence set forth in SEQ ID NO: 170 or 227, and the amino acid sequence of the light chain consists of the amino acid sequence set forth in SEQ ID NO: 187 or 228.

In another aspect, the instant disclosure provides an antibody or isolated antibody comprising a heavy chain and a light chain, wherein the amino acid sequences of the heavy chain and the light chain, respectively, consist of the amino acid sequences set forth in SEQ ID NOs: 170 and 187.

In another aspect, the instant disclosure provides an antibody or isolated antibody that specifically binds to human LAG-3, the antibody comprising a heavy chain and a light chain, wherein the amino acid sequence of the heavy chain consists of the amino acid sequence set forth in SEQ ID NO: 170 or 227, and the amino acid sequence of the light chain consists of the amino acid sequence set forth in SEQ ID NO: 187 or 228.

In another aspect, the instant disclosure provides an antibody or isolated antibody that specifically binds to human LAG-3, the antibody comprising a heavy chain and a light chain, wherein the amino acid sequences of the heavy chain and the light chain, respectively, consist of the amino acid sequences set forth in SEQ ID NOs: 170 and 187.

In certain embodiments of any one of the foregoing aspects where applicable, the X in SEQ ID NO: 225 is Q. In certain embodiments of any one of the foregoing aspects where applicable, the X in SEQ ID NO: 225 is pyroglutamate. In certain embodiments of any one of the foregoing aspects where applicable, the X in SEQ ID NO: 228 is E. In certain embodiments of any one of the foregoing aspects where applicable, the X in SEQ ID NO: 228 is pyroglutamate. In certain embodiments of any one of the foregoing aspects where applicable, the X in SEQ ID NO: 225 is Q, and the X in SEQ ID NO: 228 is E. In certain embodiments of any one of the foregoing aspects where applicable, the X in SEQ ID NO: 225 is Q, and the X in SEQ ID NO: 228 is pyroglutamate. In certain embodiments of any one of the foregoing aspects where applicable, the X in SEQ ID NO: 225 is pyroglutamate, and the X in SEQ ID NO: 228 is E. In certain embodiments of any one of the foregoing aspects where applicable, the X in SEQ ID NO: 225 is pyroglutamate, and the X in SEQ ID NO: 228 is pyroglutamate.

In certain embodiments of any one of the foregoing aspects where applicable, the X in SEQ ID NO: 226 is Q. In certain embodiments of any one of the foregoing aspects where applicable, the X in SEQ ID NO: 226 is pyroglutamate. In certain embodiments of any one of the foregoing aspects where applicable, the X in SEQ ID NO: 228 is E. In certain embodiments of any one of the foregoing aspects where applicable, the X in SEQ ID NO: 228 is pyroglutamate. In certain embodiments of any one of the foregoing aspects where applicable, the X in SEQ ID NO: 226 is Q, and the X in SEQ ID NO: 228 is E. In certain embodiments of any one of the foregoing aspects where applicable, the X in SEQ ID NO: 226 is Q, and the X in SEQ ID NO: 228 is pyroglutamate. In certain embodiments of any one of the foregoing aspects where applicable, the X in SEQ ID NO: 226 is pyroglutamate, and the X in SEQ ID NO: 228 is E. In certain embodiments of any one of the foregoing aspects where applicable, the X in SEQ ID NO: 226 is pyroglutamate, and the X in SEQ ID NO: 228 is pyroglutamate.

In certain embodiments of any one of the foregoing aspects where applicable, the X in SEQ ID NO: 227 is Q. In certain embodiments of any one of the foregoing aspects where applicable, the X in SEQ ID NO: 227 is pyroglutamate. In certain embodiments of any one of the foregoing aspects where applicable, the X in SEQ ID NO: 228 is E. In certain embodiments of any one of the foregoing aspects where applicable, the X in SEQ ID NO: 228 is pyroglutamate. In certain embodiments of any one of the foregoing aspects where applicable, the X in SEQ ID NO: 227 is Q, and the X in SEQ ID NO: 228 is E. In certain embodiments of any one of the foregoing aspects where applicable, the X in SEQ ID NO: 227 is Q, and the X in SEQ ID NO: 228 is pyroglutamate. In certain embodiments of any one of the foregoing aspects where applicable, the X in SEQ ID NO: 227 is pyroglutamate, and the X in SEQ ID NO: 228 is E. In certain embodiments of any one of the foregoing aspects where applicable, the X in SEQ ID NO: 227 is pyroglutamate, and the X in SEQ ID NO: 228 is pyroglutamate.

In certain embodiments, the antibody comprises a heavy chain constant region selected from the group consisting of human IgG$_1$, IgG$_2$, IgG$_3$, IgG$_4$, IgA$_1$, and IgA$_2$. In certain embodiments, the heavy chain constant region is IgG$_1$. In certain embodiments, the amino acid sequence of IgG$_1$ comprises a N297A mutation, numbered according to the EU numbering system. In certain embodiments, the antibody comprises a heavy chain constant region comprising the amino acid sequence of SEQ ID NO: 194. In certain embodiments, the amino acid sequence of IgG$_1$ comprises a N297Q mutation, numbered according to the EU numbering system. In certain embodiments, the IgG$_1$ is afucosylated IgG$_1$. In certain embodiments, the heavy chain constant region is IgG$_4$. In certain embodiments, the amino acid sequence of IgG$_4$ comprises a S228P mutation, numbered according to the EU numbering system. In certain embodiments, the antibody comprises a heavy chain constant region comprising the amino acid sequence of SEQ ID NO: 196.

In certain embodiments, the antibody comprises a light chain constant region selected from the group consisting of human IgGκ and IgGλ. In certain embodiments, the light chain constant region is IgGκ. In certain embodiments, the antibody comprises a light chain constant region comprising the amino acid sequence of SEQ ID NO: 198. In certain embodiments, the antibody comprises a light chain constant region comprising the amino acid sequence of SEQ ID NO: 219. In certain embodiments, the light chain constant region is IgGλ.

In another aspect, the instant disclosure provides an antibody or isolated antibody that cross-competes for binding to human LAG-3 with an antibody as disclosed herein. In certain embodiments, the instant disclosure provides an antibody or isolated antibody that cross-competes for binding to human LAG-3 with an antibody comprising the heavy and light chain variable region amino acid sequences set forth in SEQ ID NOs: 15 and 16, respectively. In certain embodiments, the instant disclosure provides an antibody or isolated antibody that cross-competes for binding to human LAG-3 with an antibody comprising the heavy and light chain variable region amino acid sequences set forth in SEQ ID NOs: 65 and 73; 220 and 73; 65 and 221; or 220 and 221, respectively.

In another aspect, the instant disclosure provides an antibody or isolated antibody that binds to the same epitope of human LAG-3 as an antibody disclosed herein. In certain embodiments, the instant disclosure provides an antibody or isolated antibody that binds to the same epitope of human LAG-3 as an antibody comprising the heavy and light chain variable region amino acid sequences set forth in SEQ ID NOs: 15 and 16, respectively. In certain embodiments, the instant disclosure provides an antibody or isolated antibody that binds to the same epitope of human LAG-3 as an antibody comprising the heavy and light chain variable region amino acid sequences set forth in SEQ ID NOs: 65 and 73; 220 and 73; 65 and 221; or 220 and 221, respectively.

In another aspect, the instant disclosure provides an antibody or isolated antibody that binds, e.g., specifically binds, to an epitope of human LAG-3. In certain embodiments, the antibody binds to an epitope located within a region of human LAG-3 consisting of the amino acid sequence of SEQ ID NO: 216. In certain embodiments, the antibody binds to an epitope located within a region of human LAG-3 consisting of the amino acid sequence of SEQ ID NO: 215. In certain embodiments, the antibody binds to an epitope located within a region of human LAG-3 consisting of the amino acid sequence of SEQ ID NO: 214. In certain embodiments, the antibody binds to an epitope located within a region of human LAG-3 consisting of the amino acid sequence of SEQ ID NO: 213. In certain embodiments, the antibody binds to an epitope located within a region of human LAG-3 consisting of the amino acid sequence of SEQ ID NO: 212. In certain embodiments, the antibody binds to an epitope located within a region of human LAG-3 consisting of the amino acid sequence of SEQ ID NO: 211.

In another aspect, the instant disclosure provides an antibody or isolated antibody that specifically binds to the same epitope of human LAG-3 as any antibody of the present invention. In certain embodiments, the antibody binds to an epitope located within a region of human LAG-3 consisting of the amino acid sequence of SEQ ID NO: 216. In certain embodiments, the antibody binds to an epitope located within a region of human LAG-3 consisting of the amino acid sequence of SEQ ID NO: 215. In certain embodiments, the antibody binds to an epitope located within a region of human LAG-3 consisting of the amino acid sequence of SEQ ID NO: 214. In certain embodiments, the antibody binds to an epitope located within a region of human LAG-3 consisting of the amino acid sequence of SEQ ID NO: 213. In certain embodiments, the antibody binds to an epitope located within a region of human LAG-3 consisting of the amino acid sequence of SEQ ID NO: 212. In certain embodiments, the antibody binds to an epitope located within a region of human LAG-3 consisting of the amino acid sequence of SEQ ID NO: 211.

In another aspect, the instant disclosure provides an antibody that, when bound to a human LAG-3 protein or fragment thereof comprising the amino acid sequence of SEQ ID NO: 217, reduces hydrogen/deuterium exchange in a region consisting of the amino acid sequence set forth in SEQ ID NO: 216 relative to hydrogen/deuterium exchange in the region consisting of the amino acid sequence set forth in SEQ ID NO: 216 in the absence of the antibody, as determined by a hydrogen/deuterium assay. In another aspect, the instant disclosure provides an antibody that, when bound to a human LAG-3 protein or fragment thereof comprising the amino acid sequence of SEQ ID NO: 217, reduces hydrogen/deuterium exchange in a region consisting of the amino acid sequence set forth in SEQ ID NO: 215 relative to hydrogen/deuterium exchange in the region consisting of the amino acid sequence set forth in SEQ ID NO: 215 in the absence of the antibody, as determined by a hydrogen/deuterium assay. In another aspect, the instant disclosure provides an antibody that, when bound to a human LAG-3 protein or fragment thereof comprising the amino acid sequence of SEQ ID NO: 217, reduces hydrogen/deuterium exchange in a region consisting of the amino acid sequence set forth in SEQ ID NO: 214 relative to hydrogen/deuterium exchange in the region consisting of the amino acid sequence set forth in SEQ ID NO: 214 in the absence of the antibody, as determined by a hydrogen/deuterium assay. In another aspect, the instant disclosure provides an antibody that, when bound to a human LAG-3 protein or fragment thereof comprising the amino acid sequence of SEQ ID NO: 217, reduces hydrogen/deuterium exchange in a region consisting of the amino acid sequence set forth in SEQ ID NO: 213 relative to hydrogen/deuterium exchange in the region consisting of the amino acid sequence set forth in SEQ ID NO: 213 in the absence of the antibody, as determined by a hydrogen/deuterium assay. In another aspect, the instant disclosure provides an antibody that, when bound to a human LAG-3 protein or fragment thereof comprising the amino acid sequence of SEQ ID NO: 217, reduces hydrogen/deuterium exchange in a region consisting of the amino acid sequence set forth in SEQ ID NO: 212 relative to hydrogen/deuterium exchange in the region consisting of the amino acid sequence set forth in SEQ ID NO: 212 in the absence of the antibody, as determined by a hydrogen/deuterium assay. In another aspect, the instant disclosure provides an antibody that, when bound to a human LAG-3 protein or fragment thereof comprising the amino acid sequence of SEQ ID NO: 217, reduces hydrogen/deuterium exchange in a region consisting of the amino acid sequence set forth in SEQ ID NO: 211 relative to hydrogen/deuterium exchange in the region consisting of the amino acid sequence set forth in SEQ ID NO: 211 in the absence of the antibody, as determined by a hydrogen/deuterium assay. In some embodiments, the reduction in hydrogen/deuterium exchange is measured using hydrogen-deuterium exchange (HDX), for example as described herein in the examples.

In another aspect, the instant disclosure provides an antibody or isolated antibody that specifically binds to the same epitope of human LAG-3 as any antibody of the present invention. In certain embodiments, the antibody, when bound to a human LAG-3 protein or fragment thereof comprising the amino acid sequence of SEQ ID NO: 217, reduces hydrogen/deuterium exchange in a region consisting of the amino acid sequence set forth in SEQ ID NO: 216 relative to hydrogen/deuterium exchange in the region consisting of the amino acid sequence set forth in SEQ ID NO: 216 in the absence of the antibody, as determined by a hydrogen/deuterium assay. In certain embodiments, the antibody, when bound to a human LAG-3 protein or fragment thereof comprising the amino acid sequence of SEQ ID NO: 217, reduces hydrogen/deuterium exchange in a region consisting of the amino acid sequence set forth in SEQ ID NO: 215 relative to hydrogen/deuterium exchange in the region consisting of the amino acid sequence set forth in SEQ ID NO: 215 in the absence of the antibody, as determined by a hydrogen/deuterium assay. In certain embodiments, the antibody, when bound to a human LAG-3 protein or fragment thereof comprising the amino acid sequence of SEQ ID NO: 217, reduces hydrogen/deuterium exchange in a region consisting of the amino acid sequence set forth in SEQ ID NO: 214 relative to hydrogen/deuterium exchange in the region consisting of the amino acid sequence set forth in SEQ ID NO: 214 in the absence of the antibody, as determined by a hydrogen/deuterium assay. In certain embodiments, the antibody, when bound to a human LAG-3 protein or fragment thereof comprising the amino acid sequence of SEQ ID NO: 217, reduces hydrogen/deuterium exchange in a region consisting of the amino acid sequence set forth in SEQ ID NO: 213 relative to hydrogen/deuterium exchange in the region consisting of the amino acid sequence set forth in SEQ ID NO: 213 in the absence of the antibody, as determined by a hydrogen/deuterium assay. In certain embodiments, the antibody, when bound to a human LAG-3 protein or fragment thereof comprising the amino acid sequence of SEQ ID NO: 217, reduces hydrogen/deuterium exchange in a region consisting of the amino acid sequence set forth in SEQ ID NO: 212 relative to hydrogen/deuterium exchange in the region consisting of the amino acid sequence set forth in SEQ ID NO: 212 in the absence of the antibody, as determined by a hydrogen/deuterium assay. In certain embodiments, the antibody, when bound to a human LAG-3 protein or fragment thereof comprising the amino acid sequence of SEQ ID NO: 217, reduces hydrogen/deuterium exchange in a region consisting of the amino acid sequence set forth in SEQ ID NO: 211 relative to hydrogen/deuterium exchange in the region consisting of the amino acid sequence set forth in SEQ ID NO: 211 in the absence of the antibody, as determined by a hydrogen/deuterium assay. In some embodiments, the reduction in hydrogen/deuterium exchange is measured using hydrogen-deuterium exchange (HDX), for example as described herein in the examples.

In certain embodiments, the antibody is a humanized antibody. In certain embodiments, the antibody is a murine antibody. In certain embodiments, the antibody is a chimeric antibody. In certain embodiments, the antibody is antagonistic to human LAG-3. In certain embodiments, the antibody deactivates, reduces, or inhibits an activity of human LAG-3. In certain embodiments, the antibody inhibits binding of human LAG-3 to MHC class II. In certain embodiments, the antibody induces IL-2 production by peripheral blood mononuclear cells (PBMCs) stimulated with staphylococcal enterotoxin A (SEA). In certain embodiments, the antibody induces TNFα production by tumor infiltrating lymphocytes (TILs) stimulated with anti-CD3 and anti-CD28 antibodies.

In another aspect, the instant disclosure provides an antibody or isolated antibody as disclosed herein conjugated to a cytotoxic agent.

In another aspect, the instant disclosure provides an antibody or isolated antibody as disclosed herein conjugated to a cytostatic agent.

In another aspect, the instant disclosure provides an antibody or isolated antibody as disclosed herein conjugated to a toxin.

In another aspect, the instant disclosure provides an antibody or isolated antibody as disclosed herein conjugated to a radionuclide.

In another aspect, the instant disclosure provides an antibody or isolated antibody as disclosed herein conjugated to a detectable label.

In another aspect, the instant disclosure provides an antibody or isolated antibody as disclosed herein, wherein the N-terminal amino acid residue of the heavy chain variable region is pyroglutamate (e.g., as a result of post-translational cyclization of the free amino group of the N-terminal E or Q residue of the heavy chain variable region). In another aspect, the instant disclosure provides an antibody or isolated antibody as disclosed herein, wherein the N-terminal amino acid residue of the heavy chain is pyroglutamate (e.g., as a result of post-translational cyclization of the free amino group of the N-terminal E or Q residue of the heavy chain).

In another aspect, the instant disclosure provides an antibody or isolated antibody as disclosed herein, wherein the N-terminal amino acid residue of the light chain variable region is pyroglutamate (e.g., as a result of post-translational cyclization of the free amino group of the N-terminal E or Q residue the light chain variable region). In another aspect, the instant disclosure provides an antibody or isolated antibody as disclosed herein, wherein the N-terminal amino acid residue of the light chain is pyroglutamate (e.g., as a result of post-translational cyclization of the free amino group of the N-terminal E or Q residue the light chain).

In another aspect, the instant disclosure provides an antibody or isolated antibody as disclosed herein, in which the heavy chain is aglycosylated.

In another aspect, the instant disclosure provides a pharmaceutical composition comprising an antibody as disclosed herein and a pharmaceutically acceptable carrier or excipient.

In another aspect, the instant disclosure provides a polynucleotide isolated polynucleotide encoding a heavy and/or light chain of an antibody as disclosed herein. In another aspect, the instant disclosure provides a vector comprising the polynucleotide. In another aspect, the instant disclosure provides a recombinant host cell comprising the polynucleotide. In another aspect, the instant disclosure provides a recombinant host cell comprising the vector. In another aspect, the instant disclosure provides a method of producing an antibody as disclosed herein, the method comprising culturing the host cell so that the polynucleotide is expressed and the antibody is produced. In one embodiment, the method is an in vitro method.

In one embodiment, the present invention relates to an antibody of the invention, or a pharmaceutical composition of the invention, or a polynucleotide of the invention, or a vector of the invention, or a recombinant host cell of the invention for use as a medicament.

In one embodiment, the present invention relates to an antibody of the invention, or a pharmaceutical composition of the invention, or a polynucleotide of the invention, or a vector of the invention, or a recombinant host cell of the invention for use as a diagnostic.

In another aspect, the instant disclosure provides a method of increasing T cell activation in response to an antigen in a subject, the method comprising administering to the subject an effective amount of an antibody or pharmaceutical composition as disclosed herein. In another aspect, the instant disclosure provides a method of treating cancer in a subject, the method comprising administering to the subject an effective amount of an antibody or pharmaceutical composition as disclosed herein. In certain embodiments of the foregoing methods, the antibody or pharmaceutical composition is administered subcutaneously. In certain embodiments of the foregoing methods, the antibody or pharmaceutical composition is administered intravenously. In certain embodiments of the foregoing methods, the antibody or pharmaceutical composition is administered intratumorally. In certain embodiments of the foregoing methods, the antibody or pharmaceutical composition is delivered to a tumor draining lymph node. In certain embodiments of the foregoing methods, the antibody or pharmaceutical composition is administered intra-arterially. In certain embodiments of the foregoing methods, the antibody or pharmaceutical composition is administered intranasally.

In one aspect, the present invention relates to an antibody, polynucleotide, vector, recombinant host cell, and/or pharmaceutical composition of the present invention for use in a method for increasing T cell activation in response to an antigen.

In one aspect, the present invention relates to an antibody, polynucleotide, vector, recombinant host cell, and/or pharmaceutical composition of the present invention for use in a method for increasing T cell activation in response to an antigen in a subject.

In one aspect, the present invention relates to an antibody, polynucleotide, vector, recombinant host cell, and/or pharmaceutical composition of the present invention for use in a method for increasing T cell activation in response to an antigen in a subject comprising administering to the subject an effective amount of an antibody, polynucleotide, vector, recombinant host cell, and/or pharmaceutical composition of the invention.

In one aspect, the present invention relates to an antibody, polynucleotide, vector, recombinant host cell, and/or pharmaceutical composition of the present invention for use in a method for the treatment of cancer.

In one aspect, the present invention relates to an antibody, polynucleotide, vector, recombinant host cell, and/or pharmaceutical composition of the present invention for use in a method for the treatment of cancer in a subject.

In one aspect, the present invention relates to an antibody, polynucleotide, vector, recombinant host cell, and/or pharmaceutical composition of the present invention for use in a method for the treatment of cancer in a subject comprising administering to the subject an effective amount of an antibody, polynucleotide, vector, recombinant host cell, and/or pharmaceutical composition of the invention.

In one embodiment of an antibody, polynucleotide, vector, recombinant host cell, and/or pharmaceutical composition for use of the present invention, the antibody, polynucleotide, vector, recombinant host cell, and/or pharmaceutical composition is administered subcutaneously or intravenously. In one embodiment of an antibody, polynucleotide, vector, recombinant host cell, and/or pharmaceutical composition for use of the present invention, the antibody, polynucleotide, vector, recombinant host cell, and/or pharmaceutical composition is administered intratumorally or intra-arterially. In one embodiment of an antibody, polynucleotide, vector, recombinant host cell, and/or pharmaceutical composition for use of the present invention, the antibody, polynucleotide, vector, recombinant host cell, and/or pharmaceutical composition is administered intranasally.

In certain embodiments, the foregoing methods further comprise administering an additional therapeutic agent to the subject. Therefore, in one embodiment of an antibody, polynucleotide, vector, recombinant host cell, and/or pharmaceutical composition for use in a method of the present invention, the method further comprises administering an additional therapeutic agent to the subject.

In one aspect, the present invention relates to (a) an antibody, polynucleotide, vector, recombinant host cell, and/or pharmaceutical composition of the present invention and (b) an additional therapeutic agent for use as a medicament.

In one aspect, the present invention relates to (a) an antibody, polynucleotide, vector, recombinant host cell, and/or pharmaceutical composition of the present invention and (b) an additional therapeutic agent for use in a method for the treatment of cancer.

In one aspect, the present invention relates to a pharmaceutical composition, kit or kit-of-parts comprising (a) an antibody, polynucleotide, vector, recombinant host cell, and/or pharmaceutical composition of the present invention and (b) an additional therapeutic agent.

In certain embodiments, the additional therapeutic agent is a chemotherapeutic. In certain embodiments, the additional therapeutic agent is a radiotherapeutic.

In certain embodiments, the additional therapeutic agent is a checkpoint targeting agent. In certain embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, an agonist anti-OX40 antibody, an antagonist anti-TIGIT antibody, an agonist anti-CD137 antibody, an antagonist anti-VISTA antibody, an antagonist anti-CD73 antibody, and an antagonist anti-CD96 antibody. In certain embodiments, the additional therapeutic agent is an anti-PD-1 antibody. In certain embodiments, the anti-PD-1 antibody is pembrolizumab. In certain embodiments, the anti-PD-1 antibody is nivolumab. In certain embodiments, the additional therapeutic agent is an anti-PD-L1 antibody. In certain embodiments, the additional therapeutic agent is an anti-CTLA-4 antibody.

In certain embodiments, the additional therapeutic agent comprises a small molecule. In certain embodiments, the additional therapeutic agent is a small molecule inhibitor of the PD-1 pathway. In certain embodiments, the additional therapeutic agent is a small molecule inhibitor of PD-1 or PD-L1.

In certain embodiments, the additional therapeutic agent is an inhibitor of indoleamine-2,3-dioxygenase (IDO). In certain embodiments, the inhibitor is selected from the group consisting of epacadostat, BMS-986205 (also known as F001287, see Example 19 of WO2016/073770, which is incorporated by reference herein in its entirety), indoximod, and NLG919. In certain embodiments, the inhibitor is epacadostat. In certain embodiments, the inhibitor is BMS-986205. In certain embodiments, the inhibitor is indoximod. In certain embodiments, the inhibitor is NLG919.

In certain embodiments, the additional therapeutic agent is an inhibitor of ARG, LSD1, CD112, CD112R, or VEGF. In certain embodiments, the additional therapeutic agent is a Stimulator of Interferon Genes (STING) agonist. In certain embodiments, the additional therapeutic agent is a CD80-Fc protein.

In certain embodiments, the additional therapeutic agent is a vaccine. In certain embodiments, the vaccine comprises a heat shock protein peptide complex (HSPPC) comprising a heat shock protein complexed with an antigenic peptide. In certain embodiments, the heat shock protein is hsc70 and is complexed with a tumor-associated antigenic peptide. In certain embodiments, the heat shock protein is gp96 protein and is complexed with a tumor-associated antigenic peptide, wherein the HSPPC is derived from a tumor obtained from a subject. In certain embodiments, the heat shock protein is gp96 protein and is complexed with a tumor-associated antigenic peptide, wherein the HSPPC is derived from a tumor obtained from a subject. In certain embodiments, the additional therapeutic agent comprises a TCR. In certain embodiments, the additional therapeutic agent is a soluble TCR. In certain embodiments, the additional therapeutic agent is a cell expressing a TCR. In certain embodiments, the additional therapeutic agent is a cell expressing a chimeric antigen receptor. In certain embodiments, the additional therapeutic agent is an antibody that specifically binds to a peptide-MHC complex. In certain embodiments, the additional therapeutic agent is an adjuvant. In one aspect, the present invention relates to (a) an antibody, polynucleotide, vector, recombinant host cell, and/or pharmaceutical composition of the present invention and (b) a vaccine for use as a medicament, for example, for use in a method for the treatment of cancer, optionally wherein the vaccine comprises a heat shock protein peptide complex (HSPPC) comprising a heat shock protein complexed with an antigenic peptide. In one aspect, the present invention relates to a pharmaceutical composition, kit or kit-of-parts comprising (a) an antibody, polynucleotide, vector, recombinant host cell, and/or pharmaceutical composition of the present invention and (b) a vaccine, optionally wherein the vaccine comprises a heat shock protein peptide complex (HSPPC) comprising a heat shock protein complexed with an antigenic peptide.

5. BRIEF DESCRIPTION OF THE DRAWINGS

FIGS. 1A, 1B, and 1C are a set of histograms showing the binding of anti-LAG-3 Fabs to wild type Jurkat cells or Jurkat cells engineered to express human LAG-3, as measured by flow cytometry. The anti-LAG-3 Fabs tested in this study include P01A12, P01C09, P05E01, P13A04, P13A06, P13B01, P13B02, P13B03, P13B11, P13C06, P13C08, P13C10, P13D04, P13D05, P13E02, P13F01, P13F02, P13F06, P13F09, P13G01, P13G04, P13G05, P13H05, P14A04, P14B07, P14C04, P14F01, P14F06, P14G01, P14G03, P15B06, P15C02, P15E06, P15F06, P15G05, P16D04, and P16H05.

FIGS. 2A and 2B are graphs showing results from assays testing the ability of anti-LAG-3 Fabs or a negative control Fab not specific for LAG-3 to block the binding of cross-linked recombinant LAG-3-6His to MHC class II expressing Raji cells. FIG. 2A is a bar graph showing the percentage of blocking mediated by the negative control Fab or anti-LAG-3 Fab P13B02, P13C08, P13C10, P13E02, P13F02, P01A12, P13B01, P05E01, or P01C09. FIG. 2B is a line graph showing the percentage of LAG-3 binding in the presence of a dose titration of anti-LAG-3 Fab P01A12, P13A06, P13B01, P13B02, P13C06, P13C08, P13C10, P13E02, or P14C04, or the negative control Fab.

Figure 5A:
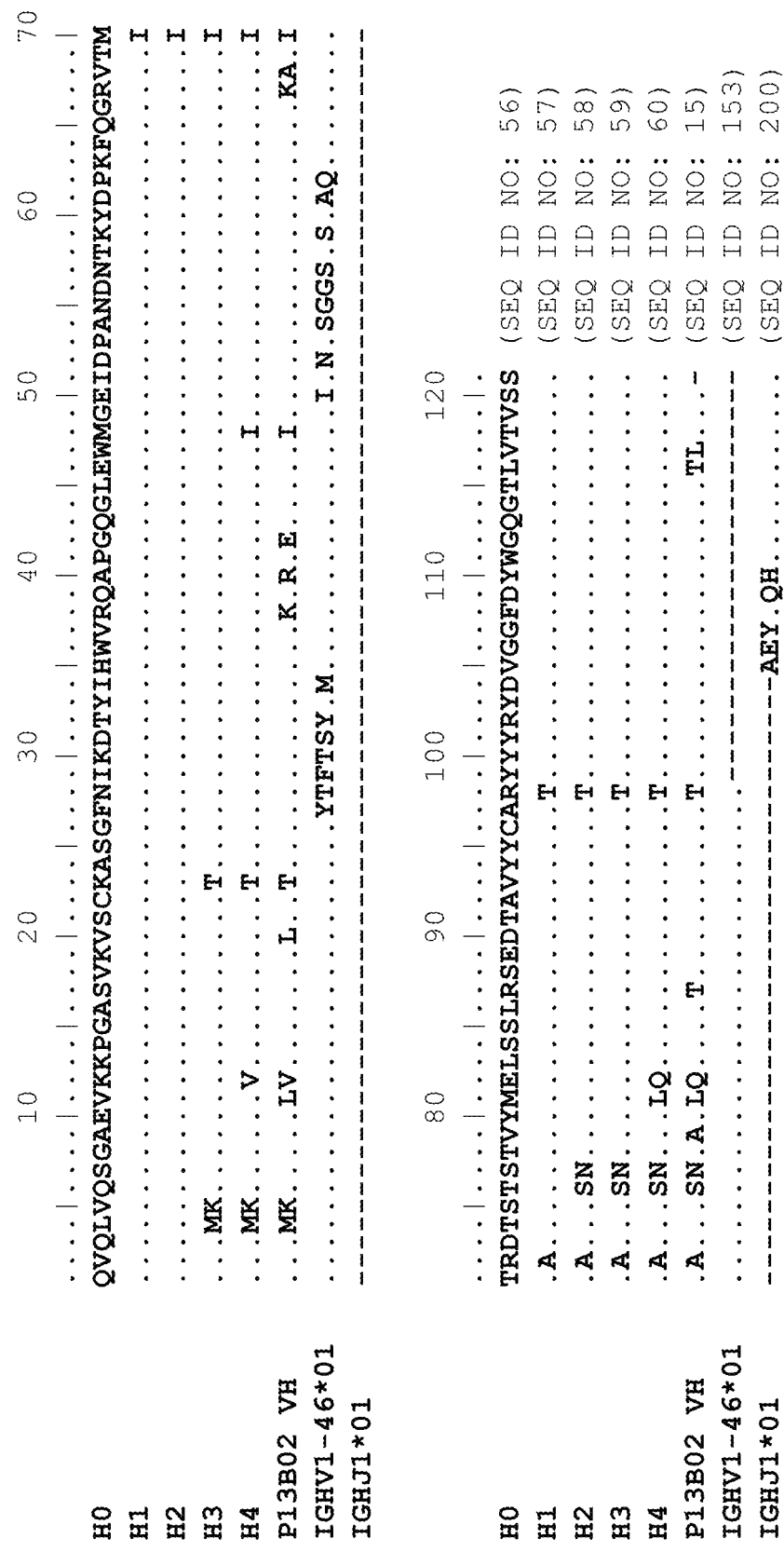

FIGS. 5A and 5B are sequence alignments of humanized variable regions with corresponding murine sequences and human germline sequences. FIG. 5A is a sequence alignment comparing the humanized heavy chain variable regions H0-H4 (SEQ ID NOs: 56-60, respectively), the murine antibody P13B02 heavy chain variable region (SEQ ID NO: 15), and the human germline sequences IGHV1-46*01 (SEQ ID NO: 153) and IGHJ1*01 (SEQ ID NO: 200). FIG. 5B is a sequence alignment comparing the humanized light chain variable regions L0-L4 (SEQ ID NOs: 73-77, respectively), the murine antibody P13B02 light chain variable region (SEQ ID NO: 16), and the human germline sequences IGKV3-20*01 (SEQ ID NO: 160) and IGKJ1*01 (SEQ ID NO: 201). Dots represent residues identical to corresponding residues in H0 (FIG. 5A) or L0 (FIG. 5B). Dashes represent lack of amino acid residues compared with H0 (FIG. 5A) or L0 (FIG. 5B).

Figure 6B:
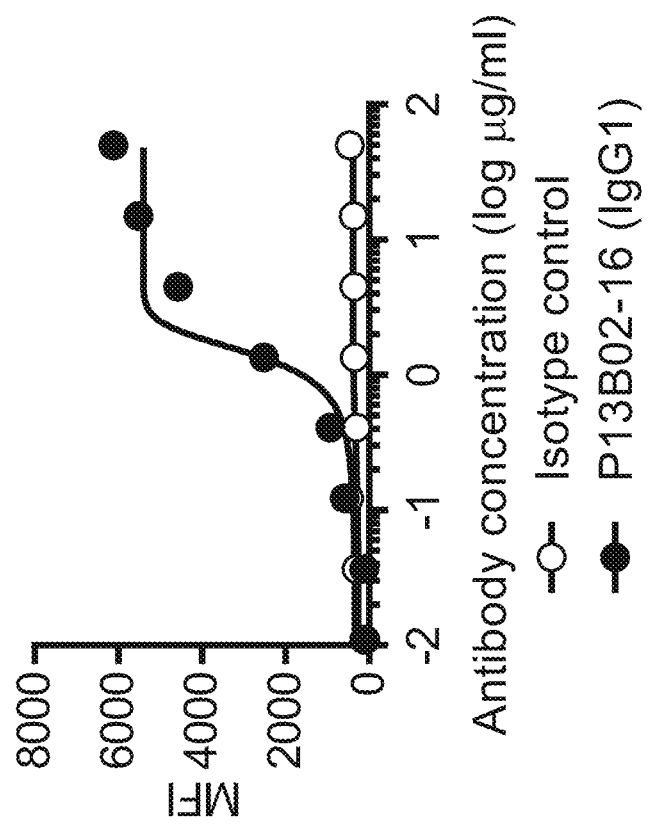

FIGS. 6A and 6B are graphs showing the binding of anti-LAG-3 antibodies to human T cells activated by *Staphylococcus* Enterotoxin A (SEA), as measured by flow cytometry. FIG. 6A is a set of histograms testing the chimeric antibody P13B02 (IgG$_1$), and the humanized antibodies P13B02-06 (IgG$_1$), P13B02-07 (IgG$_1$), P13B02-16 (IgG$_1$), P13B02-25 (IgG$_1$), P13B02-26 (IgG$_1$), P13B02-27 (IgG$_1$), P13B02-30 (IgG$_1$ Glm17 N297A), and P13B02-30 (IgG$_1$). FIG. 6B is a graph showing the binding of the anti-LAG-3 antibody P13B02-16 (IgG$_1$) or an isotype control antibody to activated primary human CD4+ T cells. The median fluorescence intensity (MFI) values are plotted against antibody concentrations.

Figure 7A:
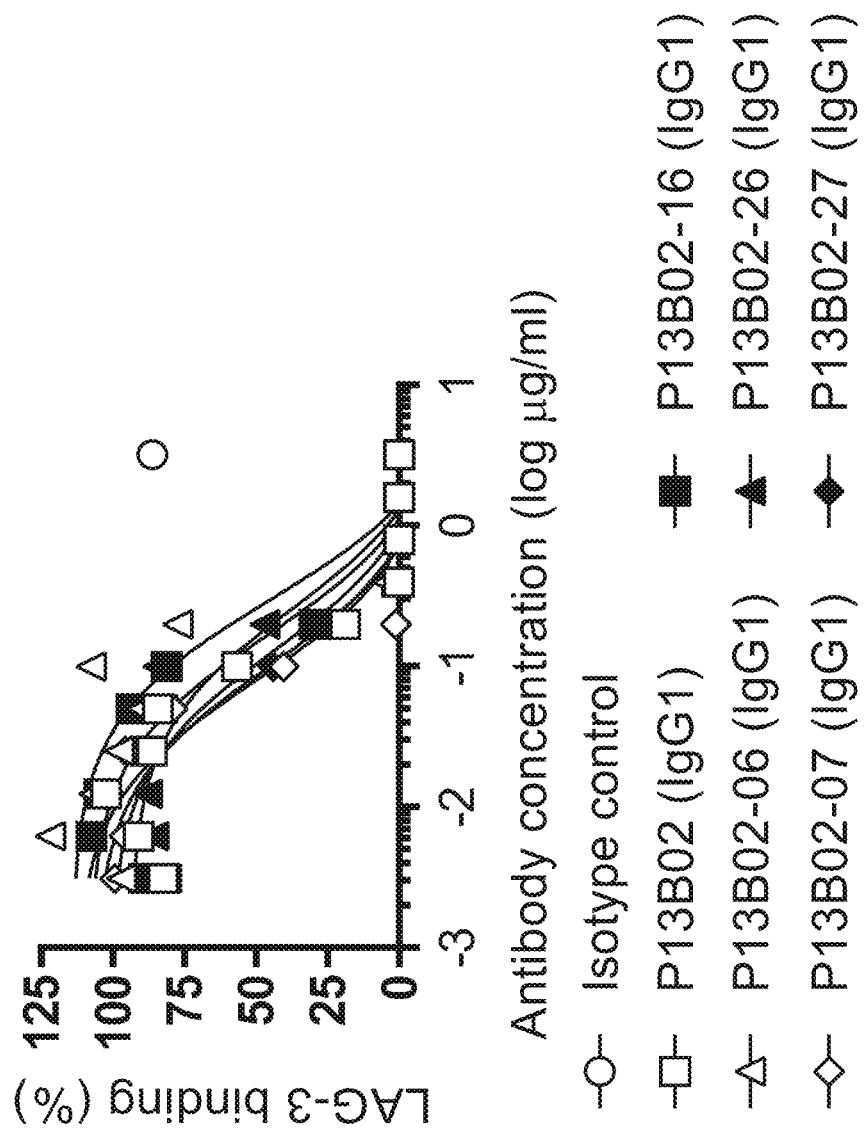
Figure 7B:
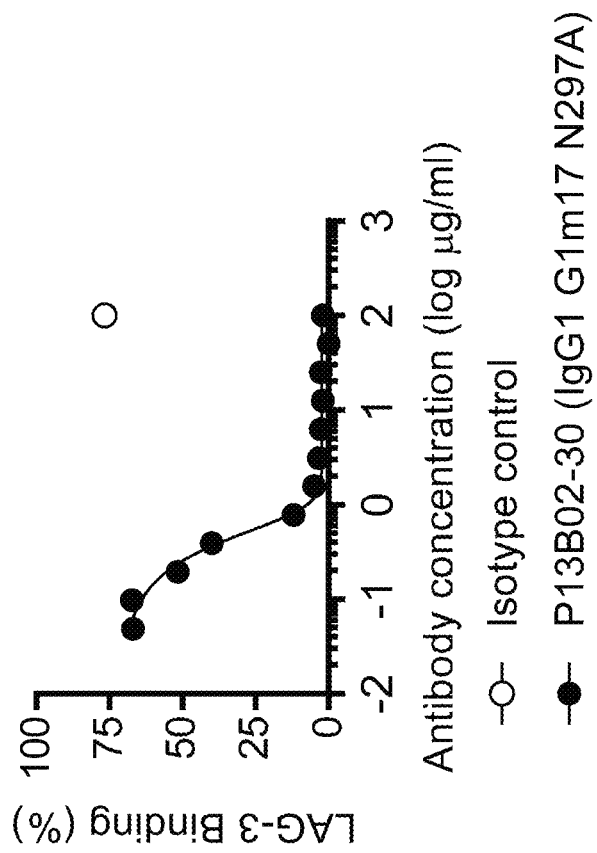

FIGS. 7A and 7B are line graphs similar to the one shown in FIG. 2B, in which the percentage of LAG-3 binding is plotted against different doses of an isotype control antibody, the chimeric antibody P13B02 (IgG$_1$), the humanized antibody P13B02-06 (IgG$_1$), P13B02-07 (IgG$_1$), P13B02-16 (IgG$_1$), P13B02-26 (IgG$_1$), or P13B02-27 (IgG$_1$) (FIG. 7A) or the humanized antibody P13B02-30 (IgG$_1$ Glm17 N297A) (FIG. 7B).

Figure 8A:
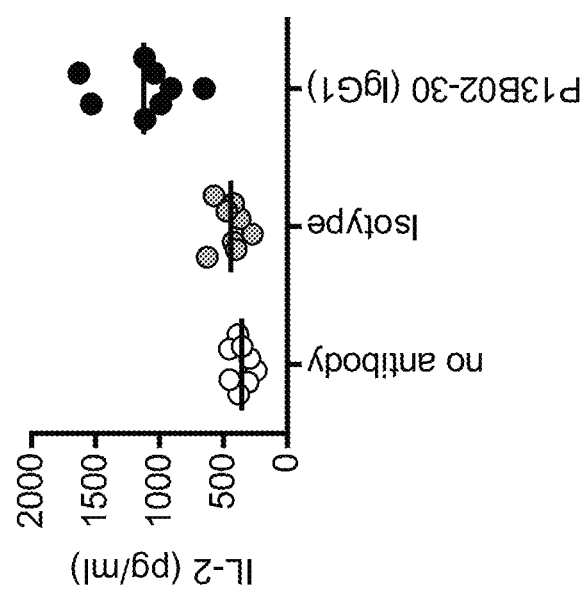
Figure 8B:
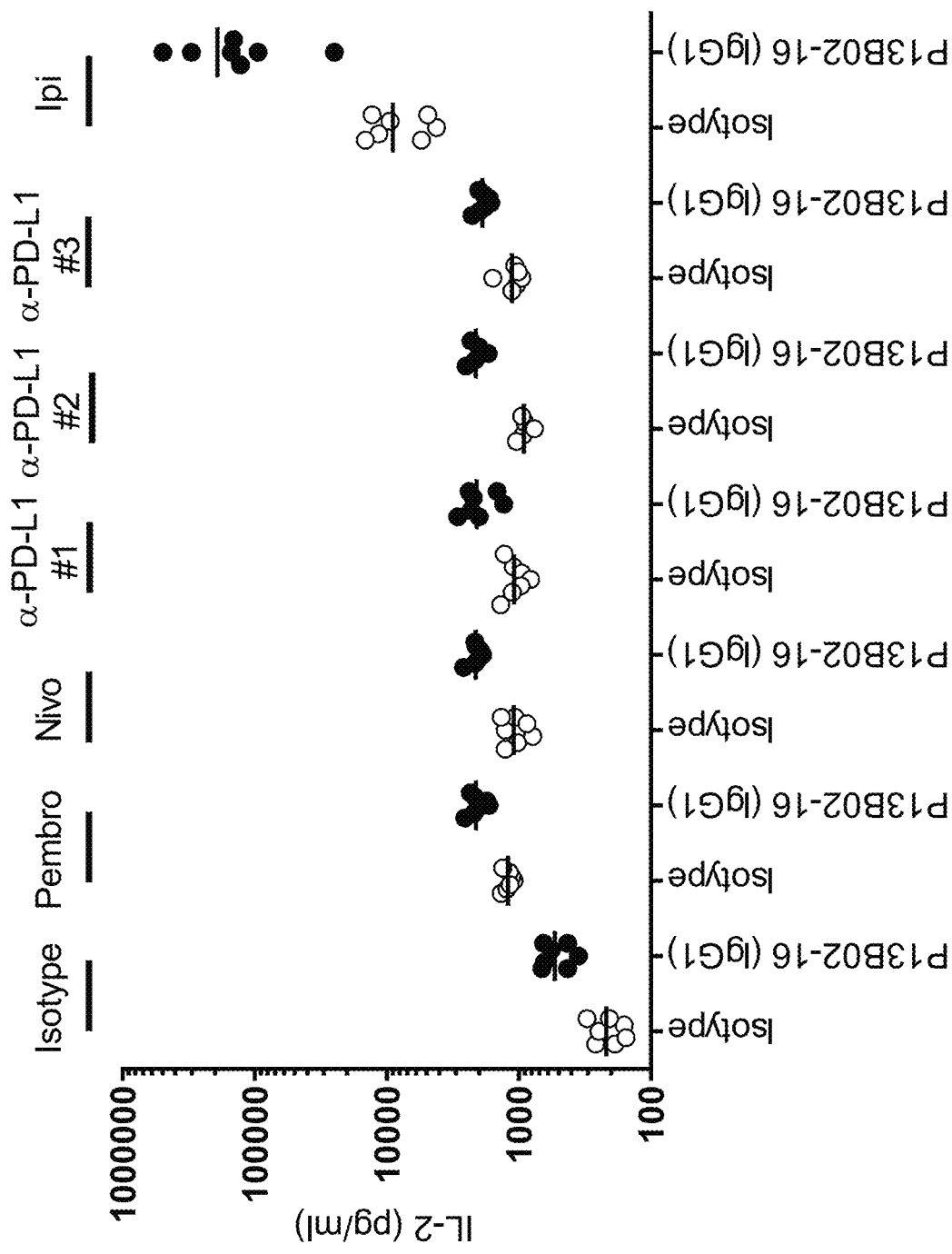

FIGS. 8A and 8B are graphs showing the production of IL-2 induced by anti-LAG-3 antibody or isotype control antibody in human peripheral blood mononuclear cells (PBMCs) upon *Staphylococcus* Enterotoxin A (SEA) stimulation. In FIG. 8A, the anti-LAG-3 antibody tested is P13B02-30 (IgG$_1$). In FIG. 8B, the anti-LAG-3 antibody P13B02-16 (IgG$_1$) or an isotype control antibody was tested in the presence or absence of anti-PD-1 antibody pembrolizumab (Pembro) or nivolumab (Nivo), anti-PD-L1 antibody #1, #2, or #3, or anti-CTLA-4 antibody ipilimumab (Ipi).

Figure 9B:
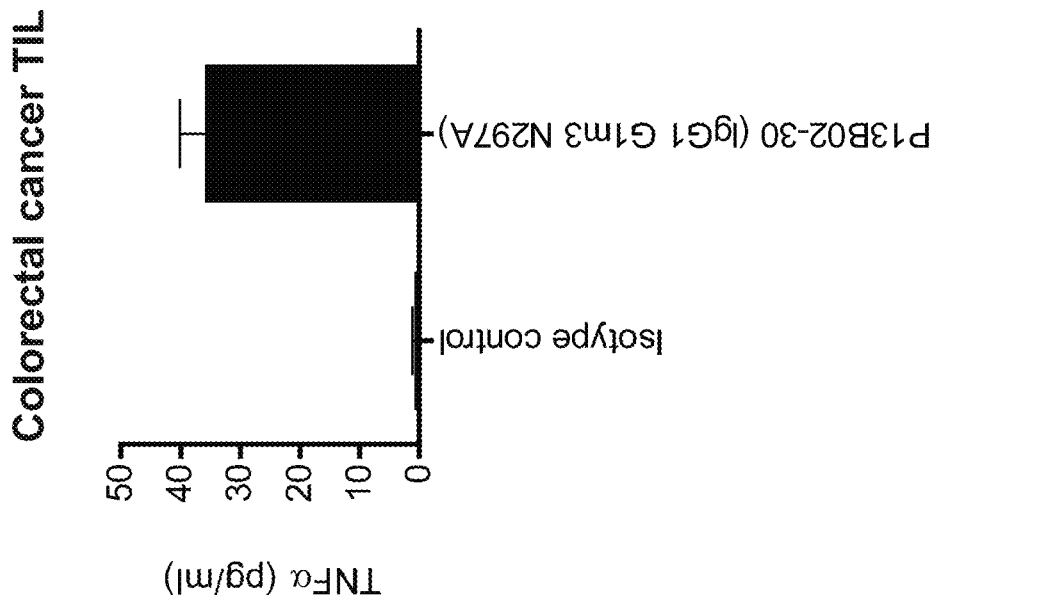
Figure 9A:
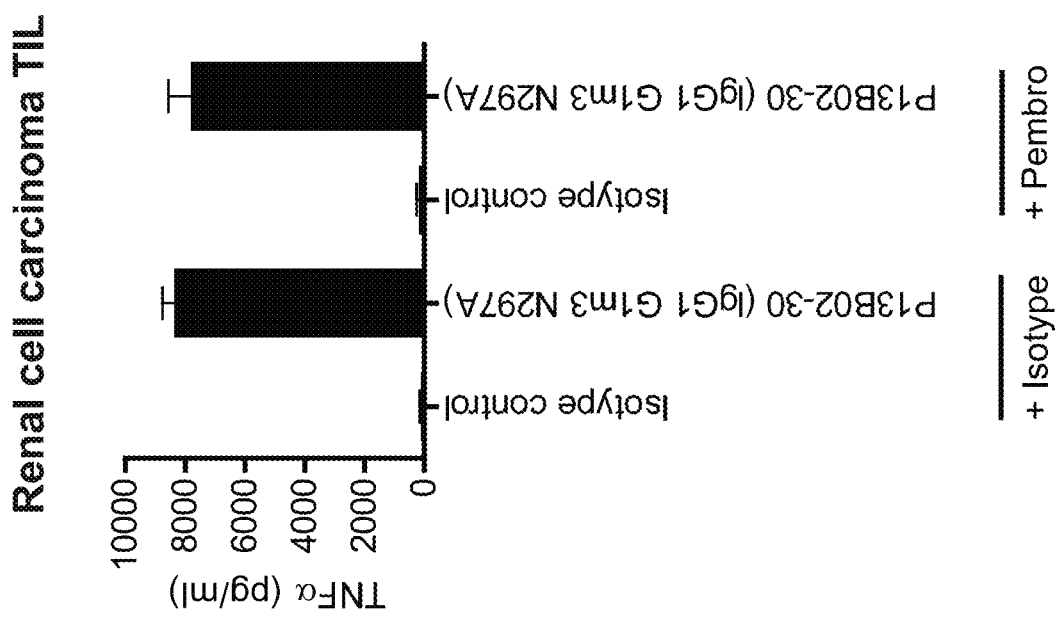

FIGS. 9A and 9B are graphs showing TNFα production of primary tumor infiltrating lymphocytes (TILs) induced by anti-LAG-3 antibody P13B02-30 (IgG$_1$ Glm3 N297A) or an isotype control antibody, either alone or in combination with the anti-PD-1 antibody pembrolizumab (Pembro). The TILs were isolated from renal cell carcinoma (FIG. 9A) or colorectal cancer (FIG. 9B) tumors and activated with anti-CD3/CD28 microbeads.

Figure 10A:
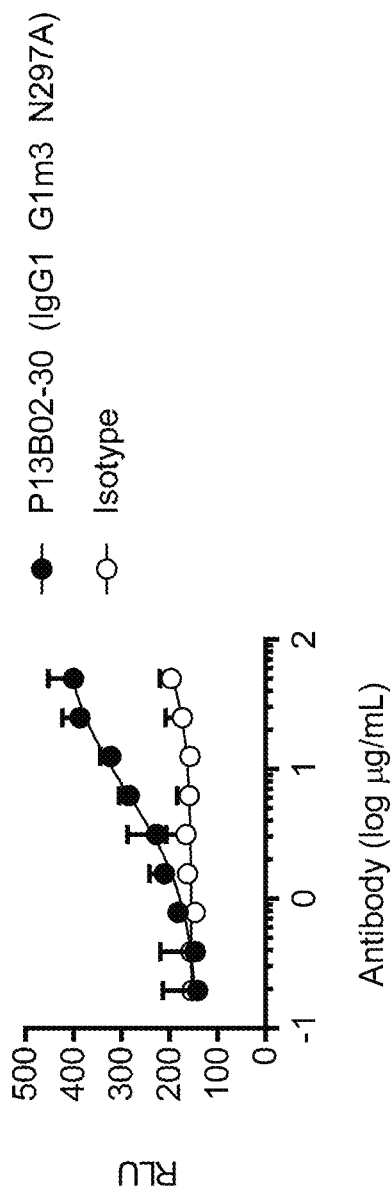
Figure 10B:
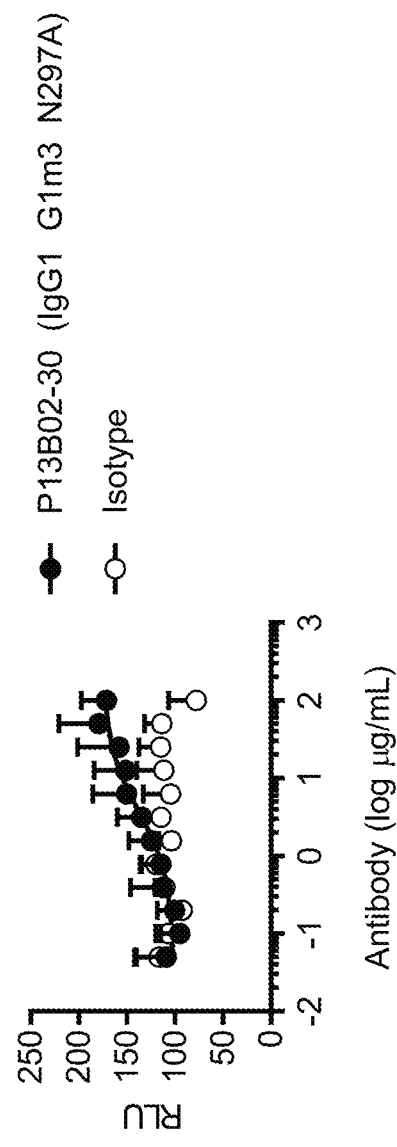

FIGS. 10A and 10B are graphs showing that the anti-LAG-3 antibody P13B02-30 (IgG$_1$ Glm3 N297A) enhanced T cell activation in a LAG-3-mediated cell suppression assay. Jurkat-NFAT-luciferase-LAG-3 cells were incubated in the presence of sextuplet dose titrations of either an anti-LAG-3 antibody (black dots) or an isotype control antibody (white dots), a fixed concentration of Raji cells, and a fixed concentration of Staphylococcal Enterotoxin E (SEE) peptide. In a first experiment, antibody concentrations between 0.2-50 µg/mL were tested (FIG. 10A). In a second experiment, antibody concentrations between 0.1-100 µg/mL were tested (FIG. 10B). RLU=relative light units of luciferase reporter.

6. DETAILED DESCRIPTION

The instant disclosure provides antibodies that specifically bind to LAG-3 (e.g., human LAG-3) and antagonize LAG-3 function, e.g., LAG-3-mediated immune suppression. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for increasing T cell activation in response to an antigen (e.g., a tumor antigen or an infectious disease antigen), and hence for treating cancer in a subject or treating or preventing an infectious disease in a subject. All instances of "isolated antibodies" described herein are additionally contemplated as antibodies that may be, but need not be, isolated. All instances of "isolated polynucleotides" described herein are additionally contemplated as polynucleotides that may be, but need not be, isolated. All instances of "antibodies" described herein are additionally contemplated as antibodies that may be, but need not be, isolated. All instances of "polynucleotides" described herein are additionally contemplated as polynucleotides that may be, but need not be, isolated.

6.1 Definitions

As used herein, the terms "about" and "approximately," when used to modify a numeric value or numeric range, indicate that deviations of 5% to 10% above (e.g., up to 5% to 10% above) and 5% to 10% below (e.g., up to 5% to 10% below) the value or range remain within the intended meaning of the recited value or range.

As used herein, the term "LAG-3" refers to Lymphocyte activation gene 3 (also known as CD223). As used herein, the term "human LAG-3" refers to a human LAG-3 protein encoded by a wild type human LAG-3 gene, e.g., GenBank™ accession number NM_002286.5. An exemplary immature amino acid sequence of human LAG-3 is provided as SEQ ID NO: 166. Exemplary mature amino acid sequences of human LAG-3 are provided as SEQ ID NO: 167 and SEQ ID NO: 210.

As used herein, the terms "antibody" and "antibodies" include full length antibodies, antigen-binding fragments of full length antibodies, and molecules comprising antibody CDRs, VH regions or VL regions. Examples of antibodies include monoclonal antibodies, recombinantly produced antibodies, monospecific antibodies, multispecific antibodies (including bispecific antibodies), human antibodies, humanized antibodies, chimeric antibodies, murine antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, antibodies described herein are IgG antibodies, or a class (e.g., human IgG$_1$ or IgG$_4$) or subclass thereof. In a specific embodiment, the antibody is a humanized monoclonal antibody. In another specific embodiment, the antibody is a human monoclonal antibody.

As used herein, the terms "VH region" and "VL region" refer to single antibody heavy and light chain variable regions, respectively, comprising FR (Framework Regions) 1, 2, 3 and 4 and CDR (Complementarity Determining Regions) 1, 2 and 3 (see Rabat et al., (1991) Sequences of Proteins of Immunological Interest (NIH Publication No. 91-3242, Bethesda), which is herein incorporated by reference in its entirety).

As used herein, the term "CDR" or "complementarity determining region" means the noncontiguous antigen combining sites found within the variable region of both heavy and light chain polypeptides. These particular regions have been described by Rabat et al., J. Biol. Chem. 252, 6609-6616 (1977) and Rabat et al., Sequences of protein of immunological interest. (1991), by Chothia et al., J. Mol. Biol. 196:901-917 (1987), and by MacCallum et al., J. Mol. Biol. 262:732-745 (1996), all of which are herein incorporated by reference in their entireties, where the definitions include overlapping or subsets of amino acid residues when compared against each other. In certain embodiments, the term "CDR" is a CDR as defined by Rabat et al., J. Biol. Chem. 252, 6609-6616 (1977) and Rabat et al., Sequences of protein of immunological interest. (1991). In certain embodiments, the term "CDR" is a CDR as defined by Chothia et al., J. Mol. Biol. 196:901-917 (1987). In certain embodiments, the term "CDR" is a CDR as defined by MacCallum et al., J. Mol. Biol. 262:732-745 (1996) and Martin A. "Protein Sequence and Structure Analysis of Antibody Variable Domains," in *Antibody Engineering*, Rontermann and Dübel, eds., Chapter 31, pp. 422-439, Springer-Verlag, Berlin (2001).

As used herein, the term "framework (FR) amino acid residues" refers to those amino acids in the framework region of an immunoglobulin chain. The term "framework region" or "FR region" as used herein, includes the amino acid residues that are part of the variable region, but are not part of the CDRs (e.g., using the Rabat or Chothia definition of CDRs).

As used herein, the terms "variable region" and "variable domain" are used interchangeably and are common in the art. The variable region typically refers to a portion of an antibody, generally, a portion of a light or heavy chain, typically about the amino-terminal 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable and are common in the art. The constant region is an antibody portion, e.g., a carboxyl terminal portion of a light and/or heavy chain which is not directly involved in binding of an antibody to antigen but which can exhibit various effector functions, such as interaction with an Fc receptor (e.g., Fc gamma receptor). The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa (κ) or lambda (λ) based on the amino acid sequence of the constant domains. Light chain amino acid sequences are well known in the art.

As used herein, the term "EU numbering system" refers to the EU numbering convention for the constant regions of an antibody, as described in Edelman, G. M. et al, Proc. Natl. Acad. USA, 63, 78-85 (1969) and Rabat et al, Sequences of Proteins of Immunological Interest, U.S. Dept. Health and Human Services, 5th edition, 1991, each of which is herein incorporated by reference in its entirety.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation rate constant of, e.g., an antibody to an antigen. The $k_{on}$ and $k_{off}$ can be determined by techniques known to one of ordinary skill in the art, such as BIAcore® or KinExA. As used herein, a "lower affinity" refers to a larger $K_D$.

As used herein, the terms "specifically binds," "specifically recognizes," "immunospecifically binds," and "immunospecifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), or other assays known in the art. In a specific embodiment, molecules that specifically bind to an antigen bind to the antigen with a $K_A$ that is at least 2 logs (i.e., factors of 10), 2.5 logs, 3 logs, 4 logs or greater than the $K_A$ when the molecules bind non-specifically to another antigen.

In another specific embodiment, molecules that specifically bind to an antigen do not cross react with other proteins under similar binding conditions. In another specific embodiment, molecules that specifically bind to LAG-3 do not cross react with other non-LAG-3 proteins. In a specific embodiment, provided herein is an antibody that binds to LAG-3 (e.g., human LAG-3) with higher affinity than to another unrelated antigen. In certain embodiments, provided herein is an antibody that binds to LAG-3 (e.g., human LAG-3) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasm on resonance, or kinetic exclusion assay. In a specific embodiment, the extent of binding of an anti-LAG-3 antibody described herein to an unrelated, non-LAG-3 protein is less than 10%, 15%, or 20% of the binding of the antibody to LAG-3 protein as measured by, e.g., a radioimmunoassay.

As used herein, the term "afucosylation" or "afucosylated" in the context of an Fc refers to a substantial lack of a fucose covalently attached, directly or indirectly, to residue 297 of the human $IgG_1$ Fc region, numbered according to the EU numbering system, or the corresponding residue in non-$IgG_1$ or non-human $IgG_1$ immunoglobulins. Thus, in a composition comprising a plurality of afucosylated antibodies, at least 70% of the antibodies will not be fucosylated, directly or indirectly (e.g., via intervening sugars) at residue 297 of the Fc region of the antibodies, and in some embodiments at least 80%, 85%, 90%, 95%, or 99% will not be fucosylated, directly or indirectly, at residue 297 of the Fc region.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays (e.g., constraining peptides using CLIPS (Chemical Linkage of Peptides onto Scaffolds) to map discontinuous or conformational epitopes), and/or mutagenesis mapping (e.g., site-directed mutagenesis mapping). For X-ray crystallography, crystallization may be accomplished using any of the known methods in the art (e.g., Giege R el al, (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, all of which are herein incorporated by reference in their entireties). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al, (2000) Acta Crystallogr D Biol Crystallogr 56(Pt 10): 1316-1323), all of which are herein incorporated by reference in their entireties. Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085, each of which is herein incorporated by reference in its entirety, for a description of mutagenesis techniques, including alanine scanning mutagenesis techniques. CLIPS (Chemical Linkage of Peptides onto Scaffolds) is a technology to present one or more peptides in a structurally constrained configuration to behave as functional mimics of complex protein domains. See, e.g., U.S. Publication Nos. US 2008/0139407 A1 and US 2007/099240 A1, and U.S. Pat. No. 7,972,993, each of which is herein incorporated by reference in its entirety. In a specific embodiment, the epitope of an antibody is determined using alanine scanning mutagenesis studies. In a specific embodiment, the epitope of an antibody is determined using hydrogen/deuterium exchange coupled with mass spectrometry. In a specific embodiment, the epitope of an antibody is determined using CLIPS Epitope Mapping Technology from Pepscan Therapeutics.

As used herein, the term "an epitope located within a region of human LAG-3" consisting of a particular amino acid sequence or a set of amino acid residues refers to an epitope comprising one or more of the amino acid residues of the specified region, wherein the specified region includes the first specified amino acid residue and the last specified amino acid residue of the region of human LAG-3. In certain embodiments, the epitope comprises each one of the amino acid residues located within the specified region. In certain embodiments, one or more additional amino acid residues of human LAG-3 outside the specified region bind to an antibody together with an epitope located within the specified region.

As used herein, the terms "T cell receptor" and "TCR" are used interchangeably and refer to full length heterodimeric αβ or γδ TCRs, antigen-binding fragments of full length TCRs, and molecules comprising TCR CDRs or variable regions. Examples of TCRs include, but are not limited to, full length TCRs, antigen-binding fragments of full length TCRs, soluble TCRs lacking transmembrane and cytoplasmic regions, single-chain TCRs containing variable regions of TCRs attached by a flexible linker, TCR chains linked by an engineered disulfide bond, monospecific TCRs, multi-specific TCRs (including bispecific TCRs), TCR fusions, human TCRs, humanized TCRs, chimeric TCRs, recombinantly produced TCRs, and synthetic TCRs. The term encompasses wild-type TCRs and genetically engineered TCRs (e.g., a chimeric TCR comprising a chimeric TCR chain which includes a first portion from a TCR of a first species and a second portion from a TCR of a second species).

As used herein, the terms "major histocompatibility complex" and "MHC" are used interchangeably and refer to an MHC class I molecule and/or an MHC class II molecule.

As used herein, the term "peptide-MHC complex" refers to an MHC molecule (MHC class I or MHC class II) with a peptide bound in the art-recognized peptide binding pocket of the MHC.

As used herein, the term "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In one embodiment, the subject is a human or non-human mammal. In one embodiment, the subject is a human.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and XBLAST programs of Altschul S F et al., (1990) J Mol Biol 215: 403, which is herein incorporated by reference in its entirety. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389-3402, which is herein incorporated by reference in its entirety. Alternatively, PSI BLAST can be used to perform an iterated search which detects distant relationships between molecules (Id). When utilizing BLAST, Gapped BLAST, and PSI Blast programs, the default parameters of the respective programs (e.g., of XBLAST and NBLAST) can be used (see, e.g., National Center for Biotechnology Information (NCBI) on the world-wide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

6.2 Anti-LAG-3 Antibodies

In one aspect the instant disclosure provides antibodies that specifically bind to LAG-3 (e.g., human LAG-3) and antagonize LAG-3 function. The amino acid sequences of exemplary antibodies are set forth in Tables 1-7 herein.

The skilled worker will appreciate that the N-terminal E or Q amino acid residue can, under certain conditions, spontaneously convert to pyroglutamate by post-translational cyclization of the free amino group to form a lactam. Accordingly, in certain embodiments, the instant disclosure provides antibodies comprising an antibody heavy chain variable region or light chain variable region disclosed herein (e.g. SEQ ID NOs: 56-72 and 73-77, respectively) or full length heavy chain or light chain disclosed herein (e.g. SEQ ID NOs: 168-186 and 187-191, respectively), wherein the N-terminal E or Q amino acid residue has been converted to pyroglutamate (e.g., as a result of post-translational cyclization of the free amino group of the N-terminal E or Q residue).

TABLE 1

Amino acid sequences of exemplary anti-LAG-3 antibodies.

| SEQ ID NO: | Description | Amino acid sequence |
|---|---|---|
| 1 | P01C09 VH | QVQLKQSGAELVKPGASVKLSCTASGFNIKDTYMYWV KQRPEQGLEWIGRIDPANGNTKYDPKLQGKATITADT SSNTVYLQLSSLTSEDTAVFYCVIYSYRYDVGGFDYW GQGTTLTVS |
| 2 | P01C09 VL, P13F01 VL, P13G05 VL, P05E03 VL | EIVLTQSPALMAASPGEKVTITCSVSSSISSSNLHWY QQKSGTSPKLWIYGTSNLASGVPVRFSGSGSGTSYSL TISSMEAEDAATYYCQQWSSYPFTFGSGTKLEIK |
| 3 | P05E01 VH | DVQLVESGAELVKPGASVKLSCTASGFTIKDTYIHWV KQRPEQGLEWIGEIDPANGNTKYDPKFQGKATITADT SSNTAYLQLSSLTSEDTAVYYCATYYYRYDVGGFDYW GQGTTLTVS |
| 4 | P05E01 VL | DIVLTQSPALMAASPGEKVTITCSVSSSISSSNLHWF QQKSGTSPKLWIYGTSNLASGVPVRFSGSGSGTSYSL TISNMEAEDAATYYCQQWNSYPLTFGAGTKLELK |
| 5 | P01A12 VH | EVQLQQSGAELVKPGASVKLSCTASGFNIKDTYMYWV KQRPEQGLDWIGRIDPANGNTKFDPKFQGKATITADT SSNTAYLQLSSLTSEDTAVYYCSTYYYRYDVGGFDYW GQGTTLTVS |
| 6 | P01A12 VL | DIVLTQSPALMAASPGEKVTITCSVSSSISSSNLHWY QQKSGTSPKLWIYGTSNLASGVPVRFSGSGSGTSYSL TISSMEAEDAATYYCQQWSSYPFTFGSGTKLEIK |
| 7 | P13B01 VH | EVQLQQSGAELVKPGASVKLSCTASGFNIKDTYIYWV KQRPERGLEWIGRIDPANGNTKFDPKFQGTATITADT SSNTAYLQLSSLTSEDTAVYYCTTYFYRYDVGGFDYW GQGTTLTVS |
| 8 | P13B01 VL, P14C04 VL, P14B07 VL | ENVLTQSPALMAASPGEKVTITCSVSSSISSSNLHWY QQKSGTSPKLWIYGTSNLASGVPVRFSGSGSGTSYSL TISSMEAEDAATYYCQQWSSYPFTFGSGTKLEIK |
| 9 | P13C10 VH, P15C02 VH, P16D04 VH, P13G05 VH, P13F06 VH, P14F01 VH, P16H01 VH | QVQLQQSGAELVKPGASVELSCTASGFNIRDTYMYWV KQRPEQGLEWIGRIDPANGNTKFDPKFQDRATMTADT SSNTAYLQLSSLTSEDTAVYYCTTYFYRYDVGGFDYW GQGTTLTVS |
| 10 | P13C10 VL, P13E02 VL, P13F02 VL, P13B03 VL, P13H05 VL, P13G04 VL | ENVLTQSPALMAASPGEKVTITCSVSSSISSSNLHWF QQKSGTSPKLWIYGTSNLASGVPVRFSGSGSGTSYSL TISSMEAEDAATYYCQQWSSYPFTFGSGTKLEIK |
| 11 | P13C08 VH | QVQLKQSGAELVKPGASVKLSCTASGFNIKDNYIHWV KQRPEQGLEWIGSIDPANGNTKYDPKFQGKASITADT SSNTAYLQLSSLTSEDTAVYYCASYFYRYDVGGFDYW GQGTTLTVS |
| 12 | P13C08 VL | DVVMTQTPALMAASPGEKVTITCSVSSSISSSNLHWF QQKSGTSPKLWIYGTSNLASGVPVRFSGSGSGTSYSL TISSMEAEDAATYYCQQWSSYPFTFGSGTKLEIK |
| 13 | P13E02 VH | QVQLQQPGAELVKPGASVKLSCTVSGFNIKDTYIHWV KQRPEQGLEWIGEIDPANGNSKYAPRFQGKATITADT SSNTAYLQLSSLTSEDTAVYYCATYYYRYDVGGFDYW GQGTTLTVS |
| 14 | P13F02 VH | QVQLQQPGAELVKPGASVKLSCTASGFNIKDTYIHWV KQRPEQGLDWVGEIDPANGHTKYDPKFQGKATITADT SSNTAYLQLSSLTSEDTAVYYCATYYYRYDVGGFDYW GQGTTLTVS |
| 15 | P13B02 VH | QVQMKQSGAELVKPGASVKLSCTASGFNIKDTYIHWV KQRPEQGLEWIGEIDPANDNTKYDPKFQGKATITADT SSNTAYLQLSSLTSEDTAVYYCATYYYRYDVGGFDYW GQGTTLTVS |
| 16 | P13B02 VL | EILLTQSPALMAASPGEKVTITCSVSSSISSSNLHWF QQKSGTSPKLWIYGTSNLASGVPVRFSGSGSGTSYSL TISSMEAEDAATYYCQQWSSYPFTFGSGTKLEIK |
| 17 | P13A06 VH | QVQLKQSGAELVKPGASVKLSCTASGFNIKDTYMYWV KQRPEQGLEWIGRIDPANGNTKYDPKFQGKATITADT |

TABLE 1-continued

Amino acid sequences of exemplary anti-LAG-3 antibodies.

| SEQ ID NO | Description | Amino acid sequence |
|---|---|---|
|  |  | SSNTVYLQLSSLTSEDTAVFYCVIYSYRYDVGGFDYW GQGTTLTVS |
| 18 | P13A06 VL | ENVLTQSPALMAASPGEKVTITCSVSSSISSSNLHWY QQKSGTSPKLWIYGTSNLASGVPVRFSGSGSGTSYSL TISSMEAEDAATYYCQQWSSYPHTFGGGTKLEIK |
| 19 | P14C04 VH | QVQLQQPGAELVKPGASVKLSCTASGFNIKDTYMYWV KQRPEQGLDWIGRIDPANGNTHFDPKFQGKATITADT SSNTAYLQLSSLISEDTAVYYCSTYFYRYDVGGFDYW GQGTTLTVS |
| 20 | P14A04 VH, P13F01 VH, P15E06 VH | QVQLQQPGAELVKPGASVELSCTASGFNIRDTYMYWV KQRPEQGLEWIGRIDPANGNTKFDPKFQDRATMTADT SSNTAYLQLSSLISEDTAVYYCTTYFYRYDVGGFDYW GQGTTLTVS |
| 21 | P14A04 VL, P14G01 VL | DIVLTQSPALMAASPGEKVTITCSVSSSISSSNLHWF QQKSGTSPKLWIYGTSNLASGVPVRFSGSGSGTSYSL TISSMEAEDAATYYCQQWSSYPFTFGSGTKLEIK |
| 22 | P15F06 VH | QVQLKQSGAELVKPGASVELSCTASGFNIRDTYMYWV KQRPEQGLEWIGRIDPANGNTKFDPKFQDRATMTADT SSNTAYLQLSSLISEDTAVYYCTTYFYRYDVGGFDYW GQGTTLTVS |
| 23 | P15F06 VL | ENVLTQSPALMAASPGEKVTITCSVSSSISSSTLHWF QQKSGTSPKLWIYGTSNLASGVPVRFSGSGSGTSYSL TISSMEAEDAATYYCQQWSSYPWTFGGGTKLEIK |
| 24 | P13B03 VH | EVQLQQSGAELVKPGASVKLSCTASGFNIKDTYIHWV KQRPEQGLEWIGEIDPANGNTKYDPKFQGKATITADT SSNTAYLQLSSLTSEDTAVYYCATYYYRYDVGGFDYW GQGTTLTVS |
| 25 | P15C02 VL | DVVMTQTPALMAASPGEKVTITCSVSSSISSSNLHWY QQKSGTSPKLWIYGTSNLASGVPVRFSGSGSGTSYSL TISSMEAEDAATYYCQQWSSYPFTFGSGTKLEIK |
| 26 | P16D04 VL, P16H01 VL | ENVLTQSPALMAASPGEKVTITCSVSSSISSSNLHWY QQKSGTSPKLWIYGTSNLASGVPVRFSGSGSGTSYSL TISSMEAEDAATYYCQQWSSYPLTFGAGTKLELK |
| 27 | P13A04 VH | QVQLQQPGAELVKPGASVELSCTASGFNIRDTYMYWV KQRPEQGLEWIGRIDPANGNTKFDPKFQDRATMTADT SSNTAYLQLSSLTSADTAVYYCTTYFYRYDVGGFDYW GQGTTLTVS |
| 28 | P13A04 VL | DIVLTQSPALMAASPGEKVTITCSVSSSISSSNLHWY QQKSGTSPKLWIYGTSNLASGVPVRFSGSGSGTSYSL TISNMEAEDAATYYCQQWSSYPFTFGSGTKLEIK |
| 29 | P16H05 VH | QVQLQQPGAELVKPGASVKLSCTASGFNIKDNYIHWV KQRPEQGLEWIGSIDPANGNTKYDPKFQGKASITADT SSNTAYLQLSSLTSEDTAVYYCASYFYRYDVGGFDYW GQGTTLTVS |
| 30 | P16H05 VL | EIVLTQSPALMAASPGEKVTITCSVSSSISSSNLHWY QQKSGTSPKLWIYGTSNLASGVPVRFSGSGSGTSYSL TISSMEAEDAATYYCQQWSSYPHTFGGGTKLEIK |
| 31 | P13F09 VH | QVQLQQSGAELVKPGASVKLSCTASGFNIKDNYIHWV KQRPEQGLEWIGSIDPANGNTKYDPKFQGKASITADT SSNTAYLQLSSLTSEGTAVYYCASYFYRYDVGGFDYW GQGTTLTVS |
| 32 | P13F09 VL, P14F06 VL | EIVLTQSPALMAASPGEKVTITCSVSSSISSSNLHWF QQKSGTSPKLWIYGTSNLASGVPVRFSGSGSGTSYSL TISSMEAEDAATYYCQQWSSYPFTFGSGTKLEIK |
| 33 | P13G01 VH, P15G05 VH | EVQLQQSGAELVKPGASVELSCTASGFNIRDTYMYWV KQRPEQGLEWIGRIDPANGNTKFDPKFQDRATMTADT SSNTAYLQLSSLTSEDTAVYYCTTYFYRYDVGGFDYW GQGTTLTVS |

TABLE 1-continued

Amino acid sequences of exemplary anti-LAG-3 antibodies.

| SEQ ID NO: | Description | Amino acid sequence |
|---|---|---|
| 34 | P13G01 VL | QIVLTQSPALMAASPGEKVTITCSVSSSISSSNLHWYQQKSGTSPKLWIYGTSNLASGVPVRFSGSGSGTSYSLTISSMEAEDAATYYCQQWSSYPFTFGSGTKLEIK |
| 35 | P13H05 VH | QVQLQQPGAELVKPGASVKLSCTASGFNIKDTYIHWVKQRPEQGLEWIGEIDPANDNTKYDPKFQGKATITADTSSNTAYLQLSSLTSEDTAVYYCATYYYRYDVGGFDYWGQGTTLTVS |
| 36 | P13D04 VH | QVQLQQSGAELVKPGASVKLSCTASGFNIKDNYMDWVKQRPEQGLEWIGKIDPANGNTKYDPKFQGKATITADTSSNTAYLQLSSLTSEDTAVYYCATYYYRYDVGGFDYWGQGTTLTVS |
| 37 | P13D04 VL | DIVLTQSPALMAASPGEKVTITCSVSSSISSSNLHWFQQKSGTPPKLWIYGTSNLASGVPVRFSGSGSGTSYSLTISSMEAEDAATYYCQQWSSYPFTFGSGTKLEIK |
| 38 | P14G01 VH, P05E03 VH | QVQLKESGAELVKPGASVELSCTASGFNIRDTYMYWVKQRPEQGLEWIGRIDPANGNTKFDPKFQDRATMTADTSSNTAYLQLSSLTSEDTAVYYCTTYFYRYDVGGFDYWGQGTTLTVS |
| 39 | P14G03 VH | QVQMKQSGAELVKPGASVKLSCTASGFNIKDTYIHWVKQRPGQGLEWIGEIDPANGNTKYDPKFQGKATITADTSSNTAYLQLSSLTSEDTAVYYCATYYYRYDVGGFDYWGQGTTLTVS |
| 40 | P14G03 VL | DIVLTQSPALMAASPGEKVTITCSVSSSISSSNLYWFQQKSGTSPKLWIYGTSNLASGVPVRFSGSGSGTSYSLTISSMEAEDAATYYCQQWSSYPFTFGSGTKLEIK |
| 41 | P13F06 VL | EILLTQSPALMAASPGEKVTITCSVSSSISSSNLHWYQQKSGTSPKLWIYGTSNLASGVPVRFSGSGSGTSYSLTISSMEAEDAATYYCQQWSSYPFTFGSGTKLEIK |
| 42 | P13B11 VH | QVQLQQPGAELVKPGASVKLSCTASGFNIKDNYMDWVKQRPEQGLEWIGKIDPANGNTKYDPKFQGKATITADTSSNTAYLQLSSLTSEDTAVYYCATYYYRYDVGGFDYWGQGTTLTVS |
| 43 | P13B11 VL | QIVLTQSPALMAASPGEKVTITCSVSSSISSSNLHWFQQKSGTSPKLWIYGTSNLASGVPVRFSGSGSGTSYSLTISSMEAEDAATYYCQQWSSYPFTFGSGTKLEIK |
| 44 | P14F01 VL | ENVLTQSPALMAASPGEKVTITCSVSSSISSSNLHWYQQKSGTSPKLWIYGTSNLASGVPVRFSGSGSGTSYSLTISSMEAEDAATYYCQQWSTYPFTFGSGTKLEIK |
| 45 | P14F06 VH | QVQMKQSGAELVKPGASVKLSCTASGFNIKDNYIHWVKQRPEQGLEWIGSIDPANGNTKYDPKFQGKASITADTSSNTAYLQLSSLTSEDTAVYYCASYFYRYDVGGFDYWGQGTTLTVS |
| 46 | P13D05 VH | QVQLQQPGAELVKPGASVELSCTASGFNIRDTYMYWVKQRPEQGLGWIGRIDPANGNTKFDPKFQDRATMTADTSSNTAYLQLSSLTSEDTAVYYCTTYFYRYDVGGFDYWGQGTTLTVS |
| 47 | P13D05 VL | EIVLTQSPALMAASPGEKVTITCSVSSSISSSNLHWFRQKSGTSPKLWIYGTSNLASGVPVRFSGSGSGTSYSLTISSMEAEDAATYYCQQWSSYPFTFGSGTKLEIK |
| 48 | P13G04 VH | EVKLMESGAELVKPGASAELSCTASGFNIRDTYMYWVKQRPEQGLEWIGRIDPANGNTKFDPKFQDRATMTADTSSNTAYLQLSSLTSEDTAVYYCTTYFYRYDVGGFDYWGQGTTLTVS |
| 49 | P15E06 VL | ENVLTQSPALMAASPGEKVTITCSVSSGISSSNLHWYQQKSGTSPKLWIYGTSNLASGVPVRFSGSGSGTSYSLTISSMEAEDAATYYCQQWSRYPWTFGGGTKLEIK |
| 50 | P15G05 VL | EIVLTQSPALMAASPGEKVTITCSVSSSISSSNLHWYQQKSGTSPKLWIYGTSNLASGVPVRFSGSGSGTSYSLTISSMEAEDAATYYCQQWSSYPLTFGAGTKLELK |

TABLE 1-continued

Amino acid sequences of exemplary anti-LAG-3 antibodies.

| SEQ ID NO: | Description | Amino acid sequence |
|---|---|---|
| 51 | P15B06 VH | EVQLQQSGAELVKPGASVKLSCTASGFNIKDTYMYWV KQRPEQGLDWIGRIDPANGNTHFDPKFQGKATITADT SSNTAYLQLSSLTSEDTAVYYCSTYFYRYDVGGFDYW GQGTTLTVS |
| 52 | P15B06 VL | QILLTQSPALMAASPGEKVTITCSVSSSISSSNLHWY QQKSGTSPKLWIYGTSNLASGVPVRFSGSGSGTSYSL TISSMEAEDAATYYCQQWSSYPLTFGAGTKLELK |
| 53 | P14B07 VH | QVQLQQPGAELVKPGASVKLSCTASGFNIKDNYIHWV KQRPEQGLEWIGSIDPANGNTKYDPKFQGKASITADT SSNTAYLQLSSLTSEDTTVYYCASYFYRYDVGGFDYW GQGTTLTVS |
| 54 | P13C06 VH | QVQMKQSGAELVKPGASVELSCTASGFNITDTYMYWV KQRPEQGLEWIGRIDPANGNTKFDPKFQDRATMTADT SSNTAYLQLSSLTSEDTAVYYCTTYFDKYDVGGCDYW GQGTTLTVS |
| 55 | P13C06 VL | EIVLTQSPALMAASPGEKVTITCSVSSSISSSNLYWF QHKSGTSPKLWIYGTSNLASGVPVRFSGSGSGTSYSL TISSMDAENAATYYCQQWRSYPFTFGSGTKLEIK |
| 56 | H0 | QVQLVQSGAEVKKPGASVKVSCKASGFNIKDTYIHWV RQAPGQGLEWMGEIDPANDNTKYDPKFQGRVTMTRDT STSTVYMELSSLRSEDTAVYYCARYYYRYDVGGFDYW GQGTLVTVSS |
| 57 | H1 | QVQLVQSGAEVKKPGASVKVSCKASGFNIKDTYIHWV RQAPGQGLEWMGEIDPANDNTKYDPKFQGRVTITADT STSTVYMELSSLRSEDTAVYYCATYYYRYDVGGFDYW GQGTLVTVSS |
| 58 | H2 | QVQLVQSGAEVKKPGASVKVSCKASGFNIKDTYIHWV RQAPGQGLEWMGEIDPANDNTKYDPKFQGRVTITADT SSNTVYMELSSLRSEDTAVYYCATYYYRYDVGGFDYW GQGTLVTVSS |
| 59 | H3 | QVQMKQSGAEVKKPGASVKVSCTASGFNIKDTYIHWV RQAPGQGLEWMGEIDPANDNTKYDPKFQGRVTITADT SSNTVYMELSSLRSEDTAVYYCATYYYRYDVGGFDYW GQGTLVTVSS |
| 60 | H4 | QVQMKQSGAEVKKPGASVKVSCTASGFNIKDTYIHWV RQAPGQGLEWIGEIDPANDNTKYDPKFQGRVTITADT SSNTVYLQLSSLRSEDTAVYYCATYYYRYDVGGFDYW GQGTLVTVSS |
| 61 | H4_R98K | QVQMKQSGAEVKKPGASVKVSCTASGFNIKDTYIHWV RQAPGQGLEWIGEIDPANDNTKYDPKFQGRVTITADT SSNTVYLQLSSLRSEDTAVYYCATYYYKYDVGGFDYW GQGTLVTVSS |
| 62 | H4_D100E | QVQMKQSGAEVKKPGASVKVSCTASGFNIKDTYIHWV RQAPGQGLEWIGEIDPANDNTKYDPKFQGRVTITADT SSNTVYLQLSSLRSEDTAVYYCATYYYRYEVGGFDYW GQGTLVTVSS |
| 63 | H1_R98K | QVQLVQSGAEVKKPGASVKVSCKASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSS |
| 64 | H1_R98K_K23T | QVQLVQSGAEVKKPGASVKVSCTASGFNIKDTYIHWV RQAPGQGLEWMGEIDPANDNTKYDPKFQGRVTITADT SISTVYMELSSLRSEDTAVYYCATYYYKYDVGGFDYW GQGTLVTVSS |
| 65 | H1_R98K_L4M | QVQMVQSGAEVKKPGASVKVSCKASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSS |

TABLE 1-continued

Amino acid sequences of exemplary anti-LAG-3 antibodies.

| SEQ ID NO: | Description | Amino acid sequence |
|---|---|---|
| 220 | H1_R98K_L4M | XVQMVQSGAEVKKPGASVKVSCKASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSS, wherein X = glutamine (Q) or pyroglutamate (pE) |
| 66 | H1_R98K_L4M_K23T | QVQMVQSGAEVKKPGASVKVSCTASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSS |
| 67 | H1_R98K_L4M_V5K | QVQMKQSGAEVKKPGASVKVSCKASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSS |
| 68 | H1_R98K_L4M_V5K_K23T | QVQMKQSGAEVKKPGASVKVSCTASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSS |
| 69 | H1_R98K_V5K | QVQLKQSGAEVKKPGASVKVSCKASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSS |
| 70 | H1_R98K_V5K_K23T | QVQLKQSGAEVKKPGASVKVSCTASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSS |
| 71 | H2_R98K | QVQLVQSGAEVKKPGASVKVSCKASGFNIKDTYIHWV RQAPGQGLEWMGEIDPANDNTKYDPKFQGRVTITADT SSNTVYMELSSLRSEDTAVYYCATYYYKYDVGGFDYW GQGTLVTVSS |
| 72 | H3_R98K | QVQMKQSGAEVKKPGASVKVSCTASGFNIKDTYIHWV RQAPGQGLEWMGEIDPANDNTKYDPKFQGRVTITADT SSNTVYMELSSLRSEDTAVYYCATYYYKYDVGGFDYW GQGTLVTVSS |
| 73 | L0 | EIVLTQSPGTLSLSPGERATLSCSVSSSISSSNLHWY QQKPGQAPRLLIYGTSNLASGIPDRFSGSGSGTDFTL TISRLEPEDFAVYYCQQWSSYPFTFGQGTKVEIK |
| 221 | L0 | XIVLTQSPGTLSLSPGERATLSCSVSSSISSSNLHWY QQKPGQAPRLLIYGTSNLASGIPDRFSGSGSGTDFTL TISRLEPEDFAVYYCQQWSSYPFTFGQGTKVEIK, wherein X = glutamate (E) or pyroglutamate (pE) |
| 74 | L1 | EIVLTQSPGTLSLSPGERATLSCSVSSSISSSNLHWY QQKPGQAPRLLIYGTSNLASGIPDRFSGSGSGTSYTL TISRLEPEDFAVYYCQQWSSYPFTFGQGTKVEIK |
| 75 | L2 | EILLTQSPGTLSLSPGERATLSCSVSSSISSSNLHWF QQKPGQAPRLLIYGTSNLASGIPDRFSGSGSGTSYTL TISRLEPEDFAVYYCQQWSSYPFTFGQGTKVEIK |
| 76 | L3 | EILLTQSPGTLSLSPGERATLSCSVSSSISSSNLHWF QQKPGQAPRLWIYGTSNLASGVPDRFSGSGSGTSYTL TISRLEPEDFAVYYCQQWSSYPFTFGQGTKVEIK |
| 77 | L4 | EILLTQSPGTLSLSPGERATLTCSVSSSISSSNLHWF QQKPGQSPRLWIYGTSNLASGVPDRFSGSGSGTSYTL TISRLEPEDFAVYYCQQWSSYPFTFGQGTKVEIK |
| 78 | CDRH1 | DTYMY |
| 79 | CDRH1 | DTYIH |
| 80 | CDRH1 | DTYIY |

TABLE 1-continued

Amino acid sequences of exemplary anti-LAG-3 antibodies.

| SEQ ID NO: | Description | Amino acid sequence |
|---|---|---|
| 81 | CDRH1 | DNYIH |
| 82 | CDRH1 | DNYMD |
| 83 | CDRH2 | RIDPANGNTKYDPKLQG |
| 84 | CDRH2 | EIDPANGNTKYDPKFQG |
| 85 | CDRH2 | RIDPANGNTKFDPKFQG |
| 86 | CDRH2 | RIDPANGNTKFDPKFQD |
| 87 | CDRH2 | SIDPANGNTKYDPKFQG |
| 88 | CDRH2 | EIDPANGNSKYAPRFQG |
| 89 | CDRH2 | EIDPANGHTKYDPKFQG |
| 90 | CDRH2 | EIDPANDNTKYDPKFQG |
| 91 | CDRH2 | RIDPANGNTKYDPKFQG |
| 92 | CDRH2 | RIDPANGNTHFDPKFQG |
| 93 | CDRH2 | KIDPANGNTKYDPKFQG |
| 94 | CDRH3 | YSYRYDVGGFDY |
| 95 | CDRH3 | YYYRYDVGGFDY |
| 96 | CDRH3 | YFYRYDVGGFDY |
| 97 | CDRH3 | YFDKYDVGGCDY |
| 98 | CDRH3 | YYYKYDVGGFDY |
| 99 | CDRH3 | YYYRYEVGGFDY |
| 100 | CDRL1 | SVSSSISSSNLH |
| 101 | CDRL1 | SVSSSISSSTLH |
| 102 | CDRL1 | SVSSSISSSNLY |
| 103 | CDRL1 | SVSSGISSSNLH |
| 104 | CDRL2 | GTSNLAS |
| 105 | CDRL3 | QQWSSYPFT |
| 106 | CDRL3 | QQWNSYPLT |
| 107 | CDRL3 | QQWSSYPHT |
| 108 | CDRL3 | QQWSSYPWT |
| 109 | CDRL3 | QQWSSYPLT |
| 110 | CDRL3 | QQWSTYPFT |
| 111 | CDRL3 | QQWSRYPWT |
| 112 | CDRL3 | QQWRSYPFT |
| 113 | VH FR1 | QVQLVQSGAEVKKPGASVKVSCKASGFNIK |
| 114 | VH FR1 | QVQMKQSGAEVKKPGASVKVSCTASGFNIK |
| 115 | VH FR1 | QVQMKQSGAEVVKPGASVKVSCTASGFNIK |
| 116 | VH FR1 | QVQLVQSGAEVKKPGASVKVSCTASGFNIK |
| 117 | VH FR1 | QVQMVQSGAEVKKPGASVKVSCKASGFNIK |
| 118 | VH FR1 | QVQMVQSGAEVKKPGASVKVSCTASGFNIK |

TABLE 1-continued

Amino acid sequences of exemplary anti-LAG-3 antibodies.

| SEQ ID NO: | Description | Amino acid sequence |
|---|---|---|
| 119 | VH FR1 | QVQMKQSGAEVKKPGASVKVSCKASGFNIK |
| 120 | VH FR1 | QVQLKQSGAEVKKPGASVKVSCKASGFNIK |
| 121 | VH FR1 | QVQLKQSGAEVKKPGASVKVSCTASGFNIK |
| 122 | VH FR2 | WVRQAPGQGLEWMG |
| 123 | VH FR2 | WVRQAPGQGLEWIG |
| 124 | VH FR3 | RVTMTRDTSTSTVYMELSSLRSEDTAVYYCAR |
| 125 | VH FR3 | RVTITADTSTSTVYMELSSLRSEDTAVYYCAT |
| 126 | VH FR3 | RVTITADTSSNTVYMELSSLRSEDTAVYYCAT |
| 127 | VH FR3 | RVTITADTSSNTVYLQLSSLRSEDTAVYYCAT |
| 128 | VH FR4 | WGQGTLVTVSS |
| 129 | VL FR1 | EIVLTQSPGTLSLSPGERATLSC |
| 130 | VL FR1 | EILLTQSPGTLSLSPGERATLSC |
| 131 | VL FR1 | EILLTQSPGTLSLSPGERATLTC |
| 132 | VL FR2 | WYQQKPGQAPRLLIY |
| 133 | VL FR2 | WFQQKPGQAPRLLIY |
| 134 | VL FR2 | WFQQKPGQAPRLWIY |
| 135 | VL FR2 | WFQQKPGQSPRLWIY |
| 136 | VL FR3 | GIPDRFSGSGSGTDFTLTISRLEPEDFAVYYC |
| 137 | VL FR3 | GIPDRFSGSGSGTSYTLTISRLEPEDFAVYYC |
| 138 | VL FR3 | GVPDRFSGSGSGTSYTLTISRLEPEDFAVYYC |
| 139 | VL FR4 | FGQGTKVEIK |
| 140 | CDRH1 consensus | $DX_1YX_2X_3$, wherein:<br>$X_1$ is T or N;<br>$X_2$ is I or M; and<br>$X_3$ is H, Y or D |
| 141 | CDRH1 consensus | $DX_1YX_2X_3$, wherein:<br>$X_1$ is T or N;<br>$X_2$ is I or M; and<br>$X_3$ is H or Y |
| 142 | CDRH2 consensus | $X_1IDPANX_2X_3X_4X_5X_6X_7PX_8X_9QX_{10}$, wherein:<br>$X_1$ is E, R, S, or K;<br>$X_2$ is D or G;<br>$X_3$ is N or H;<br>$X_4$ is T or S;<br>$X_5$ is K or H;<br>$X_6$ is Y or F;<br>$X_7$ is D or A;<br>$X_8$ is K or R;<br>$X_9$ is F or L; and<br>$X_{10}$ is G or D |
| 143 | CDRH2 consensus | $X_1IDPANX_2X_3X_4KX_5X_6PX_7FQX_8$, wherein:<br>$X_1$ is E, R, or S;<br>$X_2$ is D or G;<br>$X_3$ is N or H;<br>$X_4$ is T or S;<br>$X_5$ is Y or F;<br>$X_6$ is D or A;<br>$X_7$ is K or R; and<br>$X_8$ is G or D |

TABLE 1-continued

Amino acid sequences of exemplary anti-LAG-3 antibodies.

| SEQ ID NO: | Description | Amino acid sequence |
|---|---|---|
| 144 | CDRH3 consensus | YX$_1$X$_2$X$_3$YX$_4$VGGX$_5$DY, wherein:<br>X$_1$ is Y, F, or S;<br>X$_2$ is Y or D;<br>X$_3$ is K or R;<br>X$_4$ is D or E; and<br>X$_5$ is F or C |
| 145 | CDRH3 consensus | YX$_1$X$_2$X$_3$YDVGGX$_4$DY, wherein:<br>X$_1$ is Y, F, or S;<br>X$_2$ is Y or D;<br>X$_3$ is K or R; and<br>X$_4$ is F or C |
| 146 | CDRH3 consensus | YYYX$_1$YX$_2$VGGFDY, wherein:<br>X$_1$ is K or R; and<br>X$_2$ is D or E |
| 147 | CDRL1 consensus | SVSSX$_1$ISSSX$_2$LX$_3$, wherein:<br>X$_1$ is S or G;<br>X$_2$ is N or T; and<br>X$_3$ is H or Y |
| 148 | CDRL1 consensus | SVSSSISSSNLX$_1$, wherein:<br>X$_1$ is H or Y |
| 149 | CDRL3 consensus | QQWX$_1$X$_2$YPX$_3$T, wherein:<br>X$_1$ is S, N, or R;<br>X$_2$ is S, T or R; and<br>X$_3$ is F, L, H, or W |
| 150 | CDRL3 consensus | QQWX$_1$SYPX$_2$T, wherein:<br>X$_1$ is S, N, or R; and<br>X$_2$ is F, L, or H |
| 151 | Humanized VH consensus | QVQX$_1$X$_2$QSGAEVX$_3$KPGASVKVSCKASGFNIKDTYIH<br>WVRQAPGQGLEWX$_5$GEIDPANDNTKYDPKFQGRVTX$_6$T<br>X$_7$DTSX$_8$X$_9$TVYX$_{10}$X$_{11}$LSSLRSEDTAVYYCAX$_{12}$YYYX$_{13}$<br>YX$_{14}$VGGFDYWGQGTLVTVSS, wherein:<br>X$_1$ is M or L;<br>X$_2$ is V or K;<br>X$_3$ is K or V;<br>X$_4$ is K or T;<br>X$_5$ is M or I;<br>X$_6$ is I or M;<br>X$_7$ is A or R;<br>X$_8$ is T or S;<br>X$_9$ is S or N;<br>X$_{10}$ is M or L;<br>X$_{11}$ is E or Q;<br>X$_{12}$ is T or R;<br>X$_{13}$ is K or R; and<br>X$_{14}$ is D or E |
| 218 | Humanized VH consensus | QVQX$_1$X$_2$QSGAEVX$_3$KPGASVKVSCX$_4$ASGFNIKDTYIH<br>WVRQAPGQGLEWX$_5$GEIDPANDNTKYDPKFQGRVTX$_6$T<br>X$_7$DTSX$_8$X$_9$TVYX$_{10}$X$_{11}$LSSLRSEDTAVYYCAX$_{12}$YYYX$_{13}$<br>YX$_{14}$VGGFDYWGQGTLVTVSS, wherein:<br>X$_1$ is M or L;<br>X$_2$ is V or K;<br>X$_3$ is K or V;<br>X$_4$ is K or T;<br>X$_5$ is M or I;<br>X$_6$ is I or M;<br>X$_7$ is A or R;<br>X$_8$ is T or S;<br>X$_9$ is S or N;<br>X$_{10}$ is M or L;<br>X$_{11}$ is E or Q;<br>X$_{12}$ is T or R;<br>X$_{13}$ is K or R; and<br>X$_{14}$ is D or E |
| 222 | Humanized VH consensus | X$_1$VQX$_2$X$_3$QSGAEVX$_4$KPGASVKVSCKASGFNIKDTYIH<br>WVRQAPGQGLEWX$_5$GEIDPANDNTKYDPKFQGRVTX$_6$T<br>X$_7$DTSX$_8$X$_9$TVYX$_{10}$X$_{11}$LSSLRSEDTAVYYCAX$_{12}$YYYX$_{13}$ |

TABLE 1-continued

Amino acid sequences of exemplary anti-LAG-3 antibodies.

| SEQ ID NO: | Description | Amino acid sequence |
|---|---|---|
| | | YX$_{14}$VGGFDYWGQGTLVTVSS, wherein:<br>X$_1$ is Q or pE (pyroglutamate)<br>X$_2$ is M or L;<br>X$_3$ is V or K;<br>X$_4$ is K or V;<br>X$_5$ is M or I;<br>X$_6$ is I or M;<br>X$_7$ is A or R;<br>X$_8$ is T or S;<br>X$_9$ is S or N;<br>X$_{10}$ is M or L;<br>X$_{11}$ is E or Q;<br>X$_{12}$ is T or R;<br>X$_{13}$ is K or R; and<br>X$_{14}$ is D or E |
| 223 | Humanized VH consensus | X$_1$VQX$_2$X$_3$QSGAEVX$_4$KPGASVKVSCX$_5$ASGFNIKDTYI HWVRQAPGQGLEWX$_6$GEIDPANDNTKYDPKFQGRVTX$_7$ TX$_8$DTSX$_9$X$_{10}$TVYX$_{11}$X$_{12}$LSSLRSEDTAVYYCAX$_{13}$YYY X$_{14}$YX$_{15}$VGGFDYWGQGTLVTVSS, wherein:<br>X$_1$ is Q or pE (pyroglutamate)<br>X$_2$ is M or L;<br>X$_3$ is V or K;<br>X$_4$ is K or V;<br>X$_5$ is K or T;<br>X$_6$ is M or I;<br>X$_7$ is I or M;<br>X$_8$ is A or R;<br>X$_9$ is T or S;<br>X$_{10}$ is S or N;<br>X$_{11}$ is M or L;<br>X$_{12}$ is E or Q;<br>X$_{13}$ is T or R;<br>X$_{14}$ is K or R; and<br>X$_{15}$ is D or E |
| 152 | Humanized VL consensus | EIX$_1$LTQSPGILSLSPGERATLX$_2$CSVSSSISSSNLHW X$_3$QQKPGQX$_4$PRLX$_5$IYGTSNLASGX$_6$PDRFSGSGSGTX$_7$ X$_8$TLTISRLEPEDFAVYYCQQWSSYPFTFGQGTKVEI K, wherein:<br>X$_1$ is V or L;<br>X$_2$ is S or T;<br>X$_3$ is Y or F;<br>X$_4$ is A or S;<br>X$_5$ is L or W;<br>X$_6$ is I or V;<br>X$_7$ is D or S; and<br>X$_8$ is F or Y |
| 224 | Humanized VL consensus | X$_1$IX$_2$LTQSPGILSLSPGERATLX$_3$CSVSSSISSSNLH WX$_4$QQKPGQX$_5$PRLX$_6$IYGTSNLASGX$_7$PDRFSGSGSGT X$_8$X$_9$TLTISRLEPEDFAVYYCQQWSSYPFTFGQGTKVE IK, wherein:<br>X$_1$ is E or pE (pyroglutamate)<br>X$_2$ is V or L;<br>X$_3$ is S or T;<br>X$_4$ is Y or F;<br>X$_5$ is A or S;<br>X$_6$ is L or W;<br>X$_7$ is I or V;<br>X$_8$ is D or S; and<br>X$_9$ is F or Y |
| 168 | H1_R98K_L4M full length IgG$_1$ heavy chain | QVQMVQSGAEVKKPGASVKVSCKASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYNSTYRVVSVLTVLHQDWLNGKEYKCKVSNKALP |

TABLE 1-continued

Amino acid sequences of exemplary anti-LAG-3 antibodies.

| SEQ ID NO | Description | Amino acid sequence |
|---|---|---|
| | | APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 225 | H1_R98K_L4M full length IgG$_1$ heavy chain | XVQMVQSGAEVKKPGASVKVSCKASGFNIKDTYIHWV RQAPGQGLEWMGEIDPANDNTKYDPKFQGRVTITADT SISTVYMELSSLRSEDTAVYYCATYYYKYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYNSTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG, wherein X = glutamine (Q) or pyroglutamate (pE) |
| 169 | H1_R98K_L4M full length IgG$_1$ N297A heavy chain | QVQMVQSGAEVKKPGASVKVSCKASGFNIKDTYIHWV RQAPGQGLEWMGEIDPANDNTKYDPKFQGRVTITADT SISTVYMELSSLRSEDTAVYYCATYYYKYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 226 | H1_R98K_L4M full length IgG$_1$ N297A heavy chain | XVQMVQSGAEVKKPGASVKVSCKASGFNIKDTYIHWV RQAPGQGLEWMGEIDPANDNTKYDPKFQGRVTITADT SISTVYMELSSLRSEDTAVYYCATYYYKYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG, wherein X = glutamine (Q) or pyroglutamate (pE) |
| 170 | H1_R98K_L4M full length IgG$_4$ S228P heavy chain | QVQMVQSGAEVKKPGASVKVSCKASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSSASTKGPSVFPLAPCSRSTSESTAALGC LVKDYFPEPVTVSWNSGALTSGVHTFPAVLQSSGLYS LSSVVTVPSSSLGTKTYTCNVDHKPSNTKVDKRVESK YGPPCPPCPAPEFLGGPSVFLFPPKPKDTLMISRTPE VTCVVVDVSQEDPEVQFNWYVDGVEVHNAKTKPREEQ FNSTYRVVSVLTVLHQDWLNGKEYKCKVSNKGLPSSI EKTISKAKGQPREPQVYTLPPSQEEMTKNQVSLTCLV KGFYPSDIAVEWESNGQPENNYKTTPPVLDSDGSFFL YSRLTVDKSRWQEGNVFSCSVMHEALHNHYTQKSLSL SLG |
| 227 | H1_R98K_L4M full length IgG$_4$ S228P heavy chain | XVQMVQSGAEVKKPGASVKVSCKASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSSASTKGPSVFPLAPCSRSTSESTAALGC LVKDYFPEPVTVSWNSGALTSGVHTFPAVLQSSGLYS LSSVVTVPSSSLGTKTYTCNVDHKPSNTKVDKRVESK YGPPCPPCPAPEFLGGPSVFLFPPKPKDTLMISRTPE VTCVVVDVSQEDPEVQFNWYVDGVEVHNAKTKPREEQ FNSTYRVVSVLTVLHQDWLNGKEYKCKVSNKGLPSSI EKTISKAKGQPREPQVYTLPPSQEEMTKNQVSLTCLV |

TABLE 1-continued

Amino acid sequences of exemplary anti-LAG-3 antibodies.

| SEQ ID NO: | Description | Amino acid sequence |
|---|---|---|
| | | KGFYPSDIAVEWESNGQPENNYKTTPPVLDSDGSFFL YSRLTVDKSRWQEGNVFSCSVMHEALHNHYTQKSLSL SLG, wherein X = glutamine (Q) or pyroglutamate (pE) |
| 171 | H0 full length IgG$_1$ N297A heavy chain | QVQLVQSGAEVKKPGASVKVSCKASGFNIKDTYIHWV RQAPGQGLEWMGEIDPANDNTKYDPKFQGRVTMTRDT STSTVYMELSSLRSEDTAVYYCARYYYRYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 172 | H1 full length IgG$_1$ N297A heavy chain | QVQLVQSGAEVKKPGASVKVSCKASGFNIKDTYIHWV RQAPGQGLEWMGEIDPANDNTKYDPKFQGRVTITADT STSTVYMELSSLRSEDTAVYYCATYYYRYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 173 | H2 full length IgG$_1$ N297A heavy chain | QVQLVQSGAEVKKPGASVKVSCKASGFNIKDTYIHWV RQAPGQGLEWMGEIDPANDNTKYDPKFQGRVTITADT SSNTVYMELSSLRSEDTAVYYCATYYYRYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 174 | H3 full length IgG$_1$ N297A heavy chain | QVQMKQSGAEVKKPGASVKVSCTASGFNIKDTYIHWV RQAPGQGLEWMGEIDPANDNTKYDPKFQGRVTITADT SSNTVYMELSSLRSEDTAVYYCATYYYRYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 175 | H4 full length IgG$_1$ N297A heavy chain | QVQMKQSGAEVVKPGASVKVSCTASGFNIKDTYIHWV RQAPGQGLEWIGEIDPANDNTKYDPKFQGRVTITADT SSNTVYLQLSSLRSEDTAVYYCATYYYRYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |

TABLE 1-continued

Amino acid sequences of exemplary anti-LAG-3 antibodies.

| SEQ ID NO: | Description | Amino acid sequence |
|---|---|---|
| 176 | H4_R98K full length IgG$_1$ N297A heavy chain | QVQMKQSGAEVVKPGASVKVSCTASGFNIKDTYIHWV RQAPGQGLEWIGEIDPANDNTKYDPKFQGRVTITADT SSNTVYLQLSSLRSEDTAVYYCATYYYKYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 177 | H4_D100E full length IgG$_1$ N297A heavy chain | QVQMKQSGAEVVKPGASVKVSCTASGFNIKDTYIHWV RQAPGQGLEWIGEIDPANDNTKYDPKFQGRVTITADT SSNTVYLQLSSLRSEDTAVYYCATYYYRYEVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 178 | H1_R98K full length IgG$_1$ N297A heavy chain | QVQLVQSGAEVKKPGASVKVSCKASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 179 | H1_R98K_K23T full length IgG$_1$ N297A heavy chain | QVQLVQSGAEVKKPGASVKVSCTASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 180 | H1_R98K_L4M_K23T full length IgG$_1$ N297A heavy chain | QVQMVQSGAEVKKPGASVKVSCTASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 181 | H1_R98K_L4M_V5K full length IgG$_1$ N297A heavy chain | QVQMKQSGAEVKKPGASVKVSCKASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSSASTKGPSVFPLAPSSKSTSGGTAALGC |

TABLE 1-continued

Amino acid sequences of exemplary anti-LAG-3 antibodies.

| SEQ ID NO: | Description | Amino acid sequence |
|---|---|---|
| | | LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 182 | H1_R98K_L4M_V5K_K23T full length IgG₁ N297A heavy chain | QVQMKQSGAEVKKPGASVKVSCTASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 183 | H1_R98K_V5K full length IgG₁ N297A heavy chain | QVQLKQSGAEVKKPGASVKVSCKASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 184 | H1_R98K_V5K_K23T full length IgG₁ N297A heavy chain | QVQLKQSGAEVKKPGASVKVSCTASGFNIKDTYIHWV RQAPGQGLEWMGEIDPANDNTKYDPKFQGRVTITADT STSTVYMELSSLRSEDTAVYYCATYYYKYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 185 | H2_R98K full length IgG₁ N297A heavy chain | QVQLVQSGAEVKKPGASVKVSCKASGFNIKDTYIHWV RQAPGQGLEWMGEIDPANDNTKYDPKFQGRVTITADT SSNTVYMELSSLRSEDTAVYYCATYYYKYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 186 | H3_R98K full length IgG₁ N297A heavy chain | QVQMKQSGAEVKKPGASVKVSCTASGFNIKDTYIHWV RQAPGQGLEWMGEIDPANDNTKYDPKFQGRVTITADT SSNTVYMELSSLRSEDTAVYYCATYYYKYDVGGFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKTKPR EEQYASTYRVVSVLTVLHQDWLNGKEYKCKVSNKALP |

TABLE 1-continued

Amino acid sequences of exemplary anti-LAG-3 antibodies.

| SEQ ID NO: | Description | Amino acid sequence |
|---|---|---|
| | | APIEKTISKAKGQPREPQVYTLPPSREEMTKNQVSLT CLVKGFYPSDIAVEWESNGQPENNYKTTPPVLDSDGS FFLYSKLTVDKSRWQQGNVFSCSVMHEALHNHYTQKS LSLSPG |
| 187 | L0 full length light chain | EIVLTQSPGTLSLSPGERATLSCSVSSSISSSNLHWY QQKPGQAPRLLIYGTSNLASGIPDRFSGSGSGTDFTL TISRLEPEDFAVYYCQQWSSYPFTFGQGTKVEIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC |
| 228 | L0 full length light chain | XIVLTQSPGTLSLSPGERATLSCSVSSSISSSNLHWY QQKPGQAPRLLIYGTSNLASGIPDRFSGSGSGTDFTL TISRLEPEDFAVYYCQQWSSYPFTFGQGTKVEIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC, wherein X = glutamate (E) or pyroglutamate (pE) |
| 188 | L1 full length light chain | EIVLTQSPGTLSLSPGERATLSCSVSSSISSSNLHWY QQKPGQAPRLLIYGTSNLASGIPDRFSGSGSGTSYTL TISRLEPEDFAVYYCQQWSSYPFTFGQGTKVEIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC |
| 189 | L2 full length light chain | EILLTQSPGTLSLSPGERATLSCSVSSSISSSNLHWF QQKPGQAPRLLIYGTSNLASGIPDRFSGSGSGTSYTL TISRLEPEDFAVYYCQQWSSYPFTFGQGTKVEIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC |
| 190 | L3 full length light chain | EILLTQSPGTLSLSPGERATLSCSVSSSISSSNLHWF QQKPGQAPRLWIYGTSNLASGVPDRFSGSGSGTSYTL TISRLEPEDFAVYYCQQWSSYPFTFGQGTKVEIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC |
| 191 | L4 full length light chain | EILLTQSPGTLSLSPGERATLTCSVSSSISSSNLHWF QQKPGQSPRLWIYGTSNLASGVPDRFSGSGSGTSYTL TISRLEPEDFAVYYCQQWSSYPFTFGQGTKVEIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC |
| 192 | Human IgG$_1$ G1m3 allotype (without C-terminal lysine) | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKTHTCPP CPAPELLGGPSVFLFPPKPKDTLMISRTPEVTCVVVD VSHEDPEVKFNWYVDGVEVHNAKTKPREEQYNSTYRV VSVLTVLHQDWLNGKEYKCKVSNKALPAPIEKTISKA KGQPREPQVYTLPPSREEMTKNQVSLTCLVKGFYPSD IAVEWESNGQPENNYKTTPPVLDSDGSFFLYSKLTVD KSRWQQGNVFSCSVMHEALHNHYTQKSLSLSPG |
| 193 | Human IgG$_1$ G1m3 allotype | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKTHTCPP CPAPELLGGPSVFLFPPKPKDTLMISRTPEVTCVVVD VSHEDPEVKFNWYVDGVEVHNAKTKPREEQYNSTYRV VSVLTVLHQDWLNGKEYKCKVSNKALPAPIEKTISKA KGQPREPQVYTLPPSREEMTKNQVSLTCLVKGFYPSD IAVEWESNGQPENNYKTTPPVLDSDGSFFLYSKLTVD KSRWQQGNVFSCSVMHEALHNHYTQKSLSLSPGK |
| 208 | Human IgG$_1$ G1m17 allotype (without C-terminal lysine) | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSCDKTHTCPP CPAPELLGGPSVFLFPPKPKDTLMISRTPEVTCVVVD VSHEDPEVKFNWYVDGVEVHNAKTKPREEQYNSTYRV VSVLTVLHQDWLNGKEYKCKVSNKALPAPIEKTISKA |

TABLE 1-continued

Amino acid sequences of exemplary anti-LAG-3 antibodies.

| SEQ ID NO | Description | Amino acid sequence |
|---|---|---|
| | | KGQPREPQVYTLPPSRDELTKNQVSLTCLVKGFYPSD IAVEWESNGQPENNYKTTPPVLDSDGSFFLYSKLTVD KSRWQQGNVFSCSVMHEALHNHYTQKSLSLSPG |
| 209 | Human IgG₁ G1m17 allotype | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSCDKTHTCPP CPAPELLGGPSVFLFPPKPKDTLMISRTPEVTCVVVD VSHEDPEVKFNWYVDGVEVHNAKTKPREEQYNSTYRV VSVLTVLHQDWLNGKEYKCKVSNKALPAPIEKTISKA KGQPREPQVYTLPPSRDELTKNQVSLTCLVKGFYPSD IAVEWESNGQPENNYKTTPPVLDSDGSFFLYSKLTVD KSRWQQGNVFSCSVMHEALHNHYTQKSLSLSPGK |
| 194 | IgG₁ N297A (without C-terminal lysine) | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKTHTCPP CPAPELLGGPSVFLFPPKPKDTLMISRTPEVTCVVVD VSHEDPEVKFNWYVDGVEVHNAKTKPREEQYASTYRV VSVLTVLHQDWLNGKEYKCKVSNKALPAPIEKTISKA KGQPREPQVYTLPPSREEMTKNQVSLTCLVKGFYPSD IAVEWESNGQPENNYKTTPPVLDSDGSFFLYSKLTVD KSRWQQGNVFSCSVMHEALHNHYTQKSLSLSPG |
| 195 | IgG₁ N297A | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKRVEPKSCDKTHTCPP CPAPELLGGPSVFLFPPKPKDTLMISRTPEVTCVVVD VSHEDPEVKFNWYVDGVEVHNAKTKPREEQYASTYRV VSVLTVLHQDWLNGKEYKCKVSNKALPAPIEKTISKA KGQPREPQVYTLPPSREEMTKNQVSLTCLVKGFYPSD IAVEWESNGQPENNYKTTPPVLDSDGSFFLYSKLTVD KSRWQQGNVFSCSVMHEALHNHYTQKSLSLSPGK |
| 196 | IgG₄ S228P (without C-terminal lysine) | ASTKGPSVFPLAPCSRSTSESTAALGCLVKDYFPEPV TVSWNSGALTSGVHTFPAVLQSSGLYSLSSVVTVPSS SLGTKTYTCNVDHKPSNTKVDKRVESKYGPPCPPCPA PEFLGGPSVFLFPPKPKDTLMISRTPEVTCVVVDVSQ EDPEVQFNWYVDGVEVHNAKTKPREEQFNSTYRVVSV LTVLHQDWLNGKEYKCKVSNKGLPSSIEKTISKAKGQ PREPQVYTLPPSQEEMTKNQVSLTCLVKGFYPSDIAV EWESNGQPENNYKTTPPVLDSDGSFFLYSRLTVDKSR WQEGNVFSCSVMHEALHNHYTQKSLSLSLG |
| 197 | IgG₄ S228P | ASTKGPSVFPLAPCSRSTSESTAALGCLVKDYFPEPV TVSWNSGALISGVHTFPAVLQSSGLYSLSSVVTVPSS SLGTKTYTCNVDHKPSNTKVDKRVESKYGPPCPPCPA PEFLGGPSVFLFPPKPKDTLMISRTPEVTCVVVDVSQ EDPEVQFNWYVDGVEVHNAKTKPREEQFNSTYRVVSV LTVLHQDWLNGKEYKCKVSNKGLPSSIEKTISKAKGQ PREPQVYTLPPSQEEMTKNQVSLTCLVKGFYPSDIAV EWESNGQPENNYKTTPPVLDSDGSFFLYSRLTVDKSR WQEGNVFSCSVMHEALHNHYTQKSLSLSLGK |
| 198 | Human kappa light chain constant region IGKC*01 Km3 allotype | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC |
| 219 | Human kappa light chain constant region IGKC*01 Km3 allotype | GTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC |

TABLE 2

| | Heavy chain CDR amino acid sequences of exemplary anti-LAG-3 antibodies. * | | |
|---|---|---|---|
| VH | CDRH1 (SEQ ID NO:) | CDRH2 (SEQ ID NO:) | CDRH3 (SEQ ID NO:) |
| P01C09 VH | DTYMY (78) | RIDPANGNTKYDPKLQG (83) | YSYRYDVGGFDY (94) |
| P05E01 VH | DTYIH (79) | EIDPANGNTKYDPKFQG (84) | YYYRYDVGGFDY (95) |
| P01A12 VH | DTYMY (78) | RIDPANGNTKFDPKFQG (85) | YYYRYDVGGFDY (95) |
| P13B01 VH | DTYIY (80) | RIDPANGNTKFDPKFQG (85) | YFYRYDVGGFDY (96) |
| P13C10 VH | DTYMY (78) | RIDPANGNTKFDPKFQD (86) | YFYRYDVGGFDY (96) |
| P13C08 VH | DNYIH (81) | SIDPANGNTKYDPKFQG (87) | YFYRYDVGGFDY (96) |
| P13E02 VH | DTYIH (79) | EIDPANGNSKYAPRFQG (88) | YYYRYDVGGFDY (95) |
| P13F02 VH | DTYIH (79) | EIDPANGHTKYDPKFQG (89) | YYYRYDVGGFDY (95) |
| P13B02 VH | DTYIH (79) | EIDPANDNTKYDPKFQG (90) | YYYRYDVGGFDY (95) |
| P13A06 VH | DTYMY (78) | RIDPANGNTKYDPKFQG (91) | YSYRYDVGGFDY (94) |
| P14C04 VH | DTYMY (78) | RIDPANGNTHFDPKFQG (92) | YFYRYDVGGFDY (96) |
| P14A04 VH | DTYMY (78) | RIDPANGNTKFDPKFQD (86) | YFYRYDVGGFDY (96) |
| P15F06 VH | DTYMY (78) | RIDPANGNTKFDPKFQD (86) | YFYRYDVGGFDY (96) |
| P13B03 VH | DTYIH (79) | EIDPANGNTKYDPKFQG (84) | YYYRYDVGGFDY (95) |
| P15C02 VH | DTYMY (78) | RIDPANGNTKFDPKFQD (86) | YFYRYDVGGFDY (96) |
| P16D04 VH | DTYMY (78) | RIDPANGNTKFDPKFQD (86) | YFYRYDVGGFDY (96) |
| P13F01 VH | DTYMY (78) | RIDPANGNTKFDPKFQD (86) | YFYRYDVGGFDY (96) |
| P13A04 VH | DTYMY (78) | RIDPANGNTKFDPKFQD (86) | YFYRYDVGGFDY (96) |
| P16H05 VH | DNYIH (81) | SIDPANGNTKYDPKFQG (87) | YFYRYDVGGFDY (96) |
| P13F09 VH | DNYIH (81) | SIDPANGNTKYDPKFQG (87) | YFYRYDVGGFDY (96) |
| P13G01 VH | DTYMY (78) | RIDPANGNTKFDPKFQD (86) | YFYRYDVGGFDY (96) |
| P13H05 VH | DTYIH (79) | EIDPANDNTKYDPKFQG (90) | YYYRYDVGGFDY (95) |
| P13D04 VH | DNYMD (82) | KIDPANGNTKYDPKFQG (93) | YYYRYDVGGFDY (95) |
| P14G01 VH | DTYMY (78) | RIDPANGNTKFDPKFQD (86) | YFYRYDVGGFDY (96) |
| P14G03 VH | DTYIH (79) | EIDPANGNTKYDPKFQG (84) | YYYRYDVGGFDY (95) |
| P13G05 VH | DTYMY (78) | RIDPANGNTKFDPKFQD (86) | YFYRYDVGGFDY (96) |
| P13F06 VH | DTYMY (78) | RIDPANGNTKFDPKFQD (86) | YFYRYDVGGFDY (96) |
| P13B11 VH | DNYMD (82) | KIDPANGNTKYDPKFQG (93) | YYYRYDVGGFDY (95) |
| P14F01 VH | DTYMY (78) | RIDPANGNTKFDPKFQD (86) | YFYRYDVGGFDY (96) |
| P14F06 VH | DNYIH (81) | SIDPANGNTKYDPKFQG (87) | YFYRYDVGGFDY (96) |
| P13D05 VH | DTYMY (78) | RIDPANGNTKFDPKFQD (86) | YFYRYDVGGFDY (96) |
| P13G04 VH | DTYMY (78) | RIDPANGNTKFDPKFQD (86) | YFYRYDVGGFDY (96) |
| P15E06 VH | DTYMY (78) | RIDPANGNTKFDPKFQD (86) | YFYRYDVGGFDY (96) |
| P15G05 VH | DTYMY (78) | RIDPANGNTKFDPKFQD (86) | YFYRYDVGGFDY (96) |
| P15B06 VH | DTYMY (78) | RIDPANGNTHFDPKFQD (92) | YFYRYDVGGFDY (96) |
| P14B07 VH | DNYIH (81) | SIDPANGNTKYDPKFQG (87) | YFYRYDVGGFDY (96) |
| P05E03 VH | DTYMY (78) | RIDPANGNTKFDPKFQD (86) | YFYRYDVGGFDY (96) |

TABLE 2-continued

Heavy chain CDR amino acid sequences of exemplary anti-LAG-3 antibodies. *

| VH | CDRH1 (SEQ ID NO:) | CDRH2 (SEQ ID NO:) | CDRH3 (SEQ ID NO:) |
|---|---|---|---|
| P13C06 VH | DTYMY (78) | RIDPANGNTKFDPKFQD (86) | YFDKYDVGGCDY (97) |
| H0 | DTYIH (79) | EIDPANDNTKYDPKFQG (90) | YYYRYDVGGFDY (95) |
| H1 | DTYIH (79) | EIDPANDNTKYDPKFQG (90) | YYYRYDVGGFDY (95) |
| H2 | DTYIH (79) | EIDPANDNTKYDPKFQG (90) | YYYRYDVGGFDY (95) |
| H3 | DTYIH (79) | EIDPANDNTKYDPKFQG (90) | YYYRYDVGGFDY (95) |
| H4 | DTYIH (79) | EIDPANDNTKYDPKFQG (90) | YYYRYDVGGFDY (95) |
| H4_R98K | DTYIH (79) | EIDPANDNTKYDPKFQG (90) | YYYKYDVGGFDY (98) |
| H4_D100E | DTYIH (79) | EIDPANDNTKYDPKFQG (90) | YYYRYEVGGFDY (99) |
| H1_R98K | DTYIH (79) | EIDPANDNTKYDPKFQG (90) | YYYKYDVGGFDY (98) |
| H1_R98K_K23T | DTYIH (79) | EIDPANDNTKYDPKFQG (90) | YYYKYDVGGFDY (98) |
| H1_R98K_L4M | DTYIH (79) | EIDPANDNTKYDPKFQG (90) | YYYKYDVGGFDY (98) |
| H1_R98K_L4M_K23T | DTYIH (79) | EIDPANDNTKYDPKFQG (90) | YYYKYDVGGFDY (98) |
| H1_R98K_L4M_V5K | DTYIH (79) | EIDPANDNTKYDPKFQG (90) | YYYKYDVGGFDY (98) |
| H1_R98K_L4M_V5K_K23T | DTYIH (79) | EIDPANDNTKYDPKFQG (90) | YYYKYDVGGFDY (98) |
| H1_R98K_V5K | DTYIH (79) | EIDPANDNTKYDPKFQG (90) | YYYKYDVGGFDY (98) |
| H1_R98K_V5K_K23T | DTYIH (79) | EIDPANDNTKYDPKFQG (90) | YYYKYDVGGFDY (98) |
| H2_R98K | DTYIH (79) | EIDPANDNTKYDPKFQG (90) | YYYKYDVGGFDY (98) |
| H3_R98K | DTYIH (79) | EIDPANDNTKYDPKFQG (90) | YYYKYDVGGFDY (98) |

* Defined according to the Kabat numbering system.

TABLE 3

Light chain CDR amino acid sequences of exemplary anti-LAG-3 antibodies. *

| VL | CDRL1 (SEQ ID NO:) | CDRL2 (SEQ ID NO:) | CDRL3 (SEQ ID NO:) |
|---|---|---|---|
| P01C09 VL | SVSSSISSSNLH (100) | GTSNLAS (104) | QQWSSYPFT (105) |
| P05E01 VL | SVSSSISSSNLH (100) | GTSNLAS (104) | QQWNSYPLT (106) |
| P01A12 VL | SVSSSISSSNLH (100) | GTSNLAS (104) | QQWSSYPFT (105) |
| P13B01 VL | SVSSSISSSNLH (100) | GTSNLAS (104) | QQWSSYPFT (105) |
| P13C10 VL | SVSSSISSSNLH (100) | GTSNLAS (104) | QQWSSYPFT (105) |
| P13C08 VL | SVSSSISSSNLH (100) | GTSNLAS (104) | QQWSSYPFT (105) |
| P13E02 VL | SVSSSISSSNLH (100) | GTSNLAS (104) | QQWSSYPFT (105) |
| P13F02 VL | SVSSSISSSNLH (100) | GTSNLAS (104) | QQWSSYPFT (105) |
| P13B02 VL | SVSSSISSSNLH (100) | GTSNLAS (104) | QQWSSYPFT (105) |
| P13A06 VL | SVSSSISSSNLH (100) | GTSNLAS (104) | QQWSSYPHT (107) |
| P14C04 VL | SVSSSISSSNLH (100) | GTSNLAS (104) | QQWSSYPFT (105) |
| P14A04 VL | SVSSSISSSNLH (100) | GTSNLAS (104) | QQWSSYPFT (105) |

TABLE 3-continued

Light chain CDR amino acid sequences of exemplary anti-LAG-3 antibodies. *

| VL | CDRL1 (SEQ ID NO:) | CDRL2 (SEQ ID NO:) | CDRL3 (SEQ ID NO:) |
|---|---|---|---|
| P15F06 VL | SVSSSISSSTLH (101) | GTSNLAS (104) | QQWSSYPWT (108) |
| P13B03 VL | SVSSSISSSNLH (100) | GTSNLAS (104) | QQWSSYPFT (105) |
| P15C02 VL | SVSSSISSSNLH (100) | GTSNLAS (104) | QQWSSYPFT (105) |
| P16D04 VL | SVSSSISSSNLH (100) | GTSNLAS (104) | QQWSSYPLT (109) |
| P13F01 VL | SVSSSISSSNLH (100) | GTSNLAS (104) | QQWSSYPFT (105) |
| P13A04 VL | SVSSSISSSNLH (100) | GTSNLAS (104) | QQWSSYPFT (105) |
| P16H05 VL | SVSSSISSSNLH (100) | GTSNLAS (104) | QQWSSYPHT (107) |
| P13F09 VL | SVSSSISSSNLH (100) | GTSNLAS (104) | QQWSSYPFT (105) |
| P13G01 VL | SVSSSISSSNLH (100) | GTSNLAS (104) | QQWSSYPFT (105) |
| P13H05 VL | SVSSSISSSNLH (100) | GTSNLAS (104) | QQWSSYPFT (105) |
| P13D04 VL | SVSSSISSSNLH (100) | GTSNLAS (104) | QQWSSYPFT (105) |
| P14G01 VL | SVSSSISSSNLH (100) | GTSNLAS (104) | QQWSSYPFT (105) |
| P14G03 VL | SVSSSISSSNLY (102) | GTSNLAS (104) | QQWSSYPFT (105) |
| P13G05 VL | SVSSSISSSNLH (100) | GTSNLAS (104) | QQWSSYPFT (105) |
| P13F06 VL | SVSSSISSSNLH (100) | GTSNLAS (104) | QQWSSYPFT (105) |
| P13B11 VL | SVSSSISSSNLH (100) | GTSNLAS (104) | QQWSSYPFT (105) |
| P14F01 VL | SVSSSISSSNLH (100) | GTSNLAS (104) | QQWSTYPFT (110) |
| P14F06 VL | SVSSSISSSNLH (100) | GTSNLAS (104) | QQWSSYPFT (105) |
| P13D05 VL | SVSSSISSSNLH (100) | GTSNLAS (104) | QQWSSYPFT (105) |
| P13G04 VL | SVSSSISSSNLH (100) | GTSNLAS (104) | QQWSSYPFT (105) |
| P15E06 VL | SVSSGISSSNLH (103) | GTSNLAS (104) | QQWSRYPWT (111) |
| P15G05 VL | SVSSSISSSNLH (100) | GTSNLAS (104) | QQWSSYPLT (109) |
| P15B06 VL | SVSSSISSSNLH (100) | GTSNLAS (104) | QQWSSYPLT (109) |
| P14B07 VL | SVSSSISSSNLH (100) | GTSNLAS (104) | QQWSSYPFT (105) |
| P05E03 VL | SVSSSISSSNLH (100) | GTSNLAS (104) | QQWSSYPFT (105) |
| P13C06 VL | SVSSSISSSNLY (102) | GTSNLAS (104) | QQWRSYPFT (112) |
| L0 | SVSSSISSSNLH (100) | GTSNLAS (104) | QQWSSYPFT (105) |
| L1 | SVSSSISSSNLH (100) | GTSNLAS (104) | QQWSSYPFT (105) |
| L2 | SVSSSISSSNLH (100) | GTSNLAS (104) | QQWSSYPFT (105) |
| L3 | SVSSSISSSNLH (100) | GTSNLAS (104) | QQWSSYPFT (105) |
| L4 | SVSSSISSSNLH (100) | GTSNLAS (104) | QQWSSYPFT (105) |

* Defined according to the Kabat numbering system.

TABLE 4

Heavy chain framework (FR) amino acid sequences of exemplary anti-LAG-3 antibodies. *

| VH | VH FR1 (SEQ ID NO:) | VH FR2 (SEQ ID NO:) | VH FR3 (SEQ ID NO:) | VH FR4 (SEQ ID NO:) |
|---|---|---|---|---|
| H0 | QVQLVQSGAEVKKPGASVKVSCKASGFNIK (113) | WVRQAPGQGLEWMG (122) | RVTMTRDTSTSTVYMELSSLRSEDTAVYYCAR (124) | WGQGTLVTVSS (128) |
| H1 | QVQLVQSGAEVKKPGASVKVSCKASGFNIK (113) | WVRQAPGQGLEWMG (122) | RVTITADTSTSTVYMELSSLRSEDTAVYYCAT (125) | WGQGTLVTVSS (128) |
| H2 | QVQLVQSGAEVKKPGASVKVSCKASGFNIK (113) | WVRQAPGQGLEWMG (122) | RVTITADTSSNTVYMELSSLRSEDTAVYYCAT (126) | WGQGTLVTVSS (128) |
| H3 | QVQMKQSGAEVKKPGASVKVSCTASGFNIK (114) | WVRQAPGQGLEWMG (122) | RVTITADTSSNTVYMELSSLRSEDTAVYYCAT (126) | WGQGTLVTVSS (128) |
| H4 | QVQMKQSGAEVVKPGASVKVSCTASGFNIK (115) | WVRQAPGQGLEWIG (123) | RVTITADTSSNTVYLQLSSLRSEDTAVYYCAT (127) | WGQGTLVTVSS (128) |
| H4_R98K | QVQMKQSGAEVVKPGASVKVSCTASGFNIK (115) | WVRQAPGQGLEWIG (123) | RVTITADTSSNTVYLQLSSLRSEDTAVYYCAT (127) | WGQGTLVTVSS (128) |
| H4_D100E | QVQMKQSGAEVVKPGASVKVSCTASGFNIK (115) | WVRQAPGQGLEWIG (123) | RVTITADTSSNTVYLQLSSLRSEDTAVYYCAT (127) | WGQGTLVTVSS (128) |
| H1_R98K | QVQLVQSGAEVKKPGASVKVSCKASGFNIK (113) | WVRQAPGQGLEWMG (122) | RVTITADTSTSTVYMELSSLRSEDTAVYYCAT (125) | WGQGTLVTVSS (128) |
| H1_R98K_K23T | QVQLVQSGAEVKKPGASVKVSCTASGFNIK (116) | WVRQAPGQGLEWMG (122) | RVTITADTSTSTVYMELSSLRSEDTAVYYCAT (125) | WGQGTLVTVSS (128) |
| H1_R98K_L4M | QVQMVQSGAEVKKPGASVKVSCKASGFNIK (117) | WVRQAPGQGLEWMG (122) | RVTITADTSTSTVYMELSSLRSEDTAVYYCAT (125) | WGQGTLVTVSS (128) |
| H1_R98K_L4M_K23T | QVQMVQSGAEVKKPGASVKVSCTASGFNIK (118) | WVRQAPGQGLEWMG (122) | RVTITADTSTSTVYMELSSLRSEDTAVYYCAT (125) | WGQGTLVTVSS (128) |
| H1_R98K_L4M_V5K | QVQMKQSGAEVKKPGASVKVSCKASGFNIK (119) | WVRQAPGQGLEWMG (122) | RVTITADTSTSTVYMELSSLRSEDTAVYYCAT (125) | WGQGTLVTVSS (128) |
| H1_R98K_L4M_V5K_K23T | QVQMKQSGAEVKKPGASVKVSCTASGFNIK (114) | WVRQAPGQGLEWMG (122) | RVTITADTSTSTVYMELSSLRSEDTAVYYCAT (125) | WGQGTLVTVSS (128) |
| H1_R98K_V5K | QVQLKQSGAEVKKPGASVKVSCKASGFNIK (120) | WVRQAPGQGLEWMG (122) | RVTITADTSTSTVYMELSSLRSEDTAVYYCAT (125) | WGQGTLVTVSS (128) |
| H1_R98K_V5K_K23T | QVQLKQSGAEVKKPGASVKVSCTASGFNIK (121) | WVRQAPGQGLEWMG (122) | RVTITADTSTSTVYMELSSLRSEDTAVYYCAT (125) | WGQGTLVTVSS (128) |
| H2_R98K | QVQLVQSGAEVKKPGASVKVSCKASGFNIK (113) | WVRQAPGQGLEWMG (122) | RVTITADTSSNTVYMELSSLRSEDTAVYYCAT (126) | WGQGTLVTVSS (128) |
| H3_R98K | QVQMKQSGAEVKKPGASVKVSCTASGFNIK (114) | WVRQAPGQGLEWMG (122) | RVTITADTSSNTVYMELSSLRSEDTAVYYCAT (126) | WGQGTLVTVSS (128) |

* The heavy chain framework regions described in Table 4 are determined based upon the boundaries of the Kabat numbering system for CDRs. In other words, the VH CDRs are determined by Kabat and the framework regions are the amino acid residues surrounding the CDRs in the variable region in the format FR1, CDR1, FR2, CDR2, FR3, CDR3, and FR4.

TABLE 5

Light chain framework (FR) amino acid sequences of exemplary anti-LAG-3 antibodies. *

| VL | VL FR1 (SEQ ID NO:) | VL FR2 (SEQ ID NO:) | VL FR3 (SEQ ID NO:) | VL FR4 (SEQ ID NO:) |
|---|---|---|---|---|
| L0 | EIVLTQSPGTLSLSPGERATLSC (129) | WYQQKPGQAPRLLIY (132) | GIPDRFSGSGSGTDFTLTISRLEPEDFAVYYC (136) | FGQGTKVEIK (139) |
| L1 | EIVLTQSPGTLSLSPGERATLSC (129) | WYQQKPGQAPRLLIY (132) | GIPDRFSGSGSGTSYTLTISRLEPEDFAVYYC (137) | FGQGTKVEIK (139) |

TABLE 5-continued

Light chain framework (FR) amino acid sequences of exemplary anti-LAG-3 antibodies.*

| VL | VL FR1 (SEQ ID NO:) | VL FR2 (SEQ ID NO:) | VL FR3 (SEQ ID NO:) | VL FR4 (SEQ ID NO:) |
|---|---|---|---|---|
| L2 | EILLTQSPGTLSLSPGERATLSC (130) | WFQQKPGQAPRLLIY (133) | GIPDRFSGSGSGTSYTLTISRLEPEDFAVYYC (137) | FGQGTKVEIK (139) |
| L3 | EILLTQSPGTLSLSPGERATLSC (130) | WFQQKPGQAPRLWIY (134) | GVPDRFSGSGSGTSYTLTISRLEPEDFAVYYC (138) | FGQGTKVEIK (139) |
| L4 | EILLTQSPGTLSLSPGERATLTC (131) | WFQQKPGQSPRLWIY (135) | GVPDRFSGSGSGTSYTLTISRLEPEDFAVYYC (138) | FGQGTKVEIK (139) |

* The light chain framework regions described in Table 5 are determined based upon the boundaries of the Kabat numbering system for CDRs. In other words, the VL CDRs are determined by Kabat and the framework regions are the amino acid residues surrounding the CDRs in the variable region in the format FR1, CDR1, FR2, CDR2, FR3, CDR3, and FR4.

TABLE 6

Exemplary murine anti-LAG-3 antibodies.

| Antibody | Heavy chain variable region SEQ ID NO: | Light chain variable region SEQ ID NO: |
|---|---|---|
| P01C09 | 1 | 2 |
| P05E01 | 3 | 4 |
| P01A12 | 5 | 6 |
| P13B01 | 7 | 8 |
| P13C10 | 9 | 10 |
| P13C08 | 11 | 12 |
| P13E02 | 13 | 10 |
| P13F02 | 14 | 10 |
| P13B02 | 15 | 16 |
| P13A06 | 17 | 18 |
| P14C04 | 19 | 8 |
| P14A04 | 20 | 21 |
| P15F06 | 22 | 23 |
| P13B03 | 24 | 10 |
| P15C02 | 9 | 25 |
| P16D04 | 9 | 26 |
| P13F01 | 20 | 2 |
| P13A04 | 27 | 28 |
| P16H05 | 29 | 30 |
| P13F09 | 31 | 32 |
| P13G01 | 33 | 34 |
| P13H05 | 35 | 10 |
| P13D04 | 36 | 37 |
| P14G01 | 38 | 21 |
| P14G03 | 39 | 40 |
| P13G05 | 9 | 2 |
| P13F06 | 9 | 41 |
| P13B11 | 42 | 43 |
| P14F01 | 9 | 44 |
| P14F06 | 45 | 32 |
| P13D05 | 46 | 47 |
| P13G04 | 48 | 10 |
| P15E06 | 20 | 49 |
| P15G05 | 33 | 50 |
| P15B06 | 51 | 52 |
| P14B07 | 53 | 8 |
| P05E03 | 38 | 2 |
| P13C06 | 54 | 55 |

TABLE 7

Exemplary humanized anti-LAG-3 antibodies.*

| Antibody | Heavy chain variable region (SEQ ID NO:) | Light chain variable region (SEQ ID NO:) |
|---|---|---|
| P13B02-01 | H0 (56) | L0 (73) |
| P13B02-02 | H0 (56) | L1 (74) |
| P13B02-03 | H0 (56) | L2 (75) |
| P13B02-04 | H0 (56) | L3 (76) |
| P13B02-05 | H0 (56) | L4 (77) |
| P13B02-06 | H1 (57) | L0 (73) |
| P13B02-07 | H1 (57) | L1 (74) |
| P13B02-08 | H1 (57) | L2 (75) |
| P13B02-09 | H1 (57) | L3 (76) |
| P13B02-10 | H1 (57) | L4 (77) |
| P13B02-11 | H2 (58) | L0 (73) |
| P13B02-12 | H2 (58) | L1 (74) |
| P13B02-13 | H2 (58) | L2 (75) |
| P13B02-14 | H2 (58) | L3 (76) |
| P13B02-15 | H2 (58) | L4 (77) |
| P13B02-16 | H3 (59) | L0 (73) |
| P13B02-17 | H3 (59) | L1 (74) |
| P13B02-18 | H3 (59) | L2 (75) |
| P13B02-19 | H3 (59) | L3 (76) |
| P13B02-20 | H3 (59) | L4 (77) |
| P13B02-21 | H4 (60) | L0 (73) |
| P13B02-22 | H4 (60) | L1 (74) |
| P13B02-23 | H4 (60) | L2 (75) |
| P13B02-24 | H4 (60) | L3 (76) |
| P13B02-25 | H4 (60) | L4 (77) |
| P13B02-26 | H4_R98K (61) | L4 (77) |
| P13B02-27 | H4_D100E (62) | L4 (77) |
| P13B02-28 | H1_R98K (63) | L0 (73) |
| P13B02-29 | H1_R98K_K23T (64) | L0 (73) |
| P13B02-30 | H1_R98K_L4M (65) | L0 (73) |
| P13B02-31 | H1_R98K_L4M_K23T (66) | L0 (73) |
| P13B02-32 | H1_R98K_L4M_V5K (67) | L0 (73) |
| P13B02-33 | H1_R98K_L4M_V5K_K23T (68) | L0 (73) |
| P13B02-34 | H1_R98K_V5K (69) | L0 (73) |
| P13B02-35 | H1_R98K_V5K_K23T (70) | L0 (73) |
| P13B02-36 | H2_R98K (71) | L0 (73) |
| P13B02-37 | H3_R98K (72) | L0 (73) |

TABLE 8

Human germline sequences.

| SEQ ID NO: | Description | Amino acid sequence |
|---|---|---|
| 153 | IGHV1-46*01 | QVQLVQSGAEVKKPGASVKVSCKASGYTFTSYYMHWV RQAPGQGLEWMGIINPSGGSTSYAQKFQGRVTMTRDT STSTVYMELSSLRSEDTAVYYCAR |
| 154 | IGHV1-69-2*01 | EVQLVQSGAEVKKPGATVKISCKVSGYTFTDYYMHWV QQAPGKGLEWMGLVDPEDGETIYAEKFQGRVTITADT STDTAYMELSSLRSEDTAVYYCAT |
| 155 | IGHV1-3*01 | QVQLVQSGAEVKKPGASVKVSCKASGYTFTSYAMHWV RQAPGQRLEWMGWINAGNGNTKYSQKFQGRVTITRDT SASTAYMELSSLRSEDTAVYYCAR |
| 156 | IGHV1-24*01 | QVQLVQSGAEVKKPGASVKVSCKVSGYTLTELSMHWV RQAPGKGLEWMGGFDPEDGETIYAQKFQGRVTMTEDT STDTAYMELSSLRSEDTAVYYCAT |
| 157 | IGHV1-2*01 | QVQLVQSGAEVKKPGASVKVSCKASGYTFTGYYMHWV RQAPGQGLEWMGRINPNSGGTNYAQKFQGRVTSTRDT SISTAYMELSRLRSDDTVVYYCAR |
| 158 | IGHV1-45*01 | QMQLVQSGAEVKKTGSSVKVSCKASGYTFTYRYLHWV RQAPGQALEWMGWITPFNGNTNYAQKFQDRVTITRDR SMSTAYMELSSLRSEDTAMYYCAR |
| 159 | IGHV1-18*01 | QVQLVQSGAEVKKPGASVKVSCKASGYTFTSYGISWV RQAPGQGLEWMGWISAYNGNTNYAQKLQGRVTMTTDT STSTAYMELRSLRSDDTAVYYCAR |
| 200 | IGHJ1*01 | AEYFQHWGQGTLVTVSS |
| 160 | IGKV3-20*01 | EIVLTQSPGTLSLSPGERATLSCRASQSVSSSYLAWY QQKPGQAPRLLIYGASSRATGIPDRFSGSGSGTDFTL TISRLEPEDFAVYYCQQYGSSP |
| 161 | IGKV3D-15*01 or IGKV3-15*01 | EIVMTQSPATLSVSPGERATLSCRASQSVSSNLAWYQ QKPGQAPRLLIYGASTRATGIPARFSGSGSGTEFTLT ISSLQSEDFAVYYCQQYNNWP |
| 162 | IGKV3D-20*01 | EIVLTQSPATLSLSPGERATLSCGASQSVSSSYLAWY QQKPGLAPRLLIYDASSRATGIPDRFSGSGSGTDFTL TISRLEPEDFAVYYCQQYGSSP |
| 163 | IGKV3D-7*01 | EIVMTQSPATLSLSPGERATLSCRASQSVSSSYLSWY QQKPGQAPRLLIYGASTRATGIPARFSGSGSGTDFTL TISSLQPEDFAVYYCQQDYNLPP |
| 164 | IGKV1-9*01 | DIQLTQSPSFLSASVGDRVTITCRASQGISSYLAWYQ QKPGKAPKLLIYAASTLQSGVPSRFSGSGSGTEFTLT ISSLQPEDFATYYCQQLNSYP |
| 165 | IGKV3-11*01 | EIVLTQSPATLSLSPGERATLSCRASQSVSSYLAWYQ QKPGQAPRLLIYDASNRATGIPARFSGSGSGTDFTLT ISSLEPEDFAVYYCQQRSNWP |
| 201 | IGKJ1*01 | WTFGQGTKVEIK |

TABLE 9

Exemplary sequences of LAG-3.

| SEQ ID NO: | Description | Amino acid Sequence |
|---|---|---|
| 166 | Human LAG-3 immature protein (P18627-1) | MWEAQFLGLLFLQPLWVAPVKPLQPGAEVPVVW AQEGAPAQLPCSPTIPLQDLSLLRRAGVTWQHQP DSGPPAAAPGHPLAPGPHPAAPSSWGPRPRRYTV LSVGPGGLRSGRLPLQPRVQLDERGRQRGFDSLW LRPARRADAGEYRAAVHLRDRALSCRLRLRLGQ ASMTASPPGSLRASDWVILNCSFSRPDRPASVHW FRNRGQGRVPVRESPHHHLAESFLFLPQVSPMDS GPWGCILTYRDGFNVSIMYNLTVLGLEPPTPLTVY AGAGSRVGLPCRLPAGVGTRSFLTAKWTPPGGGP |

TABLE 9-continued

Exemplary sequences of LAG-3.

| SEQ ID NO: | Description | Amino acid Sequence |
|---|---|---|
| | | DLLVTGDNGDFTLRLEDVSQAQAGTYTCHIHLQE<br>QQLNATVTLAIITVTPKSFGSPGSLGKLLCEVTPVS<br>GQERFVWSSLDTPSQRSFSGPWLEAQEAQLLSQP<br>WQCQLYQGERLLGAAVYFTELSSPGAQRSGRAP<br>GALPAGHLLLFLILGVLSLLLLVTGAFGFHLWRRQ<br>WRPRRFSALEQGIHPPQAQSKIEELEQEPEPEPEPE<br>PEPEPEPEPEQL |
| 167 | Human LAG-3 mature protein | VPVVWAQEGAPAQLPCSPTIPLQDLSLLRRAGVT<br>WQHQPDSGPPAAAPGHPLAPGPHPAAPSSWGPRP<br>RRYTVLSVGPGGLRSGRLPLQPRVQLDERGRQRG<br>DFSLWLRPARRADAGEYRAAVHLRDRALSCRLR<br>LRLGQASMTASPPGSLRASDWVILNCSFSRPDRPA<br>SVHWFRNRGQGRVPVRESPHRHHLAESFLFLPQVS<br>PMDSGPWGCILTYRDGFNVSIMYNLTVLGLEPPTP<br>LTVYAGAGSRVGLPCRLPAGVGTRSFLTAKWTPP<br>GGGPDLLVTGDNGDFTLRLEDVSQAQAGTYTCHI<br>HLQEQQLNATVTLAIITVTPKSFGSPGSLGKLLCE<br>VTPVSGQERFVWSSLDTPSQRSFSGPWLEAQEAQ<br>LLSQPWQCQLYQGERLLGAAVYFTELSSPGAQRS<br>GRAPGALPAGHLLLFLILGVLSLLLLVTGAFGFHL<br>WRRQWRPRRFSALEQGIHPPQAQSKIEELEQEPEP<br>EPEPEPEPEPEPEPEQL |
| 210 | Human LAG-3 mature protein | LQPGAEVPVVWAQEGAPAQLPCSPTIPLQDLSLLR<br>RAGVTWQHQPDSGPPAAAPGHPLAPGPHPAAPSS<br>WGPRPRRYTVLSVGPGGLRSGRLPLQPRVQLDER<br>GRQRGDFSLWLRPARRADAGEYRAAVHLRDRAL<br>SCRLRLRLGQASMTASPPGSLRASDWVILNCSFSR<br>PDRPASVHWFRNRGQGRVPVRESPHHHLAESFLF<br>LPQVSPMDSGPWGCILTYRDGFNVSIMYNLTVLG<br>LEPPTPLTVYAGAGSRVGLPCRLPAGVGTRSFLTA<br>KWTPPGGGPDLLVTGDNGDFTLRLEDVSQAQAG<br>TYTCHIHLQEQQLNATVTLAIITVTPKSFGSPGSLG<br>KLLCEVTPVSGQERFVWSSLDTPSQRSFSGPWLE<br>AQEAQLLSQPWQCQLYQGERLLGAAVYFTELSSP<br>GAQRSGRAPGALPAGHLLLFLILGVLSLLLLVTGA<br>FGFHLWRRQWRPRRFSALEQGIHPPQAQSKIEELE<br>QEPEPEPEPEPEPEPEPEPEQL |
| 217 | Human LAG-3 fragment | LQPGAEVPVVWAQEGAPAQLPCSPTIPLQDLSLLR<br>RAGVTWQHQPDSGPPAAAPGHPLAPGPHPAAPSS<br>WGPRPRRYTVLSVGPGGLRSGRLPLQPRVQLDER<br>GRQRGDFSLWLRPARRADAGEYRAAVHLRDRAL<br>SCRLRLRLGQASMTASPPGSLRASDWVILNCSFSR<br>PDRPASVHWFRNRGQGRVPVRESPHRHLAESFLF<br>LPQVSPMDSGPWGCILTYRDGFNVSIMYNLTVLG<br>LEPPTPLTVYAGAGSRVGLPCRLPAGVGTRSFLTA<br>KWTPPGGGPDLLVTGDNGDFTLRLEDVSQAQAG<br>TYTCHIHLQEQQLNATVTLAIITVTPKSFGSPGSLG<br>KLLCEVTPVSGQERFVWSSLDTPSQRSFSGPWLE<br>AQEAQLLSQPWQCQLYQGERLLGAAVYFTELSSP<br>GAQRSGRAPGALPAGHL |
| 199 | Human LAG-3 30 amino acid loop | GPPAAAPGHPLAPGPHPAAPSSWGPRPRRY |
| 211 | LAG-3 epitope | PTIPLQD |
| 212 | LAG-3 epitope | SPTIPLQD |
| 213 | LAG-3 epitope | SPTIPLQDL |
| 214 | LAG-3 epitope | SPTIPLQDLS |
| 215 | LAG-3 epitope | SPTIPLQDLSL |
| 216 | LAG-3 epitope | SPTIPLQDLSLL |

In certain embodiments, the instant disclosure provides an isolated antibody that specifically binds to LAG-3 (e.g., human LAG-3), the antibody comprising a VH domain comprising one, two, or all three of the CDRs of a VH domain set forth in Tables 1, 2, 6, and 7 herein. In certain embodiments, the antibody comprises the CDRH1 of one of the VH domains set forth in Tables 1, 2, 6, and 7. In certain embodiments, the antibody comprises the CDRH2 of one of the VH domains set forth in Tables 1, 2, 6, and 7. In certain embodiments, the antibody comprises the CDRH3 of one of the VH domains set forth in Tables 1, 2, 6, and 7.

In certain embodiments, the instant disclosure provides an isolated antibody that specifically binds to LAG-3 (e.g., human LAG-3), the antibody comprising a VL domain comprising one, two, or all three of the CDRs of a VL domain disclosed in Tables 1, 3, 6, and 7 herein. In certain embodiments, the antibody comprises the CDRL1 of one of the VL domains set forth in Tables 1, 3, 6, and 7. In certain embodiments, the antibody comprises the CDRL2 of one of the VL domains set forth in Tables 1, 3, 6, and 7. In certain embodiments, the antibody comprises the CDRL3 of one of the VL domains set forth in Tables 1, 3, 6, and 7.

In certain embodiments, the CDRs of an antibody can be determined according to Rabat et al., J. Biol. Chem. 252, 6609-6616 (1977) and Rabat et al., Sequences of protein of immunological interest (1991), each of which is herein incorporated by reference in its entirety.

In certain embodiments, the instant disclosure provides an isolated antibody that specifically binds to LAG-3 (e.g., human LAG-3), the antibody comprising the Rabat VH CDRs of a VH disclosed in Tables 1, 6, and 7 herein. In certain embodiments, the instant disclosure provides an isolated antibody that specifically binds to LAG-3 (e.g., human LAG-3), the antibody comprising the Rabat VL CDRs of a VL disclosed in Tables 1, 6, and 7 herein. In certain embodiments, the instant disclosure provides an isolated antibody that specifically binds to LAG-3 (e.g., human LAG-3), the antibody comprising the Kabat VH CDRs and Kabat VL CDRs of an antibody disclosed in Tables 1, 6, and 7 herein.

In certain embodiments, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties). Typically, when using the Kabat numbering convention, the Chothia CDRH1 loop is present at heavy chain amino acids 26 to 32, 33, or 34, the Chothia CDRH2 loop is present at heavy chain amino acids 52 to 56, and the Chothia CDRH3 loop is present at heavy chain amino acids 95 to 102, while the Chothia CDRL1 loop is present at light chain amino acids 24 to 34, the Chothia CDRL2 loop is present at light chain amino acids 50 to 56, and the Chothia CDRL3 loop is present at light chain amino acids 89 to 97. The end of the Chothia CDRH1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain embodiments, the instant disclosure provides an isolated antibody that specifically binds to LAG-3 (e.g., human LAG-3), the antibody comprising the Chothia VH CDRs of a VH disclosed in Tables 1, 6, and 7 herein. In certain embodiments, the instant disclosure provides an isolated antibody that specifically binds to LAG-3 (e.g., human LAG-3), the antibody comprising the Chothia VL CDRs of a VL disclosed in Tables 1, 6, and 7 herein. In certain embodiments, the instant disclosure provides an isolated antibody that specifically binds to LAG-3 (e.g., human LAG-3), the antibody comprising the Chothia VH CDRs and Chothia VL CDRs of an antibody disclosed in Tables 1, 6, and 7 herein. In certain embodiments, antibodies that specifically bind to LAG-3 (e.g., human LAG-3) comprise one or more CDRs, in which the Chothia and Kabat CDRs have the same amino acid sequence. In certain embodiments, the instant disclosure provides an isolated antibody that specifically binds to LAG-3 (e.g., human LAG-3) and comprises combinations of Kabat CDRs and Chothia CDRs.

In certain embodiments, the CDRs of an antibody can be determined according to the IMGT numbering system as described in Lefranc M-P, (1999) The Immunologist 7: 132-136 and Lefranc M-P et al., (1999) Nucleic Acids Res 27: 209-212, each of which is herein incorporated by reference in its entirety. According to the IMGT numbering scheme, CDRH1 is at positions 26 to 35, CDRH2 is at positions 51 to 57, CDRH3 is at positions 93 to 102, CDRL1 is at positions 27 to 32, CDRL2 is at positions 50 to 52, and CDRL3 is at positions 89 to 97.

In certain embodiments, the instant disclosure provides antibodies that specifically bind to LAG-3 (e.g., human LAG-3) and comprise CDRs of an antibody disclosed in Tables 1, 6, and 7 herein, as determined by the IMGT numbering system, for example, as described in Lefranc M-P (1999) supra and Lefranc M-P et al., (1999) supra.

In certain embodiments, the CDRs of an antibody can be determined according to the AbM numbering scheme, which refers to AbM hypervariable regions, which represent a compromise between the Rabat CDRs and Chothia structural loops, and are used by Oxford Molecular's AbM antibody modeling software (Oxford Molecular Group, Inc.). In a particular embodiment, the instant disclosure provides antibodies that specifically bind to LAG-3 (e.g., human LAG-3) and comprise CDRs of an antibody disclosed in Tables 1, 6, and 7 herein as determined by the AbM numbering scheme.

In certain embodiments, the CDRs of an antibody can be determined according to MacCallum R M et al., (1996) J Mol Biol 262: 732-745, which is herein incorporated by reference in its entirety. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001), which is herein incorporated by reference in its entirety. In a particular embodiment, the instant disclosure provides antibodies that specifically bind to LAG-3 (e.g., human LAG-3) and comprise CDRs of an antibody disclosed in Tables 1, 6, and 7 herein as described in MacCallum R M et al., (1996) supra.

In certain embodiments, the instant disclosure provides an isolated antibody that specifically binds to LAG-3 (e.g., human LAG-3), wherein the antibody comprises a heavy chain variable region comprising the CDRH1, CDRH2, and CDRH3 region amino acid sequences of a VH domain set forth in SEQ ID NO: 1, 3, 5, 7, 9, 11, 13, 14, 15, 17, 19, 20, 22, 24, 27, 29, 31, 33, 35, 36, 38, 39, 42, 45, 46, 48, 51, 53, 54, 56, 57, 58, 59, 60, 61, 62, 63, 64, 65, 66, 67, 68, 69, 70, 71, or 72, and a light chain variable region comprising the CDRL1, CDRL2, and CDRL3 region amino acid sequences of a VL domain set forth in SEQ ID NO: 2, 4, 6, 8, 10, 12, 16, 18, 21, 23, 25, 26, 28, 30, 32, 34, 37, 40, 41, 43, 44, 47, 49, 50, 52, 55, 73, 74, 75, 76, or 77, wherein each CDR is defined in accordance with the Kabat definition, the Chothia definition, the combination of the Kabat definition and the Chothia definition, the IMGT numbering system, the AbM definition, or the MacCallum definition of CDR.

In certain embodiments, the instant disclosure provides an isolated antibody that specifically binds to LAG-3 (e.g., human LAG-3), the antibody comprising:
- (a) a CDRH1 comprises the amino acid sequence of $DX_1YX_2X_3$ (SEQ ID NO: 140), wherein
  $X_1$ is T or N,
  $X_2$ is I or M, and
  $X_3$ is H, Y or D; and/or
- (b) a CDRH2 comprises the amino acid sequence of $X_1IDPANX_2X_3X_4X_5X_6X_7PX_8X_9QX_{10}$ (SEQ ID NO: 142), wherein
  $X_1$ is E, R, S, or K,
  $X_2$ is D or G,
  $X_3$ is N or H,
  $X_4$ is T or S,
  $X_5$ is K or H,
  $X_6$ is Y or F,
  $X_7$ is D or A,
  $X_8$ is K or R,
  $X_9$ is F or L, and
  $X_{10}$ is G or D; and/or
- (c) a CDRH3 comprises the amino acid sequence of $YX_1X_2X_3\ YX_4VGGX_5DY$ (SEQ ID NO: 144), wherein
  $X_1$ is Y, F, or S,
  $X_2$ is Y or D,
  $X_3$ is K or R,
  $X_4$ is D or E, and
  $X_5$ is F or C; and/or
- (d) a CDRL1 comprises the amino acid sequence of $SVSSX_1SSSX_2LX_3$ (SEQ ID NO: 147), wherein
  $X_1$ is S or G,
  $X_2$ is N or T, and
  $X_3$ is H or Y; and/or
- (e) a CDRL2 comprises the amino acid sequence of GTSNLAS (SEQ ID NO: 104); and/or
- (f) a CDRL3 comprises the amino acid sequence of $QQWX_1X_2YPX_3T$ (SEQ ID NO: 149), wherein
  $X_1$ is S, N, or R,
  $X_2$ is S, T or R, and
  $X_3$ is F, L, H, or W.

In certain embodiments, CDRH1 comprises the amino acid sequence of $DX_1YX_2X_3$ (SEQ ID NO: 141), wherein: $X_1$ is T or N; $X_2$ is I or M; and $X_3$ is H or Y. In certain embodiments, CDRH2 comprises the amino acid sequence of $X_1IDPANX_2X_3X_4KX_5X_6PX_7FQX_8$ (SEQ ID NO: 143), wherein: $X_1$ is E, R, or S; $X_2$ is D or G; $X_3$ is N or H; $X_4$ is T or S; $X_5$ is Y or F; $X_6$ is D or A; $X_7$ is K or R; and $X_8$ is G or D. In certain embodiments, CDRH3 comprises the amino acid sequence of $YX_1X_2X_3YDVGGX_4DY$ (SEQ ID NO: 145), wherein: $X_1$ is Y, F, or S; $X_2$ is Y or D; $X_3$ is K or R; and $X_4$ is F or C. In certain embodiments, CDRH3 comprises the amino acid sequence of $YYYX_1YX_2VGGFDY$ (SEQ ID NO: 146), wherein: $X_1$ is K or R; and $X_2$ is D or E. In certain embodiments, CDRL1 comprises the amino acid sequence of $SVSSSISSSNLX_1$ (SEQ ID NO: 148), wherein: $X_1$ is H or Y. In certain embodiments, CDRL3 comprises the amino acid sequence of $QQWX_1SYPX_2T$ (SEQ ID NO: 150), wherein: $X_1$ is S, N, or R; and $X_2$ is F, L, or H.

In certain embodiments, the instant disclosure provides an isolated antibody that specifically binds to LAG-3 (e.g., human LAG-3), the antibody comprising:
- (a) a CDRH1 comprises the amino acid sequence of DTYIH (SEQ ID NO: 79); and/or
- (b) a CDRH2 comprises the amino acid sequence of EIDPANDNTKYDPKFQG (SEQ ID NO: 90); and/or
- (c) a CDRH3 comprises the amino acid sequence of $YYYX_1\ YX_2VGGFDY$ (SEQ ID NO: 146), wherein: $X_1$ is K or R; and $X_2$ is D or E; and/or
- (d) a CDRL1 comprises the amino acid sequence of SVSSSISSSNLH (SEQ ID NO: 100); and/or
- (e) a CDRL2 comprises the amino acid sequence of GTSNLAS (SEQ ID NO: 104); and/or
- (f) a CDRL3 comprises the amino acid sequence of QQWSSYPFT (SEQ ID NO: 105).

In certain embodiments, CDRH1 comprises an amino acid sequence selected from the group consisting of SEQ ID NOs: 78-82. In certain embodiments, CDRH2 comprises an amino acid sequence selected from the group consisting of SEQ ID NOs: 83-93. In certain embodiments, CDRH3 comprises an amino acid sequence selected from the group consisting of SEQ ID NOs: 94-99. In certain embodiments, CDRL1 comprises an amino acid sequence selected from the group consisting of SEQ ID NOs: 100-103. In certain embodiments, CDRL3 comprises an amino acid sequence selected from the group consisting of SEQ ID NOs: 105-112.

In certain embodiments, the instant disclosure provides an isolated antibody that specifically binds to LAG-3 (e.g., human LAG-3), wherein the antibody comprises a VH domain comprising the CDRH1, CDRH2 and CDRH3 amino acid sequences set forth in SEQ ID NOs: 78, 83, and 94; 78, 85, and 95; 78, 86, and 96; 78, 86, and 97; 78, 91, and 94; 78, 92, and 96; 79, 84, and 95; 79, 88, and 95; 79, 89, and 95; 79, 90, and 95; 79, 90, and 98; 79, 90, and 99; 80, 85, and 96; 81, 87, and 96; or, 82, 93, and 95, respectively. In certain embodiments, the instant disclosure provides an isolated antibody that specifically binds to LAG-3 (e.g., human LAG-3), wherein the antibody comprises a VH domain comprising the CDRH1, CDRH2 and CDRH3 amino acid sequences set forth in SEQ ID NOs: 79, 90, and 95, respectively. In certain embodiments, the instant disclosure provides an isolated antibody that specifically binds to LAG-3 (e.g., human LAG-3), wherein the antibody comprises a VH domain comprising the CDRH1, CDRH2 and CDRH3 amino acid sequences set forth in SEQ ID NOs: 79, 90, and 98, respectively.

In certain embodiments, the instant disclosure provides an isolated antibody that specifically binds to LAG-3 (e.g., human LAG-3), wherein the antibody comprises a VL domain comprising the CDRL1, CDRL2 and CDRL3 amino acid sequences set forth in SEQ ID NOs: 100, 104, and 105; 100, 104, and 106; 100, 104, and 107; 100, 104, and 109; 100, 104, and 110; 101, 104, and 108; 102, 104, and 105; 102, 104, and 112; or, 103, 104, and 111, respectively. In certain embodiments, the instant disclosure provides an isolated antibody that specifically binds to LAG-3 (e.g., human LAG-3), wherein the antibody comprises a VL domain comprising the CDRL1, CDRL2 and CDRL3 amino acid sequences set forth in SEQ ID NOs: 100, 104, and 105, respectively.

In certain embodiments, the instant disclosure provides an isolated antibody that specifically binds to LAG-3 (e.g., human LAG-3), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 78, 83, 94, 100, 104, and 105; 78, 85, 95, 100, 104, and 105; 78, 86, 96, 100, 104, and 105; 78, 86, 96, 100, 104, and 109; 78, 86, 96, 100, 104, and 110; 78, 86, 96, 101, 104, and 108; 78, 86, 96, 103, 104, and 111; 78, 86, 97, 102, 104, and 112; 78, 91, 94, 100, 104, and 107; 78, 92, 96, 100, 104, and 105; 78, 92, 96, 100, 104, and 109; 79, 84, 95, 100, 104, and 105; 79, 84, 95, 100, 104, and 106; 79, 84, 95, 102, 104, and 105; 79, 88, 95, 100, 104, and 105; 79, 89, 95, 100, 104, and 105; 79, 90, 95, 100, 104, and 105; 79, 90, 98, 100, 104, and 105; 79, 90, 99, 100, 104, and 105; 80, 85, 96, 100, 104, and 105; 81, 87, 96, 100, 104, and 105; 81, 87, 96, 100, 104, and 107; or, 82, 93, 95, 100, 104, and 105, respectively. In certain embodiments, the instant disclosure provides an isolated antibody that specifically binds to LAG-3 (e.g., human LAG-3), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 79, 90, 95, 100, 104, and 105, respectively. In certain embodiments, the instant disclosure provides an isolated antibody that specifically binds to LAG-3 (e.g., human LAG-3), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 79, 90, 98, 100, 104, and 105, respectively.

In certain embodiments, the instant disclosure provides an isolated antibody that specifically binds to LAG-3 (e.g., human LAG-3), wherein the antibody comprises a heavy chain variable region (VH) comprising one, two or all three of the VH CDRs of an antibody in Tables 1, 2, 6, and 7. In some embodiments, the antibody comprises one, two, three or all four of the VH framework regions described herein. In specific embodiments, the antibody comprises one, two, three or all four of the VH framework regions (FRs) set forth in Table 4 (e.g., one, two, three, or four of the framework regions in one row in Table 4). In certain embodiments, the antibody comprises one, two, three or all four of the framework regions of the heavy chain variable region sequence of SEQ ID NO: 151 or 222. In certain embodiments, the antibody comprises one, two, three or all four of the framework regions of the heavy chain variable region sequence of SEQ ID NO: 218 or 223. In certain embodiments, the antibody comprises one, two, three or four of the framework regions of a heavy chain variable region sequence which is at least 75%, 80%, 85%, 90%, 95%, or 100% (e.g., at least 86, 87, 88, 89, 90, 91, 92, 93, 94, 95, 96, 97, 98 or 99%) identical to one, two, three or four of the framework regions of a heavy chain variable region sequence selected from the group consisting of SEQ ID NOs: 56-72 and 220. In certain embodiments, the antibody comprises a heavy chain variable framework region that is or is derived from an amino acid sequence encoded by a human gene, wherein the amino acid sequence is selected from the group consisting of IGHV1-46 (e.g., IGHV1-46*01, e.g., having the amino acid sequence of SEQ ID NO: 153), IGHV1-69-2 (e.g., IGHV1-69-2*01, e.g., having the amino acid sequence of SEQ ID NO: 154), IGHV1-3 (e.g., IGHV1-3*01, e.g., having the amino acid sequence of SEQ ID NO: 155), IGHV1-24 (e.g., IGHV1-24*01, e.g., having the amino acid sequence of SEQ ID NO: 156), IGHV1-2 (e.g., IGHV1-2*01, e.g., having the amino acid sequence of SEQ ID NO: 157), IGHV1-45 (e.g., IGHV1-45*01, e.g., having the amino acid sequence of SEQ ID NO: 158), and IGHV1-18 (e.g., IGHV1-18*01, e.g., having the amino acid sequence of SEQ ID NO: 159). In specific embodiments, the heavy chain variable framework region that is derived from said amino acid sequence consists of said amino acid sequence but for the presence of up to 20 amino acid substitutions, deletions, and/or insertions, preferably up to 20 amino acid substitutions. In a particular embodiment, the heavy chain variable framework region that is derived from said amino acid sequence consists of said amino acid sequence with 1, 2, 3, 4, 5, 6, 7, 8, 9, 10, 11, 12, 13, 14, 15, 16, 17, 18, 19, or 20 amino acid residues being substituted for an amino acid found in an analogous position in a corresponding non-human heavy chain variable framework region. In some embodiments, the antibody comprises a heavy chain variable framework region that is derived from the amino acid sequence of SEQ ID NO: 153), wherein at least one amino acid in the amino acid sequence of SEQ ID NO: 153 is substituted with an amino acid in an analogous position in a corresponding non-human heavy chain variable framework region. In a specific embodiment, the amino acid substitution is at an amino acid position selected from the group consisting of 4, 5, 12, 23, 27, 28, 29, 30, 48, 69, 71, 75, 76, 80, 81, and 94, wherein the amino acid position is indicated according to the Kabat numbering system. In particular embodiments, the amino acid substitution is selected from the group consisting of 4M, 5K, 12V, 23T, 27F, 28N, 29I, 30K, 48I, 69I, 71A, 75S, 76N, 80L, 81Q, and 94T, wherein the position of the amino acid substitution is indicated according to the Kabat numbering system. In another specific embodiment, the amino acid substitution is at an amino acid position selected from the group consisting of 4, 27, 28, 29, 30, 69, 71, and 94, wherein the amino acid position is indicated according to the Kabat numbering system. In particular embodiments, the amino acid substitution is selected from the group consisting of 4M, 27F, 28N, 29I, 30K, 69I, 71A, and 94T, wherein the position of the amino acid substitution is indicated according to the Kabat numbering system.

In certain embodiments, the instant disclosure provides an isolated antibody that specifically binds to LAG-3 (e.g., human LAG-3), wherein the antibody comprises a light chain variable region (VH) comprising one, two or all three of the VL CDRs of an antibody in Tables 1, 3, 6, and 7. In some embodiments, the antibody comprises one, two, three or all four of the VL framework regions described herein. In specific embodiments, the antibody comprises one, two, three or all four of the VL framework regions (FRs) set forth in Table 5 (e.g., one, two, three, or four of the framework regions in one row in Table 5). In certain embodiments, the antibody comprises one, two, three or all four of the framework regions of the light chain variable region sequence of SEQ ID NO: 152 or 224. In certain embodiments, the antibody comprises one, two, three or four of the framework regions of a light chain variable region sequence which is at least 75%, 80%, 85%, 90%, 95%, or 100% (e.g., at least 86, 87, 88, 89, 90, 91, 92, 93, 94, 95, 96, 97, 98 or 99%) identical to one, two, three or four of the framework regions of a light chain variable region sequence selected from the group consisting of SEQ ID NOs: 73-77. In certain embodiments, the antibody comprises a light chain variable framework region that is or is derived from an amino acid sequence encoded by a human gene, wherein the amino acid sequence is selected from the group consisting of IGKV3-20 (e.g., IGKV3-20*01, e.g., having the amino acid sequence of SEQ ID NO: 160), IGKV3D-15 (e.g., IGKV3D-15*01, e.g., having the amino acid sequence of SEQ ID NO: 161), IGKV3-15 (e.g., IGKV3-15*01, e.g., having the amino acid sequence of SEQ ID NO: 161), IGKV3D-20 (e.g., IGKV3D-20*01, e.g., having the amino acid sequence of SEQ ID NO: 162), IGKV3D-7 (e.g., IGKV3D-7*01, e.g., having the amino acid sequence of SEQ ID NO: 163), IGKV1-9 (e.g., IGKV1-9*01, e.g., having the amino acid sequence of SEQ ID NO: 164), and IGKV3-11 (e.g., IGKV3-11*01, e.g., having the amino acid sequence of SEQ ID NO: 165). In specific embodiments, the light chain variable framework region that is derived from said amino acid sequence consists of said amino acid sequence but for the presence of up to 20 amino acid substitutions, deletions, and/or insertions, preferably up to 20 amino acid substitutions. In a particular embodiment, the light chain variable framework region that is derived from said amino acid sequence consists of said amino acid sequence with 1, 2, 3, 4, 5, 6, 7, 8, 9, 10, 11, 12, 13, 14, 15, 16, 17, 18, 19, or 20 amino acid residues being substituted for an amino acid found in an analogous position in a corresponding non-human light chain variable framework region. In some embodiments, the antibody comprises a light chain variable framework region that is derived from the amino acid sequence of SEQ ID NO: 160, wherein at least one amino acid in the amino acid sequence of SEQ ID NO: 160 is substituted with an amino acid in an analogous position in a corresponding non-human light chain variable framework region. In a specific embodiment, the amino acid substitution is at an amino acid position selected from the group consisting of 3, 22, 36, 43, 47, 58, 70, and 71, wherein the amino acid position is indicated according to the Kabat numbering system. In particular embodiments, the amino acid substitution is selected from the group consisting of 3L, 22T, 36F, 43S, 47W, 58V, 70S, and 71Y, wherein the position of the amino acid substitution is indicated according to the Kabat numbering system.

In certain embodiments, the instant disclosure provides an isolated antibody that specifically binds to LAG-3 (e.g., human LAG-3), wherein the antibody comprises a heavy chain variable region (VH) comprising one, two or all three of the VH CDRs of an antibody in Tables 1, 2, 6, and 7 (e.g., the VH CDRs in one row of Table 2) and a light chain variable region (VL) comprising one, two or all three of the VL CDRs of an antibody in Tables 1, 3, 6, and 7 (e.g., the VL CDRs in one row of Table 3). In some embodiments, the antibody comprises the VH framework regions and the VL framework regions described herein. In specific embodiments, the antibody comprises the VH framework regions (FRs) set forth in Table 4 (e.g., one, two, three, or four of the framework regions in one row in Table 4) and the VL framework regions (FRs) set forth in Table 5 (e.g., one, two, three, or four of the framework regions in one row in Table 5).

In certain embodiments, the instant disclosure provides an isolated antibody that specifically binds to LAG-3 (e.g., human LAG-3), wherein the antibody comprises a VH domain comprising the CDRH1, CDRH2 and CDRH3 amino acid sequences set forth in SEQ ID NOs: 79, 90, and 95; or 79, 90, and 98, respectively. In certain embodiments, the antibody comprises one, two, three or all four VH framework regions derived from the VH of a human or primate antibody. In some embodiments, the antibody comprises VH framework regions of an antibody set forth in Table 4.

In certain embodiments, the instant disclosure provides an isolated antibody that specifically binds to LAG-3 (e.g., human LAG-3), wherein the antibody comprises a VL domain comprising the CDRL1, CDRL2 and CDRL3 amino acid sequences set forth in SEQ ID NOs: 100, 104, and 105, respectively. In certain embodiments, the antibody comprises one, two, three or all four VL framework regions derived from the VL of a human or primate antibody. In some embodiments, the antibody comprises VL framework regions of an antibody set forth in Table 5.

In certain embodiments, the instant disclosure provides an isolated antibody that specifically binds to LAG-3 (e.g., human LAG-3), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 79, 90, 95, 100, 104, and 105; or 79, 90, 98, 100, 104, and 105, respectively. In certain embodiments, the antibody comprises one, two, three or all four VH framework regions derived from the VH of a human or primate antibody and one, two, three or all four VL framework regions derived from the VL of a human or primate antibody. In some embodiments, the antibody comprises VH framework regions and VL framework regions of an antibody set forth in Tables 4 and 5, respectively.

In certain embodiments, the instant disclosure provides an isolated antibody that specifically binds to LAG-3 (e.g., human LAG-3), comprising a heavy chain variable region comprising an amino acid sequence of SEQ ID NO: 151 or 222. In certain embodiments, the instant disclosure provides an isolated antibody that specifically binds to LAG-3 (e.g., human LAG-3), comprising a heavy chain variable region comprising an amino acid sequence of SEQ ID NO: 218 or 223. In certain embodiments, the instant disclosure provides an isolated antibody that specifically binds to LAG-3 (e.g., human LAG-3), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 56, 57, 58, 59, 60, 61, 62, 63, 64, 65, 220, 66, 67, 68, 69, 70, 71, or 72. In certain embodiments, the antibody comprises a heavy chain variable region having the amino acid sequence set forth in SEQ ID NO: 56, 57, 58, 59, 60, 61, 62, 63, 64, 65, 220, 66, 67, 68, 69, 70, 71, or 72, optionally wherein the amino acid residue at position 1 of the heavy chain variable region has been converted to pyroglutamate. In certain embodiments, the antibody comprises a heavy chain variable region having the amino acid sequence set forth in SEQ ID NO: 65. In certain embodiments, the antibody comprises a heavy chain variable region having the amino acid sequence set forth in SEQ ID NO: 220. In certain embodiments, the X in SEQ ID NO: 220 is Q. In certain embodiments, the X in SEQ ID NO: 220 is pyroglutamate. In certain embodiments, the antibody comprises a heavy chain having the amino acid sequence set forth in SEQ ID NO: 168, 225, 169, 226, 170, 227, 171, 172, 173, 174, 175, 176, 177, 178, 179, 180, 181, 182, 183, 184, 185, or 186, optionally wherein the amino acid residue at position 1 of the heavy chain has been converted to pyroglutamate. In certain embodiments, the antibody comprises a heavy chain having the amino acid sequence set forth in SEQ ID NO: 168. In certain embodiments, the antibody comprises a heavy chain having the amino acid sequence set forth in SEQ ID NO: 225. In certain embodiments, the X in SEQ ID NO: 225 is Q. In certain embodiments, the X in SEQ ID NO: 225 is pyroglutamate. In certain embodiments, the antibody comprises a heavy chain having the amino acid sequence set forth in SEQ ID NO: 169. In certain embodiments, the antibody comprises a heavy chain having the amino acid sequence set forth in SEQ ID NO: 226. In certain embodiments, the X in SEQ ID NO: 226 is Q. In certain embodiments, the X in SEQ ID NO: 226 is pyroglutamate. In certain embodiments, the antibody comprises a heavy chain having the amino acid sequence set forth in SEQ ID NO: 170. In certain embodiments, the antibody comprises a heavy chain having the amino acid sequence set forth in SEQ ID NO: 227. In certain embodiments, the X in SEQ ID NO: 227 is Q. In certain embodiments, the X in SEQ ID NO: 227 is pyroglutamate.

In certain embodiments, the instant disclosure provides an isolated antibody that specifically binds to LAG-3 (e.g., human LAG-3), comprising a light chain variable region comprising an amino acid sequence of SEQ ID NO: 152 or 224. In certain embodiments, the instant disclosure provides an isolated antibody that specifically binds to LAG-3 (e.g., human LAG-3), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 73, 74, 75, 76, or 77. In certain embodiments, the antibody comprises a light chain variable region having the amino acid sequence set forth in SEQ ID NO: 73, 74, 75, 76, or 77, optionally wherein the amino acid residue at position 1 of the light chain variable region has been converted to pyroglutamate. In certain embodiments, the antibody comprises a light chain variable region having the amino acid sequence set forth in SEQ ID NO: 73. In certain embodiments, the antibody comprises a light chain variable region having the amino acid sequence set forth in SEQ ID NO: 221. In certain embodiments, the X in SEQ ID NO: 221 is E. In certain embodiments, the X in SEQ ID NO: 221 is pyroglutamate. In certain embodiments, the antibody comprises a light chain variable region having the amino acid sequence set forth in SEQ ID NO: 187, 188, 189, 190, or 191, optionally wherein the amino acid residue at position 1 of the light chain has been converted to pyroglutamate. In certain embodiments, the antibody comprises a light chain variable region having the amino acid sequence set forth in SEQ ID NO: 187. In certain embodiments, the antibody comprises a light chain variable region having the amino acid sequence set forth in SEQ ID NO: 228. In certain embodiments, the X in SEQ ID NO: 228 is E. In certain embodiments, the X in SEQ ID NO: 228 is pyroglutamate.

In certain embodiments, the instant disclosure provides an isolated antibody that specifically binds to LAG-3 (e.g., human LAG-3), comprising a heavy chain variable region comprising an amino acid sequence of SEQ ID NO: 151 or 222, and a light chain variable region comprising an amino acid sequence of SEQ ID NO: 152 or 224. In certain embodiments, the instant disclosure provides an isolated antibody that specifically binds to LAG-3 (e.g., human LAG-3), comprising a heavy chain variable region comprising an amino acid sequence of SEQ ID NO: 218 or 223, and a light chain variable region comprising an amino acid sequence of SEQ ID NO: 152 or 224. In certain embodiments, the instant disclosure provides an isolated antibody that specifically binds to LAG-3 (e.g., human LAG-3), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 56, 57, 58, 59, 60, 61, 62, 63, 64, 65, 220, 66, 67, 68, 69, 70, 71, or 72, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 73, 221, 74, 75, 76, or 77. In certain embodiments, the antibody comprises a heavy chain variable region having the amino acid sequence set forth in SEQ ID NO: 56, 57, 58, 59, 60, 61, 62, 63, 64, 65, 220, 66, 67, 68, 69, 70, 71, or 72, and a light chain variable region having the amino acid sequence set forth in SEQ ID NO: 73, 221, 74, 75, 76, or 77. In certain embodiments, the antibody comprises a heavy chain variable region and light chain variable region having the amino acid sequences set forth in SEQ ID NO: 56 and 73; 56 and 74; 56 and 75; 56 and 76; 56 and 77; 57 and 73; 57 and 74; 57 and 75; 57 and 76; 57 and 77; 58 and 73; 58 and 74; 58 and 75; 58 and 76; 58 and 77; 59 and 73; 59 and 74; 59 and 75; 59 and 76; 59 and 77; 60 and 73; 60 and 74; 60 and 75; 60 and 76; 60 and 77; 61 and 77; 62 and 77; 63 and 73; 64 and 73; 65 and 73; 220 and 73; 65 and 221; 220 and 221; 66 and 73; 67 and 73; 68 and 73; 69 and 73; 70 and 73; 71 and 73; or 72 and 73, respectively. In certain embodiments, the antibody comprises a heavy chain variable region and light chain variable region having the amino acid sequences set forth in SEQ ID NO: 56 and 73, respectively. In certain embodiments, the antibody comprises a heavy chain variable region and light chain variable region having the amino acid sequences set forth in SEQ ID NO: 220 and 221, respectively. In certain embodiments, the X in SEQ ID NO: 220 is Q. In certain embodiments, the X in SEQ ID NO: 220 is pyroglutamate. In certain embodiments, the X in SEQ ID NO: 221 is E. In certain embodiments, the X in SEQ ID NO: 221 is pyroglutamate. In certain embodiments, the X in SEQ ID NO: 220 is Q, and the X in SEQ ID NO: 221 is E. In certain embodiments, the X in SEQ ID NO: 220 is Q, and the X in SEQ ID NO: 221 is pyroglutamate. In certain embodiments, the X in SEQ ID NO: 220 is pyroglutamate, and the X in SEQ ID NO: 221 is E. In certain embodiments, the X in SEQ ID NO: 220 is pyroglutamate, and the X in SEQ ID NO: 221 is pyroglutamate. In certain embodiments, the antibody comprises a heavy chain variable region and light chain variable region having the amino acid sequences set forth in SEQ ID NO: 56 and 74, respectively. In certain embodiments, the antibody comprises a heavy chain variable region and light chain variable region having the amino acid sequences set forth in SEQ ID NO: 56 and 75, respectively. In certain embodiments, the antibody comprises a heavy chain variable region and light chain variable region having the amino acid sequences set forth in SEQ ID NO: 56 and 76, respectively. In certain embodiments, the antibody comprises a heavy chain variable region and light chain variable region having the amino acid sequences set forth in SEQ ID NO: 56 and 77, respectively. In certain embodiments, the antibody comprises a heavy chain variable region and light chain variable region having the amino acid sequences set forth in SEQ ID NO: 57 and 73, respectively. In certain embodiments, the antibody comprises a heavy chain variable region and light chain variable region having the amino acid sequences set forth in SEQ ID NO: 57 and 74, respectively. In certain embodiments, the antibody comprises a heavy chain variable region and light chain variable region having the amino acid sequences set forth in SEQ ID NO: 57 and 75, respectively. In certain embodiments, the antibody comprises a heavy chain variable region and light chain variable region having the amino acid sequences set forth in SEQ ID NO: 57 and 76, respectively. In certain embodiments, the antibody comprises a heavy chain variable region and light chain variable region having the amino acid sequences set forth in SEQ ID NO: 57 and 77, respectively. In certain embodiments, the antibody comprises a heavy chain variable region and light chain variable region having the amino acid sequences set forth in SEQ ID NO: 58 and 73, respectively. In certain embodiments, the antibody comprises a heavy chain variable region and light chain variable region having the amino acid sequences set forth in SEQ ID NO: 58 and 74, respectively. In certain embodiments, the antibody comprises a heavy chain variable region and light chain variable region having the amino acid sequences set forth in SEQ ID NO: 58 and 75, respectively. In certain embodiments, the antibody comprises a heavy chain variable region and light chain variable region having the amino acid sequences set forth in SEQ ID NO: 58 and 76, respectively. In certain embodiments, the antibody comprises a heavy chain variable region and light chain variable region having the amino acid sequences set forth in SEQ ID NO: 58 and 77, respectively. In certain embodiments, the antibody comprises a heavy chain variable region and light chain variable region having the amino acid sequences set forth in SEQ ID NO: 59 and 73, respectively. In certain embodiments, the antibody comprises a heavy chain variable region and light chain variable region having the amino acid sequences set forth in SEQ ID NO: 59 and 74, respectively. In certain embodiments, the antibody comprises a heavy chain variable region and light chain variable region having the amino acid sequences set forth in SEQ ID NO: 59 and 75, respectively. In certain embodiments, the antibody comprises a heavy chain variable region and light chain variable region having the amino acid sequences set forth in SEQ ID NO: 59 and 76, respectively. In certain embodiments, the antibody comprises a heavy chain variable region and light chain variable region having the amino acid sequences set forth in SEQ ID NO: 59 and 77, respectively. In certain embodiments, the antibody comprises a heavy chain variable region and light chain variable region having the amino acid sequences set forth in SEQ ID NO: 60 and 73, respectively. In certain embodiments, the antibody comprises a heavy chain variable region and light chain variable region having the amino acid sequences set forth in SEQ ID NO: 60 and 74, respectively. In certain embodiments, the antibody comprises a heavy chain variable region and light chain variable region having the amino acid sequences set forth in SEQ ID NO: 60 and 75, respectively. In certain embodiments, the antibody comprises a heavy chain variable region and light chain variable region having the amino acid sequences set forth in SEQ ID NO: 60 and 76, respectively. In certain embodiments, the antibody comprises a heavy chain variable region and light chain variable region having the amino acid sequences set forth in SEQ ID NO: 60 and 77, respectively. In certain embodiments, the antibody comprises a heavy chain variable region and light chain variable region having the amino acid sequences set forth in SEQ ID NO: 61 and 77, respectively. In certain embodiments, the antibody comprises a heavy chain variable region and light chain variable region having the amino acid sequences set forth in SEQ ID NO: 62 and 77, respectively. In certain embodiments, the antibody comprises a heavy chain variable region and light chain variable region having the amino acid sequences set forth in SEQ ID NO: 63 and 73, respectively. In certain embodiments, the antibody comprises a heavy chain variable region and light chain variable region having the amino acid sequences set forth in SEQ ID NO: 64 and 73, respectively. In certain embodiments, the antibody comprises a heavy chain variable region and light chain variable region having the amino acid sequences set forth in SEQ ID NO: 65 and 73, respectively. In certain embodiments, the antibody comprises a heavy chain variable region and light chain variable region having the amino acid sequences set forth in SEQ ID NO: 66 and 73, respectively. In certain embodiments, the antibody comprises a heavy chain variable region and light chain variable region having the amino acid sequences set forth in SEQ ID NO: 67 and 73, respectively. In certain embodiments, the antibody comprises a heavy chain variable region and light chain variable region having the amino acid sequences set forth in SEQ ID NO: 68 and 73, respectively. In certain embodiments, the antibody comprises a heavy chain variable region and light chain variable region having the amino acid sequences set forth in SEQ ID NO: 69 and 73, respectively. In certain embodiments, the antibody comprises a heavy chain variable region and light chain variable region having the amino acid sequences set forth in SEQ ID NO: 70 and 73, respectively. In certain embodiments, the antibody comprises a heavy chain variable region and light chain variable region having the amino acid sequences set forth in SEQ ID NO: 71 and 73, respectively. In certain embodiments, the antibody comprises a heavy chain variable region and light chain variable region having the amino acid sequences set forth in SEQ ID NO: 72 and 73, respectively. In certain embodiments, the amino acid residue at position 1 of the heavy chain variable region has been converted to pyroglutamate. In certain embodiments, the amino acid residue at position 1 of the light chain variable region has been converted to pyroglutamate. In certain embodiments, the amino acid residue at position 1 of the heavy chain variable region has been converted to pyroglutamate, and the amino acid residue at position 1 of the light chain variable region has been converted to pyroglutamate.

In certain embodiments, the instant disclosure provides an isolated antibody that cross-competes for binding to LAG-3 (e.g., human LAG-3) with an antibody comprising the heavy and light chain variable region amino acid sequences set forth in SEQ ID NOs: 1 and 2; 3 and 4; 5 and 6; 7 and 8; 9 and 10; 11 and 12; 13 and 10; 14 and 10; 15 and 16; 17 and 18; 19 and 8; 20 and 21; 22 and 23; 24 and 10; 9 and 25; 9 and 26; 20 and 2; 27 and 28; 29 and 30; 31 and 32; 33 and 34; 35 and 10; 36 and 37; 38 and 21; 39 and 40; 9 and 2; 9 and 41; 42 and 43; 9 and 44; 45 and 32; 46 and 47; 48 and 10; 20 and 49; 33 and 50; 51 and 52; 53 and 8; 38 and 2; or 54 and 55, respectively. In certain embodiments, the instant disclosure provides an isolated antibody that cross-competes for binding to LAG-3 (e.g., human LAG-3) with an antibody comprising the heavy and light chain variable region amino acid sequences set forth in SEQ ID NOs: 56 and 73; 56 and 74; 56 and 75; 56 and 76; 56 and 77; 57 and 73; 57 and 74; 57 and 75; 57 and 76; 57 and 77; 58 and 73; 58 and 74; 58 and 75; 58 and 76; 58 and 77; 59 and 73; 59 and 74; 59 and 75; 59 and 76; 59 and 77; 60 and 73; 60 and 74; 60 and 75; 60 and 76; 60 and 77; 61 and 77; 62 and 77; 63 and 73; 64 and 73; 65 and 73; 220 and 73; 65 and 221; 220 and 221; 66 and 73; 67 and 73; 68 and 73; 69 and 73; 70 and 73; 71 and 73; or 72 and 73, respectively.

In certain embodiments, the instant disclosure provides an isolated antibody that binds to the same or an overlapping epitope of LAG-3 (e.g., an epitope of human LAG-3) as an antibody described herein, e.g., an antibody comprising the heavy and light chain variable region amino acid sequences set forth in SEQ ID NOs: 1 and 2; 3 and 4; 5 and 6; 7 and 8; 9 and 10; 11 and 12; 13 and 10; 14 and 10; 15 and 16; 17 and 18; 19 and 8; 20 and 21; 22 and 23; 24 and 10; 9 and 25; 9 and 26; 20 and 2; 27 and 28; 29 and 30; 31 and 32; 33 and 34; 35 and 10; 36 and 37; 38 and 21; 39 and 40; 9 and 2; 9 and 41; 42 and 43; 9 and 44; 45 and 32; 46 and 47; 48 and 10; 20 and 49; 33 and 50; 51 and 52; 53 and 8; 38 and 2; or 54 and 55, respectively. In certain embodiments, the instant disclosure provides an isolated antibody that binds to the same or an overlapping epitope of LAG-3 (e.g., an epitope of human LAG-3) as an antibody described herein, e.g., an antibody comprising the heavy and light chain variable region amino acid sequences set forth in SEQ ID NOs: 56 and 73; 56 and 74; 56 and 75; 56 and 76; 56 and 77; 57 and 73; 57 and 74; 57 and 75; 57 and 76; 57 and 77; 58 and 73; 58 and 74; 58 and 75; 58 and 76; 58 and 77; 59 and 73; 59 and 74; 59 and 75; 59 and 76; 59 and 77; 60 and 73; 60 and 74; 60 and 75; 60 and 76; 60 and 77; 61 and 77; 62 and 77; 63 and 73; 64 and 73; 65 and 73; 220 and 73; 65 and 221; 220 and 221; 66 and 73; 67 and 73; 68 and 73; 69 and 73; 70 and 73; 71 and 73; or 72 and 73, respectively. In certain embodiments, the epitope of an antibody can be determined by, e.g., NMR spectroscopy, surface plasmon resonance (BIAcore®), X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giege R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, all of which are herein incorporated by reference in their entireties). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323, all of which are herein incorporated by reference in their entireties). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of an antibody is determined using alanine scanning mutagenesis studies. In addition, antibodies that recognize and bind to the same or overlapping epitopes of LAG-3 (e.g., human LAG-3) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as LAG-3 (e.g., human LAG-3). Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using 1-125 label (see Morel G A et al., (1988) Mol Immunol 25(1): 7-15); solid phase direct biotin-avidin EIA (see Cheung R C et al., (1990) Virology 176: 546-52); and direct labeled RIA (see Moldenhauer G et al., (1990) Scand J Immunol 32: 77-82), all of which are herein incorporated by reference in their entireties. Typically, such an assay involves the use of purified antigen (e.g., LAG-3 such as human LAG-3) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al, (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389, all of which are herein incorporated by reference in their entireties.

In certain embodiments, the instant disclosure provides an isolated antibody that specifically binds to LAG-3 (e.g., human LAG-3), the antibody comprising a heavy chain comprising the amino acid sequence set forth in SEQ ID NO: 168, 225, 169, 226, 170, 227, 171, 172, 173, 174, 175, 176, 177, 178, 179, 180, 181, 182, 183, 184, 185, or 186, optionally wherein the amino acid residue at position 1 of the heavy chain has been converted to pyroglutamate. In certain embodiments, the antibody comprises a heavy chain comprising the amino acid sequence set forth in SEQ ID NO: 168. In certain embodiments, the antibody comprises a heavy chain comprising the amino acid sequence set forth in SEQ ID NO: 225. In certain embodiments, the X in SEQ ID NO: 225 is Q. In certain embodiments, the X in SEQ ID NO: 225 is pyroglutamate. In certain embodiments, the antibody comprises a heavy chain comprising the amino acid sequence set forth in SEQ ID NO: 169. In certain embodiments, the antibody comprises a heavy chain comprising the amino acid sequence set forth in SEQ ID NO: 226. In certain embodiments, the X in SEQ ID NO: 226 is Q. In certain embodiments, the X in SEQ ID NO: 226 is pyroglutamate. In certain embodiments, the antibody comprises a heavy chain comprising the amino acid sequence set forth in SEQ ID NO: 170. In certain embodiments, the antibody comprises a heavy chain comprising the amino acid sequence set forth in SEQ ID NO: 227. In certain embodiments, the X in SEQ ID NO: 227 is Q. In certain embodiments, the X in SEQ ID NO: 227 is pyroglutamate. In certain embodiments, the antibody comprises a heavy chain comprising the amino acid sequence set forth in SEQ ID NO: 171. In certain embodiments, the antibody comprises a heavy chain comprising the amino acid sequence set forth in SEQ ID NO:

172. In certain embodiments, the antibody comprises a heavy chain comprising the amino acid sequence set forth in SEQ ID NO: 173. In certain embodiments, the antibody comprises a heavy chain comprising the amino acid sequence set forth in SEQ ID NO: 174. In certain embodiments, the antibody comprises a heavy chain comprising the amino acid sequence set forth in SEQ ID NO: 175. In certain embodiments, the antibody comprises a heavy chain comprising the amino acid sequence set forth in SEQ ID NO: 176. In certain embodiments, the antibody comprises a heavy chain comprising the amino acid sequence set forth in SEQ ID NO: 177. In certain embodiments, the antibody comprises a heavy chain comprising the amino acid sequence set forth in SEQ ID NO: 178. In certain embodiments, the antibody comprises a heavy chain comprising the amino acid sequence set forth in SEQ ID NO: 179. In certain embodiments, the antibody comprises a heavy chain comprising the amino acid sequence set forth in SEQ ID NO: 180. In certain embodiments, the antibody comprises a heavy chain comprising the amino acid sequence set forth in SEQ ID NO: 181. In certain embodiments, the antibody comprises a heavy chain comprising the amino acid sequence set forth in SEQ ID NO: 182. In certain embodiments, the antibody comprises a heavy chain comprising the amino acid sequence set forth in SEQ ID NO: 183. In certain embodiments, the antibody comprises a heavy chain comprising the amino acid sequence set forth in SEQ ID NO: 184. In certain embodiments, the antibody comprises a heavy chain comprising the amino acid sequence set forth in SEQ ID NO: 185. In certain embodiments, the antibody comprises a heavy chain comprising the amino acid sequence set forth in SEQ ID NO: 186. In certain embodiments, the amino acid residue at position 1 of the heavy chain has been converted to pyroglutamate.

In certain embodiments, the instant disclosure provides an isolated antibody that specifically binds to LAG-3 (e.g., human LAG-3), the antibody comprising a light chain comprising the amino acid sequence set forth in SEQ ID NO: 187, 228, 188, 189, 190, or 191, optionally wherein the amino acid residue at position 1 of the light chain has been converted to pyroglutamate. In certain embodiments, the antibody comprises a light chain comprising the amino acid sequence set forth in SEQ ID NO: 187. In certain embodiments, the antibody comprises a light chain comprising the amino acid sequence set forth in SEQ ID NO: 228. In certain embodiments, the X in SEQ ID NO: 228 is E. In certain embodiments, the X in SEQ ID NO: 228 is pyroglutamate. In certain embodiments, the antibody comprises a light chain comprising the amino acid sequence set forth in SEQ ID NO: 188. In certain embodiments, the antibody comprises a light chain comprising the amino acid sequence set forth in SEQ ID NO: 189. In certain embodiments, the antibody comprises a light chain comprising the amino acid sequence set forth in SEQ ID NO: 190. In certain embodiments, the antibody comprises a light chain comprising the amino acid sequence set forth in SEQ ID NO: 191. In certain embodiments, the amino acid residue at position 1 of the light chain has been converted to pyroglutamate.

In certain embodiments, the instant disclosure provides an isolated antibody that specifically binds to LAG-3 (e.g., human LAG-3), the antibody comprising a heavy chain comprising the amino acid sequence of SEQ ID NO: 168; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 225; and a light chain comprising the amino acid sequence of SEQ ID NO: 228. In certain embodiments, the X in SEQ ID NO: 225 is Q, and the X in SEQ ID NO: 228 is pyroglutamate. In certain embodiments, the X in SEQ ID NO: 225 is pyroglutamate, and the X in SEQ ID NO: 228 is E. In certain embodiments, the X in SEQ ID NO: 225 is pyroglutamate, and the X in SEQ ID NO: 228 is pyroglutamate.

In certain embodiments, the instant disclosure provides an isolated antibody that specifically binds to LAG-3 (e.g., human LAG-3), the antibody comprising a heavy chain comprising the amino acid sequence of SEQ ID NO: 169; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 226; and a light chain comprising the amino acid sequence of SEQ ID NO: 228. In certain embodiments, the X in SEQ ID NO: 226 is Q, and the X in SEQ ID NO: 228 is pyroglutamate. In certain embodiments, the X in SEQ ID NO: 226 is pyroglutamate, and the X in SEQ ID NO: 228 is E. In certain embodiments, the X in SEQ ID NO: 226 is pyroglutamate, and the X in SEQ ID NO: 228 is pyroglutamate.

In certain embodiments, the instant disclosure provides an isolated antibody that specifically binds to LAG-3 (e.g., human LAG-3), the antibody comprising a heavy chain comprising the amino acid sequence of SEQ ID NO: 170; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 227; and a light chain comprising the amino acid sequence of SEQ ID NO: 228. In certain embodiments, the X in SEQ ID NO: 227 is Q, and the X in SEQ ID NO: 228 is pyroglutamate. In certain embodiments, the X in SEQ ID NO: 227 is pyroglutamate, and the X in SEQ ID NO: 228 is E. In certain embodiments, the X in SEQ ID NO: 227 is pyroglutamate, and the X in SEQ ID NO: 228 is pyroglutamate.

In certain embodiments, the instant disclosure provides an isolated antibody that specifically binds to LAG-3 (e.g., human LAG-3), the antibody comprising a heavy chain comprising the amino acid sequence of SEQ ID NO: 171; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 172; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 173; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 174; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 175; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 176; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 177; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 178; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 179; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 180; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 181; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 182; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 183; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 184; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 185; and a light chain comprising the amino acid sequence of SEQ ID NO: 187. In certain embodiments, the instant disclosure provides an isolated antibody that specifically binds to LAG-3 (e.g., human LAG-3), the antibody comprising a heavy chain comprising the amino acid sequence of SEQ ID NO: 186; and a light chain comprising the amino acid sequence of SEQ ID NO: 187. In certain embodiments, the amino acid residue at position 1 of the heavy chain has been converted to pyroglutamate. In certain embodiments, the amino acid residue at position 1 of the light chain has been converted to pyroglutamate. In certain embodiments, the amino acid residue at position 1 of the heavy chain has been converted to pyroglutamate, and the amino acid residue at position 1 of the light chain has been converted to pyroglutamate.

Any Ig constant region can be used in the antibodies disclosed herein. In certain embodiments, the Ig region is a human IgG, IgE, IgM, IgD, IgA, or IgY immunoglobulin molecule, any class (e.g., $IgG_1$, $IgG_2$, $IgG_3$, $IgG_4$, $IgA_1$, and $IgA_2$), or any subclass (e.g., $IgG_{2a}$ and $IgG_{2b}$) of immunoglobulin molecule.

In certain embodiments, the instant disclosure provides an isolated antibody that specifically binds to LAG-3 (e.g., human LAG-3), the antibody comprising a heavy chain constant region comprising the amino acid sequence of SEQ ID NO: 192, 193, 194, 195, 196, 197, 208, or 209. In certain embodiments, the instant disclosure provides an isolated antibody that specifically binds to LAG-3 (e.g., human LAG-3), the antibody comprising a heavy chain constant region comprising the amino acid sequence of SEQ ID NO: 194. In certain embodiments, the instant disclosure provides an isolated antibody that specifically binds to LAG-3 (e.g., human LAG-3), the antibody comprising a heavy chain constant region comprising the amino acid sequence of SEQ ID NO: 195. In certain embodiments, the instant disclosure provides an isolated antibody that specifically binds to LAG-3 (e.g., human LAG-3), the antibody comprising a light chain constant region comprising the amino acid sequence of SEQ ID NO: 198. In certain embodiments, the instant disclosure provides an isolated antibody that specifically binds to LAG-3 (e.g., human LAG-3), the antibody comprising a light chain constant region comprising the amino acid sequence of SEQ ID NO: 219.

In certain embodiments, one, two, or more mutations (e.g., amino acid substitutions) are introduced into the Fc region of an antibody described herein (e.g., CH2 domain (residues 231-340 of human $IgG_1$) and/or CH3 domain (residues 341-447 of human $IgG_1$) and/or the hinge region, numbered according to the EU numbering system to alter one or more functional properties of the antibody, such as serum half-life, complement fixation, Fc receptor binding and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain may be altered to, e.g., facilitate assembly of the light and heavy chains, or to alter (e.g., increase or decrease) the stability of the antibody.

In a specific embodiment, one, two, or more amino acid mutations (e.g., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745, all of which are herein incorporated by reference in their entireties, for examples of mutations that will alter (e.g., decrease or increase) the half-life of an antibody in vivo. In some embodiments, one, two or more amino acid mutations (e.g., substitutions, insertions, or deletions) are introduced into an IgG constant domain, or FcRn-binding fragment thereof (preferably an Fc or hinge-Fc domain fragment) to decrease the half-life of the antibody in vivo. In other embodiments, one, two or more amino acid mutations (e.g., substitutions, insertions or deletions) are introduced into an IgG constant domain, or FcRn-binding fragment thereof (preferably an Fc or hinge-Fc domain fragment) to increase the half-life of the antibody in vivo. In a specific embodiment, the antibodies may have one or more amino acid mutations (e.g., substitutions) in the second constant (CH2) domain (residues 231-340 of human IgG$_1$) and/or the third constant (CH3) domain (residues 341-447 of human IgG$_1$), numbered according to the EU numbering system. In a specific embodiment, the constant region of the IgG$_1$ of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is herein incorporated by reference in its entirety. This type of mutant IgG, referred to as "YTE mutant" has been shown to display fourfold increased half-life as compared to wild-type versions of the same antibody (see Dall'Acqua W F et al., (2006) J Biol Chem 281: 23514-24, which is herein incorporated by reference in its entirety). In certain embodiments, an antibody comprises an IgG constant domain comprising one, two, three or more amino acid substitutions of amino acid residues at positions 251-257, 285-290, 308-314, 385-389, and 428-436, numbered according to the EU numbering system.

In some embodiments, one, two, or more mutations (e.g., amino acid substitutions) are introduced into the Fc region of an antibody described herein (e.g., CH2 domain (residues 231-340 of human IgG$_1$) and/or CH3 domain (residues 341-447 of human IgG$_1$) and/or the hinge region, numbered according to the EU numbering system to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al, (2012) PNAS 109: 6181-6186, U.S. Pat. No. 6,737,056, and International Publication Nos. WO 02/060919; WO 98/23289; and WO 97/34631, all of which are herein incorporated by reference in their entireties.

In a further embodiment, one, two, or more amino acid substitutions are introduced into an IgG constant domain Fc region to alter the effector function(s) of the antibody. For example, one or more amino acids selected from amino acid residues 234, 235, 236, 237, 297, 318, 320 and 322, numbered according to the EU numbering system, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, each of which is herein incorporated by reference in its entirety. In some embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886, each of which is herein incorporated by reference in its entirety, for a description of mutations that delete or inactivate the constant domain and thereby increase tumor localization. In certain embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604, which is herein incorporated by reference in its entirety). In various embodiments, one or more of the following mutations in the constant region of an antibody described herein may be made: an N297A substitution; an N297Q substitution; a L235A substitution and a L237A substitution; a L234A substitution and a L235A substitution; a E233P substitution; a L234V substitution; a L235A substitution; a C236 deletion; a P238A substitution; a D265A substitution; a A327Q substitution; or a P329A substitution, numbered according to the EU numbering system. In certain embodiments, a mutation selected from the group consisting of D265A, P329A, and a combination thereof may be made in the constant region of an antibody described herein.

In a specific embodiment, an antibody described herein comprises the constant domain of an IgG$_1$ with an N297Q or N297A amino acid substitution, numbered according to the EU numbering system. In one embodiment, an antibody described herein comprises the constant domain of an IgG$_1$ with a mutation selected from the group consisting of D265A, P329A, and a combination thereof, numbered according to the EU numbering system. In another embodiment, an antibody described herein comprises the constant domain of an IgG$_1$ with a mutation selected from the group consisting of L234A, L235A, and a combination thereof, numbered according to the EU numbering system. In certain embodiments, amino acid residues in the constant region of an antibody described herein in the positions corresponding to positions L234, L235, and D265 in a human IgG$_1$ heavy chain, numbered according to the EU index of numbering, are not L, L, and D, respectively. This approach is described in detail in International Publication No. WO 14/108483, which is herein incorporated by reference in its entirety. In a particular embodiment, the amino acids corresponding to positions L234, L235, and D265 in a human IgG$_1$ heavy chain are F, E, and A; or A, A, and A, respectively.

In certain embodiments, one or more amino acids selected from amino acid residues 329, 331, and 322 in the constant region of an antibody described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et of), which is herein incorporated by reference in its entirety. In some embodiments, one or more amino acid residues within amino acid positions 231 to 238 in the N-terminal region of the CH2 domain of an antibody described herein are altered to thereby alter the ability of the antibody to fix complement. This approach is described further in International Publication No. WO 94/29351, which is herein incorporated by reference in its entirety. In certain embodiments, the Fc region of an antibody described herein is modified to increase the ability of the antibody to mediate antibody dependent cellular cytotoxicity (ADCC) and/or to increase the affinity of the antibody for an Fcy receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In certain embodiments, an antibody described herein comprises the constant region of an IgG$_4$ antibody and the serine at amino acid residue 228 of the heavy chain, numbered according to the EU numbering system, is substituted for proline. In certain embodiments, the instant disclosure provides an isolated antibody that specifically binds to LAG-3 (e.g., human LAG-3), the antibody comprising a heavy chain constant region comprising the amino acid sequence of SEQ ID NO: 196. In certain embodiments, the instant disclosure provides an isolated antibody that specifically binds to LAG-3 (e.g., human LAG-3), the antibody comprising a heavy chain constant region comprising the amino acid sequence of SEQ ID NO: 197.

In certain embodiments, any of the constant region mutations or modifications described herein can be introduced into one or both heavy chain constant regions of an antibody described herein having two heavy chain constant regions.

In certain embodiments, the instant disclosure provides an isolated antibody that specifically binds to LAG-3 (e.g., human LAG-3) and functions as an antagonist.

In certain embodiments, the instant disclosure provides an isolated antibody that specifically binds to LAG-3 (e.g., human LAG-3) and decreases LAG-3 (e.g., human LAG-3) activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to LAG-3 (e.g., human LAG-3) activity without any antibody or with an unrelated antibody (e.g., an antibody that does not specifically bind to LAG-3 (e.g., human LAG-3)). In certain embodiments, the instant disclosure provides an isolated antibody that specifically binds to LAG-3 (e.g., human LAG-3) and decreases LAG-3 (e.g., human LAG-3) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to LAG-3 (e.g., human LAG-3) activity without any antibody or with an unrelated antibody (e.g., an antibody that does not specifically bind to LAG-3 (e.g., human LAG-3)). Non-limiting examples of LAG-3 (e.g., human LAG-3) activity can include LAG-3 (e.g., human LAG-3) signaling, LAG-3 (e.g., human LAG-3) binding to LAG-3 (e.g., human LAG-3) ligand (e.g., MHC class II), and inhibition of cytokine production (e.g., IL-2 and/or TNF-α). In certain embodiments, the instant disclosure provides an isolated antibody that specifically binds to LAG-3 (e.g., human LAG-3) and deactivates, reduces, or inhibits a LAG-3 (e.g., human LAG-3) activity. In specific embodiments, a decrease in a LAG-3 (e.g., human LAG-3) activity is assessed as described in the Examples, infra.

In specific embodiments, the instant disclosure provides an isolated antibody that specifically binds to LAG-3 (e.g., human LAG-3) and reduces LAG-3 (e.g., human LAG-3) binding to its ligand (e.g., MHC class II) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to LAG-3 (e.g., human LAG-3) binding to its ligand (e.g., MHC class II) without any antibody or with an unrelated antibody (e.g., an antibody that does not specifically bind to LAG-3 (e.g., human LAG-3)). In specific embodiments, the instant disclosure provides an isolated antibody that specifically binds to LAG-3 (e.g., human LAG-3) and reduces LAG-3 (e.g., human LAG-3) binding to its ligand (e.g., MHC class II) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to LAG-3 (e.g., human LAG-3) binding to its ligand (e.g., MHC class II) without any antibody or with an unrelated antibody (e.g., an antibody that does not specifically bind to LAG-3 (e.g., human LAG-3)).

In specific embodiments, the instant disclosure provides an isolated antibody that specifically binds to LAG-3 (e.g., human LAG-3) and increases cytokine production (e.g., IL-2 and/or TNF-α) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to cytokine production without any antibody or with an unrelated antibody (e.g., an antibody that does not specifically bind to LAG-3 (e.g., human LAG-3)). In specific embodiments, the instant disclosure provides an isolated antibody that specifically binds to LAG-3 (e.g., human LAG-3) and increases cytokine production (e.g., IL-2 and/or TNF-α) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to cytokine production without any antibody or with an unrelated antibody (e.g., an antibody that does not specifically bind to LAG-3 (e.g., human LAG-3)).

In specific embodiments, the instant disclosure provides an isolated antibody that specifically binds to LAG-3 (e.g., human LAG-3) and either alone or in combination with an anti-PD-1 antibody (e.g., pembrolizumab or nivolumab), an anti-PD-L1 antibody (e.g., avelumab, durvalumab, or atezolizumab), or an anti-CTLA-4 antibody (e.g., ipilimumab) increases IL-2 production in human peripheral blood mononuclear cells (PBMCs) in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to IL-2 production without any antibody or with an unrelated antibody (e.g., an antibody that does not specifically bind to LAG-3 (e.g., human LAG-3)).

In certain embodiments, human peripheral blood mononuclear cells (PBMCs) stimulated with *Staphylococcus* Enterotoxin A (SEA) in the presence of an antibody described herein, which specifically binds to LAG-3 (e.g., human LAG-3), have increased IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to PBMCs only stimulated with SEA without any antibody or with an unrelated antibody (e.g., an antibody that does not specifically bind to LAG-3 (e.g., human LAG-3)), as assessed by methods described herein (see the Examples, infra) or known to one of skill in the art.

In specific embodiments, the instant disclosure provides an isolated antibody that specifically binds to LAG-3 (e.g., human LAG-3) and either alone or in combination with an anti-PD-1 antibody (e.g., pembrolizumab or nivolumab) increases TNFα production in tumor infiltrating lymphocytes (TILs) in response to anti-CD3 antibody and anti-CD28 antibody stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to TNFα production without an antibody that specifically binds to LAG-3 (e.g., human LAG-3). In one embodiment, the TILs are from renal cell carcinoma tumor. In another embodiment, the TILs are from colorectal cancer tumor.

In certain embodiments, tumor infiltrating lymphocytes (TILs) stimulated with anti-CD3 and anti-CD28 antibodies in the presence of an antibody described herein, which specifically binds to LAG-3 (e.g., human LAG-3), have increased TNFα production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to TILs only stimulated with anti-CD3 and anti-CD28 antibodies without an antibody that specifically binds to LAG-3 (e.g., human LAG-3), as assessed by methods described herein (see the Examples, infra) or known to one of skill in the art. In one embodiment, the TILs are from renal cell carcinoma tumor. In another embodiment, the TILs are from colorectal cancer tumor.

6.3 Pharmaceutical Compositions

Provided herein are compositions (e.g., pharmaceutical compositions) comprising an anti-LAG-3 (e.g., human LAG-3) antibody described herein having the desired degree of purity in a physiologically acceptable carrier, excipient or stabilizer (Remington's Pharmaceutical Sciences (1990) Mack Publishing Co., Easton, PA). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In certain embodiments, the composition comprises one or more anti-LAG-3 (e.g., human LAG-3) antibodies as disclosed herein, wherein in a portion of the antibodies, the N-terminal amino acid residue(s) of the heavy chain and/or the light chain have been converted to pyroglutamate (e.g., as a result of post-translational cyclization of the free amino group of the N-terminal E or Q residue). In certain embodiments, the N-terminal amino acid residue of at least 50% (e.g., at least 60%, 70%, 75%, 80%, 85%, 90%, 95%, 96%, 97%, 98%, or 99%) of the heavy chains in the composition has been converted to pyroglutamate. In certain embodiments, the N-terminal amino acid residue of no more than 50% (e.g., no more than 1%, 2%, 3%, 4%, 5%, 10%, 15%, 20%, 25%, 30%, or 40%) of the light chains in the composition has been converted to pyroglutamate. In certain embodiments, the N-terminal amino acid residue of at least 50% (e.g., at least 60%, 70%, 75%, 80%, 85%, 90%, 95%, 96%, 97%, 98%, or 99%) of the heavy chains in the composition has been converted to pyroglutamate, and the N-terminal amino acid residue of no more than 50% (e.g., no more than 1%, 2%, 3%, 4%, 5%, 10%, 15%, 20%, 25%, 30%, or 40%) of the light chains in the composition has been converted to pyroglutamate.

In a specific embodiment, pharmaceutical compositions comprise an anti-LAG-3 (e.g., human LAG-3) antibody described herein, and optionally one or more additional prophylactic or therapeutic agents, in a pharmaceutically acceptable carrier. In a specific embodiment, pharmaceutical compositions comprise an effective amount of an antibody described herein, and optionally one or more additional prophylactic or therapeutic agents, in a pharmaceutically acceptable carrier. In some embodiments, the antibody is the only active ingredient included in the pharmaceutical composition. Pharmaceutical compositions described herein can be useful in inhibiting LAG-3 (e.g., human LAG-3) activity and treating a condition, such as cancer or an infectious disease.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein.

Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An anti-LAG-3 (e.g., human LAG-3) antibody described herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma and are incorporated by reference in their entireties). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An anti-LAG-3 (e.g., human LAG-3) antibody described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957, all of which are herein incorporated by reference in their entireties.

In certain embodiments, a pharmaceutical composition comprising an antibody described herein is a lyophilized powder, which can be reconstituted for administration as solutions, emulsions and other mixtures. It may also be reconstituted and formulated as solids or gels. The lyophilized powder is prepared by dissolving an antibody described herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The anti-LAG-3 (e.g., human LAG-3) antibodies described herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874, all of which are herein incorporated by reference in their entireties. In a specific embodiment, an antibody described herein is targeted to a tumor.

The compositions to be used for in vivo administration can be sterile. This is readily accomplished by filtration through, e.g., sterile filtration membranes.

6.4 Methods of Use and Uses

In another aspect, the instant disclosure provides a method of treating a subject using the anti-LAG-3 (e.g., human LAG-3) antibodies disclosed herein. Any disease or disorder in a subject that would benefit from inhibition of LAG-3 (e.g., human LAG-3) function can be treated using the anti-LAG-3 (e.g., human LAG-3) antibodies disclosed herein. The anti-LAG-3 (e.g., human LAG-3) antibodies disclosed herein are particularly useful for inhibiting immune system tolerance to tumors, and accordingly can be used as an immunotherapy for subjects with cancer. For example, in certain embodiments, the instant disclosure provides a method of increasing T cell activation in response to an antigen in a subject, the method comprising administering to the subject an effective amount of an anti-LAG-3 (e.g., human LAG-3) antibody or pharmaceutical composition thereof, as disclosed herein. In certain embodiments, the instant disclosure provides a method of treating cancer in a subject, the method comprising administering to the subject an effective amount of the antibody or pharmaceutical composition, as disclosed herein.

Cancers that can be treated with the anti-LAG-3 (e.g., human LAG-3) antibodies or pharmaceutical compositions disclosed herein include, without limitation, a solid tumor, a hematologic cancer, leukemia, lymphoma, osteosarcoma, rhabdomyosarcoma, neuroblastoma, kidney cancer, renal transitional cell cancer, bladder cancer, Wilm's cancer, ovarian cancer, pancreatic cancer, breast cancer (e.g., characterized by a mutation in BRCA1 and/or BRCA2), prostate cancer, bone cancer, lung cancer (e.g., non-small cell lung cancer or small cell lung cancer), gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer, liver cancer, epithelial cancer, and peritoneal cancer. In certain embodiments, the cancer is metastatic cancer, e.g., of the varieties described above.

In certain embodiments, the cancer is a solid tumor, a hematological cancer (e.g., leukemia, lymphoma, myeloma), and a metastatic lesion thereof. In one embodiment, the cancer is a solid tumor. Examples of solid tumors include malignancies, e.g., sarcomas and carcinomas (e.g., adenocarcinomas) of the various organ systems, such as those affecting lung, breast, lymphoid, gastrointestinal or colorectal, genitals and genitourinary tract (e.g., renal, urothelial, bladder cells), pharynx, CNS (e.g., brain, neural or glial cells), skin (e.g., melanoma), head and neck (e.g., head and neck squamous cell carcinoma (HNCC)), and pancreas. For example, melanoma, colon cancers, gastric cancer, rectal cancer, renal-cell carcinoma, breast cancer (e.g., a breast cancer that does not express one, two or all of estrogen receptor, progesterone receptor, or Her2/neu, e.g., a triple negative breast cancer), liver cancer, a lung cancer (e.g., a non-small cell lung cancer (NSCLC) (e.g., a NSCLC with squamous and/or non-squamous histology) or small cell lung cancer), prostate cancer, cancer of head or neck (e.g., HPV+ squamous cell carcinoma), cancer of the small intestine and cancer of the esophagus.

In one embodiment, the cancer is a hematological cancer, for example, a leukemia, a lymphoma, or a myeloma. In one embodiment, the cancer is a leukemia, for example, acute lymphoblastic leukemia (ALL), acute myelogenous leukemia (AML), acute myeloblastic leukemia (AML), chronic lymphocytic leukemia (CLL), chronic myelogenous leukemia (CML), chronic myeloid leukemia (CML), chronic myelomonocytic leukemia (CMML), chronic lymphocytic leukemia (CLL), or hairy cell leukemia. In one embodiment, the cancer is a lymphoma, for example, B cell lymphoma, diffuse large B-cell lymphoma (DLBCL), activated B-cell like (ABC) diffuse large B cell lymphoma, germinal center B cell (GCB) diffuse large B cell lymphoma, mantle cell lymphoma, Hodgkin lymphoma, non-Hodgkin lymphoma, relapsed non-Hodgkin lymphoma, refractory non-Hodgkin lymphoma, recurrent follicular non-Hodgkin lymphoma, Burkitt lymphoma, small lymphocytic lymphoma, follicular lymphoma, lymphoplasmacytic lymphoma, or extranodal marginal zone lymphoma. In one embodiment the cancer is a myeloma, for example, multiple myeloma.

In certain embodiments, the instant disclosure provides a method of preventing or treating an infectious disease in a subject, the method comprising administering to the subject an effective amount of an anti-LAG-3 (e.g., human LAG-3) antibody or pharmaceutical composition thereof, as disclosed herein. In one embodiment, provided herein are methods for preventing and/or treating an infection (e.g., a viral infection, a bacterial infection, a fungal infection, a protozoal infection, or a parasitic infection). The infection prevented and/or treated in accordance with the methods can be caused by an infectious agent identified herein. In a specific embodiment, an anti-LAG-3 (e.g., human LAG-3) antibody described herein or a composition thereof is the only active agent administered to a subject. In some embodiments, an anti-LAG-3 (e.g., human LAG-3) antibody described herein or a composition thereof is used in combination with anti-infective interventions (e.g., antivirals, antibacterials, antifungals, or anti-helminthics) for the treatment of infectious diseases.

Infectious diseases that can be treated and/or prevented by anti-LAG-3 (e.g., human LAG-3) antibodies or pharmaceutical compositions disclosed herein are caused by infectious agents including but not limited to bacteria, parasites, fungi, protozae, and viruses. In a specific embodiment, the infectious disease treated and/or prevented by anti-LAG-3 (e.g., human LAG-3) antibodies or pharmaceutical compositions disclosed herein is caused by a virus. Viral diseases or viral infections that can be prevented and/or treated in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial infections that can be prevented and/or treated include infections caused by *Escherichia coli, Klebsiella pneumoniae, Staphylococcus aureus, Enterococcus faecalis, Proteus vulgaris, Staphylococcus viridans*, and *Pseudomonas aeruginosa*. Bacterial diseases caused by bacteria (e.g., *Escherichia coli, Klebsiella pneumoniae, Staphylococcus aureus, Enterococcus faecalis, Proteus vulgaris, Staphylococcus viridans*, and *Pseudomonas aeruginosa*) that can be prevented and/or treated in accordance with the methods described herein include, but are not limited to, Mycobacteria *rickettsia, Mycoplasma, Neisseria, S. pneumonia, Borrelia burgdorferi* (Lyme disease), *Bacillus antracis* (anthrax), tetanus, *Streptococcus, Staphylococcus, Mycobacterium*, pertissus, cholera, plague, diptheria, *Chlamydia, S. aureus* and *Legionella*.

Protozoal diseases or protozoal infections caused by protozoa that can be prevented and/or treated in accordance with the methods described herein include, but are not limited to, *Leishmania*, coccidiosis, *Trypanosoma schistosoma* or malaria. Parasitic diseases or parasitic infections caused by parasites that can be prevented and/or treated in accordance with the methods described herein include, but are not limited to, *Chlamydia* and *Rickettsia*.

Fungal diseases or fungal infections that can be prevented and/or treated in accordance with the methods described herein include, but are not limited to, those caused by *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium* keratitis, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis.

In certain embodiments, the instant disclosure provides a method of preventing or treating a disease or disorder of the nervous system in a subject, the method comprising administering to the subject an effective amount of an anti-LAG-3 (e.g., human LAG-3) antibody or pharmaceutical composition thereof, as disclosed herein. In some embodiments, the disease or disorder of the nervous system is a synucleinopathy. In some embodiments, the disease or disorder of the nervous system is Parkinson's disease.

In certain embodiments, these methods further comprise administering an additional therapeutic agent to the subject. In certain embodiments, the additional therapeutic agent is a chemotherapeutic, radiotherapeutic, or a checkpoint targeting agent. In certain embodiments, the chemotherapeutic agent is a hypomethylating agent (e.g., azacitidine). In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-CEACAM1 antibody, an agonist anti-GITR antibody, an agonist anti-OX40 antibody, an antagonist anti-TIGIT antibody, an agonist anti-CD137 antibody, an antagonist anti-VISTA antibody, an antagonist anti-CD73 antibody, and an antagonist anti-CD96 antibody.

In one embodiment, the present invention relates to an antibody and/or pharmaceutical composition of the present invention for use in a method of the present invention, wherein the method further comprises administering an additional therapeutic agent to the subject. In one embodiment, the present invention relates to (a) an antibody and/or pharmaceutical composition of the present invention and (b) an additional therapeutic agent for use as a medicament. In one embodiment, the present invention relates to (a) an antibody and/or pharmaceutical composition of the present invention, and (b) an additional therapeutic agent for use in a method for the treatment of cancer. In a further embodiment, the present invention relates to a pharmaceutical composition, kit or kit-of-parts comprising (a) an antibody and/or pharmaceutical composition of the present invention and (b) an additional therapeutic agent. In one embodiment, the additional therapeutic agent is a chemotherapeutic, a radiotherapeutic, or a checkpoint targeting agent.

In certain embodiments, an anti-PD-1 antibody is used in methods disclosed herein. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck & Co. In certain embodiments, the anti-PD-1 antibody is pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, all of which are herein incorporated by reference in their entireties: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used in methods disclosed herein. In certain embodiments, the anti-PD-L1 antibody is atezolizumab developed by Genentech. In certain embodiments, the anti-PD-L1 antibody is durvalumab developed by AstraZeneca, Celgene and Medimmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, all of which are herein incorporated by reference in their entireties: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, an anti-CTLA-4 antibody is used in methods disclosed herein. In certain embodiments, the anti-CTLA-4 antibody is ipilimumab developed by Bristol-Myers Squibb. In certain embodiments, the anti-CTLA-4 antibody is ipilimumab developed by Bristol-Myers Squibb. In certain embodiments, the anti-CTLA-4 antibody is tremelimumab developed by Pfizer and Medimmune.

Non-limiting examples of anti-CTLA-4 antibodies that may be used in treatment methods disclosed herein are disclosed in the following patents and patent applications, all of which are herein incorporated by reference in their entireties: U.S. Pat. Nos. 6,984,720; 7,411,057; 7,034,121; 8,697,845; U.S. Publication No. US 2009/0123477 A1; U.S. Publication No. US 2014/0105914 A1; U.S. Publication No. US 2013/0267688 A1; U.S. Publication No. US 2016/0145355 A1; PCT Publication No. WO 2014/207064 A1; and PCT Publication No. WO 2016/015675 A1.

In certain embodiments, an anti-LAG-3 (e.g., human LAG-3) antibody disclosed herein is administered to a subject in combination with a compound that targets an immunomodulatory enzyme(s) such as IDO (indoleamine-(2,3)-dioxygenase) and/or TDO (tryptophan 2,3-dioxygenase). In certain embodiments, such compound is selected from the group consisting of epacadostat (Incyte Corp; see, e.g., WO 2010/005958 which is herein incorporated by reference in its entirety), BMS-986205 (Flexus Biosciences/Bristol-Myers Squibb), indoximod (NewLink Genetics), and NLG919 (NewLink Genetics). In one embodiment, the compound is epacadostat. In another embodiment, the compound is BMS-986205. In another embodiment, the compound is indoximod. In another embodiment, the compound is NLG919. In a specific embodiment, an anti-LAG-3 (e.g., human LAG-3) antibody disclosed herein is administered to a subject in combination with an IDO inhibitor for treating cancer. The IDO inhibitor as described herein for use in treating cancer is present in a solid dosage form of a pharmaceutical composition such as a tablet, a pill or a capsule, wherein the pharmaceutical composition includes an IDO inhibitor and a pharmaceutically acceptable excipient. As such, the antibody as described herein and the IDO inhibitor as described herein can be administered separately, sequentially or concurrently as separate dosage forms. In one embodiment, the antibody is administered parenterally, and the IDO inhibitor is administered orally. In particular embodiments, the inhibitor is selected from the group consisting of epacadostat (Incyte Corporation), BMS-986205 (Flexus Biosciences/Bristol-Myers Squibb), indoximod (NewLink Genetics), and NLG919 (NewLink Genetics). Epacadostat has been described in PCT Publication No. WO 2010/005958, which is herein incorporated by reference in its entirety. In one embodiment, the inhibitor is epacadostat. In another embodiment, the inhibitor is BMS-986205. In another embodiment, the inhibitor is indoximod. In another embodiment, the inhibitor is NLG919.

In certain embodiments, the instant disclosure provides an isolated antibody that specifically binds to LAG-3 (e.g., human LAG-3) in combination with an anti-PD-1 antibody (e.g., pembrolizumab or nivolumab) and an inhibitor of indoleamine-2,3-dioxygenase (IDO). In certain embodiments, the anti-PD-1 antibody is pembrolizumab. In certain embodiments, the anti-PD-1 antibody is nivolumab. In certain embodiments, the IDO inhibitor is selected from the group consisting of epacadostat, BMS-986205, indoximod, and NLG919. In certain embodiments, the IDO inhibitor is epacadostat. In certain embodiments, the IDO inhibitor is BMS-986205. In certain embodiments, the IDO inhibitor is indoximod.

In certain embodiments, an anti-LAG-3 (e.g., human LAG-3) antibody disclosed herein is administered to a subject in combination with another anti-cancer agent. Exemplary anti-cancer agents include antibody therapeutics such as trastuzumab (Herceptin), antibodies to co-stimulatory or co-inhibitory molecules such as CTLA-4, CD137, and PD-1, and antibodies to cytokines such as IL-10 and TGF-$\beta$.

In certain embodiments, the additional therapeutic agent is an inhibitor of JAK, PBKdelta, BRD, PI3Kgamma, or Axl/Mer. In certain embodiments, the additional therapeutic agent is an inhibitor of JAK, including JAK1 and/or JAK2. In certain embodiments, the additional therapeutic agent is an inhibitor of PBKdelta. In certain embodiments, the additional therapeutic agent is an inhibitor of BRD. In certain embodiments, the additional therapeutic agent is an inhibitor of PBKgamma. In certain embodiments, the additional therapeutic agent is an inhibitor of Axl/Mer.

Additional examples of anti-cancer agents include those that block immune cell migration such as antagonists to chemokine receptors, including CCR2 and CCR4, and those that augment the immune system such as adjuvants or adoptive T cell transfer.

One or more additional immune checkpoint modulators can be used in combination with an anti-LAG-3 (e.g., human LAG-3) antibody disclosed herein for treatment of any diseases, disorders, or conditions described herein, e.g., TAM-associated diseases, disorders, or conditions. Exemplary immune checkpoint modulators include modulators against immune checkpoint molecules such as CD27, CD28, CD40, CD122, CD96, CD73, CD47, CD96, CD137, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG-3, TIM-3, TIGIT, VISTA, PD-1, PD-L1, and PD-L2. In some embodiments, the immune checkpoint molecule is a co-stimulatory checkpoint molecule selected from CD27, CD28, CD40, ICOS, OX40, GITR, and CD137. In some embodiments, the immune checkpoint molecule is a co-inhibitory checkpoint molecule selected from A2AR, B7-H3, B7-H4, BTLA, CTLA-4, IDO, KIR, PD-1, TIM-3, and VISTA. In some embodiments, an anti-LAG-3 (e.g., human LAG-3) antibody disclosed herein can be used in combination with one or more agents selected from KIR inhibitors, TIGIT inhibitors, LAIR1 inhibitors, CD160 inhibitors, 2B4 inhibitors, and TGFR beta inhibitors.

In some embodiments, the modulator of an immune checkpoint molecule is an antagonistic anti-PD1 antibody, an antagonistic anti-PD-L1 antibody, or an antagonistic anti-CTLA-4 antibody.

In some embodiments, the modulator of an immune checkpoint molecule is an agonist of GITR, e.g., an agonistic anti-GITR antibody. In some embodiments, the agonistic anti-GITR antibody is TRX518 or MK-4166.

In some embodiments, the modulator of an immune checkpoint molecule is an agonist of OX40, e.g., an agonistic anti-OX40 antibody or OX40L fusion protein. In some embodiments, the agonistic anti-OX40 antibody is MEDI0562. In some embodiments, the OX40L fusion protein is MEDI6383.

An anti-LAG-3 (e.g., human LAG-3) antibody disclosed herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfdzomib. In some embodiments, the corticosteroid is dexamethasone (DEX). In some embodiments, the immunomodulatory agent is lenalidomide (LEN) or pomalidomide (POM).

In certain embodiments, an anti-LAG-3 (e.g., human LAG-3) antibody disclosed herein is administered to a subject in combination with a vaccine. The vaccine can be, e.g., a peptide vaccine, a DNA vaccine, or an RNA vaccine. In certain embodiments, the vaccine is a heat shock protein based tumor vaccine or a heat shock protein based pathogen vaccine. In a specific embodiment, an anti-LAG-3 (e.g., human LAG-3) antibody disclosed herein is administered to a subject in combination with a heat shock protein based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject. Therefore, in one embodiment, the present invention relates to (a) an antibody and/or pharmaceutical composition of the present invention and (b) a vaccine for use as a medicament, for example for use in a method for the treatment of cancer. In one embodiment, the present invention relates to a pharmaceutical composition, kit or kit-of-parts comprising (a) an antibody and/or pharmaceutical composition of the present invention and (b) a vaccine. In one embodiment, the vaccine is a heat shock protein based tumor vaccine. In one embodiment, the vaccine is a heat shock protein based pathogen vaccine.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes and Th1 and Th-2-mediated immune responses. In certain embodiments, HSPPCs used in methods disclosed herein comprise one or more heat shock proteins from the hsp60, hsp70, or hsp90 family of stress proteins complexed with antigenic peptides. In certain embodiments, HSPPCs comprise hsc70, hsp70, hsp90, hspl 10, grp 170, gp96, calreticulin, or combinations of two or more thereof.

In a specific embodiment, the heat shock protein peptide complex (HSPPC) comprises recombinant heat shock proteins (e.g., hsp70 or hsc70) or a peptide-binding domain thereof complexed with recombinant antigenic peptides. Recombinant heat shock proteins can be produced by recombinant DNA technology, for example, using human hsc70 sequence as described in Dworniczak and Mirault, Nucleic Acids Res. 15:5181-5197 (1987) and GenBank accession no. PI 1142 and/or Y00371, each of which is incorporated herein by reference in its entirety. In certain embodiments, Hsp70 sequences are as described in Hunt and Morimoto Proc. Natl. Acad. Sci. U.S.A. 82 (19), 6455-6459 (1985) and GenBank accession no. P0DMV8 and/or Ml 1717, each of which is incorporated herein by reference in its entirety. Antigenic peptides can also be prepared by recombinant DNA methods known in the art.

In certain embodiments, the antigenic peptides comprise a modified amino acid. In certain embodiments, the modified amino acid comprises a post-translational modification. In certain embodiments, the modified amino acid comprises a mimetic of a post-translational modification. In certain embodiments, the modified amino acid is a Tyr, Ser, Thr, Arg, Lys, or His that has been phosphorylated on a side chain hydroxyl or amine. In certain embodiments, the modified amino acid is a mimetic of a Tyr, Ser, Thr, Arg, Lys, or His amino acid that has been phosphorylated on a side chain hydroxyl or amine.

In a specific embodiment, an anti-LAG-3 (e.g., human LAG-3) antibody disclosed herein is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells and injection of the vaccine is intended to stimulate the subject's immune system to recognize and attack any cells with the specific cancer fingerprint. Therefore, in one embodiment, the present invention relates to an antibody and/or pharmaceutical composition of the present invention in combination with a heat shock protein peptide complex (HSPPC) for use as a medicament and/or for use in a method for the treatment of cancer.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In some embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, all of which are herein incorporated by reference in their entireties: U.S. Pat. Nos. 6,391,306, 6,383,492, 6,403,095, 6,410,026, 6,436, 404, 6,447,780, 6,447,781 and 6,610,659, all of which are herein incorporated by reference in their entireties.

In certain embodiments, an anti-LAG-3 antibody disclosed herein is administered to a subject in combination with an adjuvant. Various adjuvants can be used depending on the treatment context. Non-limiting examples of appropriate adjuvants include, but not limited to, Complete Freund's Adjuvant (CFA), Incomplete Freund's Adjuvant (IFA), montanide ISA (incomplete Seppic adjuvant), the Ribi adjuvant system (RAS), Titer Max, muramyl peptides, Syntex Adjuvant Formulation (SAF), alum (aluminum hydroxide and/or aluminum phosphate), aluminum salt adjuvants, Gerbu® adjuvants, nitrocellulose absorbed antigen, encapsulated or entrapped antigen, 3 De-O-acylated monophosphoryl lipid A (3 D-MPL), immunostimulatory oligonucleotides, toll-like receptor (TLR) ligands, mannan-binding lectin (MBL) ligands, STING agonists, immunostimulating complexes such as saponins, Quil A, QS-21, QS-7, ISCOMATRIX, and others. Other adjuvants include CpG oligonucleotides and double stranded RNA molecules, such as poly(A) and poly(U). Combinations of the above adjuvants may also be used. See, e.g., U.S. Pat. Nos. 6,645,495; 7,029,678; and 7,858,589, all of which are incorporated herein by reference in their entireties. In one embodiment, the adjuvant used herein is QS-21 STIMULON.

In certain embodiments, an anti-LAG-3 antibody disclosed herein is administered to a subject in combination with an additional therapeutic agent comprising a TCR. In certain embodiments, the additional therapeutic agent is a soluble TCR. In certain embodiments, the additional therapeutic agent is a cell expressing a TCR. Therefore, in one embodiment, the present invention relates to an antibody and/or pharmaceutical composition of the present invention in combination with an additional therapeutic agent comprising a TCR for use as a medicament and/or for use in a method for the treatment of cancer.

In certain embodiments, an anti-LAG-3 antibody disclosed herein is administered to a subject in combination with a cell expressing a chimeric antigen receptor (CAR). In certain embodiments, the cell is a T cell.

In certain embodiments, an anti-LAG-3 antibody disclosed herein is administered to a subject in combination with a TCR mimic antibody. In certain embodiments, the TCR mimic antibody is an antibody that specifically binds to a peptide-MHC complex. For non-limiting examples of TCR mimic antibodies, see, e.g., U.S. Pat. No. 9,074,000 and U.S. Publication Nos. US 2009/0304679 A1 and US 2014/0134191 A1, all of which are incorporated herein by reference in their entireties.

The anti-LAG-3 (e.g., human LAG-3) antibody and the additional therapeutic agent (e.g., chemotherapeutic, radiotherapeutic, checkpoint targeting agent, IDO inhibitor, vaccine, adjuvant, a soluble TCR, a cell expressing a TCR, a cell expressing a chimeric antigen receptor, and/or a TCR mimic antibody) can be administered separately, sequentially or concurrently as separate dosage forms. In one embodiment, an anti-LAG-3 (e.g., human LAG-3) antibody is administered parenterally, and an IDO inhibitor is administered orally.

An antibody or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival, intra-arterial, and subcutaneous routes. Pulmonary administration can also be employed, e.g., by use of an inhaler or nebulizer, and formulation with an aerosolizing agent for use as a spray. In certain embodiments, the antibody or pharmaceutical composition described herein is delivered subcutaneously or intravenously. In certain embodiments, the antibody or pharmaceutical composition described herein is delivered intratumorally. In certain embodiments, the antibody or pharmaceutical composition described herein is delivered intra-arterially. In certain embodiments, the antibody or pharmaceutical composition described herein is delivered into a tumor draining lymph node. In certain embodiments, the antibody or pharmaceutical composition described herein is delivered intranasally.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

An anti-LAG-3 (e.g., human LAG-3) antibody described herein can also be used to assay LAG-3 (e.g., human LAG-3) protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody described herein. Alternatively, a second antibody that recognizes an anti-LAG-3 (e.g., human LAG-3) antibody described herein can be labeled and used in combination with an anti-LAG-3 (e.g., human LAG-3) antibody to detect LAG-3 (e.g., human LAG-3) protein levels. Therefore, in one embodiment, the present invention relates to the use of an antibody of the present invention for in vitro detection of LAG-3 (e.g., human LAG-3) protein in a biological sample. In a further embodiment, the present invention relates to the use of an anti-LAG-3 antibody of the invention, for assaying and/or detecting LAG-3 (e.g., human LAG-3) protein levels in a biological sample in vitro, optionally wherein the anti-LAG-3 antibody is conjugated to a radionuclide or detectable label, and/or carries a label described herein, and/or wherein an immunohistological method is used.

Assaying for the expression level of LAG-3 (e.g., human LAG-3) protein is intended to include qualitatively or quantitatively measuring or estimating the level of LAG-3 (e.g., human LAG-3) protein in a first biological sample either directly (e.g., by determining or estimating absolute protein level) or relatively (e.g., by comparing to the disease associated protein level in a second biological sample). LAG-3 (e.g., human LAG-3) polypeptide expression level in the first biological sample can be measured or estimated and compared to a standard LAG-3 (e.g., human LAG-3) protein level, the standard being taken from a second biological sample obtained from an individual not having the disorder or being determined by averaging levels from a population of individuals not having the disorder. As will be appreciated in the art, once the "standard" LAG-3 (e.g., human LAG-3) polypeptide level is known, it can be used repeatedly as a standard for comparison. Therefore, in a further embodiment, the present invention relates to an in vitro method for assaying and/or detecting LAG-3 protein levels, for example human LAG-3 protein levels, in a biological sample, comprising qualitatively or quantitatively measuring or estimating the level of LAG-3 protein, for example of human LAG-3 protein, in a biological sample, by an immunohistological method.

As used herein, the term "biological sample" refers to any biological sample obtained from a subject, cell line, tissue, or other source of cells potentially expressing LAG-3 (e.g., human LAG-3). Methods for obtaining tissue biopsies and body fluids from animals (e.g., humans) are well known in the art. Biological samples include peripheral mononuclear blood cells.

An anti-LAG-3 (e.g., human LAG-3) antibody described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction or with regard to an anticipated or desired immune system response, antigen response or vaccine response. The assessment and evaluation of immune system status and/or immune response is also useful in determining the suitability of a patient for a clinical trial of a drug or for the administration of a particular chemotherapeutic agent, a radiotherapeutic agent, or an antibody, including combinations thereof, versus a different agent or antibody. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses. Therefore, in one embodiment, the present invention relates to an anti-LAG-3 antibody and/or pharmaceutical composition of the present invention for use as a diagnostic. In one embodiment, the present invention relates to an anti-LAG-3 antibody and/or pharmaceutical composition of the present invention for use in a method for the prediction, diagnosis and/or monitoring of a subject having or suspected to have an immune system-dysfunction and/or with regard to an anticipated or desired immune system response, antigen response or vaccine response. In another embodiment, the present invention relates to the use of anti-LAG-3 antibody of the invention, for predicting, diagnosing and/or monitoring of a subject having or suspected to have an immune system-dysfunction and/or with regard to an anticipated or desired immune system response, antigen response or vaccine response by assaying and/or detecting human LAG-3 protein levels in a biological sample of the subject in vitro.

In one embodiment, an anti-LAG-3 (e.g., human LAG-3) antibody can be used in immunohistochemistry of biopsy samples. In another embodiment, an anti-LAG-3 (e.g., human LAG-3) antibody can be used to detect levels of LAG-3 (e.g., human LAG-3), or levels of cells which contain LAG-3 (e.g., human LAG-3) on their membrane surface, which levels can then be linked to certain disease symptoms. Anti-LAG-3 (e.g., human LAG-3) antibodies described herein may carry a detectable or functional label. When fluorescence labels are used, currently available microscopy and fluorescence-activated cell sorter analysis (FACS) or combination of both methods procedures known in the art may be utilized to identify and to quantitate the specific binding members. Anti-LAG-3 (e.g., human LAG-3) antibodies described herein may carry a fluorescence label. Exemplary fluorescence labels include, for example, reactive and conjugated probes e.g., Aminocoumarin, Fluorescein and Texas red, Alexa Fluor dyes, Cy dyes and DyLight dyes. An anti-LAG-3 (e.g., human LAG-3) antibody may carry a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{67}Cu$, $^{90}Y$, $^{99}Tc$, $^{111}In$, $^{117}Lu$, $^{121}I$, $^{124}I$, $^{125}I$, $^{131}I$, $^{198}Au$, $^{211}At$, $^{213}Bi$, $^{225}Ac$ and $^{186}Re$. When radioactive labels are used, currently available counting procedures known in the art may be utilized to identify and quantitate the specific binding of anti-LAG-3 (e.g., human LAG-3) antibody to LAG-3 (e.g., human LAG-3). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-LAG-3 (e.g., human LAG-3) antibody under conditions that allow for the formation of a complex between the antibody and LAG-3 (e.g., human LAG-3). Any complexes formed between the antibody and LAG-3 (e.g., human LAG-3) are detected and compared in the sample and the control. In light of the specific binding of the antibodies described herein for LAG-3 (e.g., human LAG-3), the antibodies can be used to specifically detect LAG-3 (e.g., human LAG-3) expression on the surface of cells. The antibodies described herein can also be used to purify LAG-3 (e.g., human LAG-3) via immunoaffinity purification. Also included herein is an assay system which may be prepared in the form of a test kit for the quantitative analysis of the extent of the presence of, for instance, LAG-3 (e.g., human LAG-3) or LAG-3 (e.g., human LAG-3)/LAG-3 (e.g., human LAG-3) ligand complexes. The system or test kit, kit, or kit-of-parts may comprise a labeled component, e.g., a labeled antibody, and one or more additional immunochemical reagents.

6.5 Polynucleotides, Vectors and Methods of Producing Anti-LAG-3 Antibodies

In another aspect, provided herein are polynucleotides comprising a nucleotide sequence encoding an antibody described herein or a fragment thereof (e.g., a light chain variable region and/or heavy chain variable region) that specifically binds to a LAG-3 (e.g., human LAG-3) antigen, and vectors, e.g., vectors comprising such polynucleotides for recombinant expression in host cells (e.g., E. coli and mammalian cells). Provided herein are polynucleotides comprising nucleotide sequences encoding a heavy and/or light chain of any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies, which specifically bind to a LAG-3 (e.g., human LAG-3) polypeptide and comprises an amino acid sequence as described herein, as well as antibodies which compete with such antibodies for binding to a LAG-3 (e.g., human LAG-3) polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein (see, e.g., Tables 1, 3, 5, 6, and 7) or nucleotide sequences encoding a heavy chain comprising the VH FRs and CDRs of antibodies described herein (see, e.g., Tables 1, 2, 4, 6, and 7).

Also provided herein are polynucleotides encoding an anti-LAG-3 (e.g., human LAG-3) antibody that are optimized, e.g., by codon/RNA optimization, replacement with heterologous signal sequences, and elimination of mRNA instability elements. Methods to generate optimized nucleic acids encoding an anti-LAG-3 (e.g., human LAG-3) antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, all of which are herein incorporated by reference in their entireties. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of an anti-LAG-3 (e.g., human LAG-3) antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-LAG-3 (e.g., human LAG-3) antibody encoded by polynucleotides that have not been optimized.

In certain embodiments, an optimized polynucleotide sequence encoding an anti-LAG-3 (e.g., human LAG-3) antibody described herein or a fragment thereof (e.g., VL domain and/or VH domain) can hybridize to an antisense (e.g., complementary) polynucleotide of an unoptimized polynucleotide sequence encoding an anti-LAG-3 (e.g., human LAG-3) antibody described herein or a fragment thereof (e.g., VL domain and/or VH domain). In specific embodiments, an optimized nucleotide sequence encoding an anti-LAG-3 (e.g., human LAG-3) antibody described herein or a fragment hybridizes under high stringency conditions to antisense polynucleotide of an unoptimized polynucleotide sequence encoding an anti-LAG-3 (e.g., human LAG-3) antibody described herein or a fragment thereof. In a specific embodiment, an optimized nucleotide sequence encoding an anti-LAG-3 (e.g., human LAG-3) antibody described herein or a fragment thereof hybridizes under high stringency, intermediate or lower stringency hybridization conditions to an antisense polynucleotide of an unoptimized nucleotide sequence encoding an anti-LAG-3 (e.g., human LAG-3) antibody described herein or a fragment thereof. Information regarding hybridization conditions has been described, see, e.g., U.S. Patent Application Publication No. US 2005/0048549 (e.g., paragraphs 72-73), which is herein incorporated by reference in its entirety.

The polynucleotides can be obtained, and the nucleotide sequence of the polynucleotides determined, by any method known in the art. Nucleotide sequences encoding antibodies described herein, e.g., antibodies described in Tables 1, 6, and 7, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-6, which is herein incorporated by reference in its entirety), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-LAG-3 (e.g., human LAG-3) antibodies described herein can be readily isolated and sequenced using conventional procedures (e.g., by using oligonucleotide probes that are capable of binding specifically to genes encoding the heavy and light chains of the anti-LAG-3 (e.g., human LAG-3) antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-LAG-3 (e.g., human LAG-3) antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3, which is herein incorporated by reference in its entirety.

In certain aspects, provided herein are cells (e.g., host cells) expressing (e.g., recombinantly) antibodies described herein which specifically bind to LAG-3 (e.g., human LAG-3) and related polynucleotides and expression vectors. Provided herein are vectors (e.g., expression vectors) comprising polynucleotides comprising nucleotide sequences encoding anti-LAG-3 (e.g., human LAG-3) antibodies or a fragment for recombinant expression in host cells, preferably in mammalian cells. Also provided herein are host cells comprising such vectors for recombinantly expressing anti-LAG-3 (e.g., human LAG-3) antibodies described herein (e.g., human or humanized antibody). In a particular aspect, provided herein are methods for producing an antibody described herein, comprising expressing such antibody from a host cell.

Recombinant expression of an antibody described herein (e.g., a full-length antibody, heavy and/or light chain of an antibody, or a single chain antibody described herein) that specifically binds to LAG-3 (e.g., human LAG-3) involves construction of an expression vector containing a polynucleotide that encodes the antibody. Once a polynucleotide encoding an antibody molecule, heavy and/or light chain of an antibody, or a fragment thereof (e.g., heavy and/or light chain variable regions) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable region of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464, which are herein incorporated by reference in their entireties) and variable regions of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other embodiments, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific embodiments, a heavy chain/heavy chain variable region expressed by a first cell associated with a light chain/light chain variable region of a second cell to form an anti-LAG-3 (e.g., human LAG-3) antibody described herein. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-LAG-3 (e.g., human LAG-3) antibody described herein, and a second vector comprising a polynucleotide encoding a heavy chain/heavy chain variable region of an anti-LAG-3 (e.g., human LAG-3) antibody described herein.

A variety of host-expression vector systems can be utilized to express antibody molecules described herein (see, e.g., U.S. Pat. No. 5,807,715, which is herein incorporated by reference in its entirety). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS 1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are CHO cells, for example CHO cells from the CHO GS System™ (Lonza). In certain embodiments, the heavy chain and/or light chain of an antibody produced by a CHO cell may have an N-terminal glutamine or glutamate residue replaced by pyroglutamate. In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking M K & Hofstetter H (1986) Gene 45: 101-5; and Cockett M I et al., (1990) Biotechnology 8(7): 662-7, each of which is herein incorporated by reference in its entirety). In certain embodiments, antibodies described herein are produced by CHO cells or NS0 cells. In a specific embodiment, the expression of nucleotide sequences encoding antibodies described herein which specifically bind LAG-3 (e.g., human LAG-3) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like, all of which are herein incorporated by reference in their entireties. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan J & Shenk T (1984) PNAS 81(12): 3655-9, which is herein incorporated by reference in its entirety). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al, (1987) Methods Enzymol. 153: 516-544, which is herein incorporated by reference in its entirety).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT20 and T47D, NS0 (a murine myeloma cell line that does not endogenously produce any immunoglobulin chains), CRL7O3O, COS (e.g., COS 1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-LAG-3 (e.g., human LAG-3) antibodies described herein are produced in mammalian cells, such as CHO cells.

In a specific embodiment, the antibodies described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-LAG-3 (e.g., human LAG-3) antibody described herein can be engineered. In specific embodiments, a cell provided herein stably expresses a light chain/light chain variable region and a heavy chain/heavy chain variable region which associate to form an antibody described herein.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-LAG-3 (e.g., human LAG-3) antibody described herein or a fragment thereof. Such engineered cell lines can be particularly useful in screening and evaluation of compositions that interact directly or indirectly with the antibody molecule.

A number of selection systems can be used, including but not limited to the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034) and adenine phosphoribosyltransferase (Lowy I et al., (1980) Cell 22(3): 817-23) genes in tk-, hgprt- or aprt-cells, respectively, all of which are herein incorporated by reference in their entireties. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Feigner P L (1993) Trends Biotechnol 11(5): 211-5); and hygro, which confers resistance to hygromycin (Santerre R F et al., (1984) Gene 30(1-3): 147-56), all of which are herein incorporated by reference in their entireties. Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al, (eds.), Current Protocols in Human Genetics, John Wiley & Sons, N Y (1994); Colbere-Garapin F et al., (1981) J Mol Biol 150: 1-14, which are incorporated by reference herein in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987), which is herein incorporated by reference in its entirety). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66, which is herein incorporated by reference in its entirety).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Kohler G (1980) PNAS 77: 2197-2199, each of which is herein incorporated by reference in its entirety). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Antibodies or fragments thereof that specifically bind to LAG-3 (e.g., human LAG-3) can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al, (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, NY; Ausubel F M et al, Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al, (eds.) (1999) Genome Analysis: A Laboratory Manual, Cold Spring Harbor Laboratory Press, all of which are herein incorporated by reference in their entireties.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

In one aspect, provided herein is a method of making an antibody which specifically binds to LAG-3 (e.g., human LAG-3) comprising culturing a cell or host cell described herein. In one embodiment, the method is performed in vitro. In a certain aspect, provided herein is a method of making an antibody which specifically binds to LAG-3 (e.g., human LAG-3) comprising expressing (e.g., recombinantly expressing) the antibody using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody obtained from the cell or host cell.

Methods for producing polyclonal antibodies are known in the art (see, for example, Chapter 11 in: Short Protocols in Molecular Biology, (2002) 5th Ed., Ausubel F M et al, eds., John Wiley and Sons, New York, which is herein incorporated by reference in its entirety).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), each of which is herein incorporated by reference in its entirety. The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody specifically binds to LAG-3 (e.g., human LAG-3) as determined, e.g., by ELISA or other antigen-binding or competitive binding assay known in the art or in the examples provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody). Monoclonal antibodies described herein can, for example, be made by the hybridoma method as described in Kohler G & Milstein C (1975) Nature 256: 495, which is herein incorporated by reference in its entirety, or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., LAG-3 (e.g., human LAG-3)) used for immunization. Alternatively, lymphocytes may be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986), herein incorporated by reference in its entirety). Additionally, a RIMMS (repetitive immunization multiple sites) technique can be used to immunize an animal (Kilpatrick K E et al., (1997) Hybridoma 16:381-9, herein incorporated by reference in its entirety).

In some embodiments, mice (or other animals, such as rats, monkeys, donkeys, pigs, sheep, hamster, or dogs) can be immunized with an antigen (e.g., LAG-3 (e.g., human LAG-3)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC®) (Manassas, VA), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as NS0 cell line or those derived from MOPC-21 and MPC-11 mouse tumors available from the Salk Institute Cell Distribution Center, San Diego, CA, USA, and SP-2 or X63-Ag8.653 cells available from the American Type Culture Collection, Rockville, MD, USA. Human myeloma and mouse-human heteromyeloma cell lines also have been described for the production of human monoclonal antibodies (Kozbor D (1984) J Immunol 133: 3001-5; Brodeur et al, Monoclonal Antibody Production Techniques and Applications, pp. 51-63 (Marcel Dekker, Inc., New York, 1987), each of which is herein incorporated by reference in its entirety).

Culture medium in which hybridoma cells are growing is assayed for production of monoclonal antibodies directed against LAG-3 (e.g., human LAG-3). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include antibody fragments which recognize specific LAG-3 (e.g., human LAG-3) and can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al, (1995) J Immunol Methods 182: 41-50;

Ames R S et al, (1995) J Immunol Methods 184: 177-186; Kettleborough C A et al, (1994) Eur J Immunol 24: 952-958; Persic L et al, (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108, all of which are herein incorporated by reference in their entireties.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax R L et al, (1992) BioTechniques 12(6): 864-9; Sawai H et al, (1995) Am J Reprod Immunol 34: 26-34; and Better M et al, (1988) Science 240: 1041-1043, all of which are herein incorporated by reference in their entireties.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415, all of which are herein incorporated by reference in their entireties.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including IgG$_1$, IgG$_2$, IgG$_3$ and IgG$_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73, all of which are herein incorporated by reference in their entireties. See also U.S. Application Publication No. US 2005/0042664 A1 (Feb. 24, 2005), which is incorporated by reference herein in its entirety.

Methods for making multispecific (e.g., bispecific antibodies) have been described, see, for example, U.S. Pat. Nos. 7,951,917; 7,183,076; 8,227,577; 5,837,242; 5,989,830; 5,869,620; 6,132,992 and 8,586,713, all of which are herein incorporated by reference in their entireties.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301, all of which are herein incorporated by reference in their entireties.

Further, antibodies that specifically bind to a LAG-3 (e.g., human LAG-3) antigen can, in turn, be utilized to generate anti-idiotype antibodies that "mimic" an antigen using techniques well known to those skilled in the art. See, e.g., Greenspan N S & Bona C A (1989) FASEB J 7(5): 437-444; and Nissinoff A (1991) J Immunol 147(8): 2429-2438, each of which is herein incorporated by reference in its entirety.

In particular embodiments, an antibody described herein, which binds to the same epitope of LAG-3 (e.g., human LAG-3) as an anti-LAG-3 (e.g., human LAG-3) antibody described herein, is a human antibody. In particular embodiments, an antibody described herein, which competitively blocks (e.g., in a dose-dependent manner) any one of the antibodies described herein, from binding to LAG-3 (e.g., human LAG-3), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., LAG-3 (e.g., human LAG-3)). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93, herein incorporated by reference in its entirety. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598, all of which are herein incorporated by reference in their entireties. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin), all of which are herein incorporated by reference in their entireties.

Human antibodies which specifically bind to LAG-3 (e.g., human LAG-3) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741, all of which are herein incorporated by reference in their entireties.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., LAG-3 (e.g., human LAG-3)). Such methods are known and are described in the art, see, e.g., Shinmoto H et al., (2004) Cytotechnology 46: 19-23; Naganawa Y et al., (2005) Human Antibodies 14: 27-31, each of which is herein incorporated by reference in its entirety.

6.6 Kits

Also provided, are kits comprising one or more antibodies described herein, or pharmaceutical composition or conjugates thereof. In a specific embodiment, provided herein is a pharmaceutical pack or kit comprising one or more containers filled with one or more of the ingredients of the pharmaceutical compositions described herein, such as one or more antibodies provided herein. In some embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In one embodiment, a kit comprises an antibody described herein, preferably a purified antibody, in one or more containers. In a specific embodiment, kits described herein contain a substantially isolated LAG-3 (e.g., human LAG-3) antigen as a control. In another specific embodiment, the kits described herein further comprise a control antibody which does not react with a LAG-3 (e.g., human LAG-3) antigen. In another specific embodiment, kits described herein contain one or more elements for detecting the binding of an antibody to a LAG-3 (e.g., human LAG-3) antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized LAG-3 (e.g., human LAG-3) antigen. The LAG-3 (e.g., human LAG-3) antigen provided in the kit can also be attached to a solid support. In a more specific embodiment, the detecting means of the above described kit includes a solid support to which a LAG-3 (e.g., human LAG-3) antigen is attached. Such a kit can also include a non-attached reporter-labeled anti-human antibody or anti-mouse/rat antibody. In this embodiment, binding of the antibody to the LAG-3 (e.g., human LAG-3) antigen can be detected by binding of the said reporter-labeled antibody. In one embodiment, the present invention relates to the use of a kit of the present invention for in vitro assaying and/or detecting LAG-3 antigen (e.g., human LAG-3) in a biological sample.

7. EXAMPLES

The examples in this Section (i.e., Section 6) are offered by way of illustration, and not by way of limitation.

7.1 Example 1: Generation and Characterization of Novel Antibodies Against Human LAG-3

This example describes the generation and characterization of antibodies that bind to human Lymphocyte activation gene 3 (LAG-3), also known as CD223. In particular, this example describes the generation of murine antibodies that specifically bind to human LAG-3 and inhibit the function of human LAG-3.

7.1.1 Generation of Anti-LAG-3 Antibodies

Anti-LAG-3 antibodies were identified by generation and selection of an immunized Fab phage display library. First, total RNA was purified from single-cell suspension of splenocytes from three individual mice previously immunized with recombinant human LAG-3-Fc protein (R&D Systems, Cat #2319-L3-050) and recombinant cynomolgus monkey LAG-3-Fc protein (Evitria, Custom order). Per mouse, a Fab library was then generated by random-primed cDNA using total RNA as a template to amplify variable regions from mouse antibody genes. Heavy and kappa chain amplicons were combined and cloned into phagemid vectors. Three rounds of selection were performed against recombinant LAG-3 proteins (human LAG-3-Fc, human LAG-3-6His, and/or a 30 amino acid human LAG-3 peptide) and/or cells expressing cynomolgus LAG-3 to identify LAG-3-specific Fab phage clones. The 30 amino acid human LAG-3 peptide is a biotinylated peptide comprising the amino acid sequence of GPPAAAPGHPLAPGPHPAAPSS-WGPRPRRY (SEQ ID NO: 199). Periplasmic extracts of selected Fab clones were then screened by ELISA or flow cytometry. Antibody sequencing and off-rate analysis were then performed on anti-LAG-3 Fabs.

A set of murine antibodies that bind to human LAG-3 were identified and designated as P01A12, P01C09, P05E01, P05E03, P13A04, P13A06, P13B01, P13B02, P13B03, P13B11, P13C06, P13C08, P13C10, P13D04, P13D05, P13E02, P13F01, P13F02, P13F06, P13F09, P13G01, P13G04, P13G05, P13H05, P14A04, P14B07, P14C04, P14F01, P14F06, P14G01, P14G03, P15B06, P15C02, P15E06, P15F06, P15G05, P16D04, and P16H05. The sequence information of the variable regions of these antibodies is summarized in Table 6.

7.1.2 Binding of Anti-LAG-3 Fabs to LAG-3-Expressing Cells

The anti-LAG-3 Fabs from periplasmic extracts were tested for binding to LAG-3-expressing cells using flow cytometry. Briefly, wild type and human LAG-3-expressing Jurkat cells were plated at $2\times10^5$ cells/well in sample buffer (PBS (Gibco, Cat #10010-015)+0.5% FBS (Gibco, Cat #10270-106)) in 96-well U-bottom plates (Sarstedt). 22 µl of anti-LAG-3 Fab periplasmic extract and 83 µl of diluted anti-c-myc antibody (Gentaur, Clone #9E10, Cat #04-cmyc-9E10) were incubated for 30 minutes at room temperature. 100 µl of the periplasmic extract/anti-c-myc mixture was added to cells and then incubated for one hour on ice. Cells were washed three times and then incubated with a goat anti-mouse APC (BD Biosciences, Cat #550826) for 30 minutes on ice. Cells were washed three times and then analyzed with a FACS machine (BD Accuri6).

Figure 1A:
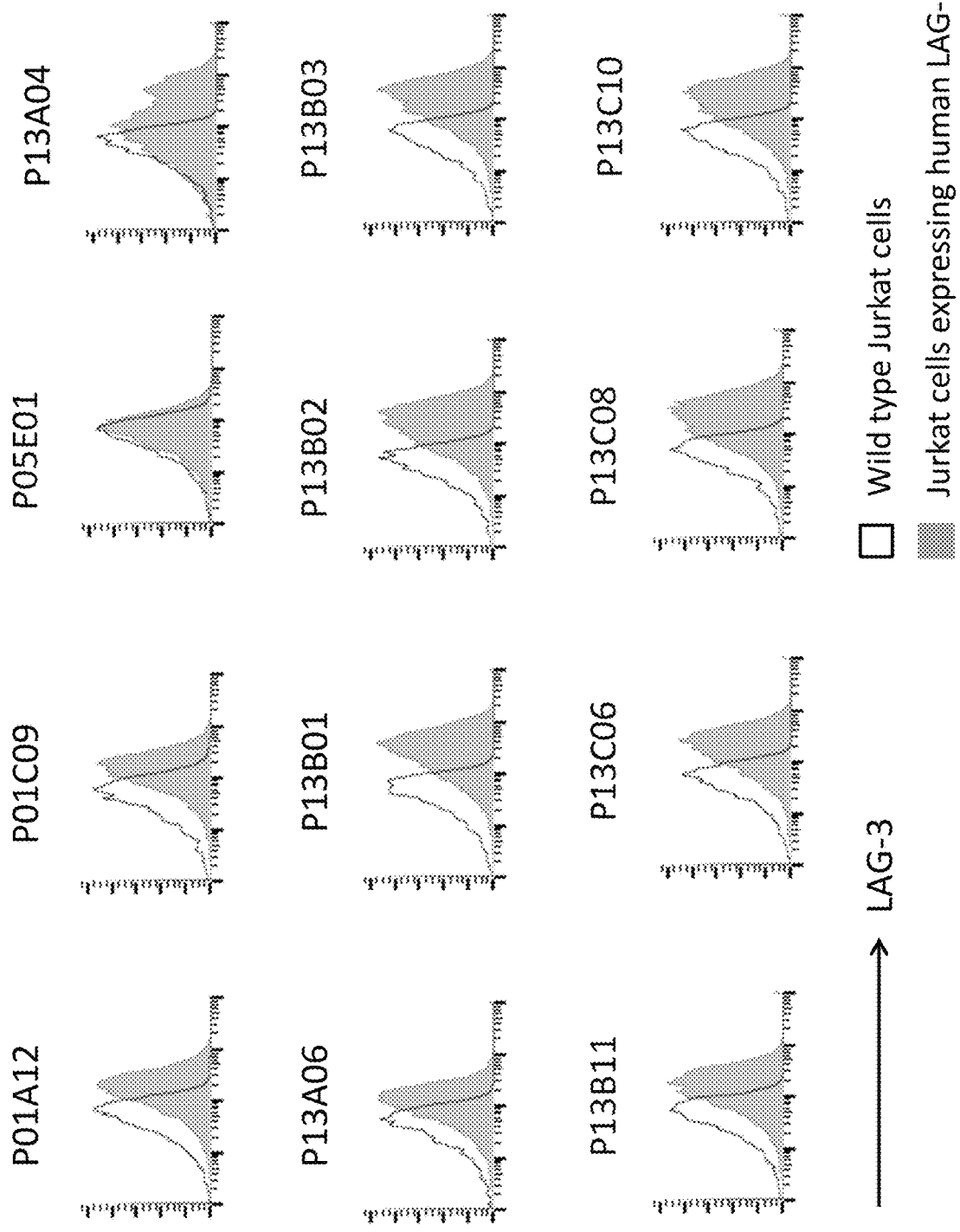
Figure 1B:
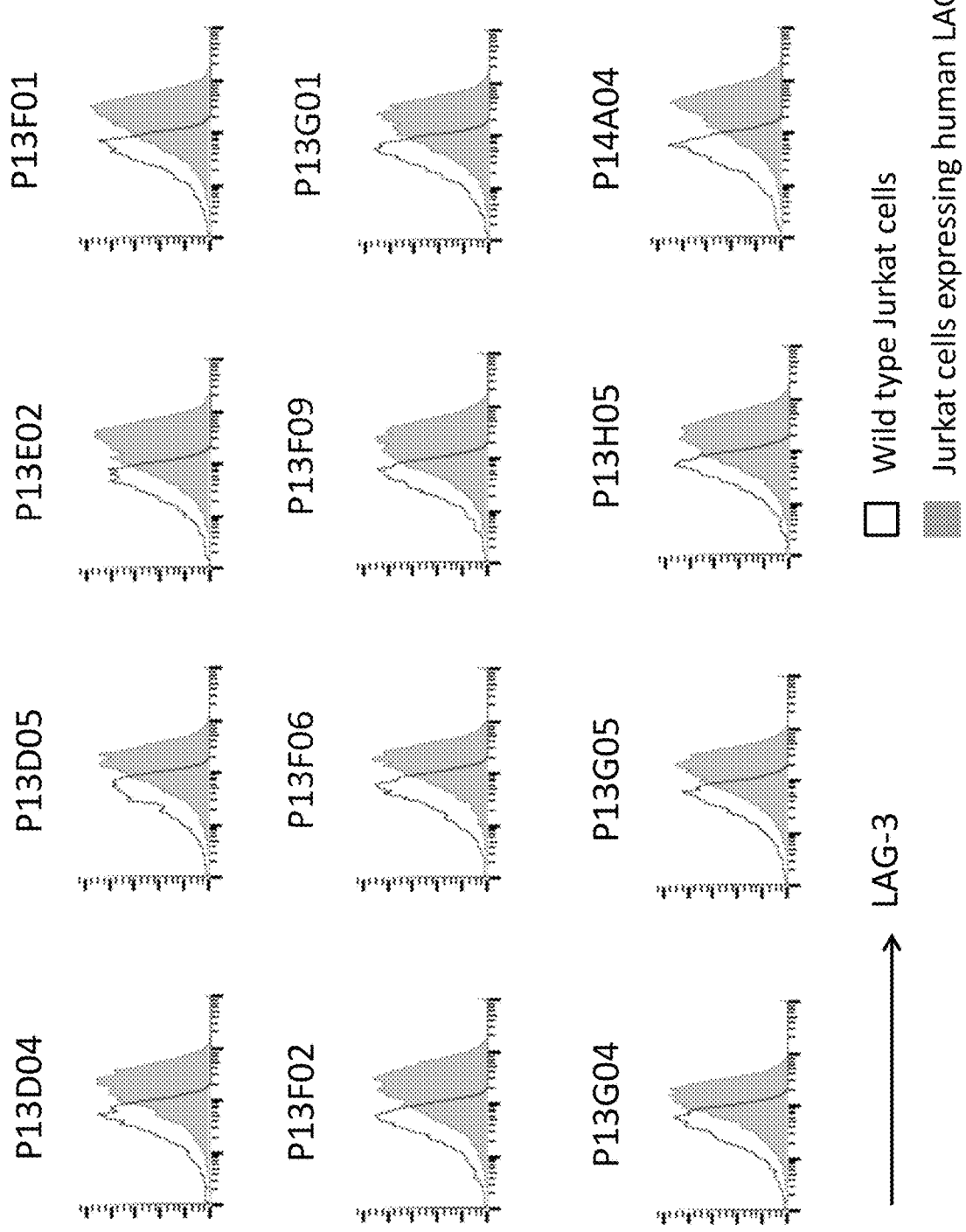
Figure 1C:
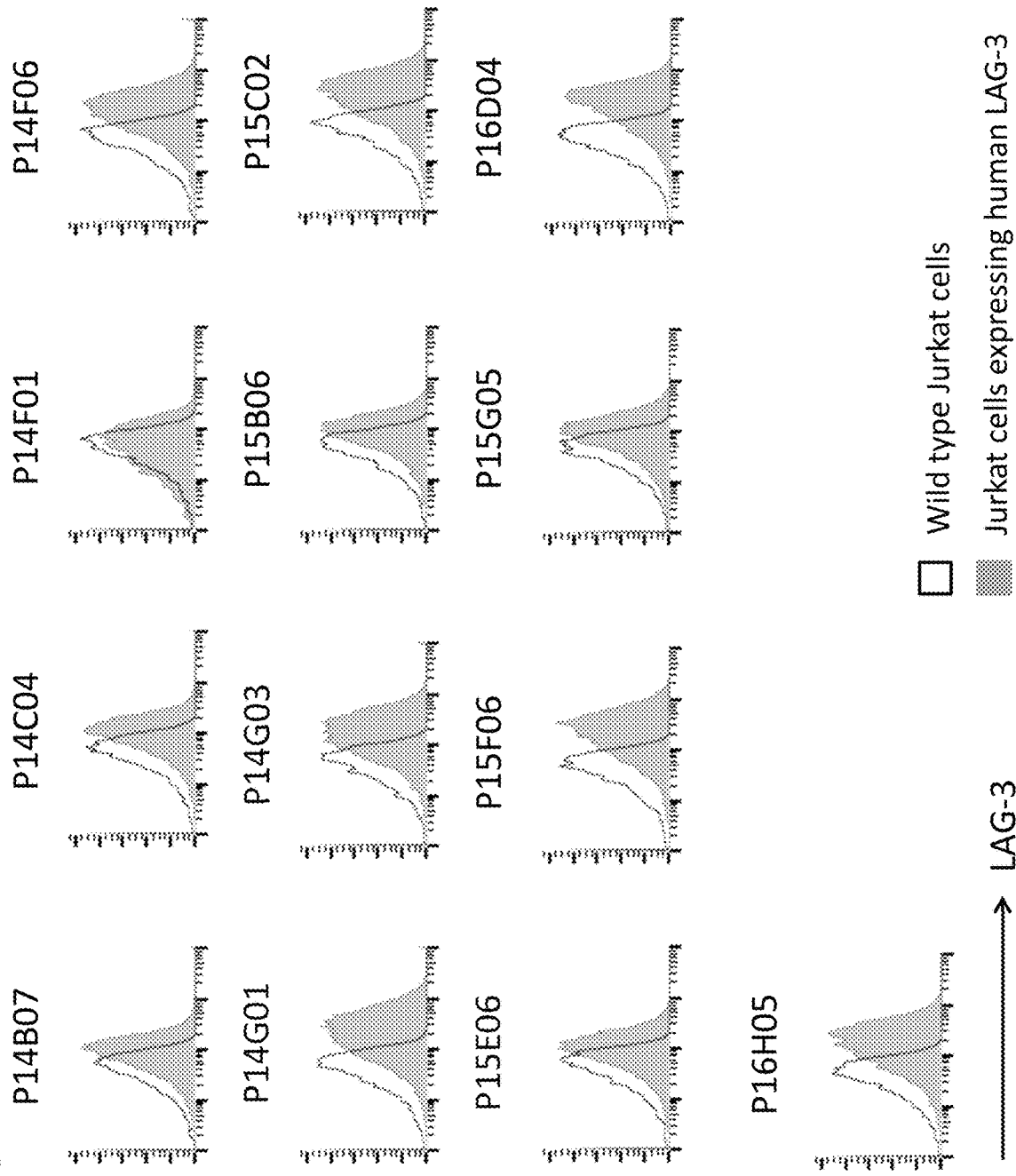

As shown in FIGS. 1A-1C, all the anti-LAG-3 Fabs tested exhibited binding to Jurkat cells expressing human LAG-3. The apparent low level of binding of P05E01 was possibly due to low Fab concentration in the periplasmic extracts. The binding of P05E01 were confirmed in later experiments (data not shown).

7.1.3 Ligand Blocking Activity of Anti-LAG-3 Fabs or Antibodies

Anti-LAG-3 Fabs were tested for their ability to block the binding of recombinant human LAG-3 to MHC class II expressing cells. LAG-3-6His (Aero Biosystems, Cat #LA3-H5222) was pre-incubated at 10 µg/ml with anti-His biotin (Genscript, Clone #A00186, Cat #A00613) at 6 µg/ml for 10 minutes at 4° C. This mixture was then incubated with either 10000 ng/ml (FIG. 2A) or a serial dilution (21170, 7056.6, 2352.2, 784.0, 261.3, 87.1, 29.0, or 9.7 ng/ml) (FIG. 2B) of anti-LAG-3 Fab or a negative control Fab not specific for LAG-3 for 60 minutes at 4° C. and then incubated with 50,000 Raji cells for another 60 minutes at 4° C. Cultures were washed twice with sample buffer (PBS+2% FBS+ 0.09% sodium azide) and then incubated with streptavidin-PE (Biolegend, Cat #405204) in sample buffer for 30 minutes at 4° C. Cells were washed twice and then analyzed with a FACS Fortessa cytometer (Becton Dickinson).

As shown in FIGS. 2A and 2B, all the anti-LAG-3 Fabs tested blocked the binding of cross-linked recombinant LAG-3-6His to MHC class II positive Raji cells.

The variable regions of selected Fabs were cloned into human heavy chain (Ch1, Ch2, and Ch3) and light chain (CL) constant regions and expressed as full-length IgG$_1$ chimeric antibodies and tested in a similar ligand blocking assay as described above at various concentrations (96360, 48180, 24090, 12045, 6022, 3011, 1505, 753, 376, 188, or 94 ng/ml).

Figure 3:
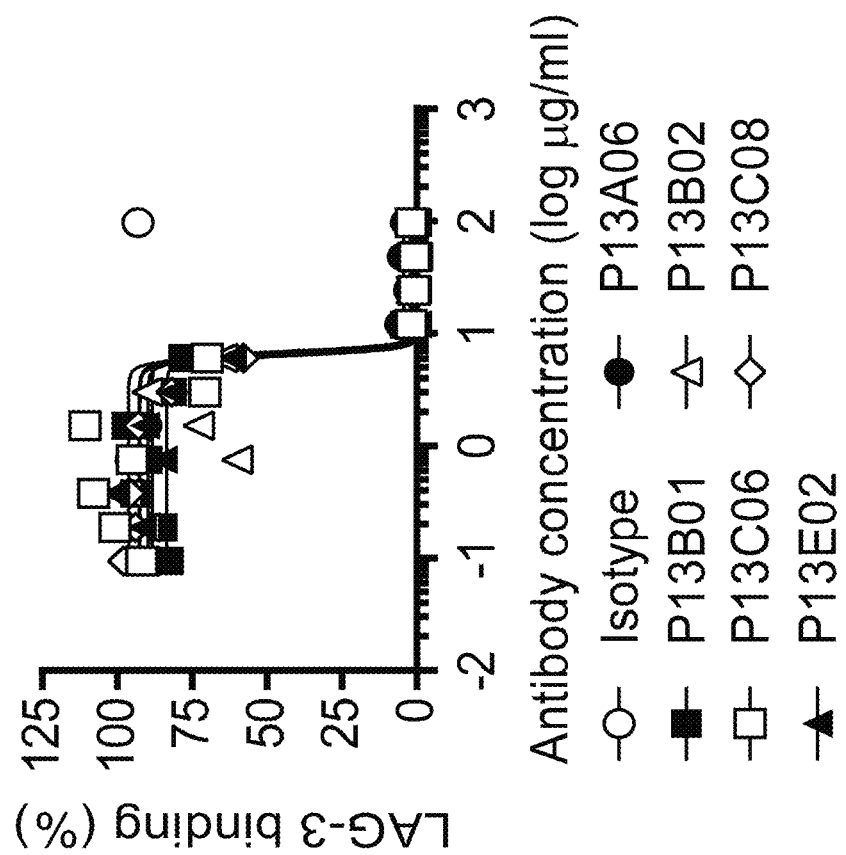
FIG. 3 is a line graph similar to the one shown in FIG. 2B, in which the percentage of LAG-3 binding is plotted against a dose titration of full length chimeric anti-LAG-3 antibody P13A06, P13B01, P13B02, P13C06, P13C08, or P13E02, or an isotype control antibody.

The full length chimeric anti-LAG-3 antibodies tested all blocked the interaction between recombinant LAG-3 and MHC class II expressing Raji cells (FIG. 3).

7.1.4 Effect of Anti-LAG-3 Antibody on Human PBMCs Upon *Staphylococcus* Enterotoxin A (SEA) Stimulation The functional activity of the chimeric anti-LAG-3 antibody P13B02 was tested using primary human peripheral blood mononuclear cells (PBMCs) stimulated with *Staphylococcus* Enterotoxin A (SEA). Briefly, cryopreserved human PBMCs (Research Blood Components) were plated at $10^5$ cells/well in RPMI1640 supplemented with Normocin™ (Invivogen, Cat #ant-nr-1) and 10% heat-inactivated FBS (Thermo Fisher Scientific, Cat #26140079) in 96-well NUNCLON delta surface plates (NUNC™). Cells were cultured with 100 ng/ml SEA (Toxin Technologies, Cat #at101red) and 10 µg/ml P13B02 or an isotype control antibody for 5 days at 37° C., 5% CO$_2$, and 97% humidity. Clarified supernatant was collected and stored at −80° C. until analysis. IL-2 levels were determined using AlphaLISA (Perkin Elmer, Cat #AL221C).

Figure 4:
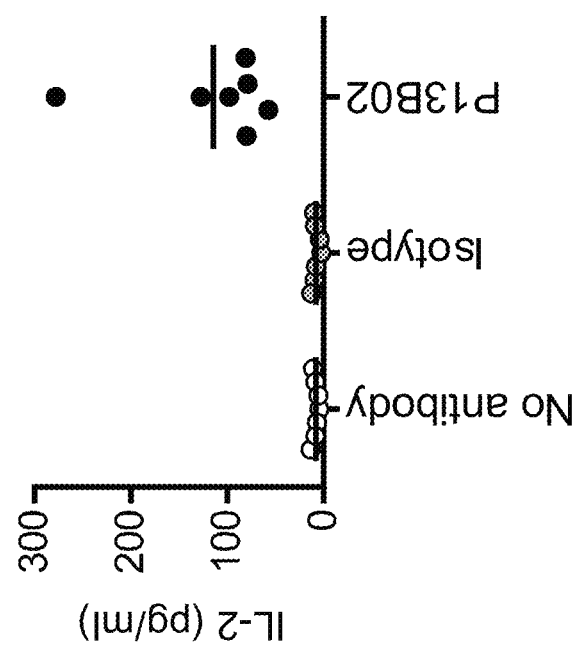
FIG. 4 is a graph showing the production of IL-2 in human peripheral blood mononuclear cells (PBMCs) upon *Staphylococcus* Enterotoxin A (SEA) stimulation in the absence of any antibody, or in the presence of an isotype control antibody or the chimeric anti-LAG-3 antibody P13B02.

As shown in FIG. 4, the anti-LAG-3 antibody P13B02 increased IL-2 production in human PBMCs stimulated with the SEA superantigen.

7.2 Example 2: Generation and Characterization of Humanized Antibodies Against Human LAG-3

This example describes the humanization of the murine antibody P13B02 and the characterization of the humanized antibodies.

7.2.1 Humanization of Murine Antibody P13B02

Homology matching was used to choose human acceptor framework regions to graft the CDRs of the murine antibody P13B02. Databases, e.g., a database of germline variable genes from the immunoglobulin loci of human and mouse (the IMGT database (the international ImMunoGeneTics Information System®; Lefranc M P et al., (1999) Nucleic Acids Res 27(1): 209-12; Ruiz M et al., (2000) Nucleic Acids Res 28(1): 219-21; Lefranc M P (2001) Nucleic Acids Res 29(1): 207-9; Lefranc M P (2003) Nucleic Acids Res 31(1): 307-10; Lefranc M P et al., (2005) Dev Compo Immunol 29(3): 185-203; Kaas Q et al., (2007) Briefings in Functional Genomics & Proteomics 6(4): 253-64) or the VBASE2 (Retter I et al., (2005) Nucleic Acids Res 33, Database issue D671-D674) or the Rabat database (Johnson G et al, (2000) Nucleic Acids Res 28: 214-218)) or publications (e.g., Rabat E A et al., (1991) Sequences of Proteins of Immunological Interest, Fifth Edition, U.S. Department of Health and Human Services, NIH Publication No. 91-3242), all of which are herein incorporated by reference in their entireties, may be used to identify the human subfamilies to which the murine heavy and light chain variable regions belong and determine the best-fit human germline framework to use as the acceptor molecule. Selection of heavy and light chain variable region sequences within these subfamilies to be used as acceptor may be based upon sequence homology and/or a match of structure of the CDR1 and CDR2 regions to help preserve the appropriate relative presentation of the six CDRs after grafting.

Searching of the IMGT database, downloaded from IMGT.org, using BioEdit Sequence Alignment Editor (Hall, T. A. 1999. BioEdit: a user-friendly biological sequence alignment editor and analysis program for Windows 95/98/NT. Nucl. Acids. Symp. Ser. 41:95-98, herein incorporated by reference in its entirety) indicated good homology between the P13B02 heavy chain variable region framework and members of the human heavy chain variable region subgroup IGHV1. Highest homologies and identities of both CDR and framework sequences were observed for germline sequences: IGHV1-46*01 (SEQ ID NO: 153) (62% identity; 61 amino acid residues out of 98); IGHV1-69-2*01 (SEQ ID NO: 154) (63% identity; 62/98); IGHV1-3*01 (SEQ ID NO: 155) (64% identity; 63/98); IGHV1-24*01 (SEQ ID NO: 156) (61% identity; 60/98); IGHV1-2*01 (SEQ ID NO: 157) (60% identity; 59/98); IGHV1-45*01 (SEQ ID NO: 158) (59% identity; 58/98); and IGHV1-18*01 (SEQ ID NO: 159) (60% identity; 59/98).

Using the same approach, P13B02 light chain variable region sequence showed good homology to members of the human light chain variable region kappa subgroups IGKV3 and IGKV1. Highest homologies and identities of both CDRs and framework sequences were observed for germline sequences: IGKV3-20*01 (SEQ ID NO: 160) (59% identity; 57 amino acid residues out of 96); IGKV3D-15*01 and IGKV3-15*01 (SEQ ID NO: 161) (58% identity; 56/96); IGKV3D-20*01 (SEQ ID NO: 162) (59% identity; 57/96); IGKV3D-7*01 (SEQ ID NO: 163) (58% identity; 56/96); IGKV1-9*01 (SEQ ID NO: 164) (63% identity; 61/96); and IGKV3-11*01 (SEQ ID NO: 165) (60% identity; 58/96).

As a starting point to the humanization process, a CDR grafted version of mouse P13B02 VH was generated using framework regions 1,2 and 3 of human IGHV1-46*01 (SEQ ID NO: 153) and framework region 4 of human IGHJ1*01 (SEQ ID NO: 200) as human framework acceptor. A number of back mutations were made at positions that may affect the conformation of CDRs or inter-variable region packing and therefore may be structurally important for maintaining the full activity of the antibody (H0-H4; SEQ ID NOs: 56-60 and 220, respectively) (FIG. 5A). Similarly, a CDR grafted version of mouse P13B02 VL was generated using framework regions 1, 2, and 3 of human IGKV3-20*01 (SEQ ID NO: 160) and framework 4 of human IGKJ1*01 (SEQ ID NO: 201) as human framework acceptor (L0; SEQ ID NO: 73) (FIG. 5B). Back mutations were generated at various positions (L1-L4; SEQ ID NOs: 74-77, respectively) (FIG. 5B). The sequences of the humanized VHs H0-H4 and the humanized VLs L0-L4 are provided in Table 1. Table 10 shows positions that are different between mouse and human antibody framework regions and are subjected to back mutation in at least one of the humanized VHs or VLs described above. Table 11 shows positions that are different between mouse and human antibody framework regions and are subjected to back mutation in H1R98KL4M.

TABLE 10

Summary of framework back mutations in at least one of the humanized VHs or VLs.

Heavy chain variable region

| Kabat position | P13B02 VH | IGHV1-46*01 (SEQ ID NO: 153) |
|---|---|---|
| H4 | M | L |
| H5 | K | V |
| H12 | V | K |
| H23 | T | K |
| H27 | F | Y |
| H28 | N | T |
| H29 | I | F |
| H30 | K | T |
| H48 | I | M |
| H69 | I | M |
| H71 | A | R |
| H75 | S | T |
| H76 | N | S |
| H80 | L | M |
| H81 | Q | E |
| H94 | T | R |

Light chain variable region

| Kabat position | P13B02 VL | IGKV3-20*01 (SEQ ID NO: 160) |
|---|---|---|
| L3 | L | V |
| L22 | T | S |
| L36 | F | Y |
| L43 | S | A |
| L47 | W | L |
| L58 | V | I |
| L70 | S | D |
| L71 | Y | F |

TABLE 11

Summary of framework back mutations in H1_R98K_L4M.

| Kabat position | P13B02 VH | IGHV1-46*01 (SEQ ID NO: 153) |
|---|---|---|
| H4 | M | L |
| H27 | F | Y |
| H28 | N | T |
| H29 | I | F |

TABLE 11-continued

Summary of framework back mutations in H1_R98K_L4M.

| Kabat position | P13B02 VH | IGHV1-46*01 (SEQ ID NO: 153) |
|---|---|---|
| H30 | K | T |
| H69 | I | M |
| H71 | A | R |
| H94 | T | R |

In addition, the HCDR3 of P13B02 contains a "RYD" motif, which has been demonstrated previously to mimic the integrin binding motif "RGD." In order to test whether the "RYD" motif could be removed without impacting binding to LAG-3, an amino acid substitution R98R or D100E, numbered according to Rabat definition, was introduced in the heavy chain.

A panel of 37 humanized antibodies, designated as P13B02-01 to P13B02-37, were designed based on the description above and generated as full length $IgG_1$ antibodies. P13B02-30 were generated in three versions: a full length antibody containing $IgG_1$ Glm17 allotype, referred to as P13B02-30 ($IgG_1$); a full length antibody containing $IgG_1$ Glm17 allotype with a N297A mutation, referred to as P13B02-30 ($IgG_1$ Glm17 N297A); and a full length antibody containing $IgG_1$ Glm3 allotype with a N297A mutation, referred to as P13B02-30 ($IgG_1$ Glm3 N297A). The sequence information of the variable regions of P13B02-01 to P13B02-37 is summarized in Table 7. Two batches of P13B02-30 ($IgG_1$ Glm3 N297A) were examined for post-translational processing in the producer cells. All these 37 humanized antibodies retained binding to recombinant human LAG-3 in surface plasmon resonance analysis (data not shown).

7.2.2 Binding of Humanized Anti-LAG-3 Antibodies to Human LAG-3

The anti-LAG-3 antibodies were tested for binding to primary human T cells using flow cytometry. Cryopreserved human PBMCs (Research Blood Components) were plated at $10^6$ cells/ml in RPMI1640 supplemented with Normocin™ (Invivogen, Cat #ant-nr-1) and 10% heat-inactivated FBS (Thermo Fisher Scientific, Cat #26140079) in a T-75 flask (Corning) in the presence of 100 ng/ml SEA (Toxin Technologies, Cat #at101red) for 5 days at 37° C., 5% $CO_2$, and 97% humidity. Cultured PBMCs were then plated at $10^5$ cells/well in 96-well U-bottom plates (Nunc). Cells were incubated with 10 µg/ml of anti-LAG-3 antibody for 30 minutes on ice. Cells were washed three times and then incubated with anti-CD4-PE/Cy7 (Biolegend, Clone #OKT4, Cat #317414), anti-CD8-FITC (Biolegend, Clone #RPA-T8, Cat #301060), anti-CD3-APC (BD Biosciences, Clone #SP34-2, Cat #557597), LIVE/DEAD® Fixable Near-IR Dead Cell Stain (Life Technologies, Cat #L10119), Fc block (BD Biosciences, Cat #422302), and goat anti-human IgG-PE (ThermoFisher, Cat #PA1-74408). Cells were incubated for 30 minutes on ice, washed, and analyzed with a FACS machine (BD Canto). As shown in FIG. 6A, the chimeric antibody P13B02 and all the humanized antibodies tested exhibited binding to primary CD4+ human T cells stimulated with the SEA superantigen.

Next, human PBMCs were activated using the SEA superantigen similarly as described above and incubated with serially diluted (50000, 15000, 4500, 1350, 407, 122, 37, or 11 ng/ml) P13B02-16 or an isotype control antibody. Binding was analyzed with a FACS Fortessa cytometer (Becton Dickinson). The humanized antibody P13B02-16 bound to activated primary human CD4+ T cells in a dose-dependent manner (FIG. 6B).

7.2.3 Ligand Blocking Activity of Humanized Anti-LAG-3 Antibodies

Next, the ability of the humanized anti-LAG-3 antibodies to block the interaction between cross-linked recombinant LAG-3-6His and MHC class II expressing Raji cells was examined as described above. The humanized antibodies P13B02-06, P13B02-07, P13B02-16, P13B02-26, and P13B02-27, all of which include a human $IgG_1$ constant region, were tested at 57820, 28910, 14455, 7228, 3613, 1807, 903, 452, 226, 113, and 56 ng/ml (FIG. 7A). The humanized antibody P13B02-30 ($IgG_1$ Glm17 N297A) was tested at 96360, 48180, 24090, 12045, 6022, 3011, 1505, 753, 376, 188, and 94 ng/ml (FIG. 7B).

As shown in FIGS. 7A and 7B, all the humanized antibodies tested effectively blocked LAG-3 binding to MHC class II positive Raji cells.

7.2.4 Effect of Humanized Anti-LAG-3 Antibody on Human PBMCs Upon *Staphylococcus* Enterotoxin A (SEA) Stimulation The functional activity of the humanized antibody P13B02-30 ($IgG_1$) was assessed using primary human PBMCs stimulated by *Staphylococcus* Enterotoxin A (SEA). Cryopreserved human PBMCs (Research Blood Components) were plated at $10^5$ cells/well in RPMI1640 supplemented with Normocin™ (Invivogen, Cat #ant-nr-1) and 10% heat-inactivated FBS (Thermo Fisher Scientific, Cat #26140079) in 96-well NUNCLON delta surface plates (NUNC™). Cells were cultured with 100 ng/ml SEA (Toxin Technologies, Cat #at101red) and 10 µg/ml P13B02-30 ($IgG_1$) or an isotype control antibody for 5 days at 37° C., 5% $CO_2$, and 97% humidity. Clarified supernatant was collected and stored at −80° C. until analysis. IL-2 levels were determined using AlphaLISA (Perkin Elmer, Cat #AL221C).

As shown in FIG. 8A, the anti-LAG-3 antibody P13B02-30 ($IgG_1$) enhanced IL-2 production in human PBMCs stimulated with the SEA superantigen.

In a similar experiment, cryopreserved human PBMCs were cultured with 100 ng/ml SEA (Toxin Technologies, Cat #at101red) and 10 µg/ml P13B02-16 ($IgG_1$) or an isotype control antibody in the presence or absence of 5 µg/ml of anti-PD-1 antibody pembrolizumab (Pembro) (Myoderm), anti-PD-1 antibody nivolumab (Nivo) (Myoderm), three different anti-PD-L1 antibodies, or anti-CTLA-4 antibody ipilimumab (Ipi) (Myoderm) for 5 days at 37° C., 5% $CO_2$, and 97% humidity. Clarified supernatant was collected and stored at −80° C. until analysis. IL-2 levels were determined using AlphaLISA (Perkin Elmer, Cat #AL221C). Anti-PD-L1 antibody #1 was generated based on the variable region sequences of antibody A09-246-2 provided in U.S. Application Publication No. US2014/0341917 (herein incorporated by reference in its entirety). Anti-PD-L1 antibody #2 was generated based on the variable region sequences of antibody 2.14H90PT provided in U.S. Pat. No. 8,779,108 (herein incorporated by reference in its entirety). Anti-PDL1 antibody #3 was generated based on sequences provided in U.S. Pat. No. 8,217,149 (herein incorporated by reference in its entirety). The sequences of these three anti-PD-L1 antibodies are listed in Table 12.

TABLE 12

Sequences of anti-PD-L1 antibodies

| SEQ ID NO: | Description | Amino acid sequence |
|---|---|---|
| 202 | anti-PD-L1 antibody #1 heavy chain | EVQLLESGGGLVQPGGSLRLSCAASGFTFSSYIMMWVRQAPGKGLE WVSSIYPSGGITFYADTVKGRFTISRDNSKNTLYLQMNSLRAEDTA VYYCARIKLGTVTTVDYWGQGTLVTVSSASTKGPSVFPLAPSSKST SGGTAALGCLVKDYFPEPVTVSWNSGALTSGVHTFPAVLQSSGLYS LSSVVTVPSSSLGTQTYICNVNHKPSNTKVDKRVEPKSCDKTHTCP PCPAPELLGGPSVFLFPPKPKDTLMISRTPEVTCVVVDVSHEDPEV KFNWYVDGVEVHNAKTKPREEQYNSTYRVVSVLTVLHQDWLNGKEY KCKVSNKALPAPIEKTISKAKGQPREPQVYTLPPSREEMTKNQVSL TCLVKGFYPSDIAVEWESNGQPENNYKTTPPVLDSDGSFFLYSKLT VDKSRWQQGNVFSCSVMHEALHNHYTQKSLSLSPG |
| 203 | anti-PD-L1 antibody #1 light chain | QSALTQPASVSGSPGQSITISCTGTSSDVGGYNYVSWYQQHPGKAP KLMIYDVSNRPSGVSNRFSGSKSGNTASLTISGLQAEDEADYYCSS YTSSSTRVFGTGTKVTVLQPKANPTVTLFPPSSEELQANKATLVCL ISDFYPGAVTVAWKADGSPVKAGVETTKPSKQSNNKYAASSYLSLT PEQWKSHRSYSCQVTHEGSTVEKTVAPTECS |
| 204 | anti-PD-L1 antibody #2 heavy chain | EVQLVESGGGLVQPGGSLRLSCAASGFTFSRYWMSWVRQAPGKGLE WVANIKQDGSEKYYVDSVKGRFTISRDNAKNSLYLQMNSLRAEDTA VYYCAREGGWFGELAFDYWGQGTLVTVSSASTKGPSVFPLAPSSKS ISGGTAALGCLVKDYFPEPVTVSWNSGALTSGVHTFPAVLQSSGLY SLSSVVTVPSSSLGTQTYICNVNHKPSNTKVDKRVEPKSCDKTHTC PPCPAPELLGGPSVFLFPPKPKDTLMISRTPEVTCVVVDVSHEDPE VKFNWYVDGVEVHNAKTKPREEQYNSTYRVVSVLTVLHQDWLNGKE YKCKVSNKALPAPIEKTISKAKGQPREPQVYTLPPSREEMTKNQVS LTCLVKGFYPSDIAVEWESNGQPENNYKTTPPVLDSDGSFFLYSKL TVDKSRWQQGNVFSCSVMHEALHNHYTQKSLSLSPG |
| 205 | anti-PD-L1 antibody #2 light chain | EIVLTQSPGTLSLSPGERATLSCRASQRVSSSYLAWYQQKPGQAPR LLIYDASSRATGIPDRFSGSGSGTDFTLTISRLEPEDFAVYYCQQY GSLPWTFGQGTKVEIKRTVAAPSVFIFPPSDEQLKSGTASVVCLLN NFYPREAKVQWKVDNALQSGNSQESVTEQDSKDSTYSLSSTLTLSK ADYEKHKVYACEVTHQGLSSPVTKSFNRGEC |
| 206 | anti-PD-L1 antibody #3 heavy chain | EVQLVESGGGLVQPGGSLRLSCAASGFTFSDSWIHWVRQAPGKGLE WVAWISPYGGSTYYADSVKGRFTISADTSKNTAYLQMNSLRAEDTA VYYCARRHWPGGFDYWGQGTLVTVSSASTKGPSVFPLAPSSKSTSG GTAALGCLVKDYFPEPVTVSWNSGALTSGVHTFPAVLQSSGLYSLS SVVTVPSSSLGTQTYICNVNHKPSNTKVDKRVEPKSCDKTHTCPPC PAPELLGGPSVFLFPPKPKDTLMISRTPEVTCVVVDVSHEDPEVKF NWYVDGVEVHNAKTKPREEQYNSTYRVVSVLTVLHQDWLNGKEYKC KVSNKALPAPIEKTISKAKGQPREPQVYTLPPSREEMTKNQVSLTC LVKGFYPSDIAVEWESNGQPENNYKTTPPVLDSDGSFFLYSKLTVD KSRWQQGNVFSCSVMHEALHNHYTQKSLSLSPG |
| 207 | anti-PD-L1 antibody #3 light chain | DIQMTQSPSSLSASVGDRVTITCRASQDVSTAVAWYQQKPGKAPKL LIYSASFLYSGVPSRFSGSGSGTDFTLTISSLQPEDFATYYCQQYL YHPATFGQGTKVEIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC |

As shown in FIG. 8B, P13B02-16 (IgG$_1$), either alone or in combination with the anti-PD-1 antibody pembrolizumab or nivolumab, the anti-PD-L1 antibody #1, #2, or #3, or the anti-CTLA-4 antibody ipilimumab, enhanced IL-2 production in human PBMCs in the presence of the SEA superantigen.

7.2.5 Effect of Humanized Anti-LAG-3 Antibody on Cytokine Production of Tumor Infiltrating Lymphocytes The anti-LAG-3 antibody P13B02-30 (IgG$_1$ Glm3 N297A) was further assessed for its ability to stimulate cytokine production of activated primary tumor infiltrating lymphocytes (TILs), alone or in combination with an anti-PD-1 antibody. Single-cell suspensions from fresh renal cell carcinoma (RCC) (stage I) or colorectal cancer (CRC) (stage II) tumors (UMass Medical School, Worcester, MA) were isolated via mechanical microdissection. In some cases, depending on the level of fibrosis, enzymatic digestion was necessary (Liberase and DNAseI, Roche). Cells were rested at 5×10$^4$ cells/well in RPMI1640 supplemented with Normocin™ (Invivogen, Cat #ant-nr-1), recombinant human IL-2 (20 U/ml, R&D Systems, Cat #202-IL-010), and 10% heat-inactivated FBS (Thermo Fisher Scientific, Cat #26140079) in 96-well NUNCLON delta surface plates (NUNC™, Cat #143761) for 1 day. On the following day, the samples were centrifuged and fresh culture media containing the antibodies of interest, P13B02-30 (IgG$_1$ Glm3 N297A) at 20 µg/ml and the anti-PD-1 antibody pembrolizumab (Pembro) (Myoderm) at 5 µg/ml, and anti-CD3/CD28 microbeads (1:1 bead:cell ratio), was added at a final volume of 100 µl and allowed to incubate for 3 days at 37° C. and 5% CO$_2$. Cell-free supernatant was collected and stored at −80° C. until analysis. TNFα levels were determined using AlphaLISA (Perkin Elmer, Cat #AL208C).

As shown in FIGS. 9A and 9B, the anti-LAG-3 antibody P13B02-30 (IgG$_1$ Glm3 N297A) enhanced TNFα production of activated primary TILs from RCC or CRC tumors.

7.2.6 Anti-LAG-3 Antibody Enhances T Cell Activation in a LAG-3-Mediated Cell Suppression Assay In this example, an NFAT-luciferase reporter line was used to assess the inhibitory effect of the anti-LAG-3 antibody P13B02-30 (IgG$_1$ Glm3 N297A) against LAG-3 in a cell suppression assay. Two experiments were performed, as described below.

In each of the two experiments, Jurkat-NFAT-LAG-3 cells were suspended to a 2.5× working concentration of 1×10$^6$ cells/mL in assay medium (RPMI+10% heat-inactivated FBS+1% Pen/Strep). Raji cells were suspended to a 3.33× working concentration of 1×10$^6$ cells/mL in assay medium. Staphylococcal Enterotoxin E (Toxin Technology) was prepared at a 10× working concentration of 0.04 ng/mL in assay medium. A serial dilution of anti-LAG-3 antibody or isotype antibody was prepared in assay medium. In the first experiment, the antibody concentrations ranged from 0.2-50 μg/mL. In the second experiment, the antibody concentrations ranged from 0.1-100 μg/mL). After the serial dilutions of the antibodies were prepared, 40 μL of Jurkat-NFAT-LAG-3 cells and 20 μL of antibody solution were pre-incubated for 30 minutes at 37° C. and 5% CO2 in U-bottom 96-well plates. 30 μL of Raji cells and 10 μL of Staphylococcal Enterotoxin E were added to the 96-well plates and incubated for 5-6 hours. 100 μL of Bio-Glo Luciferase (Promega) was then added to each well and luminescence was recorded using EnVision Plate Reader (Perkin Elmer) after 10-15 minutes.

As shown in FIGS. 10A and 10B, the anti-LAG-3 antibody significantly increased NFAT-luciferase reporter signal, relative to isotype control antibody, in a dose-dependent manner.

7.3 Example 3: Epitope Mapping of Anti-LAG-3 Antibody

In this example, the epitope of the anti-LAG-3 antibody P13B02-30 was characterized as described below.

7.3.1 Epitope Mapping of Anti-LAG-3 Antibody Using Hydrogen-Deuterium Exchange (HDX) Mass Spectrometry Anti-LAG-3 F(ab')2 was generated from P13B02-30 (IgG$_4$ S228P) using the FragIT Kit (Genovis, Cat #A2-FR2-100). The interaction of anti-LAG-3 F(ab')2 with human LAG-3 was studied using hydrogen-deuterium exchange (HDX) mass spectrometry.

For pepsin/protease XIII digestion, 7.9 μg of recombinant his-tagged human LAG-3 (Sino Biological, Cat #16498-H08H) in 125 μl control buffer (50 mM phosphate, 100 mM sodium chloride, pH 7.4) was denatured by adding 125 μl of 4 M guanidine hydrochloride, 0.85 M TCEP buffer (final pH 2.5) and incubating the mixture for 5 minutes at 20° C. The mixture was then subjected to on-column pepsin/protease XIII digestion using an in-house packed pepsin/protease XIII (w/w, 1:1) column and the resultant peptides were analyzed using a UPLC-MS system comprised of a Waters Acquity UPLC coupled to a Q Exactive™ Hybrid Quadrupole-Orbitrap Mass Spectrometer (Thermo). The peptides were separated on a 50 mm×1 mm C8 column with a 19-minute gradient from 2-30% solvent B (0.2% formic acid in acetonitrile). Peptide identification was conducted through searching MS/MS data against the human LAG-3 sequence with Mascot. The mass tolerance for the precursor and productions was 10 ppm and 0.05 Da, respectively.

20 μl human LAG-3 (7.9 μg) or 20 μl human LAG-3/F(ab')2 mixture (7.9 μg: 15.8 μg) was incubated with 105 μl deuterium oxide labeling buffer (50 mM sodium phosphate, 100 mM sodium chloride, pD 7.4) for 0 second, 60 seconds, 300 seconds, 1800 seconds, 7200 seconds, and 14400 seconds at 20° C. Hydrogen/deuterium exchange was quenched by adding 125 μl of 4 M guanidine hydrochloride, 0.85 M TCEP buffer (final pH 2.5). Subsequently, the quenched samples were subjected to on column pepsin/protease XIII digestion and LC-MS analysis as described above. The mass spectra were recorded in MS only mode. Raw MS data were processed using HDX WorkBench, software for the analysis of H/D exchange MS data (J. Am. Soc. Mass Spectrom. 2012, 23 (9), 1512-1521, herein incorporated by reference in its entirety). The deuterium levels were calculated using the average mass difference between the deuterated peptide and its native form (to).

The sequence coverage achieved for human LAG-3 was 96.6%. While most of the human LAG-3 peptides displayed identical or similar deuterium levels with and without the anti-LAG-3 F(ab')2, several peptide segments were found to have significantly decreased deuterium incorporation upon F(ab')2 binding. A strong decrease in deuterium uptake was observed at a region consisting of the amino acid sequence of SEQ ID NO: 215 (SPTIPLQDLSL). The residues are numbered according to SEQ ID NO: 166.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

What is claimed:

1. An isolated antibody that specifically binds to human LAG-3, the antibody comprising a heavy chain variable region comprising complementarity determining regions CDRH1, CDRH2 and CDRH3 and a light chain variable region comprising complementarity determining regions CDRL1, CDRL2 and CDRL3, wherein:
   (a) CDRH1 comprises the amino acid sequence of $DX_1YX_2X_3$(SEQ ID NO: 140), wherein
      $X_1$ is T or N,
      $X_2$ is I or M, and
      $X_3$ is H, Y or D;
   (b) CDRH2 comprises the amino acid sequence of $X_1IDPANX_2X_3X_4X_5X_6X_7PX_8X_9QX_{10}$ (SEQ ID NO: 142), wherein
      $X_1$ is E, R, S, or K,
      $X_2$ is D or G,
      $X_3$ is N or H,
      $X_4$ is T or S,
      $X_5$ is K or H,
      $X_6$ is Y or F,
      $X_7$ is D or A,
      $X_8$ is K or R,
      $X_9$ is F or L, and
      $X_{10}$ is G or D;
   (c) CDRH3 comprises the amino acid sequence of $YX_1X_2X_3YX_4VGGX_5DY$ (SEQ ID NO: 144), wherein
      $X_1$ is Y, F, or S,
      $X_2$ is Y or D,
      $X_3$ is K or R,
      $X_4$ is D or E, and
      $X_5$ is F or C;
   (d) CDRL1 comprises the amino acid sequence of $SVSSX_1ISSSX_2LX_3$ (SEQ ID NO: 147), wherein
      $X_1$ is S or G,
      $X_2$ is N or T, and
      $X_3$ is H or Y;
   (e) CDRL2 comprises the amino acid sequence of SEQ ID NO: 104; and
   (f) CDRL3 comprises the amino acid sequence of $QQWX_1X_2YPX_3T$ (SEQ ID NO: 149), wherein
      $X_1$ is S, N, or R,
      $X_2$ is S, T or R, and
      $X_3$ is F, L, H, or W,
   wherein the CDRH1, CDRH2, CDRH3, CDRL1, CDRL2, and CDRL3 do not comprise the amino acid sequences of SEQ ID NOs: 79, 90, 98, 100, 104, and 105, respectively.

2. The isolated antibody of claim 1, wherein:
   (a) CDRH1 comprises the amino acid sequence of $DX_1YX_2X_3$(SEQ ID NO: 141), wherein
      $X_1$ is T or N,
      $X_2$ is I or M, and
      $X_3$ is H or Y;
   (b) CDRH2 comprises the amino acid sequence of $X_1IDPANX_2X_3X_4KX_5X_6PX_7FQX_8$ (SEQ ID NO: 143), wherein
      $X_1$ is E, R, or S,
      $X_2$ is D or G,
      $X_3$ is N or H,
      $X_4$ is T or S,
      $X_5$ is Y or F,
      $X_6$ is D or A,
      $X_7$ is K or R, and
      $X_8$ is G or D;
   (c) CDRH3 comprises the amino acid sequence of $YX_1X_2X_3YDVGGX_4DY$ (SEQ ID NO: 145), wherein
      $X_1$ is Y, F, or S,
      $X_2$ is Y or D,
      $X_3$ is K or R, and
      $X_4$ is F or C;

(d) CDRH3 comprises the amino acid sequence of YYYX$_1$YX$_2$VGGFDY (SEQ ID NO: 146), wherein
X$_1$ is K or R, and
X$_2$ is D or E;
(e) CDRL1 comprises the amino acid sequence of SVSS-SISSSNLX$_1$ (SEQ ID NO: 148), wherein X$_1$ is H or Y; and/or
(f) CDRL3 comprises the amino acid sequence of QQWX$_1$SYPX$_2$T (SEQ ID NO: 150), wherein
X$_1$ is S, N, or R, and
X$_2$ is F, L, or H.

3. The isolated antibody of claim 1, wherein:
(a) CDRH1 comprises an amino acid sequence selected from the group consisting of SEQ ID NOs: 78-82;
(b) CDRH2 comprises an amino acid sequence selected from the group consisting of SEQ ID NOs: 83-93;
(c) CDRH3 comprises the amino acid sequence of YYYX$_1$YX$_2$VGGFDY (SEQ ID NO: 146), wherein
X$_1$ is K or R, and
X$_2$ is D or E;
(d) CDRH3 comprises an amino acid sequence selected from the group consisting of SEQ ID NOs: 94-99;
(e) CDRL1 comprises an amino acid sequence selected from the group consisting of SEQ ID NOs: 100-103; and/or
(f) CDRL3 comprises an amino acid sequence selected from the group consisting of SEQ ID NOs: 105-112.

4. The isolated antibody of claim 1, wherein CDRH1, CDRH2 and CDRH3 comprise the CDRH1, CDRH2 and CDRH3 amino acid sequences, respectively, set forth in SEQ ID NOs: 78, 83, and 94; 78, 85, and 95; 78, 86, and 96; 78, 86, and 97; 78, 91, and 94; 78, 92, and 96; 79, 84, and 95; 79, 88, and 95; 79, 89, and 95; 79, 90, and 95; 79, 90, and 98; 79, 90, and 99; 80, 85, and 96; 81, 87, and 96; or, 82, 93, and 95, and/or CDRL1, CDRL2 and CDRL3 comprise the CDRL1, CDRL2 and CDRL3 amino acid sequences, respectively, set forth in SEQ ID NOs: 100, 104, and 105; 100, 104, and 106; 100, 104, and 107; 100, 104, and 109; 100, 104, and 110; 101, 104, and 108; 102, 104, and 105; 102, 104, and 112; or, 103, 104, and 111.

5. The isolated antibody of claim 1, wherein:
CDRH1, CDRH2, CDRH3, CDRL1, CDRL2, and CDRL3 comprise the amino acid sequences set forth in SEQ ID NOs: 78, 83, 94, 100, 104, and 105; 78, 85, 95, 100, 104, and 105; 78, 86, 96, 100, 104, and 105; 78, 86, 96, 100, 104, and 109; 78, 86, 96, 100, 104, and 110; 78, 86, 96, 101, 104, and 108; 78, 86, 96, 103, 104, and 111; 78, 86, 97, 102, 104, and 112; 78, 91, 94, 100, 104, and 107; 78, 92, 96, 100, 104, and 105; 78, 92, 96, 100, 104, and 109; 79, 84, 95, 100, 104, and 105; 79, 84, 95, 100, 104, and 106; 79, 84, 95, 102, 104, and 105; 79, 88, 95, 100, 104, and 105; 79, 89, 95, 100, 104, and 105; 79, 90, 95, 100, 104, and 105; 79, 90, 99, 100, 104, and 105; 80, 85, 96, 100, 104, and 105; 81, 87, 96, 100, 104, and 105; 81, 87, 96, 100, 104, and 107; or 82, 93, 95, 100, 104, and 105, respectively.

6. The isolated antibody of claim 1, wherein the antibody comprises a heavy chain variable region comprising the amino acid sequence of SEQ ID NO: 151, 222, 218, or 223, and/or a light chain variable region comprising the amino acid sequence of SEQ ID NO: 152 or 224.

7. The isolated antibody of claim 1, wherein the antibody comprises a heavy chain variable region comprising an amino acid sequence selected from the group consisting of SEQ ID NOs: 56-72 and 220, and/or a light chain variable region comprising an amino acid sequence selected from the group consisting of SEQ ID NOs: 73-77 and 221.

8. The isolated antibody of claim 1, wherein the antibody comprises a heavy chain comprising an amino acid sequence selected from the group consisting of SEQ ID NOs: 168-186 and 225-227, and/or a light chain comprising an amino acid sequence selected from the group consisting of SEQ ID NOs: 187-191 and 228.

9. The isolated antibody of claim 1, wherein the antibody comprises:
(a) a heavy chain variable framework region that is or is derived from an amino acid sequence encoded by a human gene, optionally wherein said amino acid sequence is selected from the group consisting of IGHV1-46*01 (SEQ ID NO: 153), IGHV1-69-2*01 (SEQ ID NO: 154), IGHV1-3*01 (SEQ ID NO: 155), IGHV1-24*01 (SEQ ID NO: 156), IGHV1-2*01 (SEQ ID NO: 157), IGHV1-45*01 (SEQ ID NO: 158), and IGHV1-18*01 (SEQ ID NO: 159); and/or
(b) a light chain variable framework region that is or is derived from an amino acid sequence encoded by a human gene, optionally wherein said amino acid sequence is selected from the group consisting of IGKV3-20*01 (SEQ ID NO: 160), IGKV3D-15*01 (SEQ ID NO: 161), IGKV3-15*01 (SEQ ID NO: 161), IGKV3D-20*01 (SEQ ID NO: 162), IGKV3D-7*01 (SEQ ID NO: 163), IGKV1-9*01 (SEQ ID NO: 164), and IGKV3-11*01 (SEQ ID NO: 165).

10. The isolated antibody of claim 1, wherein the heavy chain variable region and the light chain variable region, respectively, comprise the amino acid sequences set forth in SEQ ID NOs: 56 and 73; 56 and 74; 56 and 75; 56 and 76; 56 and 77; 57 and 73; 57 and 74; 57 and 75; 57 and 76; 57 and 77; 58 and 73; 58 and 74; 58 and 75; 58 and 76; 58 and 77; 59 and 73; 59 and 74; 59 and 75; 59 and 76; 59 and 77; 60 and 73; 60 and 74; 60 and 75; 60 and 76; 60 and 77; or 62 and 77.

11. The isolated antibody of claim 1, wherein the antibody comprises:
(a) a heavy chain comprising the amino acid sequence of SEQ ID NO: 168 or 225, and a light chain comprising the amino acid sequence of SEQ ID NO: 187 or 228;
(b) a heavy chain comprising the amino acid sequence of SEQ ID NO: 169 or 226, and a light chain comprising the amino acid sequence of SEQ ID NO: 187 or 228; or
(c) a heavy chain comprising the amino acid sequence of SEQ ID NO: 169 or 226, and a light chain comprising the amino acid sequence of SEQ ID NO: 187 or 228.

12. The isolated antibody of claim 1, wherein the antibody comprises a heavy chain constant region selected from the group consisting of human IgG$_1$, IgG$_2$, IgG$_3$, IgG$_4$, IgA$_1$, and IgA$_2$, and optionally wherein the heavy chain constant region is:
(a) an IgG$_1$ heavy chain constant region comprising a N297A mutation, optionally wherein the heavy chain constant region comprises the amino acid sequence of SEQ ID NO: 194;
(b) an IgG$_1$ heavy chain constant region comprising a N297Q mutation;
(c) a non-fucosylated IgG$_1$ heavy chain constant region; and/or
(d) an IgG$_4$ heavy chain constant region comprises a S228P mutation, optionally wherein the heavy chain constant region comprises the amino acid sequence of SEQ ID NO: 196,
wherein the amino acid residues are numbered according to the EU numbering system.

13. The isolated antibody of claim 1, wherein the antibody comprises a light chain constant region selected from the group consisting of a human kappa light chain and a human lambda light chain, optionally wherein the light chain constant region is a human kappa light chain constant region comprising the amino acid sequence of SEQ ID NO: 198 or 219.

14. The isolated antibody of claim 1, wherein the antibody is conjugated to a cytotoxic agent, cytostatic agent, toxin, radionuclide, or detectable label.

15. A pharmaceutical composition comprising the antibody of claim 1 and a pharmaceutically acceptable carrier or excipient.

* * * * *